US 6,713,602 B1

(12) United States Patent
Buchardt et al.

(10) Patent No.: US 6,713,602 B1
(45) Date of Patent: Mar. 30, 2004

(54) SYNTHETIC PROCEDURES FOR PEPTIDE NUCLEIC ACIDS

(76) Inventors: Ole Buchardt, deceased, late of Vaerlose (DK); by D. Buchardt, legal representative, Sondergardsvej 73, 3500 Vaerlose (DK); Michael Egholm, Sindshvilevej 5, 3. tv., 2000, Frederiksburg (DK); Peter Eigil Nielsen, Hjortevaenget 509, 2980, Kokkedal (DK); Rolf Henrik Berg, Langelandsvej 20 B, 3.tv. 2000, Frederiksberg (DK)

( * ) Notice: Subject to any disclaimer, the term of this patent is extended or adjusted under 35 U.S.C. 154(b) by 0 days.

(21) Appl. No.: 08/462,977

(22) Filed: Jun. 5, 1995

Related U.S. Application Data

(63) Continuation-in-part of application No. 08/108,591, filed on Nov. 22, 1993, now Pat. No. 6,395,474.

(30) Foreign Application Priority Data

| May 24, 1991 | (DK) | 986/91 |
| May 24, 1991 | (DK) | 987/91 |
| Apr. 15, 1992 | (DK) | 510/92 |

(51) Int. Cl.$^7$ .................. A61K 38/00; C07K 1/00; C12Q 1/68; C07H 21/00
(52) U.S. Cl. .................. 530/300; 435/6; 530/350; 536/23.1
(58) Field of Search .................. 435/5, 6, 810; 436/501; 530/300, 350; 536/23.1, 24.1, 24.3–24.33, 29.3; 935/77, 78

(56) References Cited

U.S. PATENT DOCUMENTS

| 3,687,808 | A |   | 8/1972 | Merigan, Jr. et al. ..... 195/28 N |
| 5,134,066 | A |   | 7/1992 | Rogers et al. ................ 435/91 |
| 5,142,047 | A |   | 8/1992 | Summerton et al. ........ 544/118 |
| 5,324,483 | A |   | 6/1994 | Cody et al. ................. 422/131 |
| 5,340,716 | A |   | 8/1994 | Ullman et al. ................. 435/6 |
| 5,539,082 | A | * | 7/1996 | Nielsen et al. ............. 530/300 |
| 5,773,571 | A | * | 6/1998 | Nielsen et al. ............. 530/300 |

FOREIGN PATENT DOCUMENTS

| WO | WO 86/05518 | 9/1986 |
| WO | WO 86/05519 | 9/1986 |
| WO | WO 89/12060 | 12/1989 |
| WO | WO 90/02749 | 3/1990 |
| WO | WO 92/20702 | 11/1992 |
| WO | WO 92/20703 | 11/1992 |
| WO | WO 93/05180 | 3/1993 |
| WO | WO 93/07883 | 4/1993 |
| WO | WO 93/12129 | 6/1993 |
| WO | WO 93/18052 | 9/1993 |
| WO | WO 94/06815 | 3/1994 |

OTHER PUBLICATIONS

Affinity Chromatography—A practical Approach, P.D.g. Dean, W.S. Johnson and F.A. Middle, eds., IRL Press Ltd., Oxford 1986.

(List continued on next page.)

*Primary Examiner*—Ardin H. Marschel
(74) *Attorney, Agent, or Firm*—Woodcock Washburn LLP

(57) ABSTRACT

A novel class of compounds, known as peptide nucleic acids, bind complementary ssDNA and RNA strands more strongly than a corresponding DNA. The peptide nucleic acids generally comprise ligands such as naturally occurring DNA bases attached to a peptide backbone through a suitable linker.

9 Claims, 31 Drawing Sheets

OTHER PUBLICATIONS

Agrawal, S. and Tang, "Site–Specific Functionalization of Oligodeoxynucleotides for Non–Radioactive Labelling", *Tetrahedron Letters* 1990, 31(11), 143–1546.

Akashi, et al., "New Aspects of Polymer Drugs", *Adv. Polym. Sci.* 1990, 97, 108–146.

Aldrich Technical Bulletin No. AL–180, "Diazald®, MNNG and Diazomethane Generators", 1990.

Anderson et al., "t–Butyloxycarbonylamino Acids and Their Use in Peptide Synthesis", *J. Am. Chem. Soc.* 1957, 79, 6180–6183.

Atherton et al., "The Fluorenylmethoxycarbonyl Amino Protecting Group", The Peptides 9, 1987 1–38.

Atherton et al., "A Physically Supported Gel Polymer for Low Pressure, Continuous Flow Solid Phase Reactions. Application to Solid Phase Peptide Synthesis", *J. Chem. Soc. Chem. Commun* 1981, 1151–1152.

Atherton et al., "Polyamide Supports for Polypeptide Synthesis", *J. Am. Chem. Soc* 1975, 50, 6584–6585.

Atherton et al., "Peptide Synthesis. Part 2 Procedures for solid–phase Synthesis Using $N^\alpha$–Fluorenylmethoxycarbonylamino–acids on Polyamide Supports. Synthesis of Substance P and of Acyl Carrier Protein 65–74 Decapeptide", *J.C.S. Perkin* 1981, I, 538–546.

Atherton, E. et al., "The Polyamide Method of Solid Phase Peptide and Oligonucleotide Synthesis", *Bioorg. Chem.* 1979, 8, 351–370.

Baker, B., "Decapitation of a 5–capped oligoribonucleotide by o–phenanthroline:Cu(II)", *J. Am. Chem. Soc.* 1993, 115, 3378–3379.

Barany et al., "Solid–phase Peptide Synthesis: a Silver Anniversary Report", *Int. J. Peptide Protein Res.* 1987, 30, 705–739.

Barany and Merrified in "The Peptides" vol. 2, Academic Press, N.Y., 1979, pp. 1–284.

Barany et al., "A New Amino Protecting Group Removable by Reduction. Chemistry of the Dithiasuccinoyl (Dts) Function", *J. Am. Chem. Soc.* 1977, 99, 7363–7365.

Barton et al., "Solid–Phase Synthesis of Selectively Protected Peptides for Use as Building Units in the Solid–Phase Synthesis of Large Molecules", *J. Am. Chem. Soc.* 1973, 95, 4501–4506.

Bayer and Jung, "A New Support for Polypeptide Synthesis in Columns", *Tetrahedron Lett* 1970, 51, 4503–4505.

Beaucage and Caruthers, "Deoxynucleoside Phosphoramidites–A New Class of Key Intermediates for Deoxypolynucleotide Synthesis", *Tetrahedron Lett.*, 1981, 22, 1859–1862.

Beran, Mološ et al., "Substituted ω– (4–Oxo–3, 4–Dihydro–5–Pyrimidinyl) Alkanoic Acids, Their Derivatives and Analogues" *Collect. Czech. Chem. Commun.* 1983, 48, 292–298.

Berg et al., "Long–Chain Polystyrene–Grafted Polyethylene Film Matrix: A New Support for Solid–Phase Peptide Synthesis", *J. Am. Chem. Soc* 1989, 111, 8024–8026.

Blackwell, T. K. et al., "Sequence–Specific DNA Binding by the c–Myc Protein," *Science* 1990, 250, 1149–1151.

Bodánsky, "Synthesis of Peptides by Aminolysis of Nitrophenyl Esters", *Nature* 1955, 175, 685.

Bodanszky et al., "Active Esters and Resins in Peptide Synthesis", *Chem. Ind.* 1964, 1423–1424.

Bodanzsky, "Principles of Peptide Synthesis", Springer Verlag, Berlin–New York 1984.

Brady et al., "Large–Scale Synthesis of a Cyclic Hexapeptide Analogue of Somatostatin," *J. Org. Chem.* 1987, 52, 764–769.

Brady et al., "Some Novel, Acid–Labile Amine Protecting Groups", *J. Org. Chem.* 1977, 42, 143–146.

Buttrey et al., "Synthetic Analogues of Polynucleotides–XIII: The Resolution of DL–β–(Thymin–1–YL)Alanine and Polymerisation of the β–(Thymin–1–YL)Alanines", *Tetrahedron* 1975, 31, 73–75.

Carpino, "New Amino–Protecting Groups in Organic Synthesis", *Acc. Chem. Res.* 1973, 6, 191–198.

Carpino "The 9–Fluorenylmethoxycarbonyl Amino–Protecting Group" *J. Org. Chem.*, 1972, 37, 3404–3409.

Carpino, "Oxidative Reactions of Hydrazines. IV. Elimination of Nitrogen from 1,1–Disubstituted–2–arenesulfonhydrazides$^{1-4}$", *J. Am. Chem. Soc.* 1957, 79, 4427–4431.

Carpino and Han, "The 9–Fluorenylmethoxycarbonyl Function, a New Base–Sensitive Amino–Protecting Group", *J. Am. Chem. Soc.* 1970, 92, 5748–5749.

Carpino et al., "((9–Fluorenylmethyl)oxy) carbonyl (FMOC) Amino Acid Fluorides. Convenient New Peptide Coupling Reagents Applicable to the FMOC/tert–Butyl Strategy for Solution and Solid–Phase Syntheses", *J. Am. Chem. Soc.* 1990, 112, 9651–9652.

Caruthers, Marvin H., "Gene Synthesis Machines: DNA Chemistry and Its Uses" *Science*, 1985, 232, 281–285.

Chiang et al., "Antisense Oligonucleotides Inhibit Intercellular Adhesion Molecule 1 Expression by Two Distinct Mechanisms", *J.Biol.Chem.*, 1991, 266:18162–18171.

Corey et al., "Generation of a Hybrid Sequence–Specific Single–Stranded Deoxyribonuclease", *Science*, 1987, 238:1401–1403.

Cullen, B., "The HIV–1 Tat Protein: An RNA Sequence–Specific Processivity Factor?" *Cell* 1990 63, 655–657.

Daniels et al., "Membrane as Solid Supports for Peptide Synthesis", *Tetrahedron Lett.* 1989, 30, 4345–4348.

Delgado et al., "The Uses and Properties of PEG–Linked Proteins", *Critical Reviews in Therapeutic Drug Carrier Systems.* 1992, 9, 249–304.

Demidov, V. et al., "Sequence Selective Double Strand DNA Cleavage by Peptide Nucleic Acid (PNA) Targeting Using Nuclease S1" *Nucl. Acids Res.* 1993 21 (19), 2103–2107.

Depto et al., "Regulated Expression of the Human Cytomegalovirus pp65 Gene: Octamer Sequence in the Promoter Is Required for Activation by Viral Gene Products," *J. Virol.* 1989, 63, 1232–1238.

Dizio et al., "Progestin–Rhenium Complexes: Metal–Labeled Steroids with High Receptor Binding Affinity, Potential Receptor–Directed Agents for Diagnostic Imaging or Therapy" *Bioconjugate Chem.*, 1991, 2, 353–366.

Doel et al., "An Approach to the Synthesis of Peptide Analogues of Oligonucleotides (Nucleopeptides)", *Tetrahedron Letters* 1969, 27, 2285–2288.

Doel et al., "The Synthesis of Peptides Containing Purine and Pyrimidine Derivatives of DL–Alanine", *Tetrahedron* 1974, 30, 2755–2759.

Dreyer and Dervan, "Sequence–specific cleavage of single–stranded DNA: Oligodeoxynucleotide–EDTA–Fe(II)", *Proc.Natl.Acad.Sci.* USA 82, 1985, 968–972.

Dubochet et al., "A New Preparation Method for Dark–Field Electron Microscopy of Biomacromolecules," *J. Ultrastruct. Res.* 1971, 35, 147–167.

Eckstein, et al., *Oligonucleotides and Analogues, A Practical Approach*, IRL Press, 1991.

Egholm, M. "Peptide nucleic acids (PNA). Oligonucleotide analogues with an achiral peptide backbone", *J. Am. Chem. Soc.* 1992, 114, 1895–1897.

Egholm, M. et al., "Peptide Nucleic Acids Containing Adenine and Guanine Recognition Thymine and Cyhtosine in Complementary DNA Sequences" *J. Chem. Soc. Chem. Commun.* 1993 800–801.

Egholm et al., "PNA Hybridizes to Complementary Oligonucleotides Obeying the Watson–Crick Hydrogen–Bonding Rules", Nature 365 1993 566–568.

Egholm, et al., "Recognition of Guanine and Adenine in DNA by Cytosine and Thymine Containing Peptide Nucleic Acids (PNA)[1,2]" *J. Am. Chem. Soc.*, 1992, 114, 9677–9678.

Egholm et al., "Peptide Nucleic Acids (PNA): A Noel Approach to Sequence–Selective Recognition of Double–Stranded DNA" *Innovation and Perspectives in Solid Phase Synthesisi Collected Papers* (Epton, Ed. by Intercept ltd, Andover, England) 1992, 325–328.

Eichler et al., "Application of Cellulose Paper as Support Material in Simultaneous Solid Phase Peptide Synthesis", *Collect. Czech. Chem. Commun.* 1989, 54, 1746–1752.

Fissekis, John D. and Sweet, Frederick, "Synthesis of 5–Carboxymethyluridine. A Nucleoside from Transfer Ribonucleic Acid" *Biochemistry* 1970, 9, 3136–3142.

Fodor, Stephen P.A. et al., "Light–Directed, Spatially Addressable Parallel Chemical Synthesis" *Science*, 1991, 251, 767–773.

Franza, Jr., B. R. et al., "Characterization of cellular proteins recognizing the HIV enhancer using a microscale DNA–affinity precipitation assay," *Nature* 1987, 330, 391–395.

Fridkin et al., "A Synthesis of Cyclic Peptides Utilizing High Molecular Weight Carriers", *J. Am. Chem. Soc* 1965, 87, 4646–4648.

Froehler, et al., "Oligodeoxynucleotides Containing C–5 Propyne Analogs of 2'–Deoxyuridine and 2'–Deoxycytidine," *Tetrahedron Letters* 1992, 33,5307–5310.

Gait, ed., *Oligonucleotide Synthesis, A Practical Approach*, IRL Press, 1984.

Gao, et al., "6–O–(Pentafluorophenyl)–2'–Deoxyguanosine: A Versatile Synthon for Nucleoside and Oligonucleotide Synthesis", *The Journal of Organic Chemistry* 1992, 57:6954–6959.

Gewirtz, "Therapeutic Application of Antisense DNA in the Treatment of Human Leukemia", published in Antisense Strategies vol. 660 178–187 (Oct. 28, 1992) Annals of the New York Academy of Sciences (Baserga & Denhardt Eds.).

Geysen et al., "Use of Peptide Synthesis to Probe Viral Antigens for Epitopes to a Resolution of a Single Amino Acid", *Proc. Natl. Acad. Sci. USA* 1984, 81: 3998–4002.

Gilham, P. T., "The Covalent Binding of Nucleotides, Polynucleotides, and Nucleic Acids to Cellulose" in *Methods in Enzymology*, Chapter 10, L. Grossmann and K. Moldave, eds. 1971, 21, part D, 191–197, Academic Press, N.Y. and London.

Gilmore, T. D. and Temin, H. M., "Different Localization of the Product of the v–rel Oncogene in Chicken Fibroplasts and Spleen Cells Correlates with Transformation by REV–T" , *Cell* 1986 44 791–800.

Goodman and Levine, "Peptide Synthesis via Active Esters. IV. Racemization and Ring–Opening Reactions of Optically Active Oxazolones", *J. Am. Chem. Soc.* 1964, 86, 2918–2922.

Gorman, Jeffrey, "An Apparatus for Simultaneous Manual Solid–Phase Synthesis of Multiple Peptide Analogs", *Anal. Biochem* 1984 136 397–406.

Greene and Wuts, *Protective Groups in Organic Synthesis*, 2d ed. John Wiley & Sons, New York, 1991.

Greenfield et al., Thiol–Containing Cross–Linking, *Bioconjugate Chem.*, 1990, 1, 400–410.

Hahn et al., "Design and Synthesis of a Peptide Having Chymotrypsin–Like Esterase Activity", *Science* 1990, 248, 1544–1547.

Hahn et al., "Molecular cloning and characterization of the HTLV–III virus associated with AIDS," *Nature* 1984, 312, 166–169.

Haas, W.L. et al., "Adamantyloxycarbonyl, a New Blocking Group. Preparation of 1–Adamantyl Chloroformate" *J. Am. Chem. Soc.*, 1966, 88, 1988–1992.

Hanvey et al., "Antisense and Antigene Properties of Peptide Nucleic Acids", *Science* 1992, 258, 1481–1485.

Haralambidis et al., "Preparation of base–modified nucleosides suitable for non–radioactive label attachment and their incorporation into synthetic ologodeoxyribonucleotides", Nucleic Acids Research, 15, 1987, 4857–4876.

Harris et al., "New Strategy for the Synthesis", *J. Am. Chem. Soc.*, 1991, 113, 4328–4329.

Heimer, J.P. et al., "Synthesis of Analogs and Oligomers of N–(2–aminoethyl)glycine and Their Gastrointestinal Absorption in the Rat" *Int. J. Pept. Protein Res.*, 1984, 23, 203–211.

Holm and Meldal, "Multiple Column Peptide Synthesis", "*Proceedings of the 20th European Peptide Symposium*", G. Jung and E. Bayer, eds., Walter de Gruyter & Co., Berlin: 1989, 208–210.

Houghten, "General Method for the Rapid Solid–Phase Synthesis of Large Numbers of Peptides: Specificity of Antigen–Antibody Interaction at the Level of Individual Amino Acids", *Proc. Natl. Acid. Sci. USA* 1985, 82, 5131–5135.

Huang et al., "Acyclic Nucleic Acid Analogues: Synthesis and Oligomerization of γ,4–Diamino–2–oxo–1(2H)–pyrimidinepentanoic Acid and σ 4–Diamino–2–oxo–1(2H)–pyrimidinehexanoic Acid", *J. Org. Chem.* 1991, 56, 6007–6018.

Hyrup et al., "Modification of the Binding Affinity of Peptide Nucleic Acids (PNA). PNA with Extended Backbones Consisting of 2–Aminoethyl–β–alanine or 3–Aminopropylglycine Units" *J. Chem. Soc. Chem. Commun.* 1993, 518–519.

Inaki et al., "Functionality and Applicability of Synthetic Nucleic Acid Analogs", in *Current Topics in Polymer Science* 1987, Ottenbrite, Utracki, Inoue, Eds. New York : Macmillan Pub. Co., 1, 80–100.

Inaki, Y., "Synthetic Nucleic Acid Analgos", *Prog. Polym. Sci.* 1992, 17, 515–570.

Jenkins, Y. and Barton, "A Sequence–Specific Molecular Light Switch: Tethering of an Oligonucleotide to a Dipyridophonic Complex of Ruthenium (II)", *J. Am. Chem. Soc.* 1992, 114, 8736–8738.

Jeppesen, C. et al., "A Specific and Efficient Photoreaction Between E.coli RNA Polymerase and $T_{+1}$ in the lacUV5 or deoP1 Promoter", *Nucleic Acids Research* 1988, 16(20), 9545–9555.

Jones, Jr., "Hydrogenation of Protected Leucine Enkephalin from a Resin During Solid Phase Synthesis", *Tetrahedron Lett.* 1977, 33, 2853–2856.

Kent and Merrifield, "Prepartion and Properties of tert–Butyloxycarbonylaminoacyl–4–(oxymethyl) phenylacetamidomethyl–(Kel F–g–styrene) Resin, and Insoluble, Noncrosslinked Support for Solid Phase Peptide Synthesis", *Israel J. Chem* . 1978, 17, 243–247.

König et al., "Autoregulation of fos: the Dyad Symmetry Element as the Major Target of Repression," *EMBO Journal* 1989, 8, 2559–2566.

König and Geiger, "Racemisierung bei Peptidsynthesen", *Chem. Ber.* 1973, 103, 2024–2033.

König and Geiger, "Eine Neue Method Zur Synthese Von Peptiden: Aktivierung Der Carboxylgruppe Mit Dicyclohexylcarbodiimid Und 3–Hydroxy–4–oxo–3.4–dihydro–1.2.3–benzotriazin", *Chem. Ber.* 1973, 103, 2034–2040.

De Koning et al., "Unconventional Nucleotide Analgues V. Derivatives of 6–(1–pyrimidinyl)–and 6–(9–purinyl)–2–aminocaproic acid.", *Recueil* 1971, 90, 874–884.

Kovacs, J. et al., "Glutamic and Aspartic Anhydrides. Rearrangement of N–Carboxyglutamic 1,5–Anhydride to the Leuchs' Anhydride and Conversion of the Latter to Pyroglutamic Acid" J. Am. Chem. Soc. 1963 85: 1839–1844.

Krchňák et al., "Continuous–Flow Solid–Phase Peptide Synthesis", *Tetrahedron Lett* 1987, 28, 4469–4472.

Krchňák et al., "Multiple Continuous–Flow Solid Phase Peptide Synthesis", *Int. J. Peptide Protein Res.* 1989, 33, 209–213.

Kupryszewski, "O Estrach Chlorofenylowych Aminokwasow. II. Synteza Peptydow Poprzez Aminolize Aktywnych Estrow 2,4,6–Trojchlorofenylowych N–Chronionych Aminokwasow", *Rocz. Chem.* 1961, 35, 595–600.

Lal et al., "Diphenylphosphoryl Azide A Novel Reagent for the Stererospecific Synthesis of Azides from Alcohols," *Tetrahedron Letters* 1977, 23, 1977–1980.

Lebl, Michal and Eichler, Jutta, "Simulation of Continuous Solid Phase Synthesis: Synthesis of Methionine Enkephalin and its Analogs" *Peptide Research*, 1989, 2, 297–300.

Letsinger, et al., "Synthesis of Thymidine Oligonucleotides by Phosphite Triester Intermediates" *J. Am. Chem. Soc.* 1976, 98, 3655–3661.

Li et al., "The Synthesis of a Protein Possessing Growth–Promoting and Lactogenic Activities", *J. Am. Chem. Soc.* 1970, 92, 7608–7609.

Lu and et al., "Synthesis of Polyesters Containing Nucleic Acid Base Derivatives as Pending Side Chains," *J. Polym. Sci.* 1986, Part A: *Polymer Chemistry* 24: 525–536.

Mack, D. P. et al., "Design and Chemical Synthesis of a Sequence–Specific DNA–Cleaving Protein" *J. of Am. Chem. Society* 1988 110 7572–7574.

Manoharan, *Antisense Research and Applications*, Crooke and Lebleu, eds., CRC Press, Boca Raton, 1993.

McCurdy, et al., "Deoxyoligonucleotides with Inverted Polarity: Synthesis and Use in Triple–Helix Formation," *Nucleosides and Nucleotides* 1991, 10, 287–290.

McKay and Albertson, "New Amine–Masking Groups for Peptide Synthesis", *J. Am. Chem. Soc.* 1957, 79, 4686–4690.

Meier et al., "Peptide Nucleic Acids (PNAs)–Unusual Properties of Nonionic Oligonucleotide Analogues", *Angew. Chem. Int. Ed. Engl.* 1992, 31, 1008–1010.

Merrifield, "Solid Phase Peptide Synthesis. I. The Synthesis of a Tetrapeptide", *J. Am. Chem. Soc.* 1963, 85, 2149–2154.

Merrifield, "Solid Phase Synthesis", *Science* 1986, 232, 341–347.

Meyer, et al., "Efficient, Specific Cross–Linking and Cleavage of DNA by Stable, Synthetic Complementary Oligodeoxynucleotides", *J. Am. Chem. Soc.* 111, 1989 8517–8519.

Mitchell and Merrifield, "Occurrence of N–Alkylation During the Acidolytic Cleavage of Urethane Protecting Groups[1a,b]", *J. Org. Chem.* 1976, 41, 2015–2019.

Mitchell et al., "Preparation of Aminomethyl–Polystyrene Resin by Direct Amidomethylation", *Tetrahedron Lett.* 1976, 42, 3795–3798.

Mizutaniy Takaharu and Tachibana, Yoshio, "Oligo(dT)–glyceryl Porous Glass, a Better Support for the Preparation of mRNA" *J. Chromatogr*, 1987, 356, 202–205.

Mutter and Bayer, "Rapid Procedure for Liquid–Phase Peptide Synthesis: The Crystallization Method", *Angew. Chem., Int. Ed. Engl.* 1974, 13, 88–89.

Nagae et al., "Functional Monomers and Polymers. CLIV. Application of Nucleic Acid Base Containing Polymers to High Performance Liquid Chromatography," *J. Polym. Sci.: Part A: Polymer Chemistry* 1989, 27, 2593–2609.

Nefkens and Tesser, "A Novel Activated Ester in Peptide Synthesis" *J. Am. Chem. Soc.* 1961, 83, 1263.

Nielsen, P. E. et al, "Photochemical Cleavage or DNA by Nitrobenzamides" *Biochem.* 1988, 27, 6338–6343.

Nielsen, et al., "Sequence–Selective Recognition of DNA by Strand Displacement with a Thymine–Substituted Polyamide," *Science*, 254 1991 1497–1500.

Nisen, P. D. et al., "Enhanced Expression of the N–myc Gene in Wilms' Tumors," *Cancer Research* 1986, 46, 6217–6222.

Nollet et al., "Unconventional Nucleotide Analogues–III, 4–($N_1$–Pyrimidyl)–2–Aminobutyric Acids", *Tetrahedron* 1968, 25, 5989–5994.

Nollet et al., "Unconventional Nucleotide Analogues–I, $N_9$–Purinyl α–Amino Acids", *Tetrahedron* 1969, 25, 5971–5981.

Nollet et al., "Unconventional Nucleotide Analogues–II, Synthesis of the Adenyl Analogue of Willardiine", *Tetrahedron* 1969, 25, 5983–5987.

Nollet et al., "Michael Addition of 4–O–Ethyluracil. A Method for Specific $N_1$–Alkylation of Hydroxypyrimidines", *Tetrahedron Letters* 1969, 53, 4605–4606.

*Nucleic Acid Hybridization—A Practical Approach*, B. D. Harnes and S. J. Higgins, IRL Press Ltd., Oxford 1987.

Odian, "Principles of Polymerization", McGraw–Hill, N.Y. 1970.

Omura, K. and Swern, "Oxidation of Alcohols by "Activated" Dimethyl Sulfoxide. A Preparative, Steric and Mechanistic Study", *Tetrahedron* 1978, 34, 1651–1660.

Ono, A. et al., "Triplex Formation of Oligonucleotides Containing 2'–O–Methylpseudoisocytidine in Substitution for 2'–Deoycytidine" *J. Am. Chem. Soc.* 1991, 113, 4032–4033.

Ono, Akira et al., "Triplex Formation of an Oligonucleotide Containing 2'–O–Methylpseudoisocytidine with a DNA Duplex at Neutral pH" *J. Org. Chem.* 1992, 57, 3225–3230.

Ouchi, T. et al., "Synthesis and antitumor activity of poly-(ethylene glycol)s linked to 5–fluorouracil via a urethane or urea bond", *Drug Design and Discovery* 1992, 9, 93–105.

Parr and Grohmann, "Solid–Phase Peptide Synthesis on an Inorganic Matrix having Organic Groups on the Surface", *Angew. Chem. Internal. Ed.* 1972, 11, 314–315.

Petty et al., "Cytochrome Oxidase Models. 2. μ–Bipyrimidyl Mixed–Metal Complexes as Synthetic Models for the Fe/Cu Binuclear Active Site of Cytochrome Oxidase", *J. Am. Chem. Soc.* 1980, 102, 611–620.

Pietta and Marshall, "Amide Protection and Amide Supports in Solid–Phase Peptide Synthesis" *Chemical Communications*, 1970, 650–651.

Pitha et al., "Inhibition of Murine Leukemia Virus Replication by Poly(vinyluracil) and Poly(vinyladenine)", *Proc. Natl Acad. Sci. USA* 1973, 70, 1204–1208.

Pitha, J., "Physiological Activities of Synthethic Analogs of Polynucleotides", *Adv. Polym. Sci.* 1983, 50, 1–16.

Pless et al., Über die Geschwindigkeit der Aminolyse von Verschiedenen Neuen, Aktivierten, N–geschützten α–Aminosäure–phenylestern, insbesondere 2,4,5–Trichlorphenylestern) *Helv. Chim. Acta* 1963, 46, 1609–1625.

Pollack, S. J. et al., "Selective Chemical Catalysis by an Antibody" *Science*, 1986, 234, 1570–1573.

Ravasio, N. and Rossi, M., "Selective Hydrogenations Promoted by Copper Catalysts 1. Chemoselectivity, Regioselectivity, and Stereoselectivity in the Hydrogenation of 3–Substituted Steroids", *J. Org. Chem.* 1991, 56, 4329–4333.

Rich and Gurwara, "Preparation of a New o–Nitrobenzyl Resin for Solid–Phase Synthesis of tert–Butyloxycarbonyl–Protected Peptide Acids", *J. Am. Chem. Soc.* 1975, 97, 1575–1579.

Rivaille et al., "Synthesis of LH–RH Using a New Phenolic Polymer as Solid Support and "BOP" Reagent for Fragment Coupling", *Tetrahedron* 1980, 36, 3413–3419.

Ruth, J., "Oligodeoxynucleotides with Reporter Groups Attached to the Base", in *Oligonucleotides and Analogues: A Practical Approach* 1991, IRL Press, Oxford.

Sági, et al., "Base–Modified Oligodeoxynucleotides. I. Effect of 5–Alkyl, 5–(1–Alkenyl) and 5–(1–Alkynyl) Substitution of teh Pyrimidines on Duplex Stability and Hydrophobicity," *Tetrahedron Letters* 1993, 34, 2191–2194.

Sakakibara, et al., "A New Method for Releasing Oxytocin form Fully–Protected Nona–peptides Using Anhydrous Hydrogen Fluoride" *Bull. Chem. Soc. Jpn.* 1965, 38, 1412–1413.

Schlatter, James M. and Mazur, Robert H., "Hydrogenationin Solid Phase Peptide Synthesis. I. Removal of Product from the Resin" *Tet. Letts.* 1977 33: 2851–2852.

Scott et al., "The Use of Resin Coated Glass Beads in the Form of a Packed Bed for the Solid Phase Synthesis of Peptides", *J. Chromatogr. Sci* 1971, 9, 577–591.

Sheehan, "A New Method of Forming Peptide Bonds", *J. Am. Chem. Soc.* 1955, 77, 1967–1068.

Shemyakin et al., "Synthesis of Peptides in Solution on a Polymeric Support I. Synthesis of Clycylglycyl–L–Leucylglycine", *Tetrahedron Lett* 1965, 27, 2323–2327.

Shokat et al., "A New Strategy for the Generation of Catalytic Antibodies", *Nature* 1989, 338, 269–271.

Sieber and Iselin, "77. Selektive Acidolytische Spaltung von Aralkyloxycarbonyl–Aminoschutzgruppen", *Helv. Chem. Acta.* 1968, 51, 614–622.

Sigman, "Chemical Nucleases", *Biochem.* 1990, 29:9097–9105.

Simon et al., "Peptiods: A modular approach to drug discovery", *Proc. Natl. Acad. Sci. USA* 1992, 89, 9367–9371.

Sluka, J.P. et al., "Reagents and methods for the solid–phase synthesis of protein–EDTA for use in affinity cleaving", *J. Am. Chem. Soc.* 1990, 112, 6369–6374.

Smith–Jones, P. et al., "Antibody Labeling with Copper–67 Using the Bifunctional Macrocyle 4–[(1,4,8, 11–Tetraazacyclotetradec–1–yl)methyl]benzoic Acid", *Bioconjugate Chemistry* 1991, 2, 415–421.

*Solid–Phase Biochemistry—Analytical and Synthetic Aspects*, W.H. Scouten, ed., John Wiley & Sons, N.Y., 1983.

Sproat, B.S. et al., "Highly Efficient Chemical Synthesis of 2'–O–methylioligoribunocleotides and Tetrabiotinylated Derivatives; Novel Probes That are Resistant to Degradation by RNA or DNA Specific Nucleases", *Nucleic Acids Research* 1989, 17(9), 3373–3386.

Spalholtz et al., "Bovine Papillomavirus Transcriptional Regulation: Localization of the E2–Responsive Elements of the Long Control Region," *J. Virol.* 1987, 61, 2128–2137.

Stenberg et al., "Promoter–Specific trans Activation and Repression by Human Cytomegalovirus Immediate–Early Proteins Involves Common and Unique Protein Domains," *J. Virol.* 1990, 64, 1556–1565.

Stewart and Young, "Solid Phase Peptide Synthesis", 2nd Ed., Pierce Chemical Company, Ill., 1984.

Studer et al., "One Step Synthesis of Mono–N–substituted Azamacrocyles with a Carboxylic Group in the Side–Chain and their Complexes with $Cu^{2+}$ and $Ni^{2+}$", *Helvetica Chimica Acta* 69, 1986 2081–2086.

Takemoto et al., "Synthetic Nucleic Acid Analogs. Preparation and Interactions", *Adv. Polym. Sci.* 1981, 1–51.

Tam, James P., "A Gradative Deprotection Strategy for the Solid–Phase Synthesis of Peptide Amides Using p–(Acyloxy)benzyhydrylamine Resin and the $S_N2$Deprotection Method", *J. Org. Chem.* 1985, 50 5291–5298.

Tam et al., "Multi–Detachable Resin Supports for Solid Phase Fragment Synthesis", *Tetrahedron Lett.* 1979, 52, 4935–4938.

Tam et al., "$S_N2$ Deprotection of Synthetic Peptides with a Low Concentration of HF in Dimethyl Sulfide: Evidence and Application in Peptide Synthesis", *J. Am. Chem. Soc.* 1983, 105, 6442–6455.

Tam et al., "Improved Synthesis of 4–(Boc–minoacyloxymethyl)–phenylacetic Acids for Use in Solid Phase Peptide Synthesis", *Communications* 1979, 955–957.

Tam et al., "Mechanisms for the Removal of Benzyl Protecting Groups in Synthetic Peptides by Trifluoromethanesulfonic Acid–Trifluoroacetic Acid–Dimethyl Sulfide", *J. Am. Chem. Soc.* 1986, 108, 5242–5251.

Tam, "Design and Synthesis of Multidetachable Resin Supports for Solid–Phase Peptide Synthesis" *J. Am. Chem. Soc.* 1980, 102, 6117–6127.

Telser, J. et al., "DNA Oligomers and Duplexes Containing a Covalently Attached Derivative of Tris(2,2'–bipyridine)ruthenium(II): Synthesis and Characterization by Thermodynamic and Optical Spectroscopic Measurements"3, *J. Am. Chem. Soc.* 1989, 111, 7221–7226.

Tibanyenda et al, "The effect of single base–pair mismatches on the duplex stability of d(T–A–T–T–A–A–T–A–T–C–A–A–G–T–T–G) . d(C–A–A–C–T–T–G–A–T–A–T–T–A–A–T–A)," *Eur. J. Biochem.* 1984, 139, 19–27.

Tramontano et al., "Catalytic Antibodies", Science 1986, 234, 1566–1570.

Trapane, T.L. et al., "A Proposed Model for Triplex Formation at Single–Stranded Nucleic Acid Target Sites of Unrestricted Sequence", Abstracts Conference on Nucleic Acids Medical Applications, Cancun, Mexico, Jan. 1993.

Trapane, T. et al., "Formation of a purine–purine–pyrimidine triplex with purine oligomers having non–ionic methylphosphonate linkages" Abstract of J. Biomol. Strul. Struct., 1991, 8, from "Seventh Conversation in Biomolecular Stereodynamics" a229.

Trapana, T.L. and Ts'0, P.O.P. "Triplex Formation of Adenine and Thymine Deoxyoligonucleotides and Their Nonionic Methylphosphonate Analogs" Biophys. J., 1992, 61, Abstract 2437.

Tregear, "Graft Copolymers as Insoluble Supports in Peptide Synthesis", Chemistry and Biology of Peptides 1972, J. Meienhofer, ed., Ann Arbor Sci. Publ., Ann Arbor, 175–178.

Uhlmann et al., "Antisense Oligonucleotides: A New Therapeutic Principle", Chemical Reviews 1990, 90, 544–583.

van Rietschoten, "Simultaneous Synthesis of Two Peptide Analogs on Different Insoluble Supports", Peptides 1974 1975, Y. Wolman, Ed., Wiley and Sons, New York, pp. 113–116.

Vasseur et al., "Oligonucleosides: Synthesis of a Novel Methylhydroxylamine–Linked Nucleoside Dimer and Its Incorporation into Antisense Sequences," J. Am. Chem. Soc. 1992, 114, 4006–4007.

Veber, Daniel F. et al., "Isonicotinyloxycarbonyl, a Novel Amino Protecting Group for Peptide Synthesis", J. Org. Chem. 1977, 42(20), 3286–3288.

Vickers, T. et al., "Inhibition of HIV–LTR gene expression by oligonucleotides targeted to the TAR element," Nucleic Acids Research 1991, 19, 3359–3368.

Wagner, R., "Antisense Gene Inhibition by Oligonucleotides Containing C–5 Propyne Pyrimidines", Science 1993, 260, 1510–1513.

Wakelin, L. P.G. et al., "Kinetic and Equilibrium Binding Studies of Amsacrine–4–Carboxamides: A Class of Asymmetrical DNA–Intercalating Agents which Bind by Threading Through the DNA Helix" J. Med. Chem 1990, 33, 2039–2044.

Weller et al., "Molecular Modeling of Acyclic Polyamide Oligonucleotide Analogues", J. Org. Chem. 1991, 6000–6006.

Wieland et al., "Symmetrical Boc–Amino Acid Anhydrides for Economical Peptide Syntheses on a Solid Phase", Angew. Chem., Int. Ed. Engl. 1971, 10, 336.

Yajima et al., "Trifluoromethanesulphonic Acid, as a Deprotecting Reagent in Peptide Chemistry", J. Chem. Soc., Chem. Comm. 1974, 107–108.

Zervas et al., "New Methods in Peptide Synthesis. I. Tritylsulfenyl and o–Nitrophenylsulfenyl Groups as N–Protecting Groups", J. Am. Chem. Soc. 1963, 85, 3660–3666.

Zhang, Z. and McCormick, "Uptake of N–(4'–pyridoxyl)amines and Release of Amines by Renal Cells: A Model for Transporter–Enhanced Delivery of Bioactive Compounds", PNAS USA 1991, 88, 10407–10410.

Almarsson, et al., "Molecular Mechanisc Calculations of the Structures of Polyamide Nucleic Acid DNA Duplexes and Triple Helical Hybrids", Proc. Natl. Acad. Sci. USA, 1993, 90(16):7518–7522.

Almarsson, et al., "Peptide Nucleic Acid (PNA) Conformation and Polymorphism in PNA–DNA and PNA–RNA Hybrids", Proc. Natl. Acad. Sci. USA, 1993, 90(20):9542–9546.

Brown, et al., "NMR Solution Structure of a Peptide Nucleic Acid Complexed with RNA", Science, 1994, 265:777–780.

Chen, et al., "Molecular Dynamics and NMR Studies of Single–Stranded PNAs", Tetrahedron Lett., 1994, 35(29):5105–5108.

Demidov, et al., "Sequence Selective Double Strand DNA Cleavage by PNA Targeting Using Nuclease S1", Nucleic Acids Res., 1993, 21(9):2103–2107.

Demidov, et al., "Stability of Peptide Nucleic Acids in Human Serum and Cellular Extracts", Biochem Pharmacol, 1994, 48(6):1310–1313.

Dueholm, et al., "An Efficient Synthetic Approach to Boc–aminoacetaldehyde and Its Application in the Synthesis of 2–Boc–aminoethylglycine Methyl Ester", Org. Prep. Proc. Int., 1993, 25:457–461.

Dueholm, et al., "Peptide Nucleic Acid (PNA) with a Chiral Backbone Based on Alanine", Bioorg. Med. Chem. Lett., 1994, 4(8):1077–1080.

Dueholm, et al., Synthesis of Peptide Nucleic Acids Monomers Containing the Four Natural Nucleobases: Thymine, Cytosine, Adenine and Guanine, and Their Oligomerization, J. Org. Chem., 1994, 59(19):5767–5773.

Egholm, et al., "Peptide Nucleic Acids (PNA). Oligonucleotide Analogues with an Achrial Peptide Backbone", J. Chem. Soc., 1992, 114:1895–1897.

Egholm, et al., "Recognition of Guanine and Adenine in DNA by Cytosine and Thymine Containing Peptide Nucleic Acids (PNA)", J. Am. Chem. Soc., 1992, 114:9677–9678.

Egholm, et al., "Peptide Nucleic Acids Containing Adenine or Guanine Recognize Thymine and Cytosine in Complementary DNA Sequences", J. Chem. Soc. Comm., 1993, p. 800–801.

Flam, F., "Can DNA Mimics Improve on the Real Thing?", Science, 1993, 262:1647–1649.

Frank–Kamenetskii, M., "A Change of Backbone", Nature, 1991, 354(6354):505.

Griffith, et al., Single and Bis Peptide Nucleic Acids as Triplexing Agents: Binding and Stoichiometry, J. Am. Chem. Soc., 1995, 117(2):831–832.

Hyrup, et al., Modification of the Binding Affinity of Peptide Nucleic Acids (PNA). PNA With Extended Backbones Consisting of 2–aminoethyl–B–alanine or 3–aminopropylglycine Units, J. Chem. Soc. Chem. Comm., 1993, Issue 6;518–519.

Hyrup, et al., "Structure–activity Studies of the Binding of Modified Peptide Nucleic Acids (PNA) to DNA", J. Am. Chem. Soc., 1994, 116(18):7964–7970.

Kosynkina, et al., "A Convenient Synthesis of Chiral Peptide Nucleic Acid (PNA) Monomers", Tetrahedron Lett., 1994, 35(29):5173–5176.

Lagriffoul, et al., "The Synthesis, Co–oligomerization and Hybridization of a Thymine–Thymine Heterodimer Containing PNA", Bioorg. Med. Chem. Lett., 1994, 4(8):1081–1085.

Leijon, et al., "Structural Characterization of PNA–DNA Duplexes by NMR. Evidence for DNA in a B–like Conformation", Biochemistry, 1994, 33(33):9820–9825.

Mollegaard, et al., "Peptide Nucleic Acid–DNA Strand Displacement Loops as Artificial Transcription Promoters", Proc. Natl. Acad. Sci. USA, 1994, 91(9):3892–3895.

Nielsen, et al., "Peptide Nucleic Acids (PNA). Potential Anti–Sense and Anti–Gene Agents", *Anticancer Drug Des.*, 1993, 8(1):53–56.

Nielsen, P.E., "Peptide Nucleic Acids (PNA): Potential Antiviral AGents", *Int'l. Antiviral News*, 1993, 1:37–39.

Nielsen, et al., "Peptide Nucleic Acids (PNA). DNA Analogues with a Polyamide Backbone", *Antisense Research and Applications*, 1993, p. 363–367.

Nielsen, P.E., "Peptide Nucleic Acid (PNA): A Model Structure for the Primordial Genetic Material", *Orig. Life Evol. Biosph.*, 1993, 23(5–6):323–327.

Nielsen, et al., "Peptide Nucleic Acid (PNA). A DNA Mimic with a Peptide Backbone", *Bioconjugate Chem.*, 1994, 5(1):3–7.

Nielsen, et al., "Sequence–Specific Transcription Arrest by Peptide Nucleic Acid Bound to the DNA Template Strand", *Gene*, 1994, 149(1):139–145.

Orum, et al., "Single Base Pair Mutation Analysis by PNA Directed PCR Clamping", *Nucleic Acids Res.*, 1993, 21(23):5332–5336.

Peffer, et al., "Strand–Invasion of Duplex DNA by Peptide Nucleic Acid Oligomers", *Proc. Natl. Acad. Sci. USA*, 1993, 90(22):10648–10652.

Rose, D.J., "Characterization of Antisense Binding Properties of Peptide Nucleic Acids by Capillary Gel Electrophoresis", *Anal. Chem.*, 1993, 65(24):3545–3549.

Wittung, et al., "DNA–like Double Helix Formed by Peptide Nucleic Acid", *Nature*, 1994, 368(6471):561–563.

Englisch, U. and Gauss, "Chemically Modified Oligonucleotides as Probes and Inhibitors", *Angewandte Chemie International Edition* 1991, 30, 613–629.

Kemp, D.S. and Hoyng, "New Protective Groups for Peptide Synthesis. I. The BIC Group Base and Solvent Lability of the 5–benzisoxazolylmethyleneoxycarbonylamino Function", *Tetrahedron Letters* 1975, 52, 4625–4628.

Matsueda, G. and Stewart, "A p–Methylbenzyhydrylamine Resin for Improved Solid–Phase Synthesis of Peptide Amides", *Peptides* 1981, 2, 45–50.

Matthews, J. and Kricka, "Analytical Strategies for hte Use of DNA Probes", *Analytical Biochemistry* 1988, 169, 1–25.

Merrifield, R.B., "Solid Phase Peptide Synthesis. II. The Synthesis of Bradykinin", *J. Am. Chem. Soc.* 1964, 86, 304–305.

Merrifield, R.B. et al., "Synthesis of the Antibacterial Peptide Cecropoin A(1–33)", *Biochemistry* 1982, 21, 5020–5031.

Nielsen, P. et al., "Adenosine–guanosine Preferential Photocleavage of DNA by Azido–benzoyl– and Diazocyclopentadienylcarbonyloxy Derivatives of 9–aminoacridine", *Nucleic Acids Res.* 1988, 16(9), 3877–3888.

Sarin, V. et al., "Quantitative Monitoring of Solid–Phase Peptide Synthesis by the Ninhydrin Reaction", *Analytical Biochemistry* 1981, 117, 147–157.

Kroschwitz, J., ed., "Concise Encyclopedia of Polymer Science and Engineering", pp. 858–859, John Wiley & Sons, New York, 1990.

Parkanyi, C. et al,. "Synthesis of Polymethylene Chain–Bridged 6–Substituted 8–Azapurines and Related Compounds", *Collect. Czech. Chem. Commun.* 1991, 56, 2382–2388.

Pitha, J. et al., "Synthetic Analogs of Nucleic Acids", pp. 271–297 in "Biomedical Polymers", Goldberg and Nakajima, eds., Academic Press, New York, 1989.

Shvatschkin, Y.P. et al., "Uspechi i perspektivi chimij nikleoamniokislot i nikleopeptidov", *Isnechi Chimij* 1982, 2, 311–330.

Takemoto, K., "Recent Problems Concerning Functional Monomers and Polymers Containing Nucleic Acid Bases", pp. 103–129 in "Polymeric Drugs", Donaruma and Vogl, eds., Academic Press, New York, 1978.

* cited by examiner

Acr¹

$R^1$ = AMINO ACID SIDECHAIN
$R^2$ = METHYL, ETHYL, ETC.

PNA Target

5'------GGATCCAAAAAAAAAAGGATCC-------
3'------CCTAGGTTTTTTTTTTCCTAGG-------

BamH1              BamH1

COMPOUND

COMPOUND 1 IN
50% TFA: 50% METHYLENE CHLRIDE, 5 h, rt.

COMPOUND 1 IN
100% HF, 0°C, 1h

QUANTITATIVE DE-BENZYLATION

QUANTITATIVE DE-BENZYLATION
AND DE-SULFONYLATION

SYNTHETIC PROCEDURES FOR PEPTIDE NUCLEIC ACIDS

RELATED APPLICATIONS

This application is a continuation-in-part of U.S. Ser. No. 08/108,591, filed Nov. 22, 1993, now U.S. Pat. No. 6,395,474, deriving from Application PCT/EP92/01219, filed May 22, 1992, which is a continuation-in-part of the following Danish Patent Applications: No. 986/91, filed May 24, 1991, No. 987/91, filed May 24, 1991, and No. 510/92, filed Apr. 15, 1992. The disclosure of the foregoing patent applications is incorporated herein by reference.

FIELD OF THE INVENTION

This invention is directed to compounds that are not polynucleotides yet which bind to complementary DNA and RNA strands more strongly the corresponding DNA. In particular, the invention concerns compounds wherein naturally-occurring nucleobases or other nucleobase-binding moieties are covalently bound to a polyamide backbone.

BACKGROUND OF THE INVENTION

Oligodeoxyribonucleotides as long as 100 base pairs (bp) are routinely synthesized by solid phase methods using commercially available, fully automatic synthesis machines. The chemical synthesis of oligoribonucleotides, however, is far less routine. Oligoribonucleotides also are much less stable than oligodeoxyribonucleotides, a fact which has contributed to the more prevalent use of oligodeoxyribonucleotides in medical and biological research directed to, for example, gene therapy or the regulation of transcription or translation.

The function of a gene starts by transcription of its information to a messenger RNA (mRNA) which, by interaction with the ribosomal complex, directs the synthesis of a protein coded for by its sequence. The synthetic process is known as translation. Translation requires the presence of various co-factors and building blocks, the amino acids, and their transfer RNAs (tRNA), all of which are present in normal cells. Transcription initiation requires specific recognition of a promoter DNA sequence by the RNA-synthesizing enzyme, RNA polymerase. In many cases in prokaryotic cells, and probably in all cases in eukaryotic cells, this recognition is preceded by sequence-specific binding of a protein transcription factor to the promoter. Other proteins which bind to the promoter, but whose binding prohibits action of RNA polymerase, are known as repressors. Thus, gene activation typically is regulated positively by transcription factors and negatively by repressors.

Most conventional drugs function by interaction with and modulation of one or more targeted endogenous proteins, e.g., enzymes. Such drugs, however, typically are not specific for targeted proteins but interact with other proteins as well. Thus, a relatively large dose of drug must be used to effectively modulate a targeted protein. Typical daily doses of drugs are from $10^{-5}$–$10^{-1}$ millimoles per kilogram of body weight or $10^{-3}$–10 millimoles for a 100 kilogram person. If this modulation instead could be effected by interaction with and inactivation of mRNA, a dramatic reduction in the necessary amount of drug necessary could likely be achieved, along with a corresponding reduction in side effects. Further reductions could be effected if such interaction could be rendered site-specific. Given that a functioning gene continually produces mRNA, it would thus be even more advantageous if gene transcription could be arrested in its entirety.

Oligodeoxynucleotides offer such opportunities. For example, synthetic oligodeoxynucleotides could be used as antisense probes to block and eventually lead to the breakdown of mRNA. Thus, synthetic DNA could suppress translation in vivo. It also may be possible to modulate the genome of an animal by, for example, triple helix formation using oligonucleotides or other DNA recognizing agents. However, there are a number of drawbacks associated with triple helix formation. For example, it can only be used for homopurine sequences and it requires unphysiologically high ionic strength and low pH.

Furthermore, unmodified oligonucleotides are unpractical both in the antisense approach and in the triple helix approach because they have short in vivo half-lives, they are difficult to prepare in more than milligram quantities and, thus, are prohibitively costly, and they are poor cell membrane penetrators.

These problems have resulted in an extensive search for improvements and alternatives. For example, the problems arising in connection with double-stranded DNA (dsDNA) recognition through triple helix formation have been diminished by a clever "switch back" chemical linking whereby a sequence of polypurine on one strand is recognized, and by "switching back", a homopurine sequence on the other strand can be recognized. See, e.g., McCurdy, Moulds, and Froehler, *Nucleosides,* in press. Also, good helix formation has been obtained by using artificial bases, thereby improving binding conditions with regard to ionic strength and pH.

In order to improve half life as well as membrane penetration, a large number of variations in polynucleotide backbones has been undertaken, although so far not with desired results. These variations include the use of methylphosphonates, monothiophosphates, dithiophosphates, phosphoramidates, phosphate esters, bridged phosphoroamidates, bridged phosphorothioates, bridged methylenephosphonates, dephospho internucleotide analogs with siloxane bridges, carbonate bridges, carboxymethyl ester bridges, acetamide bridges, carbamate bridges, thioether, sulfoxy, sulfono bridges, various "plastic" DNAs, α-anomeric bridges, and borane derivatives.

International patent application WO 86/05518 broadly claims a polymeric composition effective to bind to a single-stranded polynucleotide containing a target sequence of bases. The composition is said to comprise non-homopolymeric, substantially stereoregular polymer molecules of the form:

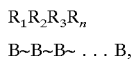

B~B~B~ ... B, where:
(a) $R_1$–$R_n$ are recognition moieties selected from purine, purine-like, pyrimidine, and pyrimidine like heterocycles effective to bind by Watson/Crick pairing to corresponding, in-sequence bases in the target sequence;
(b) n is such that the total number of Watson/Crick hydrogen bonds formed between a polymer molecule and target sequence is at least about 15;
(c) B~B are backbone moieties joined predominantly by chemically stable, substantially uncharged, predominantly achiral linkages;
(d) the backbone moiety length ranges from 5 to 7 atoms if the backbone moieties have a cyclic structure, and ranges from 4 to 6 atoms if the backbone moieties have an acyclic structure; and (e) the backbone moieties support the recognition moieties at position which allow Watson/Crick base pairing between the recognition moieties and the corresponding, in-sequence bases of the target sequence.

According to WO 86/05518, the recognition moieties are various natural nucleobases and nucleobase-analogs and the backbone moieties are either cyclic backbone moieties comprising furan or morpholine rings or acyclic backbone moieties of the following forms:

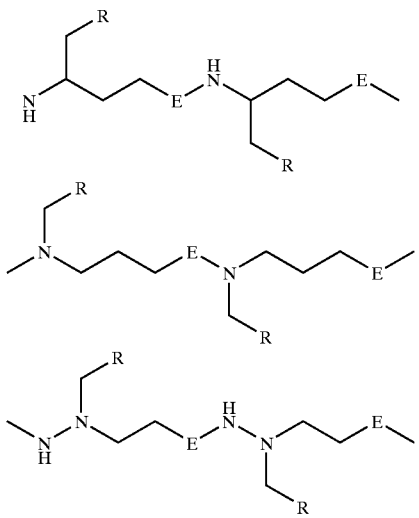

where E is —CO— or —SO$_2$—. The specification of the application provides general descriptions for the synthesis of subunits, for backbone coupling reactions, and for polymer assembly strategies. However, the specification provides no example wherein a claimed compound or structure is actually prepared. Although WO 86/05518 indicates that the claimed polymer compositions can bind target sequences and, as a result, have possible diagnostic and therapeutic applications, the application contains no data relating to the binding affinity of a claimed polymer.

International patent application WO 86/05519 claims diagnostic reagents and systems that comprise polymers described in WO 86/05518, but attached to a solid support. WO 86/05519 also provides no examples concerning actually preparation of a claimed diagnostic reagent, much less data showing the diagnostic efficiency of such a reagent.

International patent application WO 89/12060 claims various building blocks for synthesizing oligonucleotide analogs, as well as oligonucleotide analogs formed by joining such building blocks in a defined sequence. The building blocks may be either "rigid" (containing a ring) or "flexible" (lacking a ring). In both cases the building blocks contain a hydroxy group and a mercapto group, through which the building blocks are said to join to form oligonucleotide analogs. The linking moiety in the oligonucleotide analogs is selected from the group consisting of sulfide (—S—), sulfoxide (—SO—), and sulfone (—SO$_2$—). WO 89/12060 provides a general description concerning synthesis of the building blocks and coupling reactions for the synthesis of oligonucleotide analogs, along with experimental examples describing the preparation of building blocks. However, the application provides no examples directed to the preparation of a claimed oligonucleotide analog and no data confirming the specific binding of an oligonucleotide analog to a target oligonucleotide.

Furthermore, oligonucleotides or their derivatives have been linked to intercalators in order to improve binding, to polylysine or other basic groups in order to improve binding both to double-stranded and single-stranded DNA, and to peptides in order to improve membrane penetration. However, such linking has not resulted in satisfactory binding for either double-stranded or single-stranded DNA. Other problems which resulted from, for example, methylphosphonates and monothiophosphates were the occurrence of chirality, insufficient synthetic yield or difficulties in performing solid phase assisted syntheses.

In most cases only a few of these modifications could be used. Even then, only short sequences—often only dimers— or monomers could be generated. Furthermore, the oligomers actually produced have rarely been shown to bind to DNA or RNA orhave not been examined biologically.

The great majority of these backbone modifications led to decreased stability for hybrids formed between the modified oligonucleotide and its complementary native oligonucleotide, as assayed by measuring $T_m$ values. Consequently, it is generally understood in the art that backbone modifications destabilize such hybrids, i.e., result in lower $T_m$ values, and should be kept to a minimum.

OBJECTS OF THE INVENTION

It is one object of the present invention to provide compounds that bind ssDNA and RNA strands to form stable hybrids therewith.

It is a further object of the invention to provide compounds that bind ssDNA and RNA strands more strongly the corresponding DNA.

It is another object to provide compounds wherein naturally-occurring nucleobases or other nucleobase-binding moieties are covalently bound to a peptide backbone.

It is yet another object to provide compounds other than RNA that can bind one strand of a double-stranded polynucleotide, thereby displacing the other strand.

It is still another object to provide therapeutic and prophylactic methods that employ such compounds.

SUMMARY OF THE INVENTION

The present invention provides a novel class of compounds, known as peptide nucleic acids (PNAs), that bind complementary ssDNA and RNA strands more strongly than a corresponding DNA. The compounds of the invention generally comprise ligands linked to a peptide backbone via an aza nitrogen. Representative ligands include either the four main naturally occurring DNA bases (i.e., thymine, cytosine, adenine or guanine) or other naturally occurring nucleobases (e.g., inosine, uracil, 5-methylcytosine or thiouracil) or artificial bases (e.g., bromothymine, azaadenines or azaguanines, etc.) attached to a peptide backbone through a suitable linker.

In certain preferred embodiments, the peptide nucleic acids of the invention have the general formula (I):

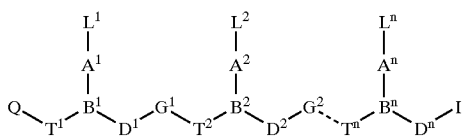

wherein:

n is at least 2, each of $L^1$–$L^n$ is independently selected from the group consisting of hydrogen, hydroxy, ($C_1$–$C_4$) alkanoyl, naturally occurring nucleobases, non-naturally occurring nucleobases, aromatic moieties, DNA intercalators, nucleobase-binding groups, heterocyclic moieties, and reporter ligands, at least one of $L^1$–$L^n$ being a naturally occurring nucleobase, a non-naturally occurring nucleobase, a DNA intercalator, or a nucleobase-binding group;

each of $A^1$–$A^n$ is a single bond, a methylene group or a group of formula (IIa) or (IIb):

$$\left[\begin{array}{c} R^1 \\ | \\ -C- \\ | \\ R^2 \end{array}\right]_p Y \left[\begin{array}{c} R^1 \\ | \\ -C- \\ | \\ R^2 \end{array}\right]_q \quad \text{or} \quad (\text{IIa})$$

$$\left[\begin{array}{c} R^1 \\ | \\ -C- \\ | \\ R^2 \end{array}\right]_r Y \left[\begin{array}{c} R^1 \\ | \\ -C- \\ | \\ R^2 \end{array}\right]_s \begin{array}{c} X \\ \| \\ C- \end{array} \quad (\text{IIb})$$

where:

X is O, S, Se, $NR^3$, $CH_2$ or C $(CH_3)_2$;

Y is a single bond, O, S or $NR^4$;

each of p and q is zero or an integer from 1 to 5, the sum p+q being not more than 10;

each of r and s is zero or an integer from 1 to 5, the sum r+s being not more than 10;

each $R^1$ and $R^2$ is independently selected from the group consisting of hydrogen, $(C_1$–$C_4)$alkyl which may be hydroxy- or alkoxy- or alkylthio-substituted, hydroxy, alkoxy, alkylthio, amino and halogen; and each $R^3$ and $R^4$ is independently selected from the group consisting of hydrogen, $(C_1$–$C_4)$alkyl, hydroxy- or alkoxy- or alkylthio-substituted $(C_1$–$C_4)$ alkyl, hydroxy, alkoxy, alkylthio and amino;

each of $B^1$–$B^n$ is N or $R^3N^+$, where $R^3$ is as defined above;

each of $T^1$–$T^n$ is $CR^6R^7$, $CHR^6CHR^7$ or $CR^6R^7CH_2$, where $R^6$ is hydrogen and $R^7$ is selected from the group consisting of the side chains of naturally occurring alpha amino acids, or $R^6$ and $R^7$ are independently selected from the group consisting of hydrogen, $(C_2$–$C_6)$alkyl, aryl, aralkyl, heteroaryl, hydroxy, $(C_1$–$C_6)$alkoxy, $(C_1$–$C_6)$alkylthio, $NR^3R^4$ and $SR^5$, where $R^3$ and $R^4$ are as defined above, and $R^5$ is hydrogen, $(C_1$–$C_6)$alkyl, hydroxy-, alkoxy-, or alkylthio-substituted $(C_1$–$C_6)$alkyl, or $R^6$ and $R^7$ taken together complete an alicyclic or heterocyclic system;

each of $D^1$–$D^n$ is $CR^6R^7$, $CH_2CR^6R^7$ or $CHR^6CHR^7$, where $R^6$ and $R^7$ are as defined above;

each of $G^1$–$G^{n-1}$ is —$NR^3CO$—, —$NR^3CS$—, —$NR^3SO$— or —$NR^3SO_2$—, Y in either orientation, where $R^3$ is as defined above;

Q is —$CO_2H$, —CONR'R", —$SO_3H$ or —$SO_2NR'R"$ or an activated derivative of —$CO_2H$ or —$SO_3H$; and I is —NHR'''R"" or —NR'''C(O)R"", where R', R", R''' and R"" are independently selected from the group consisting of hydrogen, alkyl, amino protecting groups, reporter ligands, intercalators, chelators, peptides, proteins, carbohydrates, lipids, steroids, oligonucleotides and soluble and non-soluble polymers.

The peptide nucleic acids of the invention differ from those disclosed in WO 86/05518 in that their recognition moieties are attached to an aza nitrogen atom in the backbone, rather than to an amide nitrogen atom, a hydrazine moiety or a carbon atom in the backbone.

Preferred peptide nucleic acids have general formula (III):

(III)

wherein:

each L is independently selected from the group consisting of hydrogen, phenyl, heterocyclic moieties, naturally occurring nucleobases, and non-naturally occurring nucleobases;

each $R^7$ is independently selected from the group consisting of hydrogen and the side chains of naturally occurring alpha amino acids;

n is an integer from 1 to 60;

each of k, l and m is independently zero or an integer from 1 to 5;

$R^h$ is OH, $NH_2$ or —$NHLysNH_2$; and $R^i$ is H or $COCH_3$.

Particularly preferred are compounds having formula (III) wherein each L is independently selected from the group consisting of the nucleobases thymine (T), adenine (A), cytosine (C), guanine (G) and uracil (U), k and m are zero or 1, and n is an integer from 1 to 30, in particular from 4 to 20. An example of such a compound is provided in FIG. 1, which shows the structural similarity between such compounds and single-stranded DNA.

The peptide nucleic acids of the invention are synthesized by adaptation of standard peptide synthesis procedures, either in solution or on a solid phase. The synthons used are specially designed monomer amino acids or their activated derivatives, protected by standard protecting groups. The oligonucleotide analogs also can be synthesized by using the corresponding diacids and diamines.

Thus, the novel monomer synthons according to the invention are selected from the group consisting of amino acids, diacids and diamines having general formulae:

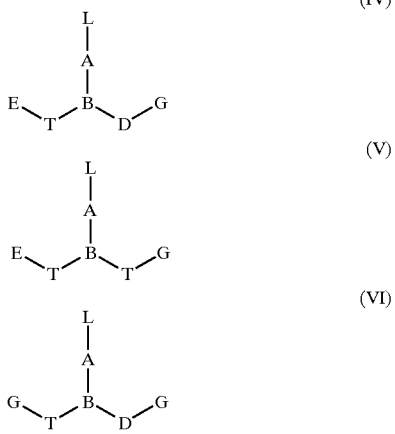

(IV)

(V)

(VI)

wherein L, A, B, T and D are as defined above, except that any amino groups therein may be protected by amino protecting groups; E is COOH, CSOH, SOOH, $SO_2OH$ or an activated derivative thereof; and G is $NHR^3$ or $NPgR^3$, where $R^3$ is as defined above and Pg is an amino protecting group.

Preferred monomer synthons according to the invention are amino acids having formula (VII):

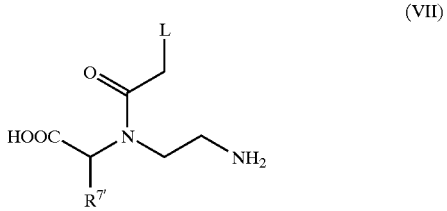

(VII)

or amino-protected and/or acid terminal activated derivatives thereof, wherein L is selected from the group consisting of hydrogen, phenyl, heterocyclic moieties, naturally occurring nucleobases, non-naturally occurring nucleobases, and protected derivatives thereof; and $R^{7'}$ is independently selected from the group consisting of hydrogen and the side chains of naturally occurring alpha amino acids. Especially preferred are such synthons having formula (VII) wherein $R^{7'}$ is hydrogen and L is selected from the group consisting of the nucleobases thymine (T), adenine (A), cytosine (C), guanine (G) and uracil (U) and protected derivatives thereof.

Unexpectedly, these compounds also are able to recognize duplex DNA by displacing one strand, thereby presumably generating a double helix with the other one. Such recognition can take place to dsDNA sequences 5–60 base pairs long. Sequences between 10 and 20 bases are of interest since this is the range within which unique DNA sequences of prokaryotes and eukaryotes are found. Reagents which recognize 17–18 bases are of particular interest since this is the length of unique sequences in the human genome. The compounds of the invention also should be able to form triple helices with dsDNA.

Whereas the improved binding of the compounds of the invention should render them efficient as antisense agents, it is expected that an extended range of related reagents may cause strand displacement, now that this surprising and unexpected new behavior of dsDNA has been discovered.

Thus, in one aspect, the present invention provides methods for inhibiting the expression of particular genes in the cells of an organism, comprising administering to said organism a reagent as defined above which binds specifically to sequences of said genes.

Further, the invention provides methods for inhibiting transcription and/or replication of particular genes or for inducing degradation of particular regions of double stranded DNA in cells of an organism by administering to said organism a reagent as defined above.

Still further, the invention provides methods for killing cells or virus by contacting said cells or virus with a reagent as defined above which binds specifically to sequences of the genome of said cells or virus.

BRIEF DESCRIPTION OF THE DRAWINGS

The numerous objects and advantages of the present invention may be better understood by those skilled in the art by reference to the accompanying figures, in which:

FIG. 12B, lanes 1–3), photofootprinting (FIG. 12A lanes 5–6), potassium permanganate probing (FIG. 12B, lanes 4–6) or probing by staphylococcus nuclease (FIG. 12B, lanes 8–10) or by nuclease $S_1$ (FIG. 12C). Either the A-strand (FIG. 12A) or the T-strand (FIGS. 12B, C) was probed.

DETAILED DESCRIPTION OF THE INVENTION

In the oligonucleotide analogs and monomer synthons according to the invention, ligand L is primarily a naturally occurring nucleobase attached at the position found in nature, i.e., position 9 for adenine or guanine, and position 1 for thymine or cytosine. Alternatively, L may be a non-naturally occurring nucleobase (nucleobase analog), another base-binding moiety, an aromatic moiety, $(C_1–C_4)$alkanoyl, hydroxy or even hydrogen. Some typical nucleobase ligands and illustrative synthetic ligands are shown in FIG. 2. Furthermore, L can be a DNA intercalator, a reporter ligand such as, for example, a fluorophor, radio label, spin label, hapten, or a protein-recognizing ligand such as biotin.

In one aspect of the invention naturally occurring and non-naturally occurring nucleobases include purines and pyrimidines. Purines and pyrimidines suitable for use include adenine, guanine, cytosine, uridine, and thymine, as well as other synthetic and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine. Further purines and pyrimidines include those disclosed in U.S. Pat. No. 3,687,808, those disclosed in the *Concise Encyclopedia Of Polymer Science And Engineering*, pages 858–859, Kroschwitz, J. I., ed. John Wiley & Sons, 1990, and those disclosed by Englisch, et al., *Angewandte Chemie, International Edition* 1991, 30, 613.

Figure 4:
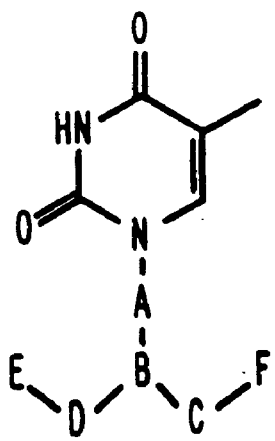
FIG. 4 provides examples of PNA monomer synthons of the invention.
Figure 4:
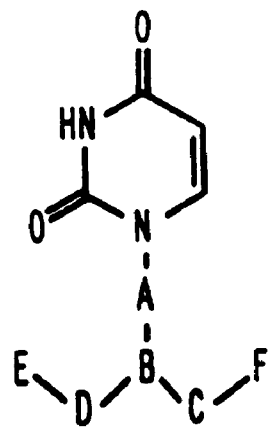
Figure 4:
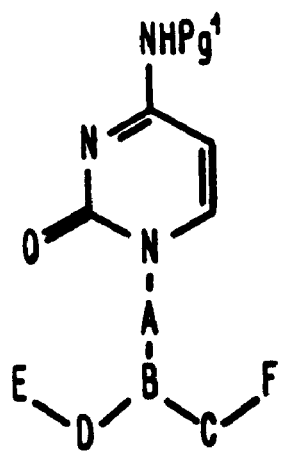
Figure 4:
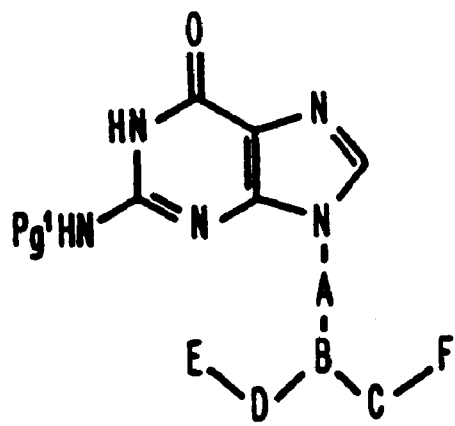
Figure 4:
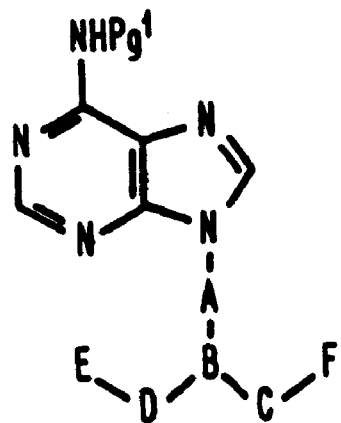
Figure 4:
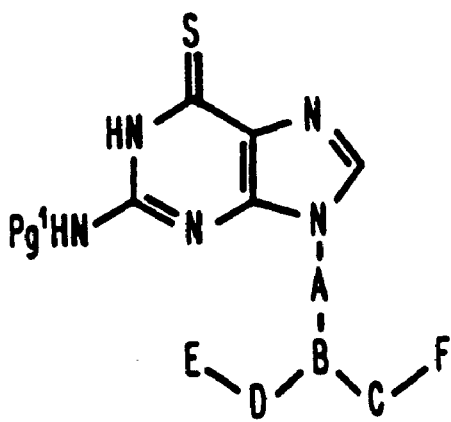

In monomer synthons, L may be blocked with protecting groups. This is illustrated in FIG. 4, where $Pg^1$ is an acid, a base or a hydrogenolytically or photochemically cleavable protecting group such as, for example, t-butoxycarbonyl (Boc), fluorenylmethyloxycarbonyl (Fmoc) or 2-nitrobenzyl (2Nb).

Linker A can be a wide variety of groups such as —$CR^1R^2CO$—, —$CR^1R^2CS$—, —$CR^1R^2CSe$—, —$CR^1R^2CNHR^3$—, —$CR^1R^2C$=$CH_2$— and —$CR^1R^2C$=$C(CH_3)_2$—, where $R^1$, $R^2$ and $R^3$ are as defined above. Preferably, A is methylenecarbonyl (—$CH_2CO$—). Also, A can be a longer chain moiety such as propanoyl, butanoyl or pentanoyl, or corresponding derivative, wherein O is replaced by another value of X or the chain is substituted with $R^1R^2$ or is heterogenous, containing Y. Further, A can be a $(C_2–C_6)$alkylene chain, a $(C_2–C_6)$alkylene chain substituted with $R^1R^2$ or can be heterogenous, containing Y. In certain cases, A can just be a single bond.

In the preferred form of the invention, B is a nitrogen atom, thereby presenting the possibility of an achiral backbone. B can also be $R^3N^+$, where $R^3$ is as defined above.

In the preferred form of the invention, C is —$CR^6R^7$—, but can also be a two carbon unit, i.e. —$CHR^6CHR^7$— or —$CR^6R^7CH_2$—, where $R^6$ and $R^7$ are as defined above. $R^6$ and $R^7$ also can be a heteroaryl group such as, for example, pyrrolyl, furyl, thienyl, imidazolyl, pyridyl, pyrimidinyl, indolyl, or can be taken together to complete an alicyclic system such as, for example, 1,2-cyclobutanediyl, 1,2-cyclopentanediyl or 1,2-cyclohexanediyl.

In the preferred form of the invention, E in the monomer synthon is COOH or an activated derivative thereof, and G in the oligomer is —$CONR^3$—. As defined above, E may also be CSOH; SOOH, $SO_2OH$ or an activated derivative thereof, whereby G in the oligomer becomes —$CSNR^3$—, —$SONR^3$— and —$SO_2NR^3$—, respectively. The activation may, for example, be achieved using an acid anhydride or an active ester derivative, wherein hydrogen in the groups represented by E is replaced by a leaving group suited for generating the growing backbone.

PNA oligomers of the invention can be synthesized with the G group in either orientation. The G group can be synthesized to have the carbonyl of —$C(O)NR^3$— aligned towards the N terminus or the C terminus of the oligomer.

The amino acids which form the backbone may be identical or different. We have found that those based on 2-aminoethylglycine are especially well suited to the purpose of the invention.

In some cases it may be of interest to attach ligands at either terminus (Q, I) to modulate the binding characteristics of the PNAs. Representative ligands include DNA intercalators which will improve dsDNA binding or basic groups, such as lysine or polylysine, which will strengthen the binding of PNA due to electrostatic interaction. To decrease negatively charged groups such as carboxy and sulfo groups could be used. The design of the synthons further allows such other moieties to be located on non-terminal positions.

In a further aspect of the invention, the PNA oligomers are conjugated to low molecular effector ligands such as ligands having nuclease activity or alkylating activity or reporter ligands (fluorescent, spin labels, radioactive, protein recognition ligands, for example, biotin or haptens). In a further aspect of the invention, the PNAs are conjugated to peptides or proteins, where the peptides have signaling activity and the proteins are, for example, enzymes, transcription factors or antibodies. Also, the PNAs can be attached to water-soluble or water-insoluble polymers. In another aspect of the invention, the PNAs are conjugated to oligonucleotides or carbohydrates. When warranted, a PNA oligomer can be synthesized onto some moiety (e.g., a peptide chain, reporter, intercalator or other type of ligand-containing group) attached to a solid support.

Such conjugates can be used for gene modulation (e.g., gene targeted drugs), for diagnostics, for biotechnology, and for scientific purposes.

As a further aspect of the invention, PNAs can be used to target RNA and ssDNA to produce both antisense-type gene regulating moieties and hybridization probes for the identification and purification of nucleic acids. Furthermore, the PNAs can be modified in such a way that they can form triple helices with dsDNA. Reagents that bind sequence-specifically to dsDNA have applications as gene targeted drugs. These are foreseen as extremely useful drugs for treating diseases like cancer, AIDS and other virus infections, and may also prove effective for treatment of some genetic diseases. Furthermore, these reagents may be used for research and in diagnostics for detection and isolation of specific nucleic acids.

The triple helix principle is believed to be the only known principle in the art for sequence-specific recognition. of dsDNA. However, triple helix formation is largely limited to recognition of homopurine-homopyrimidine sequences. Strand displacement is superior to triple helix recognition in that it allows for recognition of any sequence by use of the four natural bases. Also, in strand displacement recognition readily occurs at physiological conditions, that is, neutral pH, ambient (20–40 C.) temperature and medium (100–150 mM) ionic strength.

Gene targeted drugs are designed with a nucleobase sequence (containing 10–20 units) complementary to the regulatory region (the promoter) of the target gene. Therefore, upon administration of the drug, it binds to the promoter and block access thereto by RNA polymerase. Consequently, no mRNA, and thus no gene product (protein), is produced. If the target is within a vital gene for a virus, no viable virus particles will be produced. Alternatively, the target could be downstream from the promoter, causing the RNA polymerase to terminate at this position, thus forming a truncated mRNA/protein which is nonfunctional.

Sequence-specific recognition of ssDNA by base complementary hybridization can likewise be exploited to target specific genes and viruses. In this case, the target sequence is contained in the mRNA such that binding of the drug to the target hinders the action of ribosomes and, consequently, translation of the mRNA into protein. The peptide nucleic acids of the invention are superior to prior reagents in that they have significantly higher affinity for complementary ssDNA. Also, they possess no charge and water soluble, which should facilitate cellular uptake, and they contain amides of non-biological amino acids, which should make them biostable and resistant to enzymatic degradation by, for example, proteases.

Certain biochemical/biological properties of PNA oligomers are illustrated by the following experiments.

1. Sequence Discrimination at the dsDNA Level (Example 63, FIG. 20)

Using the $S_1$-nuclease probing technique, the discrimination of binding of the $T_{10}$, $T_5CT_4(T_9C)$ & $T_2CT_2CT_4(T_8C_2)$ PNA to the recognition sequences $A_{10}$, $A_5GA_4$ ($A_9G$) & $A_2GA_2GA_4$ ($A_8G_2$) cloned into the BamHI, SalI or PstI site of the plasmid pUC19 was analyzed. The results (FIG. 20) show that the three PNAs bind to their respective recognition sequences with the following relative efficiencies: PNA-T10: $A_{10} > A_9G >> A_8G_2$, PNA-$T_9C$: $A_9G > A_{10} \sim A_8G_2$, PNA-$T_8C_2$: $A_8G_2 \geq A_9G >> A_{10}$. Thus at 37° C. one mismatch out of ten gives reduced efficiency (5–10 times estimated) whereas two mismatches are not accepted.

2. Kinetics of PNA-$T_{10}$—dsDNA Strand Displacement Complex Formation (Example 66, FIG. 21)

Figure 21:
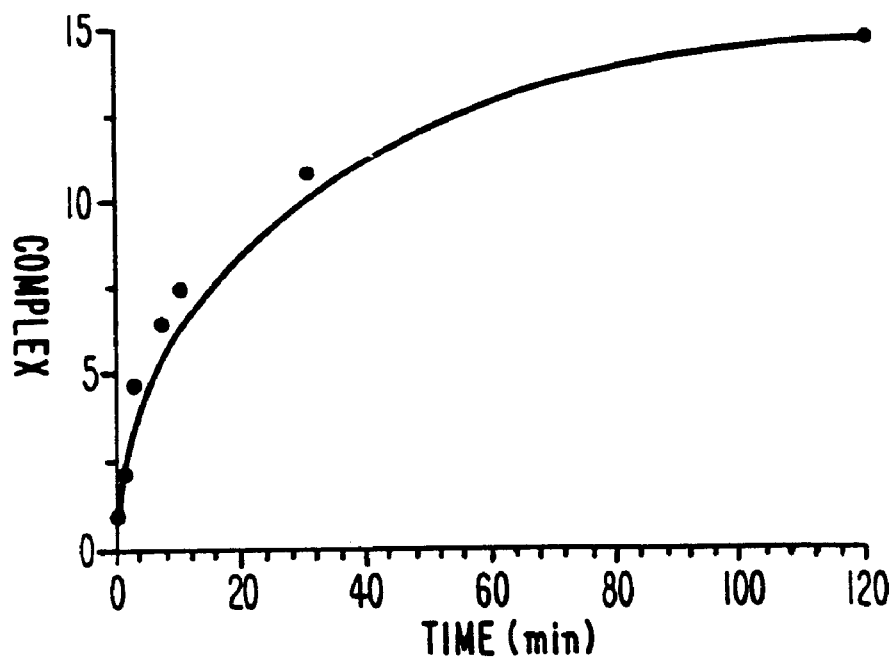
FIG. 21 shows a graph based on densitometric scanning of PAGE autoradiographs demonstrating the kinetics of the binding of PNA-$T_{10}$ to a double stranded target.

Complex formation was probed by $S_1$-nuclease at various times following mixing of PNA and $^{32}$P-endlabeled dsDNA fragment (FIG. 21).

3. Stability of PNA-dsDNA Complex (Example 67, FIG. 22)

Complexes between PNA-$T_n$ and $^{32}$P-dsDNA ($A_{10}/T_{10}$) target were formed (60 min, 37° C.). The complexes were then incubated at the desired temperature in the presence of excess oligo-$dA_{10}$ for 10 min, cooled to RT and probed with $KMnO_4$. The results (FIG. 22) show that the thermal stability of the PNA-dsDNA complexes mirror that of the PNA oligonucleotide complexes in terms of "$T_m$".

4. Inhibition of Restriction Enzyme Cleavage by PNA (Example 65, FIG. 23)

Figure 23:
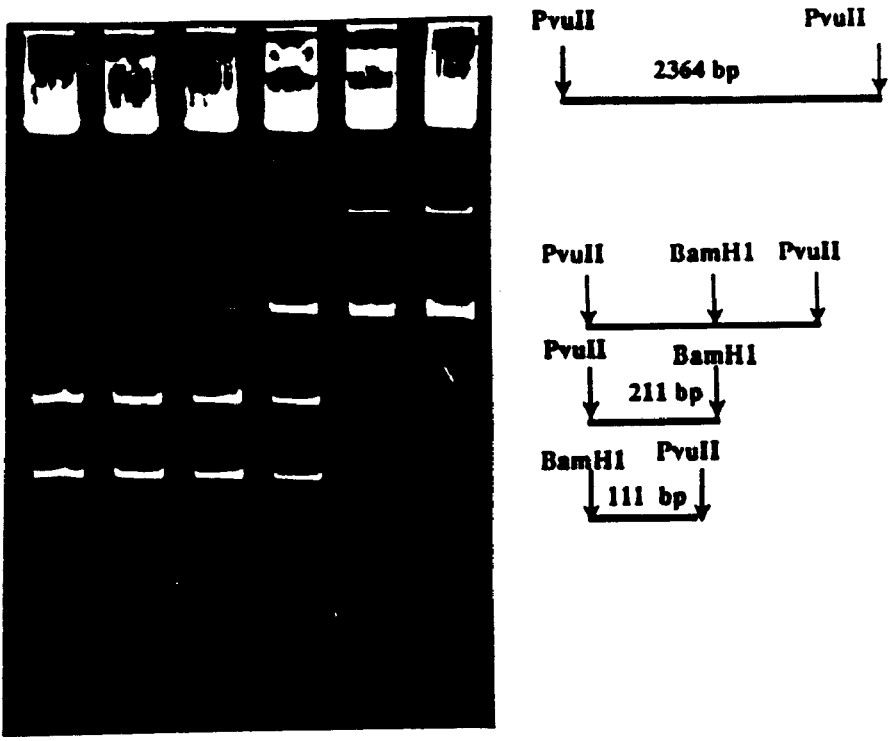
FIG. 23 shows an electrophoretic gel staining demonstrating that restriction enzyme activity towards DNA is inhibited when PNA is bound proximal to the restriction enzyme recognition site.

The plasmid construct, pT10, contains a $dA_{10}/dT_{10}$ tract cloned into the BamHI site in pUC19. Thus, cleavage of pT10 with BamHI and PvuII results in two small DNA fragments of 211 and 111 bp, respectively. In the presence of PNA-$T_{10}$, a 336 bp fragment is obtained corresponding to cleavage only by PvuII (FIG. 23). Thus cleavage by BamHI is inhibited by PNA bound proximal to the restriction enzyme site. The results also show that the PNA-dsDNA complex can be formed in 100% yield. Similar results were obtained using the pT8C2 plasmid and PNA-T8C2.

5. Binding of $^{125}$I-labeled PNA to Oligonucleotides (Example 63, FIG. 24)

Figure 24:
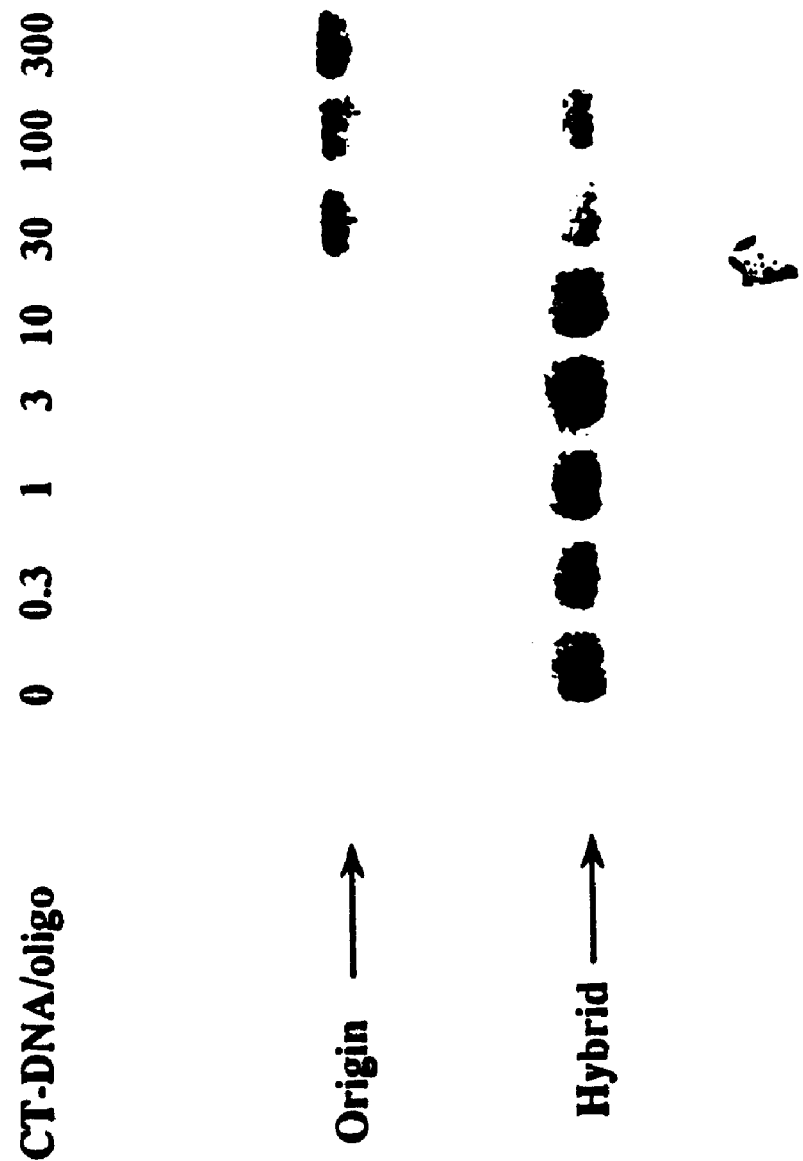
FIG. 24 shows a PAGE autoradiograph demonstrating that $^{125}$I-labeled PNA-$T_{10}$ binds to a complementary $dA_{10}$ oligonucleotide.

A Tyr-PNA-$T_{10}$-Lys-$NH_2$ was labeled with $^{125}$I using Na$^{125}$I and chloramine-T and purified by HPLC. The $^{125}$I-PNA-$T_{10}$ was shown to bind to oligo-$dA_{10}$ by PAGE and autoradiography (FIG. 24). The binding could be competed by excess denatured calf thymus DNA.

Figure 11A:
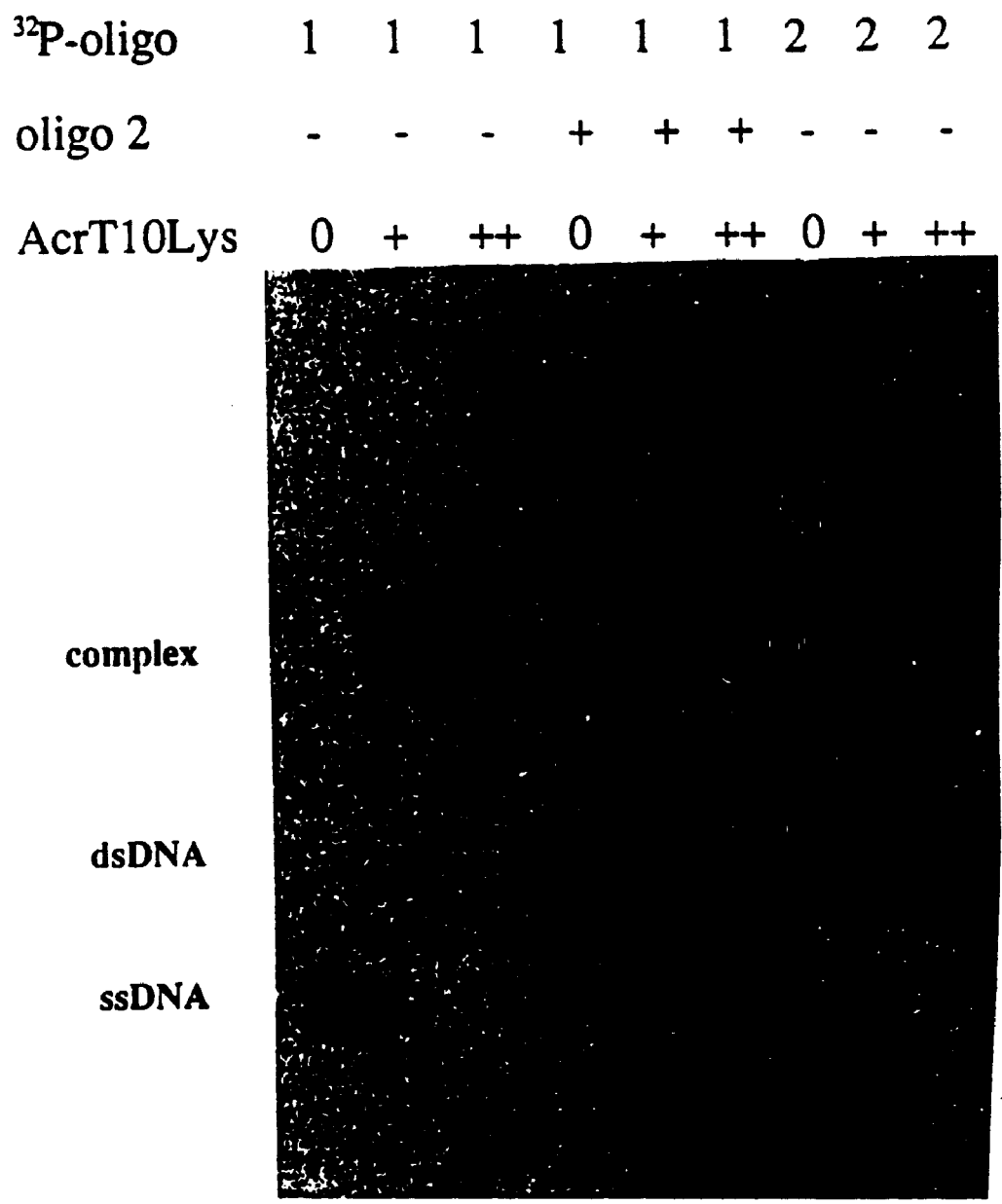
FIGS. 11A and 11B show binding of AcrT10-Lys to $dA_{10}$. 5'-$^{32}$P-labeled oligonucleotide (1) (5'-$GATCCA_{10}G$) was incubated in the absence or presence of Acr-T10-LysNH$_2$ and in the absence or presence of oligonucleotide (2) (5'-$GATCCT_{10}G$) and the samples were analyzed by polyacrylamide gel electrophoresis (PAGE) and autoradiography under "native conditions" (FIG. 11A) or under "denaturing conditions" (FIG. 11B).
Figure 11B:
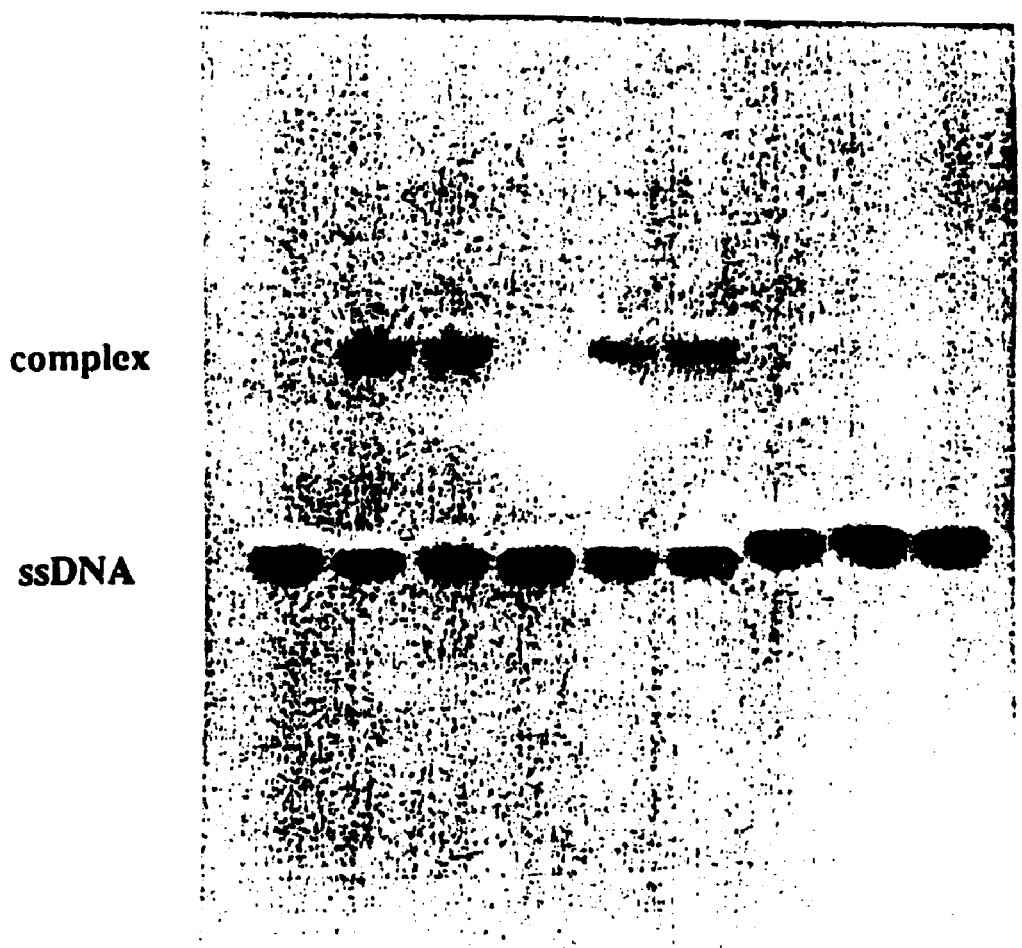

The sequence-specific recognition of dsDNA is illustrated by the binding of a PNA, consisting of 10 thymine substituted 2-aminoethylglycyl units, which C-terminates in a lysine amide and N-terminates in a complex 9-aminoacridine ligand (9-Acr$^1$-(Taeg)$_{10}$-Lys-$NH_2$, FIG. 11a, 11b) to a $dA_{10}/dT_{10}$ target sequence. The target is contained in a 248 bp $^{32}$P-end-labelled DNA-fragment.

Figure 3A:
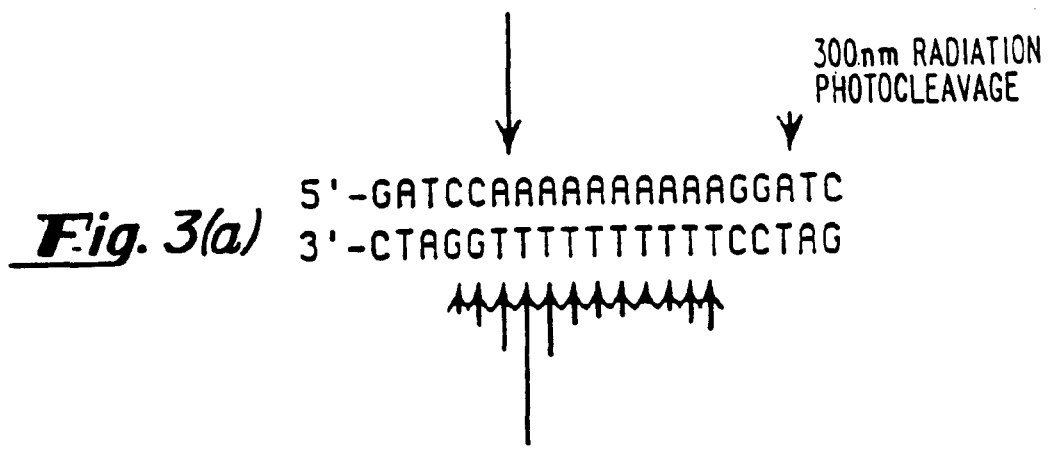
FIGS. 3(a)–3(d) provide a schematic illustration of (a) photocleavage by $Acr^1$-$(Taeg)_{10}$-Lys-$NH_2$ (Acr-T10-LysNH$_2$); (b) photofootprint by the diazo-linked acridine of $Acr^1$-$(Taeg)_{10}$-Lys-$NH_2$ and preferred $KMnO_4$-cleavage; and (c) $S_1$-nuclease enhanced cleavage and (d) micrococcus nuclease cleavage of $Acr^1$-$(Taeg)_{10}$-Lys-$NH_2$ binding site.
Figure 5:
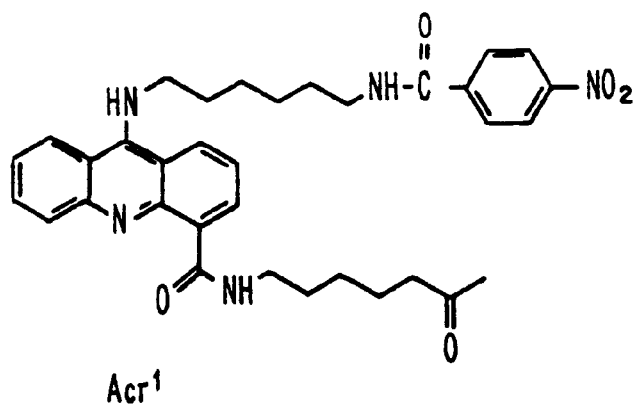
FIG. 5 shows the $Acr^1$ ligand and a PNA, $Acr^1$-$(Taeg)_{10}$-Lys-$NH_2$.
Figure 5:
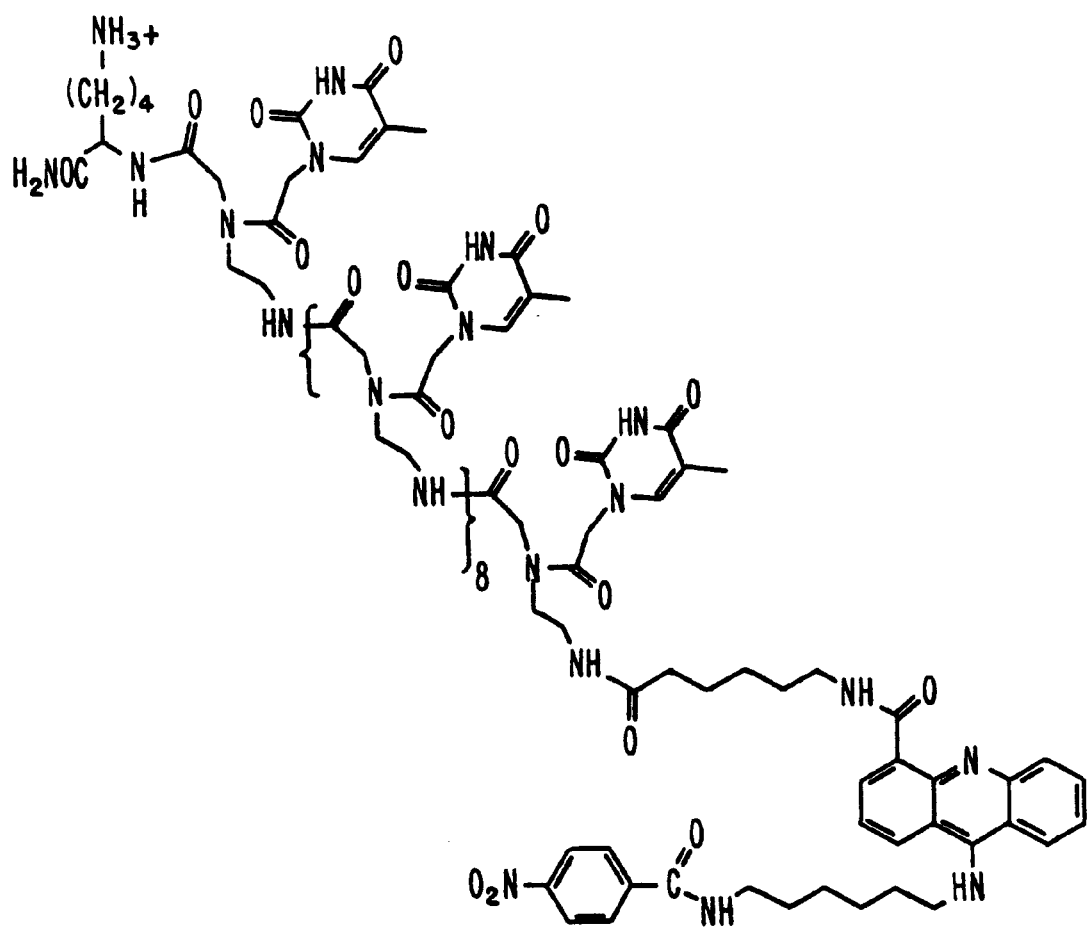
Figure 6:
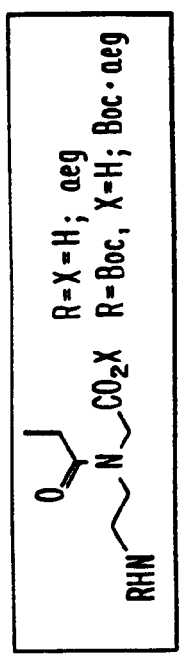
FIG. 6 provides a general scheme for the preparation of monomer synthons.
Figure 6:
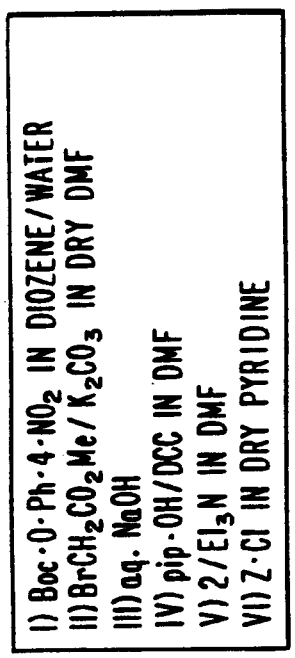
Figure 6:
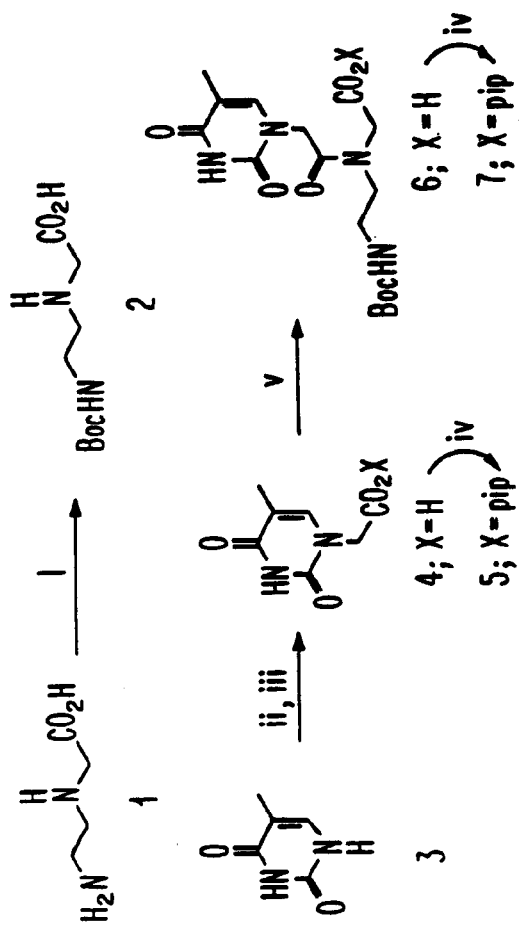
Figure 6:
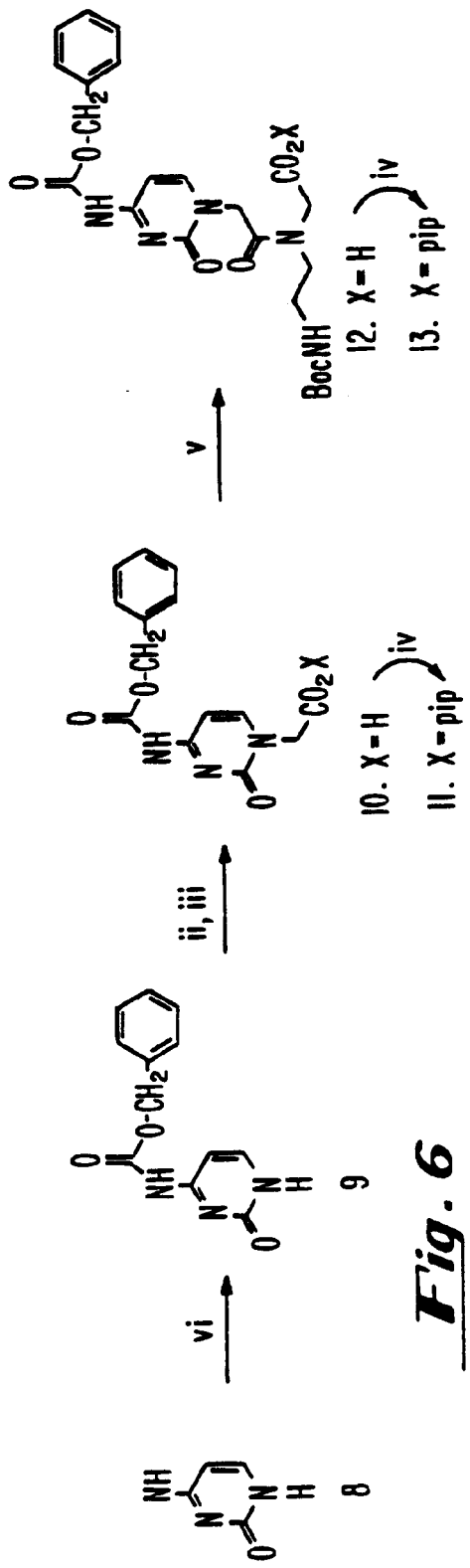
Figure 7:
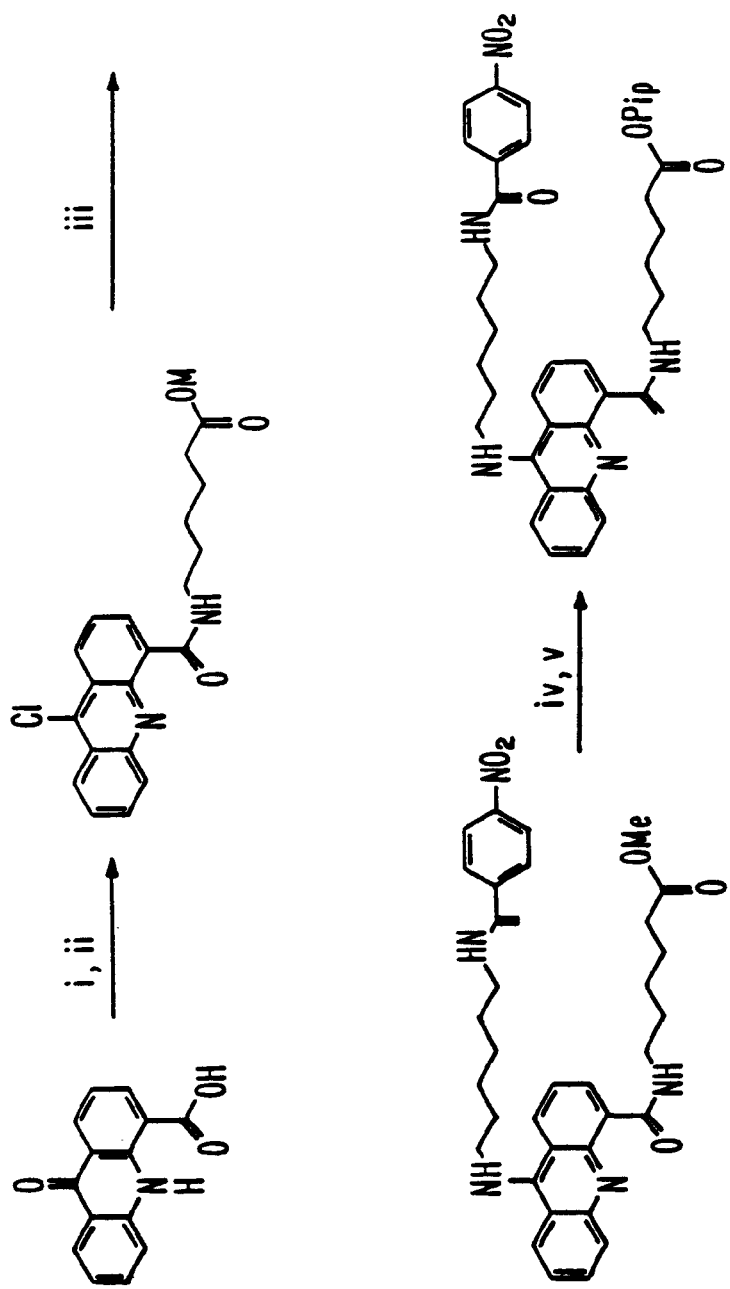
FIG. 7 provides a general scheme for the preparation of the $Acr^1$ ligand.

Strand displacement was ascertained by the following type of experiments:

1) The 9-Acr$^1$ ligand (FIG. 5), which is equipped with a 4-nitrobenzamido group to ensures cleavage of DNA upon irradiation, is expected only to cleave DNA in close proximity to its binding site. Upon irradiation of the PNA with the above 248 bp DNA fragment, selective cleavage at the $dA_{10}/dT_{10}$ sequence is observed (FIG. 3a).

2) In a so-called photofootprinting assay, where a synthetic diazo-linked acridine under irradiation cleaves DNA (except where the DNA is protected by said binding substance) upon interaction with DNA in the presence of a DNA-binding substance.

Figure 3B:
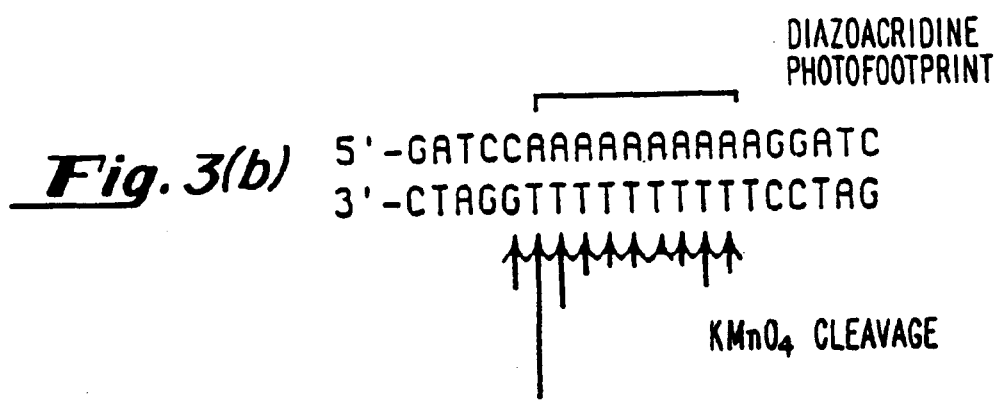

Such an experiment was performed with the above 248 bp dsDNA fragment, which showed clear protection against photocleavage of the PNA binding site (FIG. 3b).

Figure 3C:
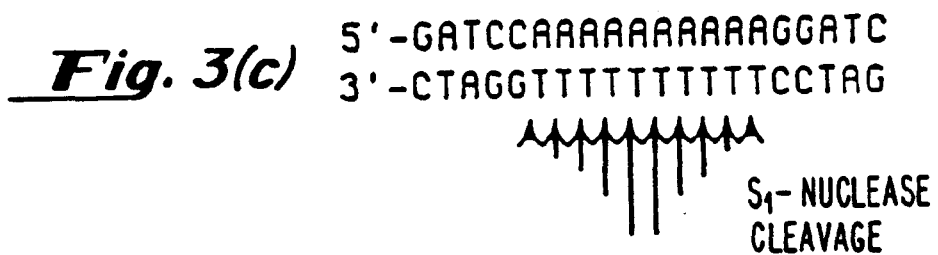

3) In a similar type of experiment, the DNA-cleaving enzyme micrococcus nuclease, which is also hindered in its action by most DNA-binding reagents, showed increased cleavage at the $T_{10}$-target (FIG. 3c).

4) In yet another type of experiment, the well-known high susceptibility of single strand thymine ligands (as opposed to double strand thymine ligands) towards potassium permanganate oxidation was employed. Oxidation of the 248 bp in the presence of the reagent showed only oxidation of the $T_{10}$-strand of the target (FIG. 3b).

Figure 3D:
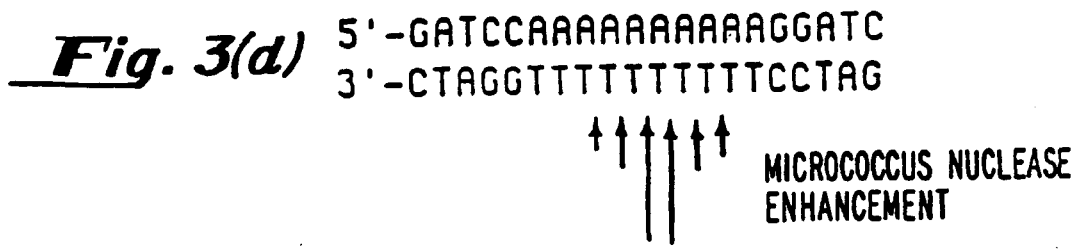

5) In a similar type of demonstration, the single strand specificity of $S_1$ nuclease clearly showed that only the $T_{10}$-strand of the target was attacked (FIG. 3d).

The very efficient binding of $(Taeg)_{10}$, $(Taeg)_{10}$-Lys-NH$_2$ and Acr$^1$-(Taeg)$_{10}$-Lys-NH$_2$ (FIGS. 11a, 11b) to the corresponding dA$_{10}$ was furthermore illustrated in two ways:

1. Ligand-oligonucleotide complexes will migrate slower than the naked oligonucleotide upon electrophoresis in polyacrylamide gels. Consequently, such experiments were performed with Acr$^1$-(Taeg)$_{10}$-Lys-NH$_2$ and $^{32}$P-end-labelled dA$_{10}$. This showed retarded migration under conditions where a normal dA$_{10}$/dT$_{10}$ duplex is stable, as well as under conditions where such a duplex is unstable (denaturing gel). A control experiment was performed with a mixture of Acr$^1$-(Taeg)$_{10}$-Lys-NH$_2$ and $^{32}$P-end-labelled dT$_{10}$ which showed no retardation under the above conditions.

2. Upon formation of DNA duplexes (dsDNA) from single strand DNA, the extinction coefficient decreases (hypochromicity). Thus, the denaturing of DNA can be followed by measuring changes in the absorbance, for example, as a function of $T_m$, the temperature where 50% of a duplex has disappeared to give single strands.

Duplexes were formed from the single-stranded oligodeoxyribonucleotides and the PNAs listed below. Typically 0.3 OD$_{260}$ of the T-rich strand was hybridized with 1 equivalent of the other strand by heating to 90 C. for 5 min, cooling to room temperature and kept for 30 min and finally stored in a refrigerator at 5 C. for at least 30 min. The buffers used were all 10 mM in phosphate and 1 mM in EDTA. The low salt buffer contained no sodium chloride, whereas the medium salt buffer contained 140 mM NaCl and the high salt buffer 500 mM NaCl. The pH of all the buffers was 7.2. The melting temperature of the hybrids were determined on a Gilford Response apparatus. The following extinction coefficients were used A: 15.4 ml/µmol.cm; T: 8.8; G: 11.7 and C: 7.3 for both normal oligonucleotides and PNA. The melting curves were recorded in steps of 0.5 C./min. The $T_m$ were determined from the maximum of the 1st derivative of the plot of A$_{260}$ vs temperature.

List of Oligodeoxyribonucleotides

| 1. | 5'-AAA-AAA-AA |
| 2. | 5'-AAA-AAA-AAA-A |
| 3. | 5'-TTT-TTT-TTT-T |
| 4. | 5'-AAA-AAG-AAA-A |
| 5. | 5'-AAG-AAG-AAA-A |
| 6. | 5'-AAA-AGA-AAA-A |
| 7. | 5'-AAA-AGA-AGA-A |
| 8. | 5'-TTT-TCT-TTT-T |
| 9. | 5'-TTT-TCT-TCT-T |
| 10. | 5'-TTT-TTC-TTT-T |
| 11. | 5'-TTT-TTC-TTC-T |
| 12. | 5'-TTC-TTC-TTT-T |
| 13. | 5'-TTT-TTT-TTT-TTT-TTT |
| 14. | 5'-AAA-AAA-AAA-AAA-AAA |

List of PNAs

| a. | TTT-TTT-TTT-T-Lys-NH$_2$ |
| b. | TTT-TTT-TT-Lys-NH$_2$ |
| c. | TTT-TTC-TTT-T-Lys-NH$_2$ |
| d. | TTC-TTC-TTT-T-Lys-NH$_2$ |
| e. | Acr-TTT-TTT-TTT-T-Lys-NH$_2$ |
| f. | Ac-TTT-TTT-TTT-T-Lys-NH$_2$ |

| Oligo/PNA | Low Salt | Medium Salt | High Salt |
|---|---|---|---|
| 1 + b | 56.0 | 51.5 | 50.0 |
| 2 + a | 73.0 | 72.5 | 73.0 |
| 2 + c |  | 41.5 and 52.0* |  |
| 2 + e | 84.5 | 86.0 | ≈90 |
| 2 + f |  | 74 |  |
| 4 + a | 60.0 | 59.0 | 61.5 |
| 4 + c | 74.5 | 72.0 | 72.5 |
| 4 + f |  | 62.0 |  |
| 5 + a |  | 47.0 |  |
| 5 + c |  | 57.5 |  |
| 5 + f |  | 46.5 |  |
| 7 + a |  | 46.0 |  |
| 7 + c |  | 58.0 |  |
| 7 + f |  | 43.5 |  |
| 7 + 12 |  | 23.0 |  |
| 13 + 14 |  | 39.0 |  |

*= Two distinct melting temperatures are seen, indicating local melting before complete denaturation.

The hybrid formed between RNA-A (poly rA) and PNA-T$_{10}$-Lys-NH$_2$ melts at such high temperature that it cannot be measured (>90 C.). But specific hybridization is demonstrated by the large drop in A$_{260}$ by mixing with RNA-A but not G,C and U. The experiment is done by mixing 1 ml of a solution of the PNA and 1 ml of a solution the RNA, each with A$_{260}$=0.6, and then measure the absorbance at 260 nm. Thereafter the sample is heated to 90 C. for 5 min, cooled to room temperature and kept at this temperature for 30 minutes and finally stored at 5 C. for 30 min.

| RNA | PNA | A$_{260}$ Before Mixing | A$_{260}$ After Mixing | A$_{260}$ After Mixing and Heating |
|---|---|---|---|---|
| RNA-A | PNA-T$_{10}$-lys-NH$_2$ | 0.600 | 0.389 | 0.360 |
| RNA-U | PNA-T$_{10}$-lys-NH$_2$ | 0.600 | 0.538 | 0.528 |
| RNA-G | PNA-T$_{10}$-lys-NH$_2$ | 0.600 | 0.514 | 0.517 |
| RNA-C | PNA-T$_{10}$-lys-NH$_2$ | 0.600 | 0.540 | 0.532 |

From the above measurements the following conclusions can be made. There is base stacking, since a melting curve is observed. The PNA-DNA hybrid is more stable than a normal DNA-DNA hybrid, and the PNA-RNA is even more stable. Mismatches cause significant drops in the $T_m$-value, whether the mispaired base is in the DNA or in the PNA-strand. The $T_m$-value is only slightly dependent on ionic strength, as opposed to normal oligonucleotides.

Figure 1A:
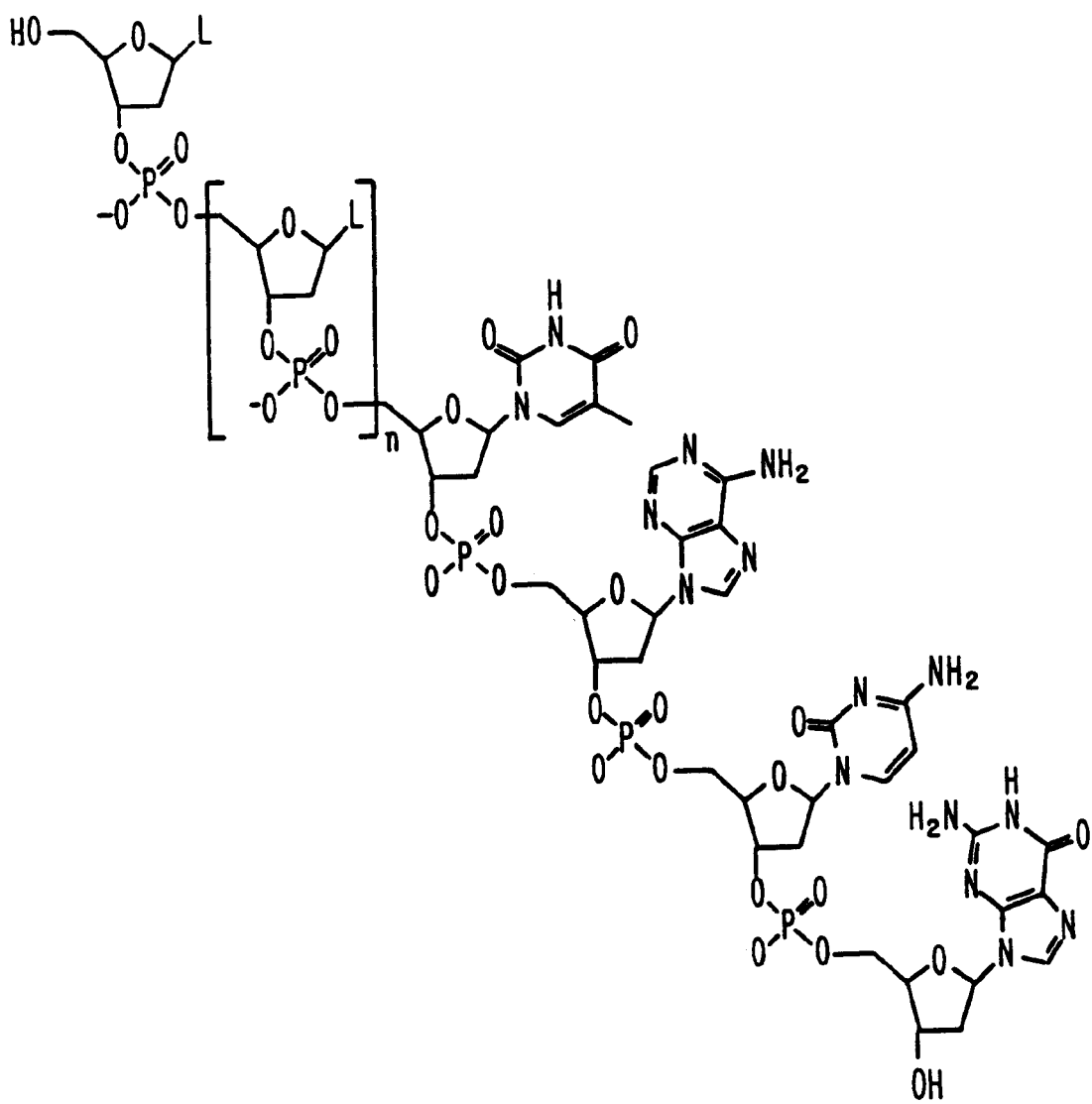
FIGS. 1(A) and 1(B) show a naturally occurring deoxyribooligonucleotide (A) and a peptide nucleic acid (PNA) of the invention (B).
Figure 1B:
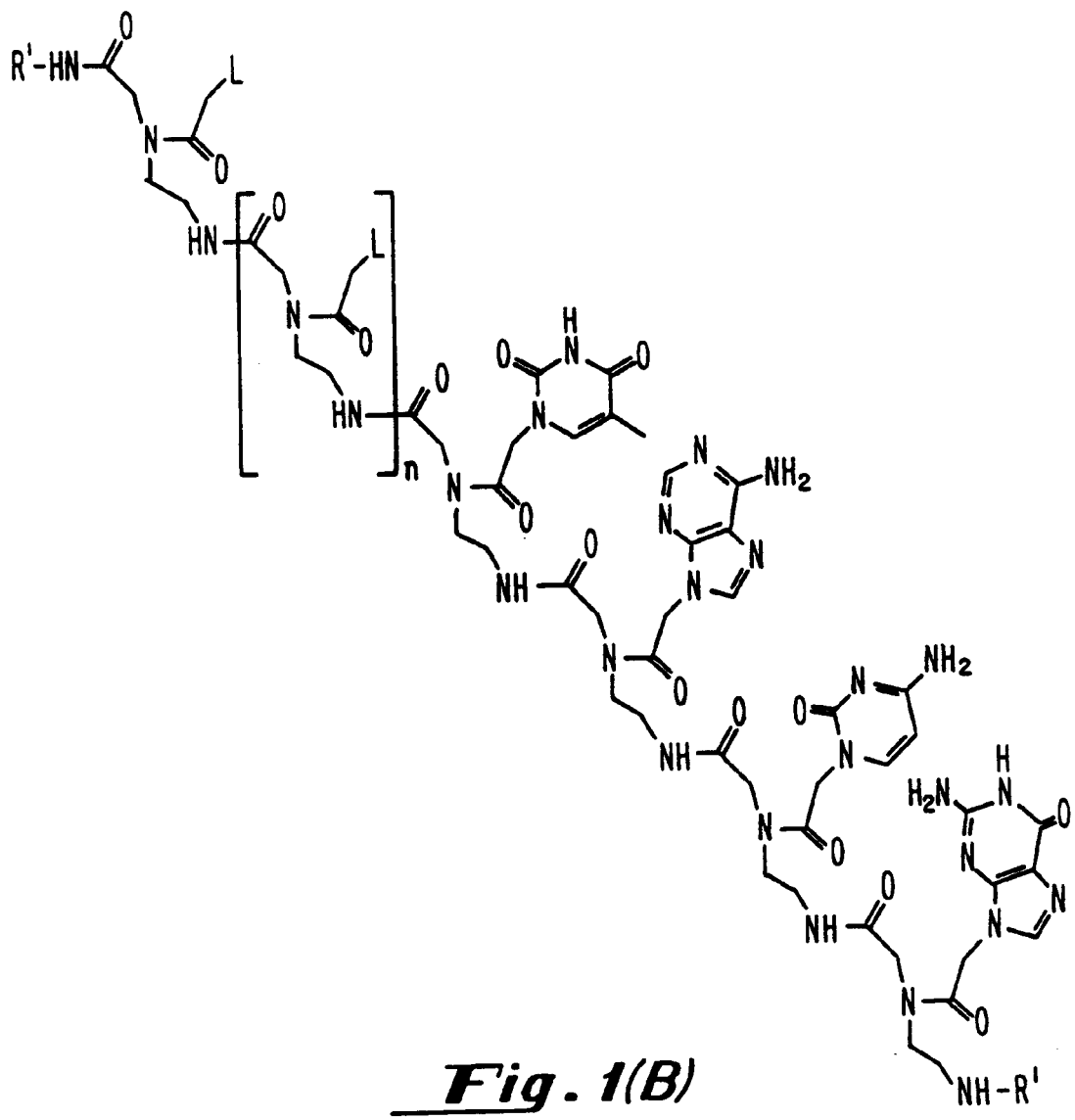
Figure 2A:
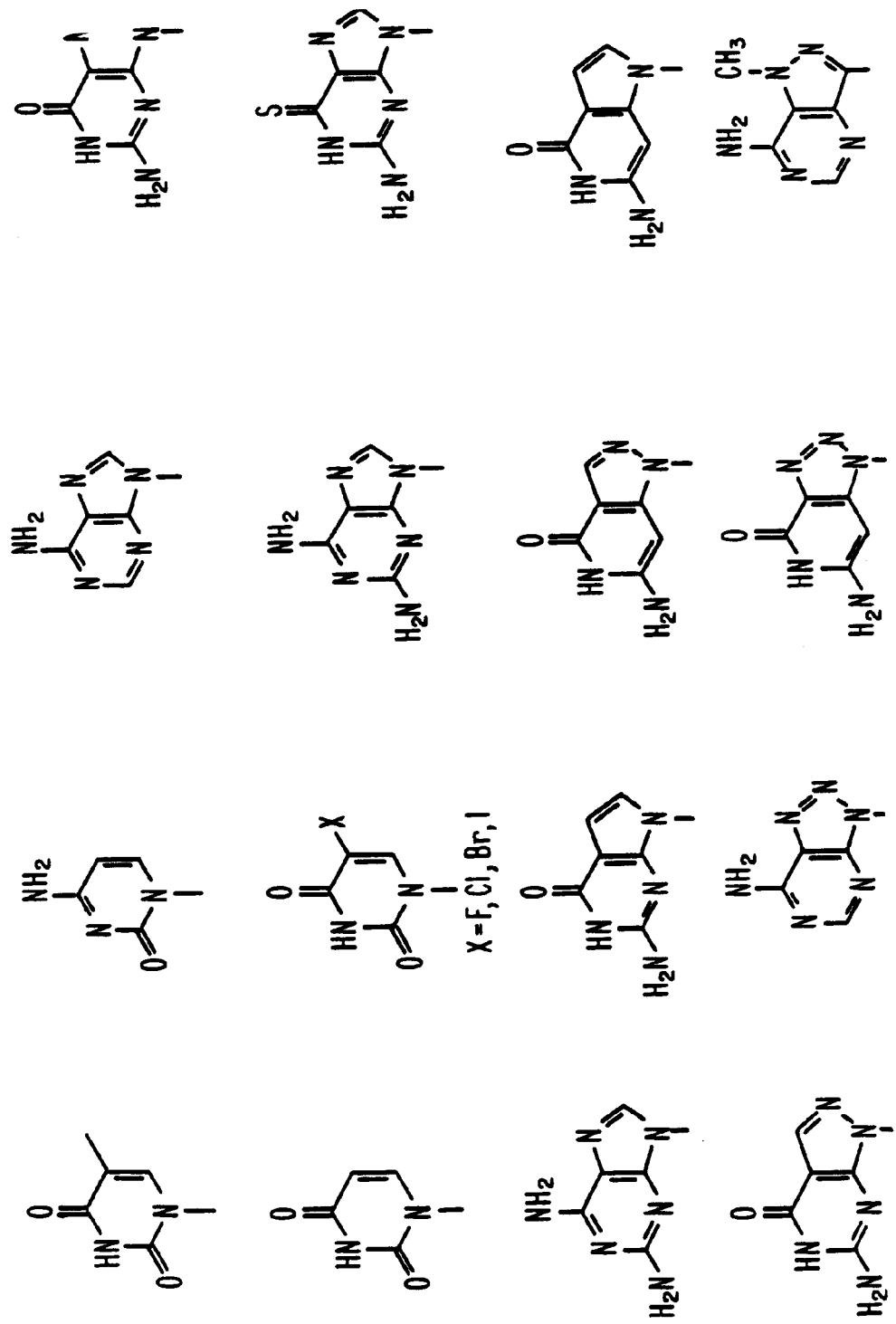
FIGS. 2(A) and 2(B) provide examples of naturally occurring and non-naturally occurring nucleobases for DNA recognition and reporter groups.
Figure 2B:
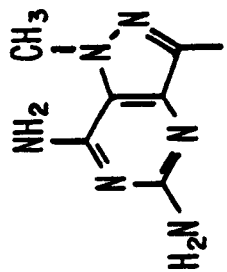
Figure 2B:
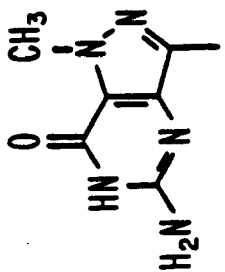
Figure 2B:
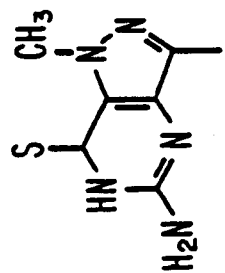
Figure 2B:
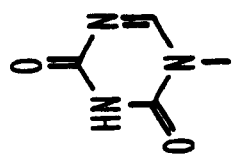
Figure 2B:
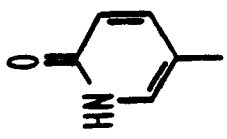
Figure 2B:
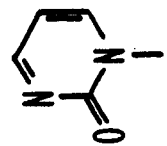
Figure 2B:
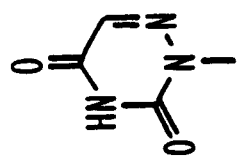
Figure 2B:
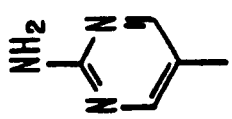
Figure 2B:
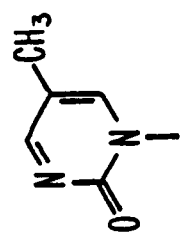
Figure 2B:
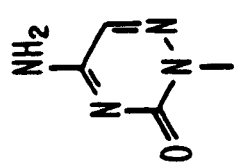
Figure 2B:
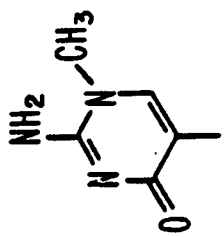
Figure 2B:
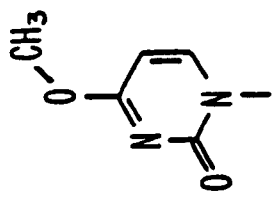

The synthesis of the PNAs according to the invention is discussed in detail in the following, where FIG. 1 illustrates one of the preferred PNA examples and compares its structure to that of a complementary DNA.

Synthesis of PNA Oligomers and Polymers

Figure 8:
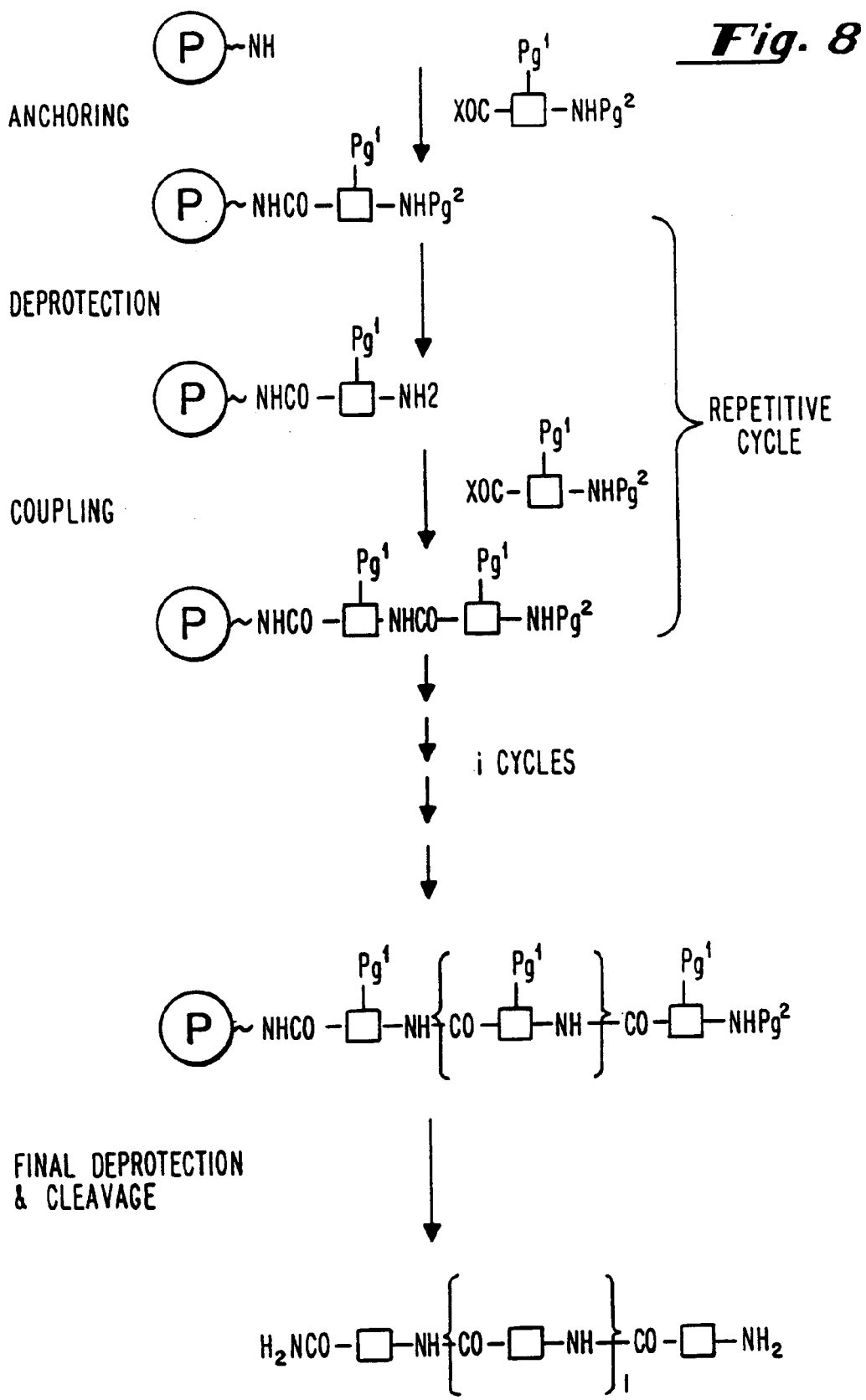
FIG. 8 provides a general scheme for solid-phase PNA synthesis illustrating the preparation of linear unprotected PNA amides.
Figure 9:
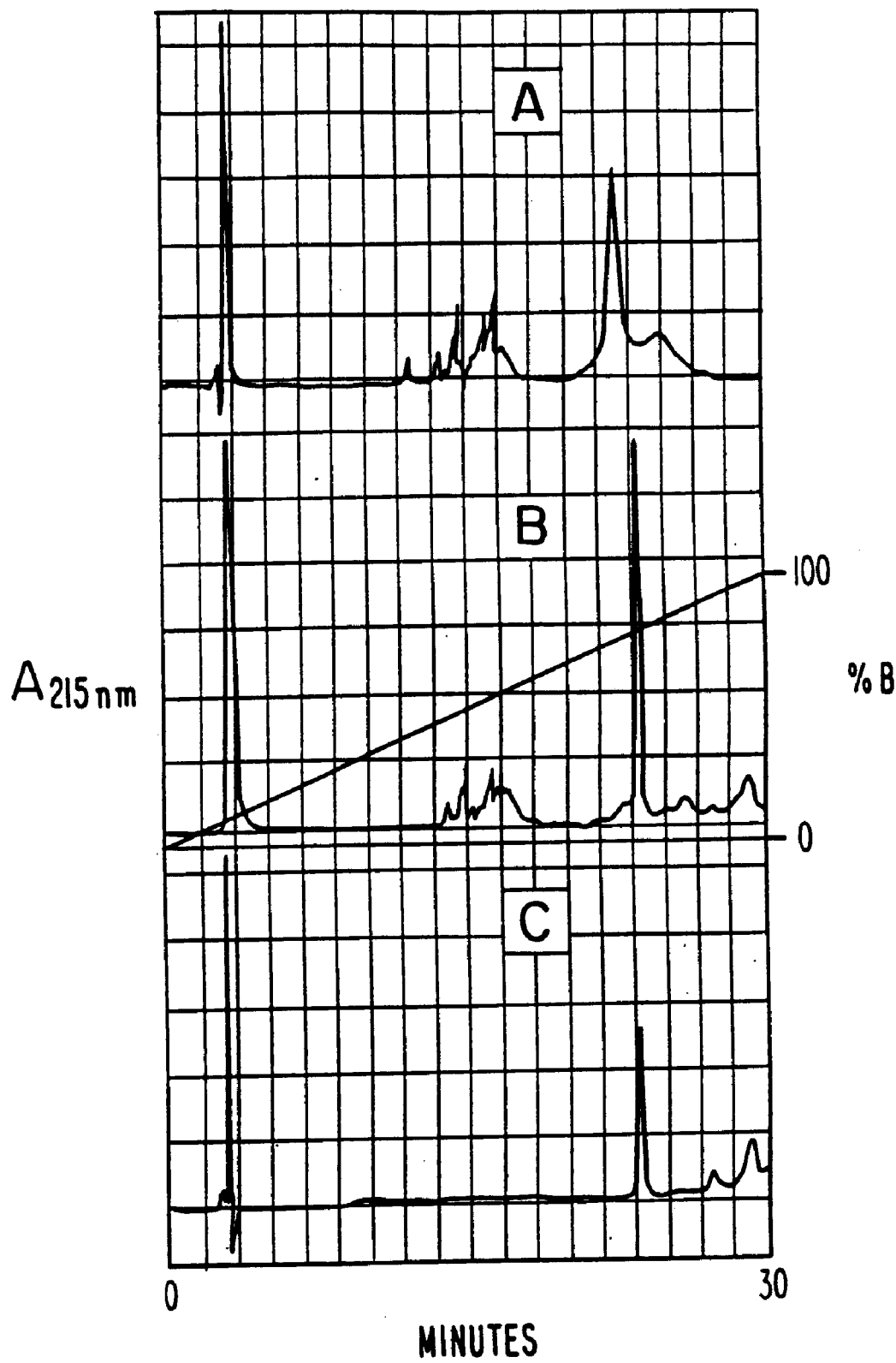
FIG. 9 shows analytical HPLC chromatograms of: (A) crude H-$[Taeg]_{15}$-$NH_2$ after HF-cleavage (before lyophilization); (B) crude $Acr^1$-$[Taeg]_{15}$-$NH_2$ after HF-cleavage (before lyophilization); and (C) purified $Acr^1$-$[Taeg]_{15}$-$NH_2$. Buffer A, 5% $CH_3CN$/95% $H_2O$/0.0445% TFA; buffer B, 60% $CH_3CN$/40% $H_2O$/0.0390% TFA; linear gradient, 0–100% of B in 30 min; flow rate, 1.2 ml/min; column, Vydac $C_{18}$ (5 μm, 0.46×25 cm).
Figure 10:
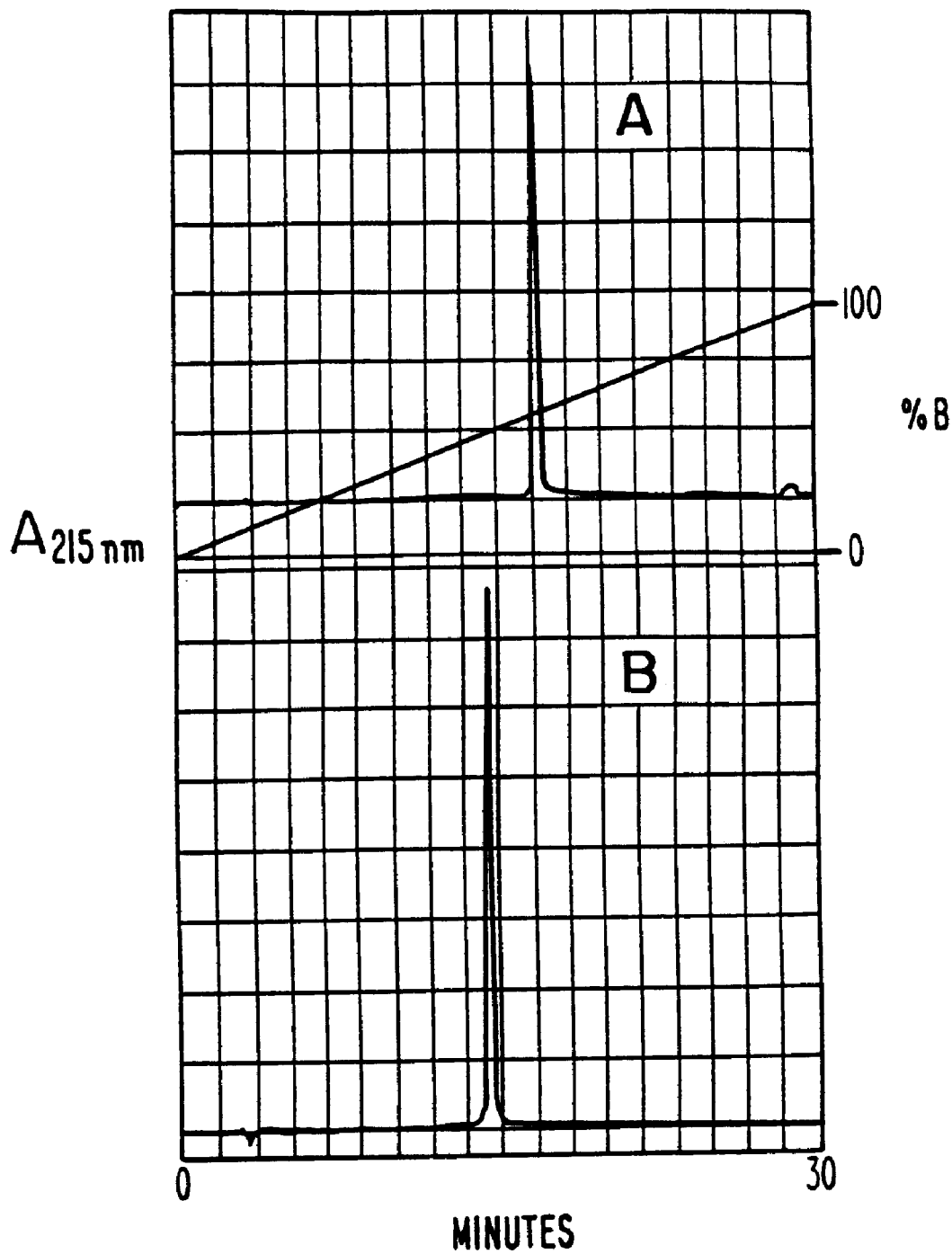
FIG. 10 shows analytical HPLC chromatograms of: (A) purified H-$[Taeg]_{10}$-Lys-$NH_2$ and (B) purified H-$[Taeg]_5$-Caeg-$[Taeg]_4$-Lys-$NH_2$ employing the same conditions as in FIG. 9.

The principle of anchoring molecules onto a solid matrix, which helps in accounting for intermediate products during chemical transformations, is known as Solid-Phase Synthesis or Merrifield Synthesis (see, e.g., Merrifield, *J. Am. Chem. Soc.*, 1963, 85, 2149 and *Science*, 1986, 232, 341). Established methods for the stepwise or fragmentwise solid-phase assembly of amino acids into peptides normally employ a beaded matrix of slightly cross-linked styrene-divinylbenzene copolymer, the cross-linked copolymer having been formed by the pearl polymerization of styrene monomer to which has been added a mixture of divinylbenzenes. A level of 1–2% cross-linking is usually employed. Such a matrix also can be used in solid-phase PNA synthesis in accordance with the present invention (FIG. 8).

Concerning the initial functionalization of the solid phase, more than fifty methods have been described in connection with traditional solid-phase peptide synthesis (see, e.g., Barany and Merrifield in "The Peptides" Vol. 2, Academic Press, New York, 1979, pp. 1–284, and Stewart and Young, "Solid Phase Peptide Synthesis", 2nd Ed., Pierce Chemical Company, Illinois, 1984). Reactions for the introduction of chloromethyl functionality (Merrifield resin; via a chloromethyl methyl ether/$SnCl_4$ reaction), aminomethyl functionality (via an N-hydroxymethylphthalimide reaction; see, Mitchell, et al., *Tetrahedron Lett.*, 1976, 3795), and benzhydrylamino functionality (Pietta, et al., *J. Chem. Soc.*, 1970, 650) are the most widely applied. Regardless of its nature, the purpose of the functionality is normally to form an anchoring linkage between the copolymer solid support and the C-terminus of the first amino acid to be coupled to the solid support. As will be recognized, anchoring linkages also can be formed between the solid support and the amino acid N-terminus. It is generally convenient to express the "concentration" of a functional group in terms of millimoles per gram (mmol/g). Other reactive functionalities which have been initially introduced include 4-methylbenzhydrylamino and 4-methoxybenzhydrylamino. All of these established methods are in principle useful within the context of the present invention. Preferred methods for PNA synthesis employ aminomethyl as the initial functionality, in that aminomethyl is particularly advantageous with respect to the incorporation of "spacer" or "handle" groups, owing to the reactivity of the amino group of the aminomethyl functionality with respect to the essentially quantitative formation of amide bonds to a carboxylic acid group at one end of the spacer-forming reagent. A vast number of relevant spacer- or handle-forming bifunctional reagents have been described (see, Barany, et al., *Int. J. Peptide Protein Res.*, 1987, 30, 705), especially reagents which are reactive towards amino groups such as found in the aminomethyl function. Representative bifunctional reagents include 4-(haloalkyl)aryl-lower alkanoic acids such as 4-(bromomethyl)phenylacetic acid, Boc-aminoacyl-4-(oxymethyl)aryl-lower alkanoic acids such as Boc-aminoacyl-4-(oxymethyl)phenylacetic acid, N-Boc-p-acylbenzhydrylamines such as N-Boc-p-glutaroylbenzhydrylamine, N-Boc-4'-lower alkyl-p-acylbenzhydrylamines such as N-Boc-4'-methyl-p-glutaroylbenzhydrylamine, N-Boc-4'-lower alkoxy-p-acylbenzhydrylamines such as N-Boc-4'-methoxy-p-glutaroyl-benzhydrylamine, and 4-hydroxymethylphenoxyacetic acid. One type of spacer group particularly relevant within the context of the present invention is the phenylacetamidomethyl (Pam) handle (Mitchell and Merrifield, *J. Org. Chem.*, 1976, 41, 2015) which, deriving from the electron withdrawing effect of the 4-phenylacetamidomethyl group, is about 100 times more stable than the classical benzyl ester linkage towards the Boc-amino deprotection reagent trifluoroacetic acid (TFA).

Certain functionalities (e.g., benzhydrylamino, 4-methylbenzhydrylamino and 4-methoxybenzhydrylamino) which may be incorporated for the purpose of cleavage of a synthesized PNA chain from the solid support such that the C-terminal of the PNA chain is in amide form, require no introduction of a spacer group. Any such functionality may advantageously be employed in the context of the present invention.

An alternative strategy concerning the introduction of spacer or handle groups is the so-called "preformed handle" strategy (see, Tam, et al., *Synthesis*, 1979, 955–957), which offers complete control over coupling of the first amino acid, and excludes the possibility of complications arising from the presence of undesired functional groups not related to the peptide or PNA synthesis. In this strategy, spacer or handle groups, of the same type as described above, are reacted with the first amino acid desired to be bound to the solid support, the amino acid being N-protected and optionally protected at the other side-chains which are not relevant with respect to the growth of the desired PNA chain. Thus, in those cases in which a spacer or handle group is desirable, the first amino acid to be coupled to the solid support can either be coupled to the free reactive end of a spacer group which has been bound to the initially introduced functionality (for example, an aminomethyl group) or can be reacted with the spacer-forming reagent. The space-forming reagent is then reacted with the initially introduced functionality. Other useful anchoring schemes include the "multidetachable" resins (Tam, et al., *Tetrahedron Lett.*, 1979, 4935 and *J. Am. Chem. Soc.*, 1980, 102, 611; Tam, *J. Org. Chem.*, 1985, 50, 5291), which provide more than one mode of release and thereby allow more flexibility in synthetic design.

Suitable choices for N-protection are the tert-butyloxycarbonyl (Boc) group (Carpino, *J. Am. Chem. Soc.*, 1957, 79, 4427; McKay, et al., *J. Am. Chem. Soc.*, 1957, 79, 4686; Anderson, et al., *J. Am. Chem. Soc.*, 1957, 79, 6180) normally in combination with benzyl-based groups for the protection of side chains, and the 9-fluorenylmethyloxycarbonyl (Fmoc) group (Carpino, et al., *J. Am. Chem. Soc.*, 1970, 92, 5748 and *J. Org. Chem.*, 1972, 37, 3404), normally in combination with tert-butyl (tBu) for the protection of any side chains, although a number of other possibilities exist which are well known in conventional solid-phase peptide synthesis. Thus, a wide range of other useful amino protecting groups exist, some of which are Adoc (Hass, et al., *J. Am. Chem. Soc.*, 1966, 88, 1988), Bpoc (Sieber, *Helv. Chem. Acta.*, 1968, 51, 614), Mcb (Brady, et al., *J. Org. Chem.*, 1977, 42, 143), Bic (Kemp, et al., *Tetrahedron*, 1975, 4624), the o-nitrophenylsulfenyl (Nps) (Zervas, et al., *J. Am. Chem. Soc.*, 1963, 85, 3660), and the dithiasuccinoyl (Dts) (Barany, et al., *J. Am. Chem. Soc.*, 1977, 99, 7363). These amino protecting groups, particularly those based on the widely-used urethane functionality, successfully prohibit racemization (mediated by tautomerization of the readily formed oxazolinone (azlactone) intermediates (Goodman, et al., *J. Am. Chem. Soc.,* 1964, 86, 2918)) during the coupling of most α-amino acids. In addition to such amino protecting groups, a whole range of otherwise "worthless" nonurethane-type of amino protecting groups are applicable when assembling PNA molecules, especially those built from achiral units. Thus, not only the above-mentioned amino protecting groups (or those derived from any of these groups) are useful within the context of the present invention, but virtually any amino protecting group which largely fulfills the following requirements: (1) stability to mild acids (not significantly attacked by carboxyl groups); (2) stability to mild bases or nucleophiles (not significantly attacked by the amino group in question); (3) resistance to acylation (not significantly attacked by activated amino acids). Additionally: (4) the protecting group must be close to quantitatively removable, without serious side reactions, and (5) the optical integrity, if any, of the incoming amino acid should preferably be highly preserved upon coupling. Finally, the choice of side-chain protecting groups, in general, depends on the choice of the amino protecting group, since the protection of side-chain functionalities must withstand the conditions of the repeated amino deprotection cycles. This is true whether the overall strategy for chemically assembling PNA molecules relies on, for example, differential acid stability of amino and side-chain protecting groups (such as is the case for the above-mentioned "Boc-benzyl" approach) or employs an orthogonal, that is, chemoselective, protection scheme (such as is the case for the above-mentioned "Fmoc-tBu" approach).

Following coupling of the first amino acid, the next stage of solid-phase synthesis is the systematic elaboration of the desired PNA chain. This elaboration involves repeated deprotection/coupling cycles. The temporary protecting group, such as a Boc or Fmoc group, on the last-coupled amino acid is quantitatively removed by a suitable treatment, for example, by acidolysis, such as with trifluoroacetic acid, in the case of Boc, or by base treatment, such as with piperidine, in the case of Fmoc, so as to liberate the N-terminal amine function.

The next desired N-protected amino acid is then coupled to the N-terminal of the last-coupled amino acid. This coupling of the C-terminal of an amino acid with the N-terminal of the last-coupled amino acid can be achieved in several ways. For example, it can be bound by providing the incoming amino acid in a form with the carboxyl group activated by any of several methods, including the initial formation of an active ester derivative such as a 2,4,5-trichlorophenyl ester (Pless, et al., *Helv. Chim. Acta,* 1963, 46, 1609), a phthalimido ester (Nefkens, et al., *J. Am. Chem. Soc.,* 1961, 83, 1263), a pentachlorophenyl ester (Kupryszewski, *Rocz. Chem.,* 1961, 35, 595), a pentafluorophenyl ester (Kovacs, et al., *J. Am. Chem. Soc.,* 1963, 85, 183), an o-nitrophenyl ester (Bodanzsky, *Nature,* 1955, 175, 685), an imidazole ester (Li, et al., *J. Am. Chem. Soc.,* 1970, 92, 7608), and a 3-hydroxy-4-oxo-3,4-dihydroquinazoline (Dhbt-OH) ester (Konig, et al., *Chem. Ber.,* 1973, 103, 2024 and 2034), or the initial formation of an anhydride such as a symmetrical anhydride (Wieland, et al., *Angew. Chem., Int. Ed. Engl.,* 1971, 10, 336). Alternatively, the carboxyl group of the incoming amino acid can be reacted directly with the N-terminal of the last-coupled amino acid with the assistance of a condensation reagent such as, for example, dicyclohexylcarbodiimide (Sheehan, et al., *J. Am. Chem. Soc.,* 1955, 77, 1067) or derivatives thereof. Benzotriazolyl N-oxytrisdimethylaminophosphonium hexafluorophosphate (BOP), "Castro's reagent" (see, e.g., Rivaille, et al., *Tetrahedron,* 1980, 36, 3413) is recommended when assembling PNA molecules containing secondary amino groups. Finally, activated PNA monomers analogous to the recently-reported amino acid fluorides (Carpino, *J. Am. Chem. Soc.,* 1990, 112, 9651) hold considerable promise to be used in PNA synthesis as well.

Following assembly of the desired PNA chain, including protecting groups, the next step will normally be deprotection of the amino acid moieties of the PNA chain and cleavage of the synthesized PNA from the solid support. These processes can take place substantially simultaneously, thereby providing the free PNA molecule in the desired form. Alternatively, in cases in which condensation of two separately synthesized PNA chains is to be carried out, it is possible by choosing a suitable spacer group at the start of the synthesis to cleave the desired PNA chains from their respective solid supports (both peptide chains still incorporating their side-chain protecting groups) and finally removing the side-chain protecting groups after, for example, coupling the two side-chain protected peptide chains to form a longer PNA chain.

In the above-mentioned "Boc-benzyl" protection scheme, the final deprotection of side-chains and release of the PNA molecule from the solid support is most often carried out by the use of strong acids such as anhydrous HF (Sakakibara, et al., *Bull. Chem. Soc. Jpn.,* 1965, 38, 4921), boron tris (trifluoroacetate) (Pless, et al., *Helv. Chim. Acta,* 1973, 46, 1609.), and sulfonic acids such as trifluoromethanesulfonic acid and methanesulfonic acid (Yajima, et al., *J. Chem. Soc., Chem. Comm.,* 1974, 107). This conventional strong acid (e.g., anhydrous HF) deprotection method, produces very reactive carbocations that may lead to alkylation and acylation of sensitive residues in the PNA chain. Such side-reactions are only partly avoided by the presence of scavengers such as anisole, phenol, dimethyl sulfide, and mercaptoethanol and, therefore, the sulfide-assisted acidolytic $S_N2$ deprotection method (Tam, et al., *J. Am. Chem. Soc.,* 1983, 105, 6442 and *J. Am. Chem. Soc.,* 1986, 108, 5242), the so-called "low", which removes the precursors of harmful carbocations to form inert sulfonium salts, is frequently employed in peptide and PNA synthesis, either solely or in combination with "high" methods. Less frequently, in special cases, other methods used for deprotection and/or final cleavage of the PNA-solid support bond are, for example, such methods as base-catalyzed alcoholysis (Barton, et al., *J. Am. Chem. Soc.,* 1973, 95, 4501), and ammonolysis as well as hydrazinolysis (Bodanszky, et al., *Chem. Ind.,* 1964 1423), hydrogenolysis (Jones, *Tetrahedron Lett.* 1977 2853 and Schlatter, et al., *Tetrahedron Lett.* 1977 2861)), and photolysis (Rich and Gurwara, *J. Am. Chem. Soc.,* 1975 97, 1575)).

Finally, in contrast with the chemical synthesis of "normal" peptides, stepwise chain building of achiral PNAs such as those based on aminoethylglycyl backbone units can start either from the N-terminus or the C-terminus, because the coupling reactions are free of racemization. Those skilled in the art will recognize that whereas syntheses commencing at the C-terminus typically employ protected amine groups and free or activated acid groups, syntheses commencing at the N-terminus typically employ protected acid groups and free or activated amine groups.

Based on the recognition that most operations are identical in the synthetic cycles of solid-phase peptide synthesis (as is also the case for solid-phase PNA synthesis), a new matrix, PEPS, was recently introduced (Berg, et al., *J. Am. Chem. Soc.,* 1989, 111, 8024 and International Patent Application WO 90/02749) to facilitate the preparation of large numbers of peptides. This matrix is comprised of a polyethylene (PE) film with pendant long-chain polystyrene (PS) grafts (molecular weight on the order of $10^6$). The loading capacity of the film is as high as that of a beaded matrix, but PEPS has the additional flexibility to suit multiple syntheses simultaneously. Thus, in a new configuration for solid-phase peptide synthesis, the PEPS film is fashioned in the form of discrete, labeled sheets, each serving as an individual compartment. During all the identical steps of the synthetic cycles, the sheets are kept together in a single reaction vessel to permit concurrent preparation of a multitude of peptides at a rate close to that of a single peptide by conventional methods. It was reasoned that the PEPS film support, comprising linker or spacer groups adapted to the particular chemistry in question, should be particularly valuable in the synthesis of multiple PNA molecules, these being conceptually simple to synthesize since only four different reaction compartments are normally required, one for each of the four "pseudo-nucleotide" units. Thus, the PEPS film support has been successfully tested in a number of PNA syntheses carried out in a parallel and substantially simultaneous fashion. The yield and quality of the products obtained from PEPS were comparable to those obtained by using the traditional polystyrene beaded support. Also, experiments with other geometries of the PEPS polymer such as, for example, non-woven felt, knitted net, sticks or microwellplates have not indicated any limitations of the synthetic efficacy.

Two other methods proposed for the simultaneous synthesis of large numbers of peptides also apply to the preparation of multiple, different PNA molecules. The first of these methods (Geysen, et al., *Proc. Natl. Acad. Sci. USA*, 1984, 81, 3998) utilizes acrylic acid-grafted polyethylenerods and 96-microtiter wells to immobilize the growing peptide chains and to perform the compartmentalized synthesis. While highly effective, the method is only applicable on a microgram scale. The second method (Houghten, *Proc. Natl. Acad. Sci. USA,* 1985, 82, 5131) utilizes a "tea bag" containing traditionally-used polymer beads. Other relevant proposals for multiple peptide or PNA synthesis in the context of the present invention include the simultaneous use of two different supports with different densities (Tregear, in "*Chemistry and Biology of Peptides*", J. Meienhofer, ed., Ann Arbor Sci. Publ., Ann Arbor, 1972 pp. 175–178), combining of reaction vessels via a manifold (Gorman, *Anal. Biochem.,* 1984, 136, 397), multicolumn solid-phase synthesis (e.g. Krchnak, et al., *Int. J. Peptide Protein Res.,* 1989, 33, 209), and Holm and Meldal, in "*Proceedings of the* 20*th European Peptide Symposium*", G. Jung and E. Bayer, eds., Walter de Gruyter & Co., Berlin, 1989 pp. 208–210), and the use of cellulose paper (Eichler, et al., Collect. *Czech. Chem. Commun.,* 1989, 54, 1746).

While the conventional cross-linked styrene/divinylbenzene copolymer matrix and the PEPS support are presently preferred in the context of solid-phase PNA synthesis, a non-limiting list of examples of solid supports which may be of relevance are: (1) Particles based upon copolymers of dimethylacrylamide cross-linked with N,N'-bisacryloylethylenediamine, including a known amount of N-tertbutoxycarbonyl-beta-alanyl-N'-acryloylhexamethylenediamine. Several spacer molecules are typically added via the beta alanyl group, followed thereafter by the amino acid residue subunits. Also, the beta alanyl-containing monomer can be replaced with an acryloyl sarcosine monomer during polymerization to form resin beads. The polymerization is followed by reaction of the beads with ethylenediamine to form resin particles that contain primary amines as the covalently linked functionality. The polyacrylamide-based supports are relatively more hydrophilic than are the polystyrene-based supports and are usually used with polar aprotic solvents including dimethylformamide, dimethylacetamide, N-methylpyrrolidone and the like (see Atherton, et al., *J. Am. Chem. Soc.,* 1975, 97, 6584, *Bioorg. Chem.* 1979, 8, 351), and J. C. S. Perkin I 538 (1981)); (2) a second group of solid supports is based on silica-containing particles such as porous glass beads and silica gel. One example is the reaction product of trichloro-[3-(4-chloromethyl)phenyl] propylsilane and porous glass beads (see Parr and Grohmann, *Angew. Chem. Internal. Ed.* 1972, 11, 314) sold under the trademark "PORASIL E" by Waters Associates, Framingham, Mass., USA. Similarly, a mono ester of 1,4-dihydroxymethylbenzene and silica (sold under the trademark "BIOPAK" by Waters Associates) has been reported to be useful (see Bayer and Jung, *Tetrahedron Lett.,* 1970, 4503); (3) a third general type of useful solid supports can be termed composites in that they contain two major ingredients: a resin and another material that is also substantially inert to the organic synthesis reaction conditions employed. One exemplary composite (see Scott, et al., *J. Chrom. Sci.,* 1971, 9, 577) utilized glass particles coated with a hydrophobic, cross-linked styrene polymer containing reactive chloromethyl groups, and was supplied by Northgate Laboratories, Inc., of Hamden, Conn., USA. Another exemplary composite contains a core of fluorinated ethylene polymer onto which has been grafted polystyrene (see Kent and Merrifield, *Israel J. Chem.* 1978, 17, 243) and van Rietschoten in "*Peptides* 19741", Y. Wolman, Ed., Wiley and Sons, New York, 1975, pp. 113–116); and (4) contiguous solid supports other than PEPS, such as cotton sheets (Lebl and Eichler, *Peptide Res.* 1989, 2, 232) and hydroxypropylacrylate-coated polypropylene membranes (Daniels, et al., *Tetrahedron Lett.* 1989, 4345), are suited for PNA synthesis as well.

Whether manually or automatically operated, solid-phase PNA synthesis in the context of the present invention is normally performed batchwise. However, most of the syntheses may equally well be carried out in the continuous-flow mode, where the support is packed into columns (Bayer, et al., *Tetrahedron Lett.,* 1970, 4503 and Scott, et al., *J. Chromatogr. Sci.,* 1971, 9, 577). With respect to continuous-flow solid-phase synthesis, the rigid poly (dimethylacrylamide)-Kieselguhr support (Atherton, et al., *J. Chem. Soc. Chem. Commun.,* 1981, 1151) appears to be particularly successful, but another valuable configuration concerns the one worked out for the standard copoly (styrene-1%-divinylbenzene) support (Krchnak, et al., *Tetrahedron Lett.,* 1987, 4469).

While the solid-phase technique is presently preferred in the context of PNA synthesis, other methodologies or combinations thereof, for example, in combination with the solid-phase technique, apply as well: (1) the classical solution-phase methods for peptide synthesis (e.g., Bodanszky, "*Principles of Peptide Synthesis*", Springer-Verlag, Berlin-New York 1984), either by stepwise assembly or by segment/fragment condensation, are of particular relevance when considering especially large scale productions (gram, kilogram, and even tons) of PNA compounds; (2) the so-called "liquid-phase" strategy, which utilizes soluble polymeric supports such as linear polystyrene (Shemyakin, et al., *Tetrahedron Lett.,* 1965, 2323) and polyethylene glycol (PEG) (Mutter and Bayer, *Angew. Chem., Int. Ed. Engl.,* 1974, 13, 88), is useful; (3) random polymerization (see, e.g., Odian, "*Principles of Polymerization*", McGraw-Hill, New York (1970)) yielding mixtures of many molecular weights ("polydisperse") peptide or PNA molecules are particularly relevant for purposes such as screening for antiviral effects; (4) a technique based on the use of polymer-supported amino acid active esters (Fridkin, et al., *J. Am. Chem. Soc.*, 1965, 87, 4646), sometimes referred to as "inverse Merrifield synthesis" or "polymeric reagent synthesis", offers the advantage of isolation and purification of intermediate products, and may thus provide a particularly suitable method for the synthesis of medium-sized, optionally protected, PNA molecules, that can subsequently be used for fragment condensation into larger PNA molecules; (5) it is envisaged that PNA molecules may be assembled enzymatically by enzymes such as proteases or derivatives thereof with novel specificities (obtained, for example, by artificial means such as protein engineering). Also, one can envision the development of "PNA ligases" for the condensation of a number of PNA fragments into very large PNA molecules; (6) since antibodies can be generated to virtually any molecule of interest, the recently developed catalytic antibodies (abzymes), discovered simultaneously by the groups of Lerner (Tramantano, et al., *Science*, 1986, 234, 1566) and of Schultz (Pollack, et al., *Science*, 1986, 234, 1570), should also be considered as potential candidates for assembling PNA molecules. Thus, there has been considerable success in producing abzymes catalyzing acyl-transfer reactions (see for example Shokat, et al., *Nature*, 1989, 338, 269) and references therein). Finally, completely artificial enzymes, very recently pioneered by Stewart's group (Hahn, et al., *Science*, 1990, 248, 1544); may be developed to suit PNA synthesis. The design of generally applicable enzymes, ligases, and catalytic antibodies, capable of mediating specific coupling reactions, should be more readily achieved for PNA synthesis than for "normal" peptide synthesis since PNA molecules will often be comprised of only four different amino acids (one for each of the four native nucleobases) as compared to the twenty natural by occurring (proteinogenic) amino acids constituting peptides. In conclusion, no single strategy may be wholly suitable for the synthesis of a specific PNA molecule, and therefore, sometimes a combination of methods may work best.

The present invention also is directed to therapeutic or prophylactic uses for peptide nucleic acids. Likely therapeutic and prophylactic targets include herpes simplex virus (HSV), human papillomavirus (HPV), human immunodeficiency virus (HIV), candidia albicans, influenza virus, cytomegalovirus (CMV), intracellular adhesion molecules (ICAM), 5-lipoxygenase (5-LO), phospholipase $A_2$ ($PLA_2$), protein kinase C (PKC), and RAS oncogene. Potential applications of such targeting include treatments for ocular, labial, genital, and systemic herpes simplex I and II infections; genital warts; cervical cancer; common warts; Kaposi's sarcoma; AIDS; skin and systemic fungal infections; flu; pneumonia; retinitis and pneumonitis in immunosuppressed patients; mononucleosis; ocular, skin and systemic inflammation; cardiovascular disease; cancer; asthma; psoriasis; cardiovascular collapse; cardiac infarction; gastrointestinal disease; kidney disease; rheumatoid arthritis; osteoarthritis; acute pancreatitis; septic shock; and Crohn's disease.

For therapeutic or prophylactic treatment, the peptide nucleic acids of the invention can be formulated in a pharmaceutical composition, which may include carriers, thickeners, diluents, buffers, preservatives, surface active agents and the like. Pharmaceutical compositions may also include one or more active ingredients such as antimicrobial agents, antiinflammatory agents, anesthetics, and the like in addition to peptide nucleic acid.

The pharmaceutical composition may be administered in a number of ways depending on whether local or systemic treatment is desired, and on the area to be treated. Administration may be done topically (including ophthalmically, vaginally, rectally, intranasally), orally, by inhalation,or parenterally, for example by intravenous drip or subcutaneous, intraperitoneal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine optimum dosages, dosing methodologies and repetition rates.

Treatments of this type can be practiced one a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, since each cell of multicellular eukaryotes can be treated since they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic phosphorothioate oligonucleotides. As used herein, therapeutics is meant to include the eradication of a disease state, by killing an organism or by control of erratic or harmful cellular growth or expression.

The present invention also pertains to the advantageous use of PNA molecules in solid-phase biochemistry (see, e.g., "*Solid-Phase Biochemistry—Analytical and Synthetic Aspects*", W. H. Scouten, ed., John Wiley & Sons, New York, 1983), notably solid-phase biosystems, especially bioassays or solid-phase techniques which concerns diagnostic detection/quantitation or affinity purification of complementary nucleic acids (see, e.g., "*Affinity Chromatography—A Practical Approach*", P. D. G. Dean, W. S. Johnson and F. A. Middle, eds., IRL Press Ltd., Oxford 1986; "*Nucleic Acid Hybridization—A Practical Approach*", B. D. Harnes and S. J. Higgins, IRL Press Ltd., Oxford 1987). Present day methods for performing such bioassays or purification techniques almost exclusively utilize "normal" or slightly modified oligonucleotides either physically adsorbed or bound through a substantially permanent covalent anchoring linkage to beaded solid supports such as cellulose, glass beads, including those with controlled porosity (Mizutani, et al., *J. Chromatogr.,* 1986, 356, 202), "Sephadex", "Sepharose", agarose, polyacrylamide, porous particulate alumina, hydroxyalkyl methacrylate gels, diol-bonded silica, porous ceramics, or contiguous materials such as filter discs of nylon and nitrocellulose. One example employed the chemical synthesis of oligo-dT on cellulose beads for the affinity isolation of poly A tail containing mRNA (Gilham in "*Methods in Enzymology,*" L. Grossmann and K. Moldave, eds., vol. 21, part D, page 191, Academic Press, New York and London, 1971). All the above-mentioned methods are applicable within the context of the present invention. However, when possible, covalent linkage is preferred over the physical adsorption of the molecules in question, since the latter approach has the disadvantage that some of the immobilized molecules can be washed out (desorbed) during the hybridization or affinity process. There is, thus, little control of the extent to which a species adsorbed on the surface of the support material is lost during the various treatments to which the support is subjected in the course of the bioassay/purification procedure. The severity of this problem will, of course, depend to a large extent on the rate at which equilibrium between adsorbed and "free" species is established. In certain cases it may be virtually impossible to perform a quantitative assay with acceptable accuracy and/or reproducibility. Loss of adsorbed species during treatment of the support with body fluids, aqueous reagents or washing media will, in general, be expected to be most pronounced for species of relatively low molecular weight. In contrast with oligonucleotides, PNA molecules are easier to attach onto solid supports because they contain strong nucleophilic and/or electrophilic centers. In addition, the direct assembly of oligonucleotides onto solid supports suffers from an extremely low loading of the immobilized molecule, mainly due to the low surface capacity of the materials that allow the successful use of the state-of-the-art phosphoramidite chemistry for the construction of oligonucleotides. (Beaucage and Caruthers, *Tetrahedron Lett.,* 1981, 22, 1859; Caruthers, *Science,* 1985, 232, 281). It also suffers from the fact that by using the alternative phosphite triester method (Letsinger and Mahadevan, *J. Am. Chem. Soc.* 1976, 98, 3655), which is suited for solid supports with a high surface/loading capacity, only relatively short oligonucleotides can be obtained. As for conventional solid-phase peptide synthesis, however, the latter supports are excellent materials for building up immobilized PNA molecules (the side-chain protecting groups are removed from the synthesized PNA chain without cleaving the anchoring linkage holding the chain to the solid support). Thus, PNA species benefit from the above-described solid-phase techniques with respect to the much higher (and still sequence-specific) binding affinity for complementary nucleic acids and from the additional unique sequence-specific recognition of (and strong binding to) nucleic acids present in double-stranded structures. They also can be loaded onto solid supports in large amounts, thus further increasing the sensitivity/capacity of the solid-phase technique. Further, certain types of studies concerning the use of PNA in solid-phase biochemistry can be approached, facilitated, or greatly accelerated by use of the recently-reported "light-directed, spatially addressable, parallel chemical synthesis" technology (Fodor, et al., *Science,* 1991, 251, 767), a technique that combines solid-phase chemistry and photolithography to produce thousands of highly diverse, but identifiable, permanently immobilized compounds (such as peptides) in a substantially simultaneous way.

Additional objects, advantages, and novel features of this invention will become apparent to those skilled in the art upon examination of the following examples thereof, which are not intended to be limiting.

Synthesis of Monomeric Building Blocks

Figure 13:
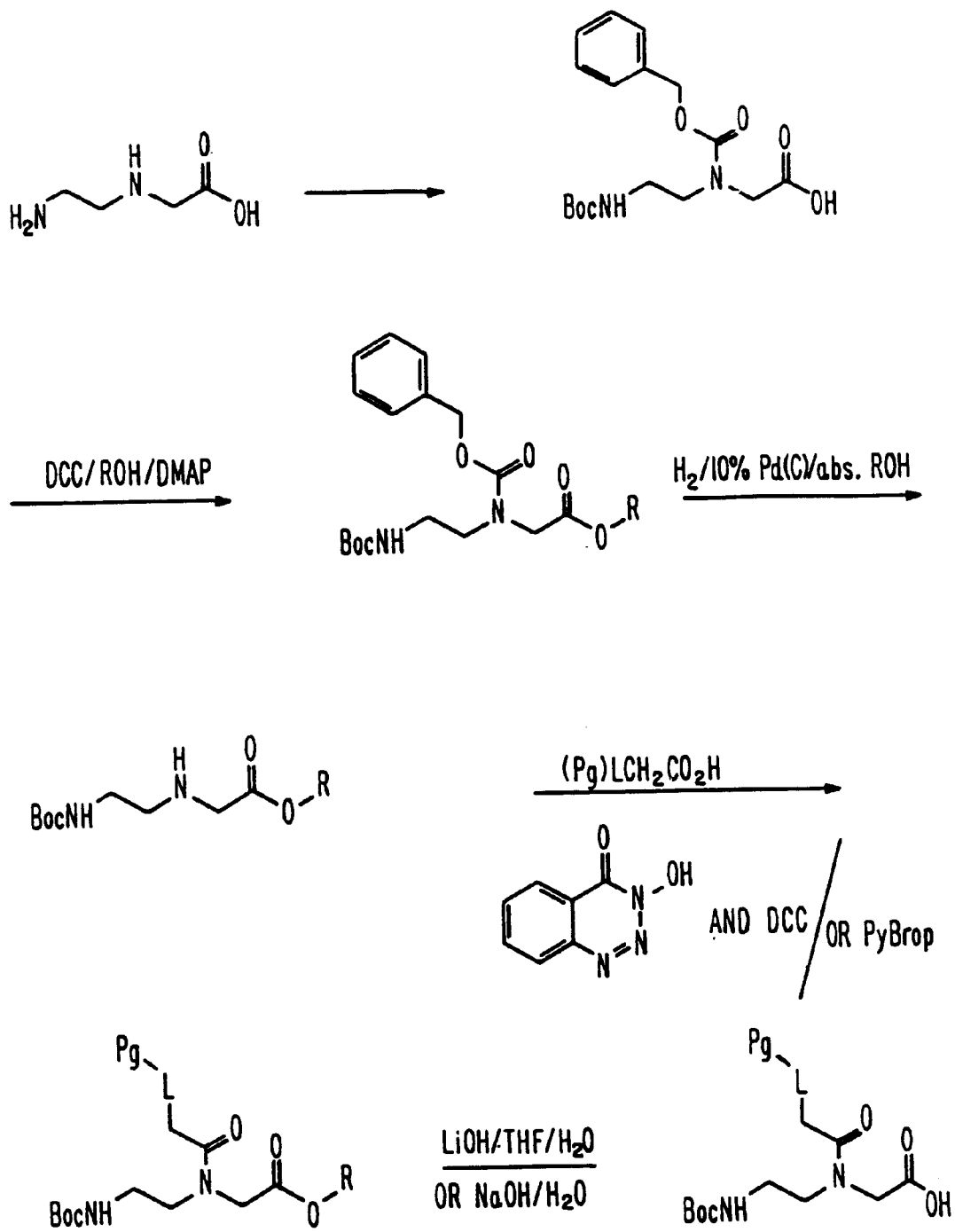
FIG. 13 provides a procedure for the synthesis of protected PNA synthons.

The monomers preferably are synthesized by the general scheme outlined in FIG. 13. This involves preparation of either the methyl or ethyl ester of (Bocaminoethyl)glycine, by a protection/deprotection procedure as described in Examples 24–26. The synthesis of thymine monomer is described in Examples 27–28, and that of the protected cytosine monomer is described in Example 29.

Figure 14:
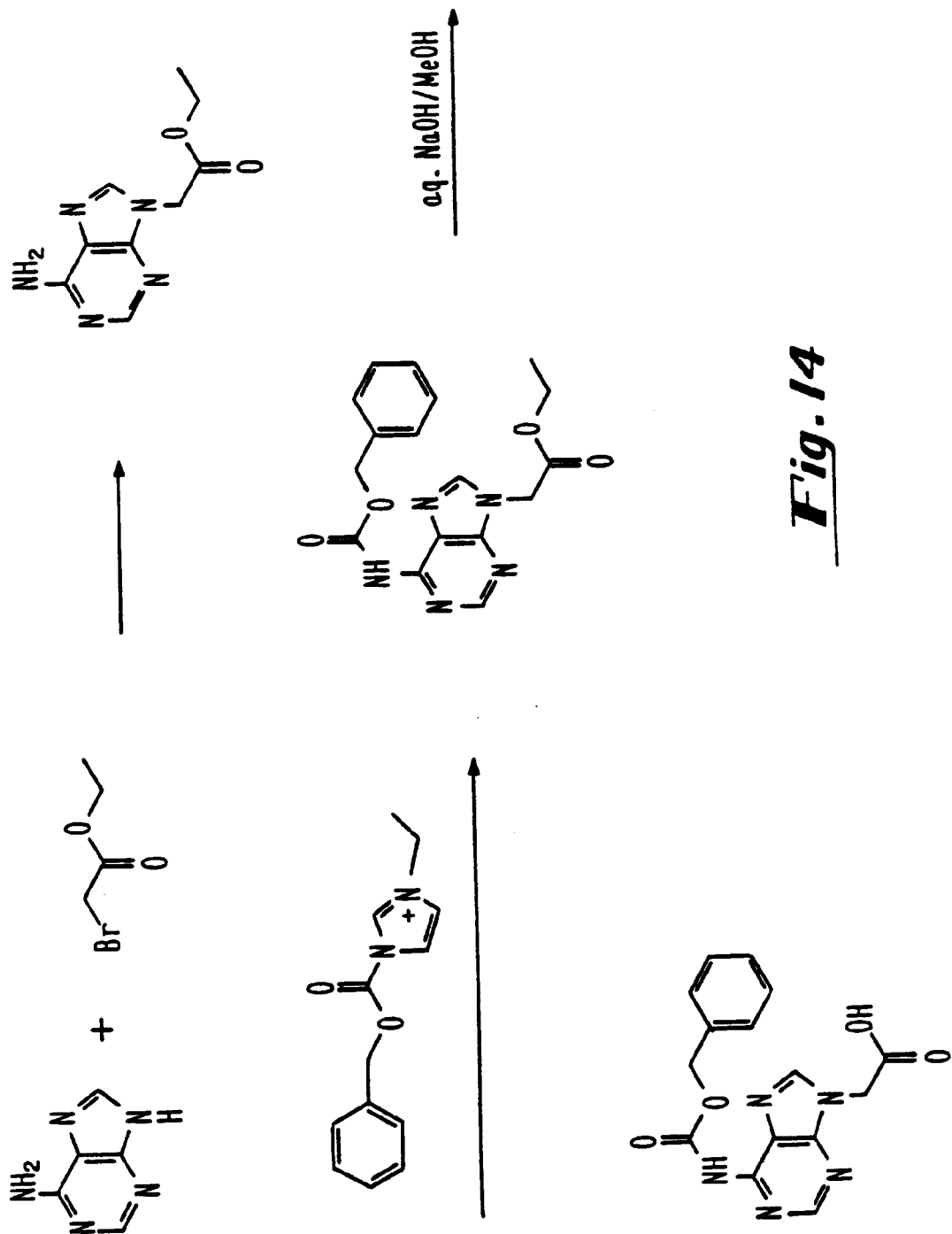
FIG. 14 provides a procedure for the synthesis of a protected adenine monomer synthon.

The synthesis of the protected adenine monomer (FIG. 14) involved alkylation with ethyl bromoacetate (Example 30) and verification of the position of substitution by X-ray crystallography, as being the wanted 9-position. The $N^6$-amino group then was protected with the benzyloxycarbonyl group by the use of the reagent N-ethyl-benzyloxycarbonylimidazole tetrafluoroborate (Example 31). Simple hydrolysis of the product ester (Example 32) gave $N^6$-benzyloxycarbonyl-9-carboxymethyl adenine, which then was used in the standard procedure (Examples 33–34, FIG. 13). The adenine monomer has been built into two different PNA-oligomers (Examples 56, 57, 71 and 73).

Figure 15:
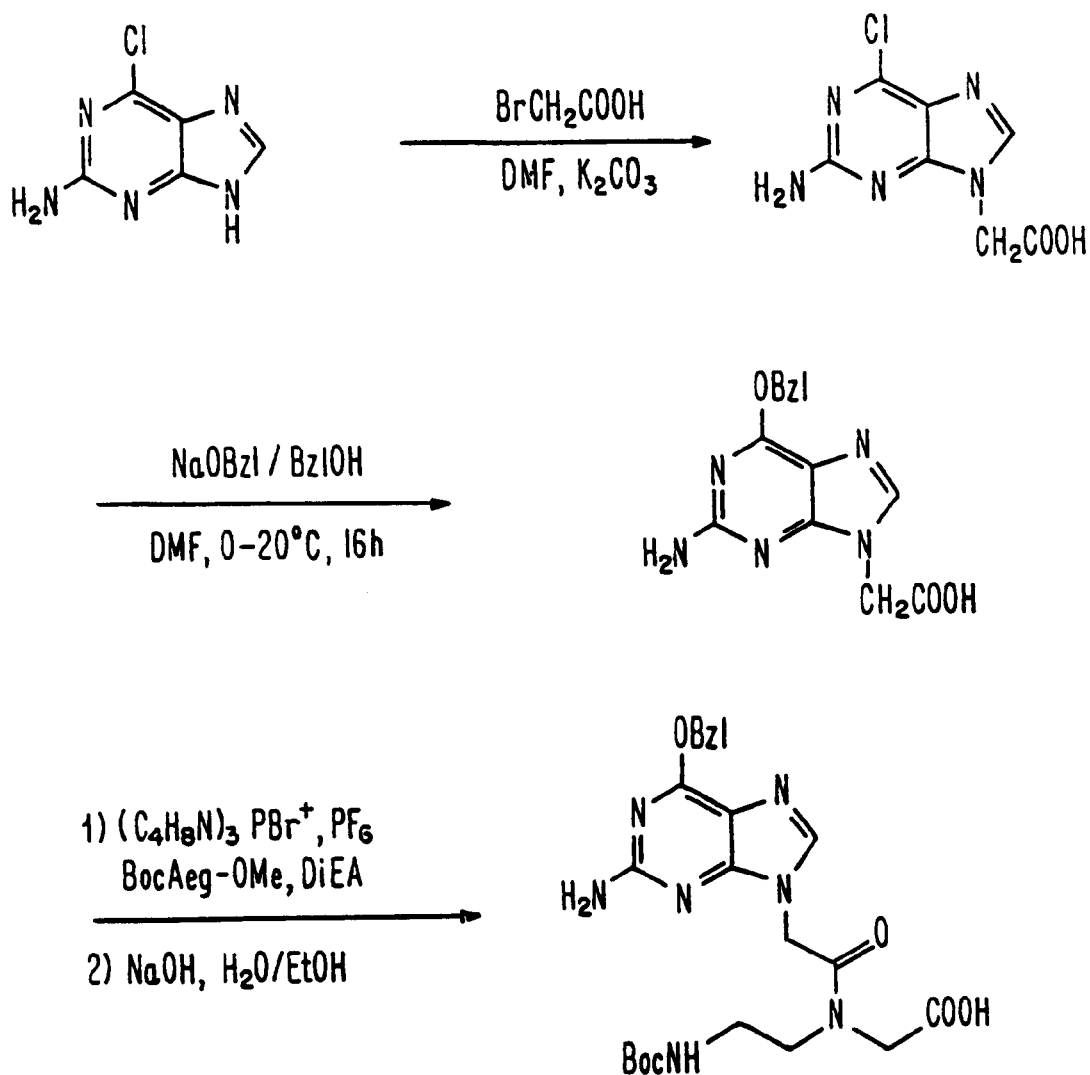
FIG. 15 provides a procedure for the synthesis of a protected guanine monomer synthon.

The synthesis of the protected G-monomer is outlined in FIG. 15. The starting material, 2-amino-6-chloropurine, was alkylated with bromoacetic acid (Example 35) and the chlorine atom was then substituted with a benzyloxy group (Example 36). The resulting acid was coupled to the (bocaminoethyl) glycine methyl ester (from Example 26) with agent PyBrop™, and the resulting ester was hydrolysed (Example 37). The $O^6$-benzyl group was removed in the final HF-cleavage step in the synthesis of the PNA-oligomer. Cleavage was verified by finding the expected mass of the final PNA-oligomer, upon incorporation into an PNA-oligomer using diisopropyl carbodiimide as the condensation agent (Examples 55 and 71).

Extended Backbones

Figure 16:
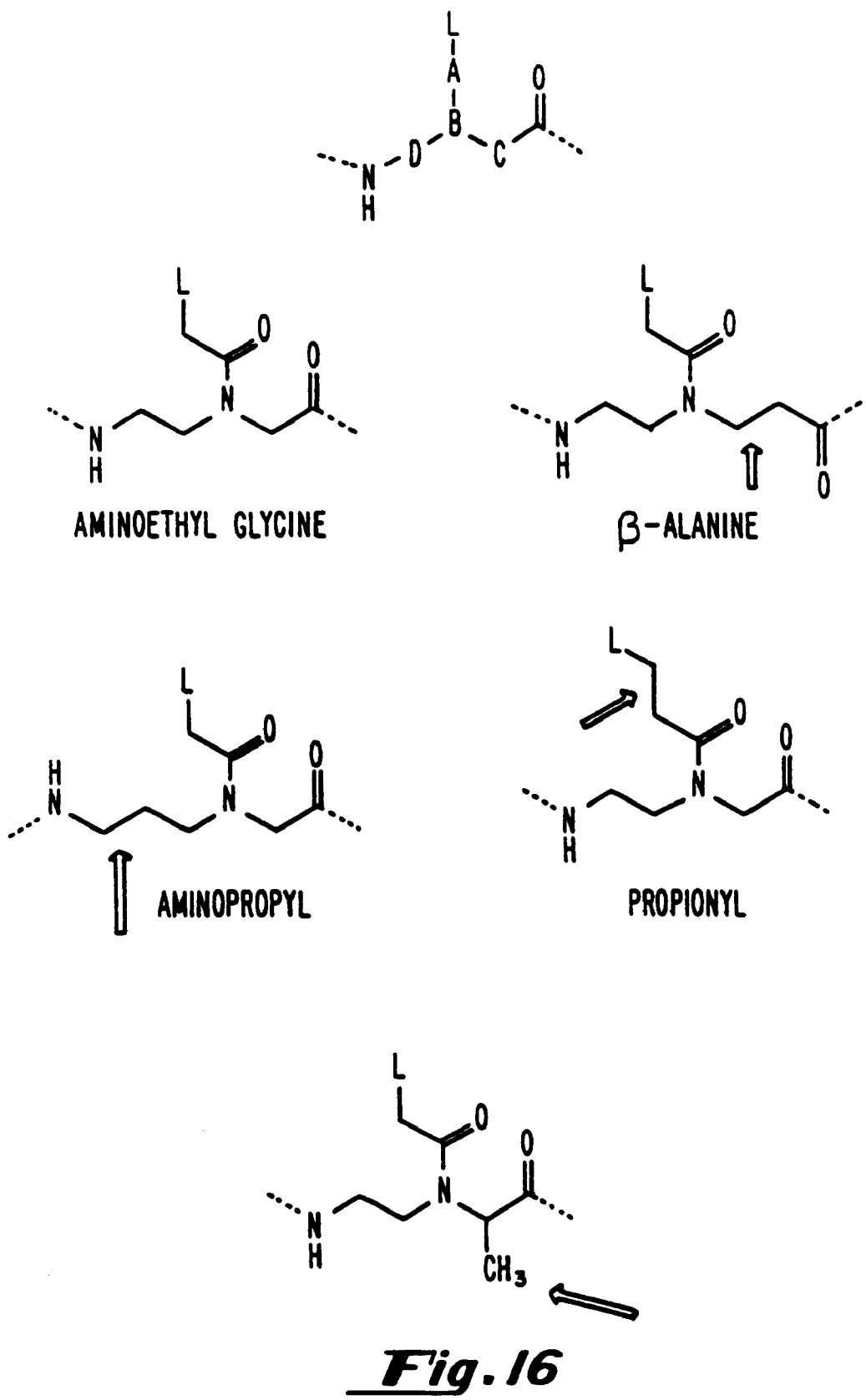
FIG. 16 provides examples of PNA backbone alterations.

Alterations of the groups A, C and D (FIG. 16) is demonstrated by the synthesis of monomeric building blocks and incorporation into PNA-oligomers.

Figure 17:
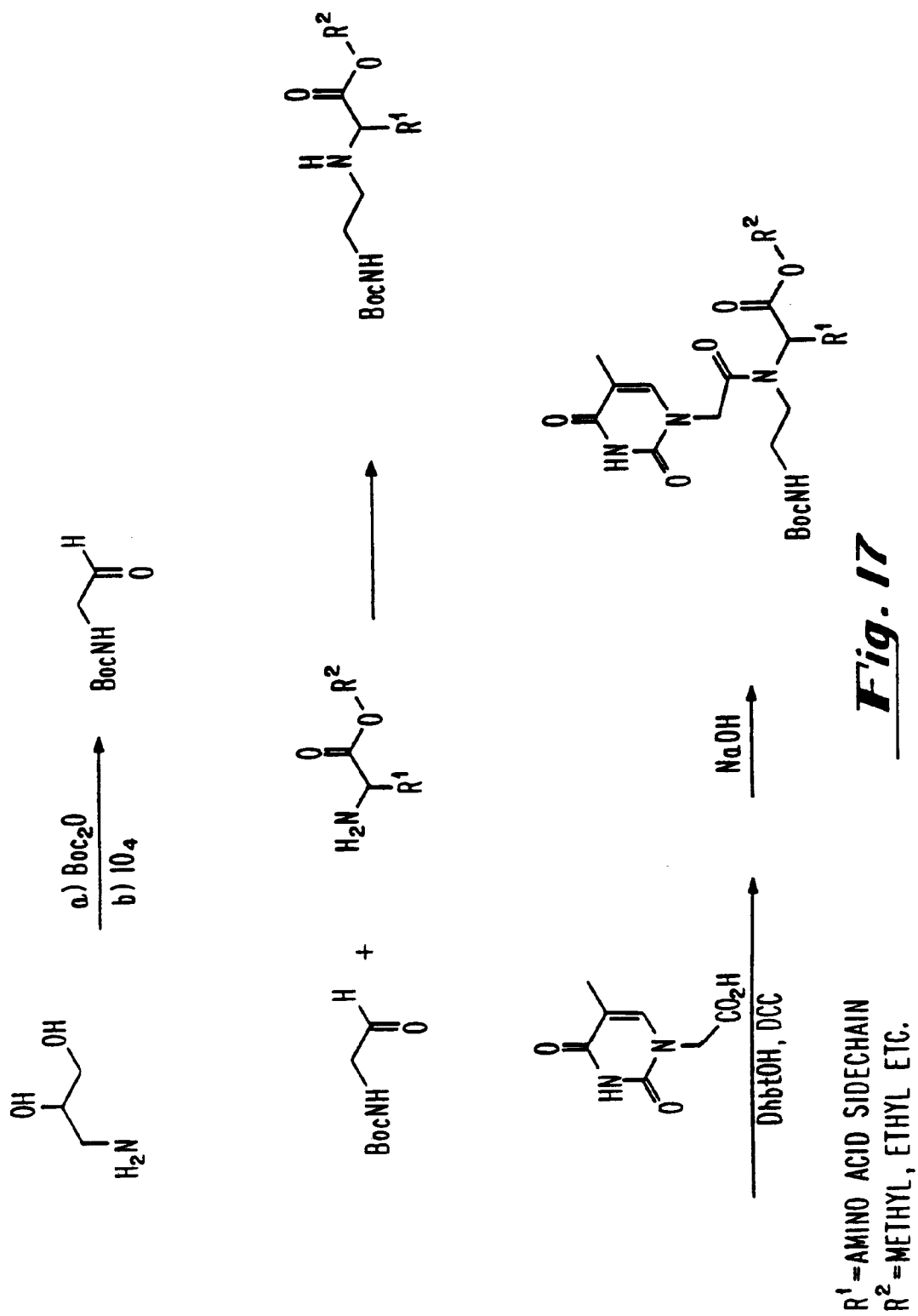
FIG. 17 provides a procedure for synthesis of thymine monomer synthons with side chains corresponding to the normal amino acids.

In one example, the C group was a $CH(CH_3)$ group. The synthesis of the corresponding monomer is outlined in FIG. 17. It involves preparation of Boc-protected 1-amino-2,3-propanediol (Example 38), which is cleaved by periodate to give bocaminoacetaldehyde, which is used directly in the next reaction. The bocaminoacetaldehyde can be condensed with a variety of amines; in Example 39, alanine ethyl ester was used. In Examples 40–42, the corresponding thymine monomers were prepared. The monomer has been incorporated into an 8-mer (Example 60) by the DCC-coupling protocol (Examples 56 and 57).

Figure 18A:
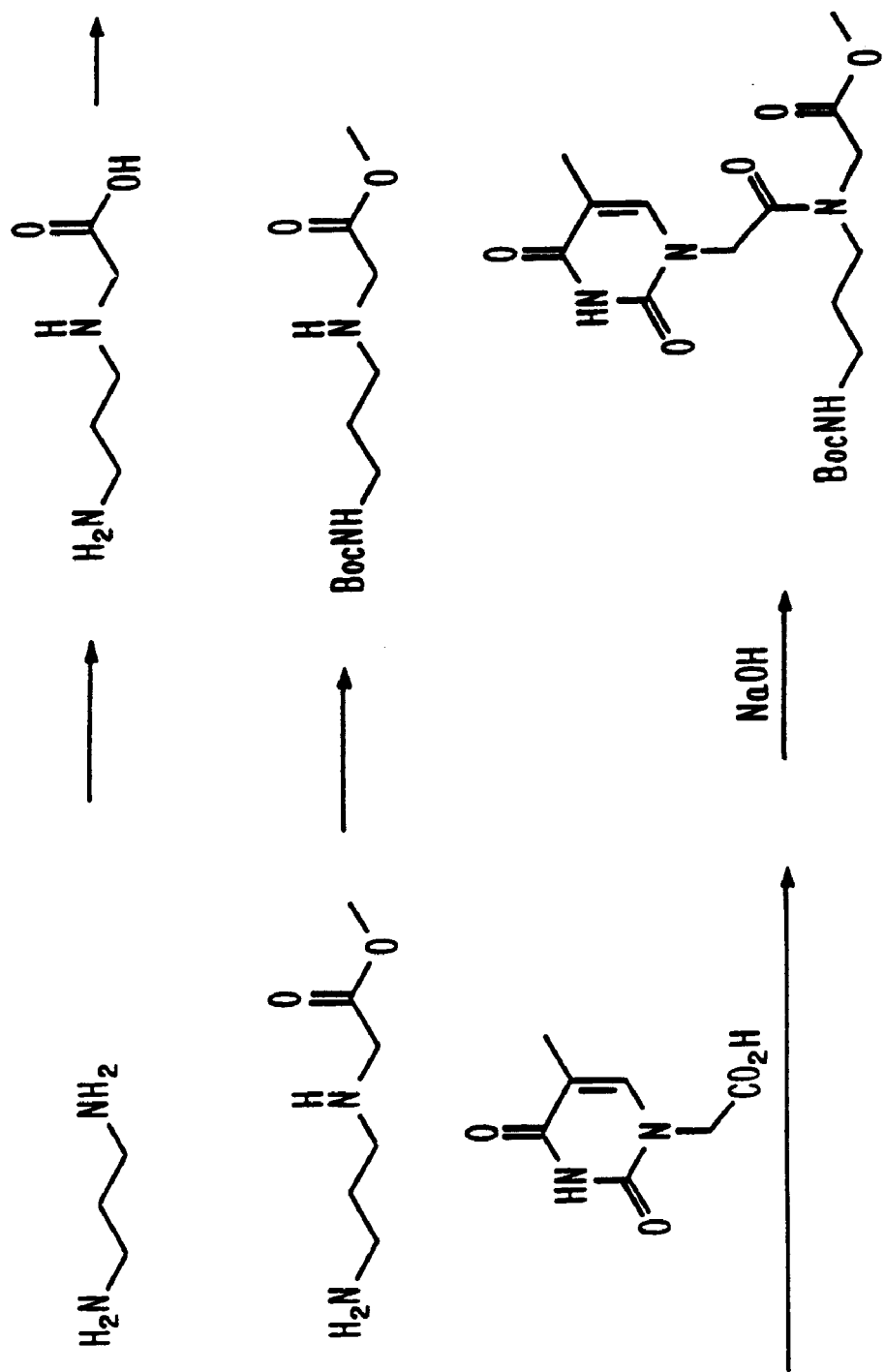
FIGS. 18(*a*) and 18(*b*) provide procedures for synthesis of an aminopropyl analogue and a propionyl analogue, respectively, of a thymine monomer synthon.
Figure 18B:
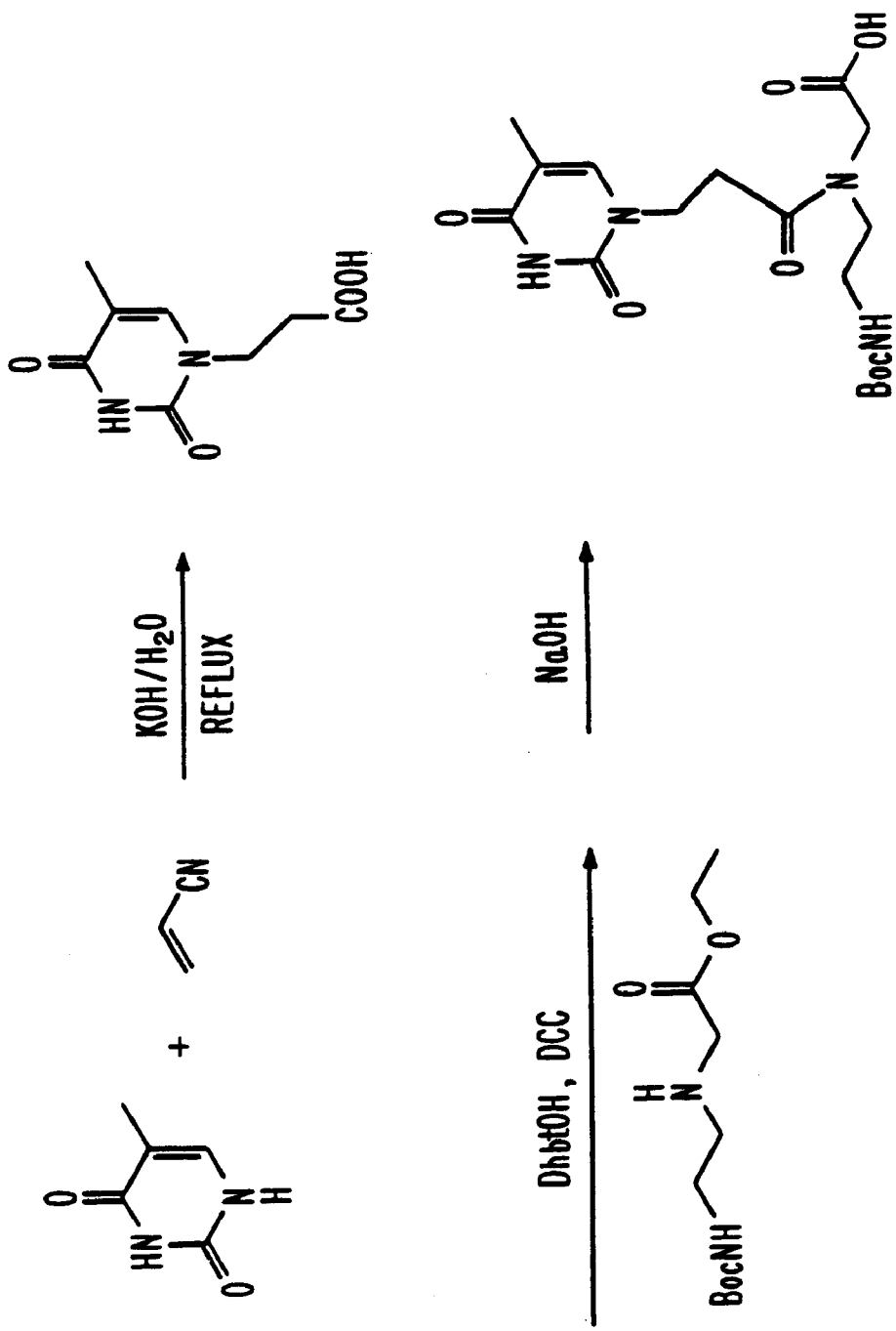

In another example, the D group is a $(CH_2)_3$ group. The synthesis of the corresponding monomer is outlined in FIG. 18.A and described in Examples 43–44.

In another example, the A group is a $(CH_2)_2CO$ group. The synthesis of the corresponding thymine monomer is outlined FIG. 18.B and Examples 46 through 48.

Figure 19:
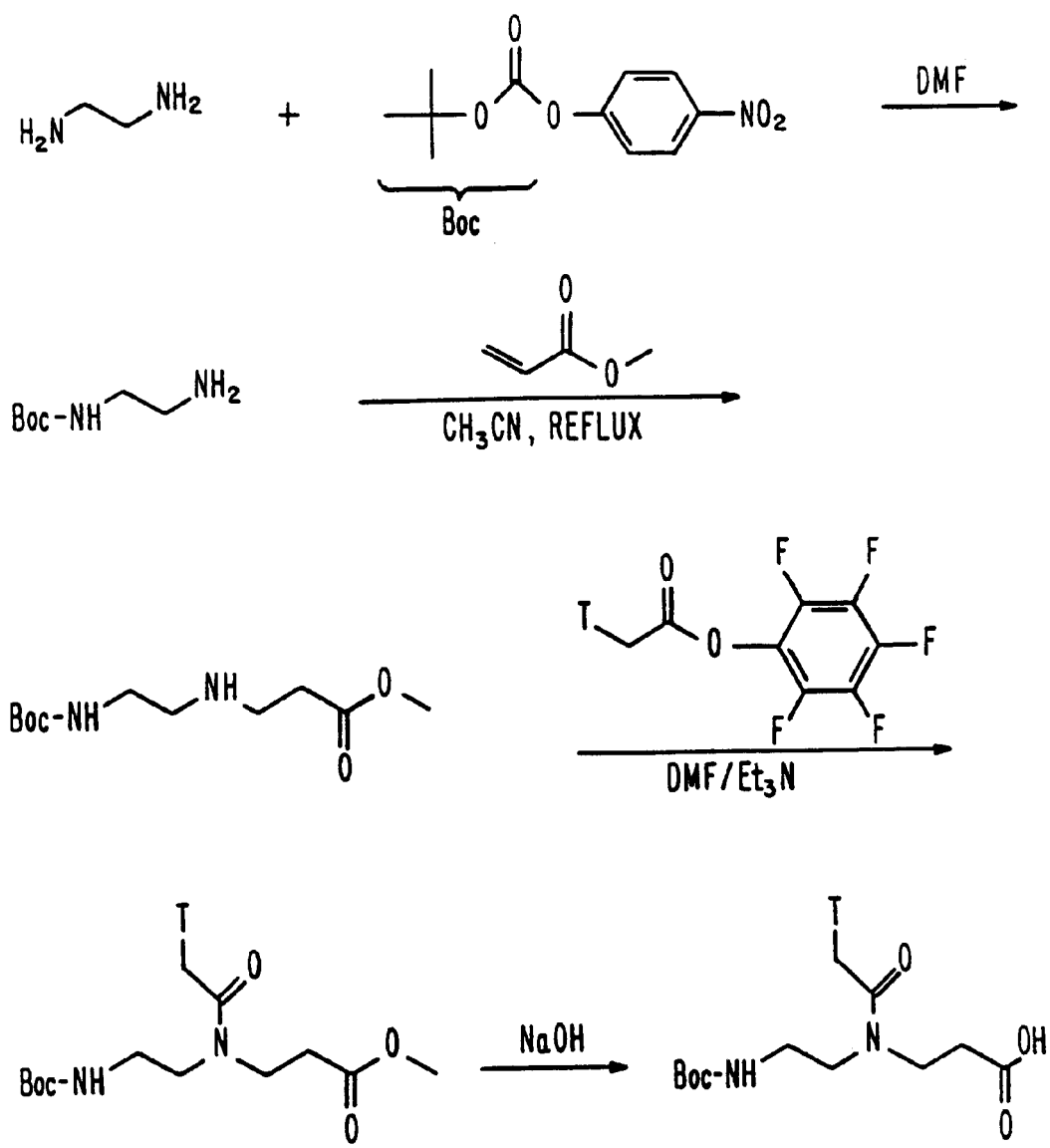
FIG. 19 provides a procedure for synthesis of an aminoethyl-β-alanine analogue of thymine monomer synthon.

In yet another example, the C group is a $(CH_2)_2$ group. The synthesis of the thymine and protected cytosine monomer is outlined in FIG. 19 and Examples 49 through 54. Hybridization experiments with a PNA-oligomer containing one unit is described in Examples 61 and 81, which shows a significant lowering of affinity but a retention of specificity.

General Remarks

The following abbreviations are used in the experimental examples: DMF, N,N-dimethylformamide; DCC, N,N-dicyclohexyl carbodiimide; DCU, N,N-dicyclohexyl urea; THF, tetrahydrofuran; aeg, N-acetyl (2'-aminoethyl)glycine; pfp, pentafluorophenyl; Boc, tert-butoxycarbonyl; Z, benzyloxycarbonyl; NMR, nuclear magnetic resonance; s, singlet; d, doublet; dd, doublet of doublets; t; triplet; q, quartet; m, multiplet; b, broad; δ, chemical shift;

NMR spectra were recorded on either a JEOL FX 90Q spectrometer, or a Bruker 250 MHz with tetramethylsilane as internal standard. Mass spectrometry was performed on a MassLab VG 12–250 quadropole instrument fitted with a VG FAB source and probe. Melting points were recorded on Buchi melting point apparatus and are uncorrected. N,N-Dimethylformamide was dried over 4 Å molecular sieves, distilled and stored over 4 Å molecular sieves. Pyridine (HPLC quality) was dried and stored over 4 Å molecular sieves. Other solvents used were either the highest quality obtainable or were distilled before use. Dioxane was passed through basic alumina prior to use. Bocanhydride, 4-nitrophenol, methyl bromoacetate,, benzyloxycarbonyl chloride, pentafluorophenol were all obtained through Aldrich Chemical Company. Thymine, cytosine, adenine were all obtained through Sigma.

Thin layer chromatography (Tlc) was performed using the following solvent systems: (1) chloroform:triethyl amine:methanol, 7:1:2; (2) methylene chloride:methanol, 9:1; (3) chloroform:methanol:acetic acid 85:10:5. Spots were visualized by UV (254 nm) or/and spraying with a ninhydrin solution (3 g ninhydrin in 1000 ml 1-butanol and 30 ml acetic acid), after heating at 120° C. for 5 min and, after spraying, heating again.

EXAMPLE 1 tert-Butyl 4-nitrophenyl Carbonate

Sodium carbonate (29.14 g; 0.275 mol) and 4-nitrophenol (12.75 g; 91.6 mmol) were mixed with dioxane (250 ml). Boc-anhydride (20.0 g; 91.6 mmol) was transferred to the mixture with dioxane (50 ml). The mixture was refluxed for 1 h, cooled to 0° C., filtered and concentrated to ⅓, and then poured into wat.82 ml;82.6 mmol) and a suspension of $N^4$-benzyloxycarbonyl-cytosine (9, 21.0 g;82.6 mmol) and potassium carbonate (11.4 g;82.6 mmol) in dry DMF (900 ml). The mixture was stirred vigorously overnight, filtered, and evaporated to dryness, in vacuo. Water (300 ml) and 4 N hydrochloric acid (10 ml) were added, the mixture was stirred for 15 minutes at 0° C., filtered, and washed with water (2×75 ml). The isolated precipitate was treated with water (120 ml), 2N sodium hydroxide (60 ml), stirred for 30 min, filtered, cooled to 0° C., and 4 N hydrochloric acid (35 ml) was added. The title compound was isolated by filtration, washed thoroughly with water, recrystallized from methanol (1000 ml) and washed thoroughly with ether. This afforded 7.70 g (31%) of pure compound. The mother liquor from the recrystallization was reduced to a volume of 200 ml and cooled to 0° C. This afforded an additional 2.30 g of a material that was pure by tlc but had a reddish color. M.p. 266–274° C. Anal., for $C_{14}H_{13}N_3O_5$. Found(calc.); C, 55.41 (55.45); H, 4.23(4.32); N, 14.04(13.86) $^1$H-NMR (90 MHz; DMSO-$d_6$): 8.02 ppm (d,J=7.32 Hz,1H,H-6); 7.39 (s,5H, Ph); 7.01 (d,J=7.32 Hz,1H,H-5); 5.19 (s,2H,PhC$\underline{H}_2$—); 4.52. (s,2H).

EXAMPLE 9

$N^4$-Benzyloxycarbonyl-$N^1$-carboxymethyl-cytosine Pentafluorophenyl Ester (11)

$N^4$-Benzyloxycarbonyl-$N^1$-carboxymethyl-cytosine (10, 4.00 g; 13.2 mmol) and pentafluorophenol (2.67 g; 14.5 mmol) were mixed with DMF (70 ml), cooled to 0° C. with ice-water, and DCC (3.27 g; 15.8 mmol) was added. The ice bath was removed after 3 min and the mixture was stirred for 3 h at room temperature. The precipitated DCU was removed by filtration, washed with DMF, and the filtrate was evaporated to dryness, in vacuo (0.2 mmHg). The solid residue was treated with methylene chloride (250 ml), stirred vigorously for 15 min, filtered, washed twice with diluted sodium hydrogen carbonate and once with saturated sodium chloride, dried over magnesium sulfate, and evaporated to dryness, in vacuo. The solid residue was recrystallized from 2-propanol (150 ml) and the crystals were washed thoroughly with ether. Yield 3.40 g (55%). M.p. 241–245° C. Anal. for $C_{20}H_{12}N_3F_5O_5$. Found(calc.); C, 51.56(51.18); H, 2.77(2.58); N, 9.24(8.95). $^1$H-NMR (90 MHz; CDCl$_3$): 7.66 ppm (d,J=7.63 Hz,1H,H-6); 7.37 (s,5H, Ph); 7.31 (d,J=7.63 Hz,1H,H-5); 5.21 (s,2H,PhC$\underline{H}_2$—); 4.97 (s,2H,NC$\underline{H}_2$—). FAB-MS: 470 (M+1)

EXAMPLE 10

$N^4$-Benzyloxycarbonyl-1-Boc-aeg-cytosine (12)

To a solution of (N-Boc-2-aminoethyl)glycine (2) in DMF, prepared as described above, was added triethyl amine (7.00 ml; 50.8 mmol) and $N^1$-benzyloxycarbonyl-N'-carboxymethyl-cytosine pentafluorophenyl ester (11, 2.70 g; 5.75 mmol) After stirring the solution for 1 h at room temperature, methylene chloride (150 ml), saturated sodium chloride (250 ml), and 4 N hydrochloric acid to pH~1 were added. The organic layer was separated and washed twice with saturated sodium chloride, dried over magnesium sulfate, and evaporated to dryness, in vacuo, first with a water aspirator and then with an oil pump. The oily residue was treated with water (25 ml) and was again evaporated to dryness, in vacuo. This procedure then was repeated. The oily residue (2.80 g) was then dissolved in methylene chloride (100 ml), petroleum ether (250 ml) was added, and the mixture was stirred overnight. The title compound was isolated by filtration and washed with petroleum ether. Tlc (system 1) indicated substantial quantities of pentafluorophenol, but no attempt was made to remove it. Yield: 1.72 g (59%). M.p. 156° C.(decomp.). $^1$H-NMR (250 MHz, CDCl$_3$): Due to the limited rotation around the secondary amide bond several of the signals were doubled in the ratio 2:1, (indicated in the list by mj. for major and mi. for minor). 7.88 ppm (dd,1H,H-6); 7.39 (m, 5H, Ph); 7.00 (dd,1H,H-5); 6.92 (b,1H,BocN$\underline{H}$); 6.74 (b,1H,ZN$\underline{H}$)-?; 5.19 (s,2H,Ph—C$\underline{H}_3$); 4.81 ppm (s, mj., Cyt-CH$_2$—CO—); 4.62 ppm (s, mi., Cyt-CH$_2$—CO—); 4.23 (s, mi., CONRC$\underline{H}_2$CO$_2$H); 3.98 ppm (s, mj., CONRC$\underline{H}_2$CO$_2$H); 3.42–3.02 (unres. m, —CH$_2$CH$_2$— and water);1.37 (s,9H,tBu). FAB-MS: 504 (M+1); 448 (M+1-tBu).

EXAMPLE 11

$N^4$-Benzyloxycarbonyl-1-Boc-aeg-cytosine pentafluorophenyl Ester (13)

$N^4$-Benzyloxycarbonyl-1-Boc-aeg-cytosine (12, 1.50 g; 2.98 mmol) and pentafluorophenol (548 mg; 2.98 mmol) was dissolved in DMF (10 ml) Methylene chloride (10 ml) was added, the reaction mixture was cooled to 0° C. in an ice bath, and DCC (676 mg; 3.28 mmol) was added. The ice bath was removed after 3 min and the mixture was stirred for 3 h at ambient temperature. The precipitate was isolated by filtration and washed once with methylene chloride. The precipitate was dissolved in boiling dioxane (150 ml) and the solution was cooled to 15° C., whereby DCU precipitated. The DCU was removed by filtration and the resulting filtrate was poured into water (250 ml) at 0° C. The title compound was isolated by filtration, was washed with water, and dried over sicapent, in vacuo. Yield 1.30 g (65%). Analysis for $C_{29}H_{28}N_5O_8F_5$. Found(calc.); C, 52.63(52.02); H, 4.41(4.22); N, 10.55(10.46). $^1$H-NMR (250 MHz; DMSO-$d_6$): showed essentially the spectrum of the above acid, most probably due to hydrolysis of the ester. FAB-MS: 670 (M+1); 614 (M+1-tBu)

EXAMPLE 12

4-Chlorocarboxy-9-chloroacridine

4-Carboxyacridone (6.25 g; 26.1 mmol), thionyl chloride (25 ml), and 4 drops of DMF were heated gently under a flow of nitrogen until all solid material had dissolved. The solution then was refluxed for 40 min. The solution was cooled and excess thionyl chloride was removed in vacuo. The last traces of thionyl chloride were removed by coevaporation with dry benzene (dried over Na—Pb) twice. The remaining yellow powder was used directly in the next reaction.

EXAMPLE 13

4-(5-Methoxycarbonylpentylamidocarbonyl)-9-chloroacridine

Methyl 6-aminohexanoate hydrochloride (4.70 g; 25.9 mmol) was dissolved in methylene chloride (90 ml), cooled to 0° C., triethyl amine (15 ml) was added, and the resulting solution then was immediately added to the acid chloride from above. The roundbottomed flask containing the acid chloride was cooled to 0° C. in an ice bath. The mixture was stirred vigorously for 30 min at 0° C. and 3 h at room temperature. The resulting mixture was filtered to remove the remaining solids, which were washed with methylene chloride (20 ml). The red-brown methylene chloride filtrate was subsequently washed twice with saturated sodium hydrogen carbonate, once with saturated sodium chloride, dried over magnesium sulfate, and evaporated to dryness, in vacuo. To the resulting oily substance was added dry benzene (35 ml) and ligroin (60–80° C., dried over Na—Pb). The mixture was heated to reflux. Activated carbon and celite were added and mixture was refluxed for 3 min. After filtration, the title compound crystallised upon cooling with magnetic stirring. It was isolated by filtration and washed with petroleum ether. The product was stored over solid potassium hydroxide. Yield 5.0 g (50%).

EXAMPLE 14

4-(5-Methoxycarbonylpentyl)amidocarbonyl-9-[6'-(4"-nitrobenzamido)hexylamino]-aminoacridine 4-(5-Methoxycarbonylpentylamidocarbonyl)-9-chloroacridine (1.30 g; 3.38 mmol) and phenol (5 g) were heated to 80° C. for 30 min under a flow of nitrogen, after which 6-(4'-nitrobenzamido)-1-hexylamine (897 mg; 3.38 mmol) was added. The temperature raised to 120° C. for 2 h. The reaction mixture was cooled and methylene chloride (80 ml) was added. The resulting solution was washed three times with 2N sodium hydroxide (60 ml portions) and once with water, dried over magnesium sulfate, and evaporated to dryness, in vacuo. The resulting red oil (1.8 g) was dissolved in methylene chloride (40 ml), cooled to 0° C. Ether (120 ml) was added and the resultant solution was stirred overnight. This results in a mixture of solid material and an oil. The solid was isolated by filtration. The solid and the oil were re-dissolved in methylene chloride (80 ml) and added dropwise to cold ether (150 ml). After 20 minutes of stirring, the title compound was isolated by filtration in the form of orange crystals. The product was washed with ether and dried in vacuo over potassium hydroxide. Yield 1.60 g (77%). M.p. 145–147° C.

EXAMPLE 15

4-(5-Carboxypentyl)amidocarbonyl-9-[6'-(4"-nitrobenzamido)hexylamino]-aminoacridine 4-(5-Methoxycarbonylpentyl)amidocarbonyl-9-[6'-(4"-nitrobenzamido)hexylamino]aminoacridine (503 mg; 0.82 mmol) was dissolved in DMF (30 ml), and 2 N sodium hydroxide (30 ml) was added. After stirring for 15 min, 2 N hydrochloric acid (35 ml) and water (50 ml) were added at 0° C. After stirring for 30 min, the solution was decanted, leaving an oily substance which was dissolved in boiling methanol (150 ml), filtered and concentrated to ⅓ volume. To the methanol solution were added ether (125 ml) and 5–6 drops of HCl in ethanol. The solution was decanted after 1 h of stirring at 0° C. The oily substance was redissolved in methanol (25 ml) and precipitated with ether (150 ml). The title compound was isolated as yellow crystals after stirring overnight. Yield 417 mg (80%). M.p. 173° C. (decomp.)

EXAMPLE 16

(a) 4-(5-pentafluorophenyloxycarbonylpentyl)amidocarbonyl-9-[6'-(4'-nitrobenzamido)hexylamino]-aminoacridine ($Acr^1$Opfp)

The acid from above (300 mg; 0.480 mmol) was dissolved in DMF (2 ml) and methylene chloride (8 ml) was added. Pentafluorophenol (97 mg; 0.53 mmol), transferred with 2×2 ml of the methylene chloride, was added. The resulting solution was cooled to 0° C. after which DCC (124 mg; 0.60 mmol) was subsequently added. The ice bath was removed after 5 minutes and the mixture was left with stirring overnight. The precipitated DCU was removed by centrifugation and the centrifugate was evaporated to dryness, in vacuc, first by a water aspirator and then by an oil pump. The residue was dissolved in methylene chloride (20 ml), filtered, and evaporated to dryness, in vacuo. The residue was again dissolved in methylene chloride and petroleum ether (150 ml). A 1 ml portion of 5M HCl in ether was added. The solvent was removed by decanting after 30 min of stirring at 0° C. The residual oily substance was dissolved in methylene chloride (100 ml). Petroleum ether (150 ml) was added and the mixture was left with stirring overnight. The next day the yellow precipitated crystalline material was isolated by filtration and was washed with copious amounts of petroleum ether. Yield, after drying, 300 mg (78%). M.p. 97.5° C. (decomp.) All samples showed satisfactory elemental analysis, $^1$H- and $^{13}$C-NMR and mass spectra.

(b) Experimental for the Synthesis of PNA Compounds, of. FIG. 8

Materials: Boc-Lys(ClZ), benzhydrylamine-copoly(styrene-1%-divinylbenzene) resin (BHA resin), and p-methylbenzhydrylamine-copoly(styrene-1%-divinylbenzene) resin (MBHA resin) were purchased from Peninsula Laboratories. Other reagents and solvents were: Biograde trifluoroacetic acid from Halocarbon Products; diisopropylethylamine (99%; was not further distilled) and N-acetylimidazole (98%) from Aldrich; $H_2O$ was distilled twice; anhydrous HF from Union Carbide; synthesis grade N,N-dimethylformamide and analytical grade methylene chloride (was not further distilled) from Merck; HPLC grade acetonitrile from Lab-Scan; purum grade anisole, N,N'-dicyclohexylcarbodiimide, and puriss. grade 2,2,2-trifluoroethanol from Fluka.

(b) General Methods and Remarks

Except where otherwise stated, the following applies. The PNA compounds were synthezised by the stepwise solid-phase approach (Merrifield, *J. Am. Chem. Soc.,* 1963, 85, 2149) employing conventional peptide chemistry utilizing the TFA-labile tert-butyloxycarbonyl (Boc) group for "temporary" N-protection (Merrifield, *J. Am. Chem. Soc.,* 1964, 86, 304) and the more acid-stable benzyloxycarbonyl (Z) and 2-chlorobenzyloxycarbonyl (ClZ) groups for "permanent" side chain protection. To obtain C-terminal amides, the PNAs were assembled onto the HF-labile BHA or MBHA resins (the MBHA resin has increased susceptibility to the final HF cleavage relative to the unsubstituted BHA resin (Matsueda, et al., *Peptides,* 1981, 2, 45). All reactions (except HF reactions) were carried out in manually operated standard solid-phase reaction vessels fitted with a coarse glass frit (Merrifield, et al., *Biochemistry,* 1982, 21, 5020). The quantitative ninhydrin reaction (Kaiser test), originally developed by Merrifield and co-workers (Sarin, et al., *Anal. Biochem.,* 1981, 117, 147) for peptides containing "normal" amino acids, was successfully applied (see Table I–III) using the "normally" employed effective extinction coefficient $\epsilon=15000$ M$^{-1}$cm$^{-1}$ for all residues to determine the completeness of the individual couplings as well as to measure the number of growing peptide chains. The theoretical substitution $S_{n-1}$ upon coupling of residue number n (assuming both complete deprotection and coupling as well as neither chain termination nor loss of PNA chains during the synthetic cycle) is calculated from the equation:

$$S_n = S_{n-1} \times (1 + (S_{n-1} \times \Delta MW \times 10^{-3} \text{ mmol/mol}))^{-1}$$

where ΔMW is the gain in molecular weight ([ΔMW]=g/mol) and $S_{n-1}$ is the theoretical substitution upon coupling of the preceding residue n−1 ([S]=mmol/g). The estimated value (%) on the extent of an individual coupling is calculated relative to the measured substitution (unless S was not determined) and include correction for the number of remaining free amino groups following the previous cycle. HF reactions were carried out in a Diaflon HF apparatus from Toho Kasei (Osaka, Japan). Vydac C$_{18}$ (5 μm, 0.46×25 cm and 5 μm, 1.0×25 cm) reverse-phase columns, respectively were used for analytical and semi-preparative HPLC on an SP8000 instrument. Buffer A was 5 vol % acetonitrile in water containing 445 μl trifluoroacetic acid per liter, and buffer B was 60 vol % acetonitrile in water containing 390 μl trifluoroacetic acid per liter. The linear gradient was 0–100% of buffer B in 30 min, flow rates 1.2 ml/min (analytical) and 5 ml/min (semi-preparative). The eluents were monitored at 215 nm (analytical) and 230 nm (semi-preparative). Molecular weights of the PNAs were determined by $^{252}$Cf plasma desorption time-of-flight mass spectrometry from the mean of the most abundant isotopes.

EXAMPLE 17

Solid-Phase Synthesis of Acr$^1$-[Taeg]$_{15}$-NH$_2$ and Shorter Derivatives (a) Stepwise Assembly of Boc-[Taeg]$_{15}$-BHA Resin The synthesis was initiated on 100 mg of preswollen and neutralized BHA resin (determined by the quantitative ninhydrin reaction to contain 0.57 mmol NH$_2$/g) employing single couplings ("Synthetic Protocol 1") using 3.2 equivalents of BocTaeg-OPfp in about 33% DMF/CH$_2$Cl$_2$. The individual coupling reactions were carried out by shaking for at least 12 h in a manually operated 6 ml standard solid-phase reaction vessel and unreacted amino groups were blocked by acetylation at selected stages of the synthesis. The progress of chain elongation was monitored at several stages by the quantitative ninhydrin reaction (see Table I). Portions of protected Boc-[Taeg]$_5$-BHA, Boc-[Taeg]$_{10}$-BHA, and Boc-[Taeg]$_{15}$-BHA resins were taken out after assembling 5, 10, and 15 residues, respectively.

| Synthetic Step | Residue Coupled | Substitution After Deprotection (mmol/g) | | Remaining Free Amino Groups After (μmol/g) | | Estimated Extent of Coupling (%) |
|---|---|---|---|---|---|---|
| | | Measd | Theoretol | Single Coupling | Acetylation | |
| "0" | | 0.57 | | | | |
| 1 | BocTaeg | ND | 0.50 | 1.30 | | <99.7 |
| 2 | BocTaeg | ND | 0.44 | 1.43 | | <99.9 |
| 3 | BocTaeg | 0.29 | 0.39 | 3.33 | | 99.3 |
| 4 | BocTaeg | 0.27 | 0.35 | 13.30 | | 96.3 |
| 5 | BocTaeg | 0.26 | 0.32 | 8.33 | | >99.9 |
| 6 | BocTaeg | ND | 0.30 | 7.78 | | >99.9 |
| 7 | BocaTeg | ND | 0.28 | 13.81 | 7.22 | <97.8 |
| 8 | BocTaeg | ND | 0.26 | 14.00 | | <99.9 |
| 9 | BocTaeg | ND | 0.24 | 30.33 | | 93.2 |
| 10 | BocTaeg | 0.16 | 0.23 | 11.67 | 2.67 | >99.9 |
| 11 | BocTaeg | ND | 0.21 | 4.58 | | >99.9 |
| 12 | BocTaeg | ND | 0.20 | 5.87 | | <99.4 |
| 13 | BocTaeg | ND | 0.19 | 1.67 | | >99.9 |
| 14 | BocTaeg | ND | 0.18 | 14.02 | | <93.1 |
| 15 | BocTaeg | 0.07 | 0.17 | 4.20 | 3.33 | >99.9 |

(b) Synthesis of Acr$^1$-[Taeg]$_{15}$-BHA Resin

Following deprotection of the residual Boc-[Taeg]$_{15}$-BHA resin (estimated dry weight is about 30 mg; ~0.002 mmol growing chains), the H-[Taeg]$_{15}$-BHA resin was reacted with about 50 equivalents (80 mg; 0.11 mmol) of Acr$^1$-OPfp in 1 ml of about 66% DMF/CH$_2$Cl$_2$ (i.e., a 0.11 M solution of the pentafluorophenylester) in a 3 ml solid-phase reaction vessel. As judged by a qualitative ninhydrin reaction, coupling of the acridine moiety was close to quantitative.

(c) Cleavage, Purification, and Identification of H-[Taeg]$_5$-NH$_2$

A portion of protected Boc-[Taeg]$_5$-BHA resin was treated with 50% trifluoroacetic acid in methylene chloride to remove the N-terminal Boc group (which is a precursor of the potentially harmful tert-butyl cation) prior to the HF cleavage. Following neutralization and washing (performed in a way similar to those of steps 2–4 in "Synthetic Protocol 1"), and drying for 2 h in vacuum, the resulting 67.1 mg (dry weight) of H-[Taeg]$_5$-BHA resin was cleaved with 5 ml of HF:anisole (9:1, v/v) stirring at 0° C. for 60 min. After removal of HF, the residue was stirred with dry diethyl ether (4×15 ml, 15 min each) to remove anisole, filtered under gravity through a fritted glass funnel, and dried. The PNA was then extracted into a 60 ml (4×15 ml, stirring 15 min each) 10% aqueous acetic acid solution. Aliquots of this solution were analyzed by analytical reverse-phase HPLC to establish the purity of the crude PNA. The main peak at 13.0 min accounted for about 93% of the total absorbance. The remaining solution was frozen and lyophilized to afford about 22.9 mg of crude material. Finally, 19.0 mg of the crude product was purified from five batches, each containing 3.8 mg in 1 ml of H$_2$O. The main peak was collected by use of a semi-preparative reverse-phase column. Acetonitrile was removed on a speed vac and the residual solution was frozen (dry ice) and subsequently lyophilized to give 13.1 mg of >99% pure H-[Taeg]$_5$-NH$_2$. The PNA molecule readily dissolved in water and had the correct molecular weight based on mass spectral determination. For (M+H)$^+$ the calculated m/z value was 1349.3 and the measured m/z value was 1347.8.

(d) Cleavage, Purification, and Identification of H-[Taeg]$_{10}$-NH$_2$

A portion of protected Boc-[Taeg]$_{10}$-BHA resin was treated as described in section (c) to yield 11.0 mg of crude material upon HF cleavage of 18.9 mg dry H-[Taeg]$_{10}$-BHA resin. The main peak at 15.5 min accounted for about 53% of the total absorbance. About 1 mg of the crude product was purified repeatedly (for reasons described below) to give approximately 0.1 mg of at least 80% but presumably >99% pure H-[Taeg]$_{10}$-NH$_2$. A rather broad tail eluting after the target peak and accounting for about 20% of the total absorbance could not be removed (only slightly reduced) upon the repeated purification. Judged by the mass spectrum, which only confirms the presence of the correct molecular weight H-[Taeg]$_{10}$-NH$_2$, the tail phenomonen is ascribed to more or less well-defined aggregational/conformational states of the target molecule. Therefore, the crude product is likely to contain more than the above-mentioned 53% of the target molecule. H-[Taeg]$_{10}$-NH$_2$ is readily dissolved in water. For (M+H)$^+$ the calculated m/z value was 2679.6 and the measured m/z value was 2681.5.

(e) Cleavage, Purification, and Identification of H-[Taeg]$_{15}$-NH$_2$.

Figure 12A:
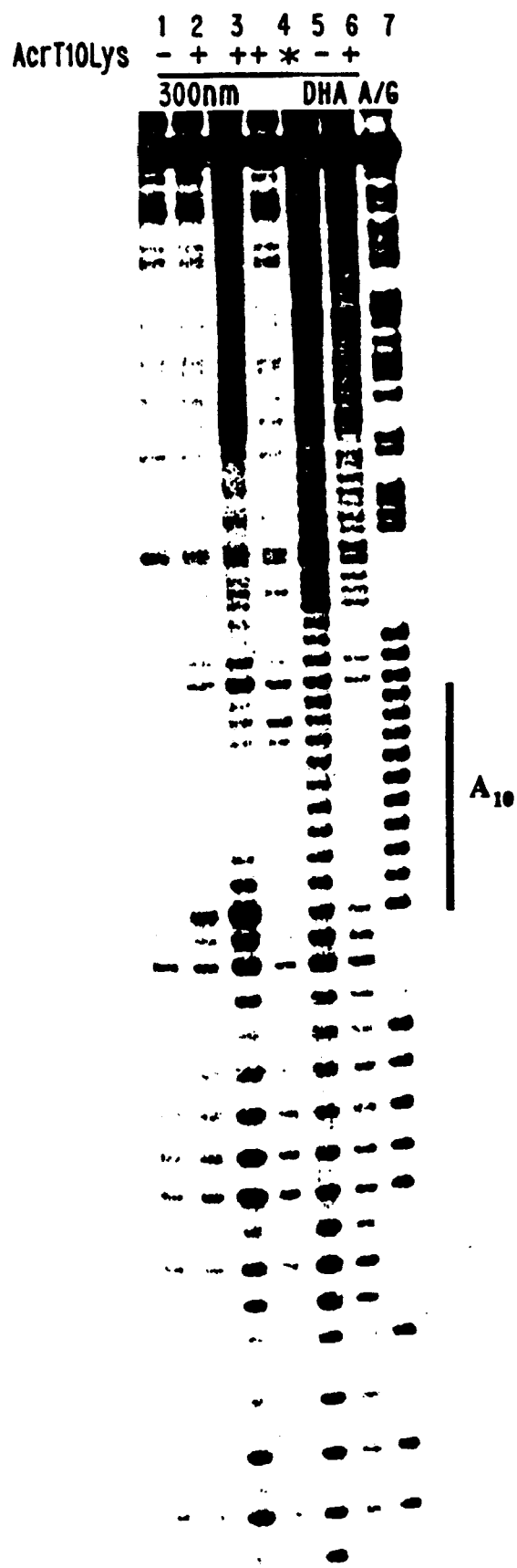
FIGS. 12A, 12B, and 12C show chemical, photochemical and enzymatic probing of dsDNA-Acr-T10-LysNH$_2$ complex. Complexes between Acr-T10-LysNH$_2$ and a $^{32}$P-endlabeled DNA fragment containing a $dA_{10}/dT_{10}$ target sequence were probed by affinity photocleavage (FIG. 12A, lanes 1–3.

A portion of protected Boc-[Taeg]$_{15}$-BHA resin was treated as described in section (c) to yield 3.2 mg of crude material upon HF cleavage of 13.9 mg dry H-[Taeg]$_{15}$-BHA resin. The main peak at 22.6 min was located in a broad bulge accounting for about 60% of the total absorbance (FIG. 12a). Again (see the preceding section), this bulge is ascribed to aggregational/conformational states of the target molecule H-[Taeg]$_{15}$-NH$_2$ since mass spectral analysis of the collected "bulge" did not significantly reveal the presence of other molecules. All of the crude product was purified collecting the "bulge" to give approximately 2.8 mg material. For (M+Na)$^+$ the calculated m/z value was 4033.9 and the measured m/z value was 4032.9.

(f) Cleavage, Purification, and Identification of Acr$^1$-[Taeg]$_{15}$-NH$_2$.

Figure 12B:
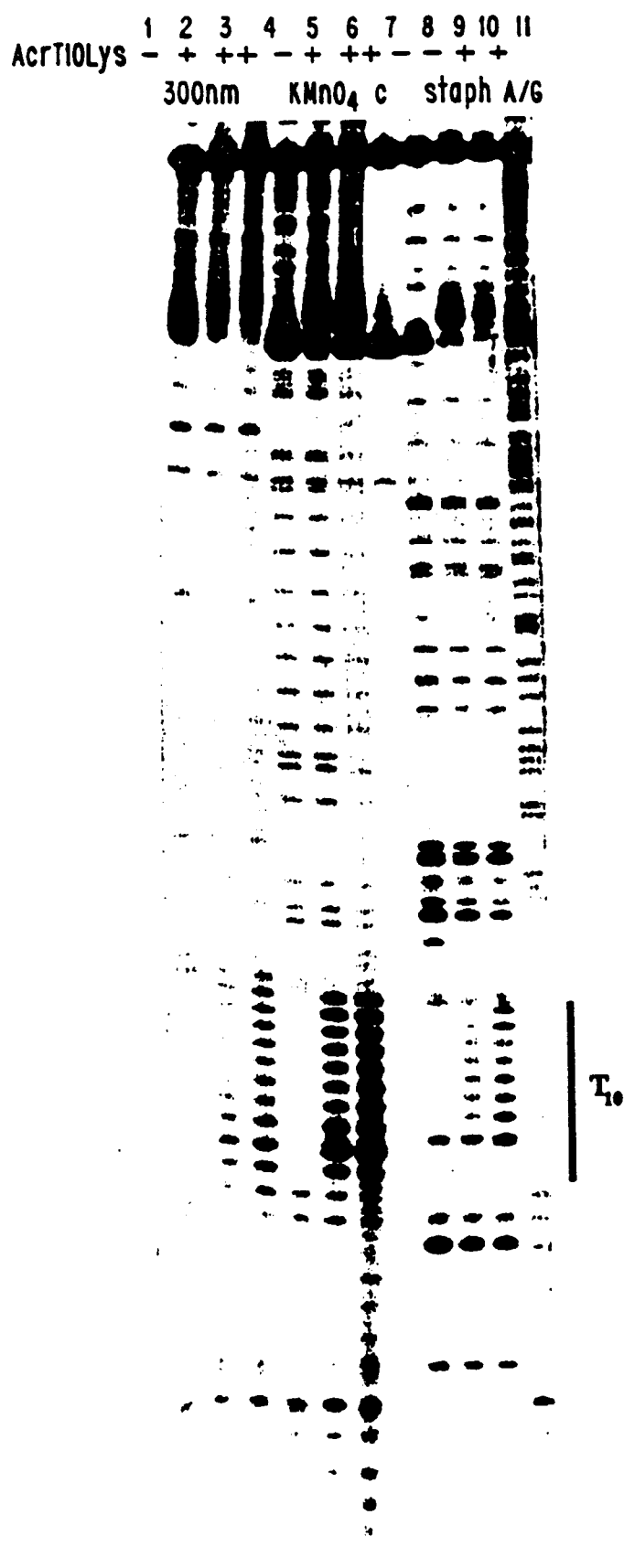
Figure 12C:
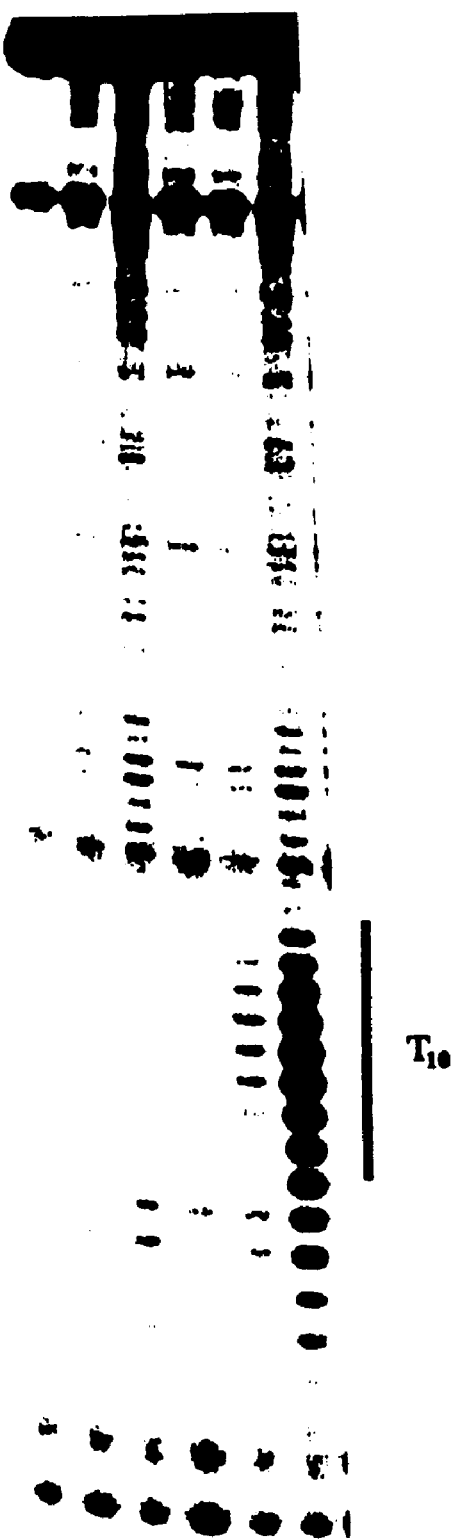

A portion of protected Acr$^1$-[Taeg]$_{15}$-BHA resin was treated as described in section (b) to yield 14.3 mg of crude material upon HF cleavage of 29.7 mg dry Acr$^1$-[Taeg]$_{15}$-BHA resin. Taken together, the main peak at 23.7 min and a "dimer" (see below) at 29.2 min accounted for about 40% of the total absorbance (FIG. 12b). The crude product was purified repeatedly to give approximately 1 mg of presumably >99% pure Acr$^1$-[Taeg]$_{15}$-NH$_2$ "contaminated" with self-aggregated molecules eluting at 27.4 min, 29.2 min, and finally as a huge broad bulge eluting with 100% buffer B (FIG. 12c). This interpretation is in agreement with the observation that those peaks grow upon standing (for hours) in aqueous acetic acid solution, and finally precipitate: out quantitatively. For (M+H)$^+$ the calculated m/z value was 4593.6 and the measured m/z value was 4588.7.

(g) Synthetic Protocol 1

(1) Boc-deprotection with TFA/CH$_2$Cl$_2$ (1:1, v/v), 3 ml, 3×1 min and 1×30 min; (2) washing with CH$_2$Cl$_2$, 3 ml, 6×1 min; (3) neutralization with DIEA/CH$_2$Cl$_2$ (1:19, v/v), 3 ml, 3×2 min; (4) washing with CH$_2$Cl$_2$, 3 ml, 6×1 min, and drain for 1 min; (5) 2–5 mg sample of PNA-resin may be taken out and dried thoroughly for a quantitative ninhydrin analysis to determine the substitution; (6) addition of 3.2 equiv. (0.18 mmol; 100 mg) BocTaeg-OPfp dissolved in 1 ml CH$_2$Cl$_2$ followed by addition of 0.5 ml DMF (final concentration of pentafluorophenylester~0.12 M); the coupling reaction was allowed to proceed for a total of 12–24 h shaking at room temperature; (7) washing with DMF, 3 ml, 1×2 min; (8) washing with CH$_2$Cl$_2$, 3 ml, 4×1 min; (9) neutralization with DIEA/CH$_2$Cl$_2$ (1:19, v/v), 3 ml, 2×2 min; (10) washing with CH$_2$Cl$_2$, 3 ml, 6×1 min; (11) 2–5 mg sample of protected PNA-resin is taken out for a rapid qualitative ninhydrin test and further 2–5 mg is dried thoroughly for a quantitative ninhydrin analysis to determine the extent of coupling (after cycles 7, 10, and 15 unreacted amino groups were blocked by acetylation with N-acetylimidazol in methylene chloride).

EXAMPLE 18

Solid-Phase Synthesis of Acr$^1$-[Taeg]$_{15}$-Lys-NH$_2$ and Shorter Derivatives (a) Stepwise Assembly of Boc-[Taeg]$_{15}$-Lys(ClZ)-BHA Resin The synthesis was initiated by a quantitative loading (standard DCC in situ coupling in neat CH$_2$Cl$_2$) of Boc-Lys (ClZ) onto 100 mg of preswollen and neutralized BHA resin (0.57 mmol NH$_2$/g). Further extension of the protected PNA chain employed single couplings ("Synthetic Protocol 2") for cycles 1 to 5 and cycles 10 to 15 using 3.2 equivalents of BocTaeg-OPfp in about 33% DMF/CH$_2$Cl$_2$. Cycles 5 to 10 employed an extra straight DCC (i.e., in situ) coupling of the free acid BocTaeg-OH in about 33% DMF/CH$_2$Cl$_2$. All coupling reactions were carried out by shaking for at least 12 h in a manually operated 6 ml standard solid-phase reaction vessel. Unreacted amino groups were blocked by acetylation at the same stages of the synthesis, as was done in Example 17. Portions of protected Boc-[Taeg]$_5$-Lys(ClZ)-BHA and Boc-[Taeg]$_{10}$-Lys(ClZ)-BHA resins were taken out after assembling 5 and 10 PNA residues, respectively. As judged by the analytical HPLC chromatogram of the crude cleavage product from the Boc-[Taeg]$_{10}$-Lys(ClZ)-BHA resin (see section (e)), an additional "free acid" coupling of PNA residues 5 to 10 gave no significant improvement of the synthetic yield as compared to the throughout single-coupled, residues in Example 17.

(b) Synthesis of Acr$^1$-[Taeg]$_{10}$-Lys(ClZ)-BHA Resin

Following deprotection of a portion of Boc-[Taeg]$_{10}$-Lys (ClZ)-BHA resin (estimated dry weight is about 90 mg; ~0.01 mmol growing chains), the H-[Taeg]$_{15}$-BHA resin was reacted with about 20 equivalents (141 mg; 0.19 mmol) of Acr$^1$-OPfp in 1 ml of about 66% DMF/CH$_2$Cl$_2$ in a 3 ml solid-phase reaction vessel. As judged by a qualitative ninhydrin reaction, coupling of the acridine moiety was close to quantitative.

(c) Synthesis of Acr$^1$-[Taeg]$_{15}$-Lys(ClZ)-BHA Resin

Following deprotection of the residual Boc-[Taeg]$_{15}$-Lys (ClZ)-BHA resin (estimated dry weight about 70 mg; ~0.005 mmol growing chains), the H-[Taeg]$_{15}$-Lys(ClZ)-BHA resin was reacted with about 25 equivalents (91 mg; 0.12 mmol) of Acr$^1$-OPfp in 1 ml of about 66% DMF/CH$_2$Cl$_2$ in a 3 ml solid-phase reaction vessel. As judged by a qualitative ninhydrin reaction, coupling of the acridine moiety was close to quantitative.

(d) Cleavage, Purification, and Identification of H-[Taeg]$_5$-Lys-NH$_2$

A portion of protected Boc-[Taeg]$_5$-Lys(ClZ)-BHA resin was treated as described in Example 17c to yield 8.9 mg of crude material upon HF cleavage of 19.0 mg dry H-[Taeg]$_5$-Lys(ClZ)-BHA resin. The main peak at 12.2 min (eluted at 14.2 min if injected from an aqueous solution instead of the 10% aqueous acetic acid solution) accounted for about 90% of the total absorbance. About 2.2 mg of the crude product was purified to give approximately 1.5 mg of 99% pure H-[Taeg]$_5$-Lys-NH$_2$.

(e) Cleavage, Purification, and Identification of H-[Taeg]$_{10}$-Lys-NH$_2$

A portion of protected Boc-[Taeg]$_{10}$-Lys(ClZ)-BHA resin was treated as described in Example 17c to yield 1.7 mg of crude material upon HF cleavage of 7.0 mg dry H-[Taeg]$_{10}$-Lys(ClZ)-BHA resin. The main peak at 15.1 min (eluted at 17.0 min if injected from an aqueous solution instead of the 10% aqueous acetic acid solution) accounted for about 50% of the total absorbance. About 1.2 mg of the crude product was purified to give approximately 0.2 mg of >95% pure H-[Taeg]$_{10}$-Lys-NH$_2$. FIG. 13a. For (M+H)$^+$ the calculated m/z value was 2807.8 and the measured m/z value was 2808.2.

(f) Cleavage, Purification, and Identification of Acr$^1$-[Taeg]$_{10}$-Lys-NH$_2$ 99.1 mg protected Acr$^1$-[Taeg]$_{10}$-Lys(ClZ)-BHA resin (dry weight) was cleaved as described in Example 17c to yield 42.2 mg of crude material. The main peak at 25.3 min (eluted at 23.5 min if injected from an aqueous solution instead of the 10% aqueous acetic acid solution) accounted for about 45% of the total absorbance. An 8.87 mg portion of the crude product was purified to give approximately 5.3 mg of >97% pure H-[Taeg]$_{10}$-Lys-NH$_2$. For (M+H)$^+$ the calculated m/z value was 2850.8 and the measured m/z value was 2849.8.

(g) Cleavage and Purification of Acr$^1$-[Taeg]$_{15}$-Lys-NH$_2$

A 78.7 mg portion of protected Acr$^1$-[Taeg]$_{15}$-Lys(ClZ)-BHA resin (dry weight) was cleaved as described in Example I section (c) to yield 34.8 mg of crude material. The main peak at 23.5 min (about the same elution time if injected from an aqueous solution instead of the 10% aqueous acetic acid solution) and a "dimer" at 28.2 min accounted for about 35% of the total absorbance. About 4.5 mg of the crude product was purified to give approximately 1.6 mg of presumably >95% pure H-[Taeg]$_{10}$-Lys-NH$_2$. This compound could not be free of the "dimer" peak, which grew upon standing in aqueous acetic acid solution.

(h) Synthetic Protocol 2

(1) Boc-deprotection with TFA/CH$_2$Cl$_2$ (1:1, v/v), 3 ml, 3×1 min and 1×30 min; (2) washing with CH$_2$Cl$_2$, 3 ml, 6×1 min; (3) neutralization with DIEA/CH$_2$Cl$_2$ (1:19, v/v), 3 ml, 3×2 min; (4) washing with CH$_2$Cl$_2$, 3 ml, 6×1 min, and drain for 1 min; (5) 2–5 mg sample of PNA-resin can be taken out and dried thoroughly for a qualitative ninhydrin analysis; (6) for cycles 1 to 5 and cycles 10 to 15 the coupling reaction was carried out by addition of 3.2 equiv. (0.18 mmol; 100 mg) BocTaeg-OPfp dissolved in 1 ml CH$_2$Cl$_2$ followed by addition of 0.5 ml DMF (final concentration of pentafluorophenylester ~0.12 M); the coupling reaction was allowed to proceed for a total of 12–24 h with shaking; cycles 5 to 10 employed an additional 0.12 M DCC coupling of 0.12 M BocTaeg-OH in 1.5 ml DMF/CH$_2$Cl$_2$ (1:2, v/v); (7) washing with DMF, 3 ml, 1×2 min; (8) washing with CH$_2$Cl$_2$, 3 ml, 4×1 min; (9) neutralization with DIEA/CH$_2$Cl$_2$ (1:19, v/v), 3 ml, 2×2 min; (10) washing with CH$_2$Cl$_2$, 3 ml, 6×1 min; (11) 2–5 mg sample of protected PNA-resin is taken out for a qualitative ninhydrin test (after cycles 7, 10, and 15 unreacted amino groups were blocked by acetylation with N-acetylimidazol-in methylene chloride).

EXAMPLE 19

Improved Solid-Phase Synthesis of H-[Taeg]$_{10}$-Lys-NH$_2$

The protected PNA was assembled onto an MBHA resin, using approximately half the loading of the BHA resin used in the previous examples. Furthermore, all cycles except one was followed by acetylation of uncoupled amino groups. The following describes the synthesis in full detail:

(a) Preparation of Boc-Lys(ClZ)-NH—CH(p-CH$_3$—C$_6$H$_4$)—C$_6$H$_4$ Resin (MBHA Resin) with an Initial Substitution of 0.3 mmol/g The desired substitution of Boc-Lys(ClZ)-MBHA resin was 0.25–0.30 mmol/g. In order to get this value, 1.5 mmol of Boc-Lys(ClZ) was coupled to 5.0 g of neutralized and preswollen MBHA resin (determined by the quantitative ninhydrin reaction to contain 0.64 mmol NH$_2$/g) using a single "in situ" coupling (1.5 mmol of DCC) in 60 ml of CH$_2$Cl$_2$. The reaction was carried out by shaking for 3 h in a manually operated, 225 ml, standard, solid-phase reaction vessel. Unreacted amino groups were then blocked by acetylation with a mixture of acetic anhydride/pyridine/CH$_2$Cl$_2$ (1:1:2, v/v/v) for 18 h. A quantitative ninhydrin reaction on the neutralized resin showed that only 0.00093 mmol/g free amine remained (see Table I), i.e. 0.156 of the original amino groups. The degree of substitution was estimated by deprotection and ninhydrin analysis, and was found to be 0.32 mmol/g for the neutralized H-Lys(ClZ)-MBHA resin. This compares well with the maximum value of 0.28 mmol/g for a quantitative coupling of 0.30 mmol Boc-Lys(ClZ)/g resin (see Table II).

(b) Stepwise Assembly of Boc-[Taeg]$_3$-Lys(ClZ)-MBHA Resin

The entire batch of H-Lys(ClZ)-MBHA resin prepared in section (a) was used directly (in the same reaction vessel) to assemble Boc-[Taeg]$_3$-Lys(ClZ)-MBHA resin by single couplings ("Synthetic Protocol 3") utilizing 2.5 equivalents of BocTaeg-OPfp in neat CH$_2$Cl$_2$. The quantitative ninhydrin reaction was applied throughout the synthesis (see Table II).

(c) Stepwise Assembly of Boc-[Taeg]$_8$-Lys(ClZ)-MBHA Resin

About 4.5 g of wet Boc-[Taeg]$_3$-Lys(ClZ)-MBHA resin (~0.36 mmol growing chains; taken out of totally ~19 g wet resin prepared in section (b)) was placed in a 55 ml SPPS reaction vessel. Boc-[Taeg]$_8$-Lys(ClZ)-MBHA resin was assembled by single couplings ("Synthetic Protocol 4") utilizing 2.5 equivalents of BocTaeg-OPfp in about 30% DMF/CH$_2$Cl$_2$. The progress of the synthesis was monitored at all stages by the quantitative ninhydrin reaction (see Table II).

(d) Stepwise Assembly of Boc-[Taeg]$_{10}$-Lys(ClZ)-MBHA Resin

About 1 g of wet Boc-[Taeg]$_8$-Lys(ClZ)-MBHA resin (~0.09 mmol growing chains; taken out of totally ~4 g wet resin prepared in section (c)) was placed in a 20 ml SPPS reaction vessel. Boc-[Taeg]$_{10}$-Lys(ClZ)-MBHA resin was assembled by the single-coupling protocol employed in the preceding section utilizing 2.5 equivalents of BocTaeg-OPfp in about 30% DMF/CH$_2$Cl$_2$. The reaction volume was 3 ml (vigorous shaking). The synthesis was monitored by the quantitative ninhydrin reaction (see Table II).

| Synthetic Step | Residue Coupled | Substitution After Deprotection (mmol/g) Measd | Substitution After Deprotection (mmol/g) Theoret | Remaining Free Amino Groups After (μmol/g) Single Coupling | Remaining Free Amino Groups After (μmol/g) Acetylation | Estimated Extent of Coupling (%) |
|---|---|---|---|---|---|---|
| "0" | BocLys (ClZ) | 0.32 | 0.28 | | 0.93 | |

-continued

| Syn-thetic Step | Residue Coupled | Substitution After Deprotection (mmol/g) | | Remaining Free Amino Groups After (μmol/g) | | Estimated Extent of Coupling (%) |
| --- | --- | --- | --- | --- | --- | --- |
| | | Measd | Theo-ret | Single Coupling | Acetylation | |
| 1 | BocTaeg | 0.23 | 0.26 | 0.97 | 0.54 | >99.9 |
| 2 | BocTaeg | 0.21 | 0.24 | 0.92 | 0.46 | 99.8 |
| 3 | BocTaeg | 0.19 | 0.23 | 1.00 | 0.57 | 99.7 |
| 4 | BocTaeg | 0.18 | 0.21 | 1.85 | | 99.3 |
| 5 | BocTaeg | 0.17 | 0.20 | 2.01 | 0.19 | 99.9 |
| 6 | BocTaeg | 0.15 | 0.19 | 1.69 | 0.10 | 99.0 |
| 7 | BocaTeg | 0.11 | 0.18 | 1.11 | 0.66 | 99.1 |
| 8 | BocTaeg | 0.12 | 0.17 | 1.82 | 0.44 | 99.0 |
| 9 | BocTaeg | 0.10 | 0.17 | 5.63 | 0.56 | 94.8 |
| 10 | BocTaeg | 0.11 | 0.16 | 1.54 | 0.67 | 99.1 |

(e) Synthesis of Ac-[Taeg]$_{10}$-Lys(ClZ)-MBHA Resin

Following deprotection of a portion of Boc-[Taeg]$_{10}$-Lys (ClZ)-MBHA resin (estimated dry weight is about 45 mg), the resin was next acetylated quantitatively with a 2 ml mixture of acetic anhydride/pyridine/CH$_2$Cl$_2$ (1:1:2, v/v/v) for 2 h in a 3 ml solid-phase reaction vessel.

(f) Cleavage, Purification, and Identification of H-[Taeg]$_{10}$-Lys-NH$_2$

A portion of protected Boc-[Taeg]$_{10}$-Lys(ClZ)-BHA resin was treated as described in Example 17c to yield about 24 mg of crude material upon HF cleavage of 76 mg dry H-[Taeg]$_5$-Lys(ClZ)-BHA resin. The main peak at 15.2 min (which includes impurities such as deletion peptides and various byproducts) accounted for about 78% of the total absorbance. The main peak also accounted for about 88% of the "main peak plus deletion peaks", absorbance, which is in good agreement with the overall estimated coupling yield of 90.1% obtained by summarizing the individual coupling yields in Table II. A 7.2 mg portion of the crude product was purified from two batches by use of a semi-preparative reserve-phase column, (collecting the main peak in a beaker cooled with dry ice/2-propanol). Each contained 3.6 mg in 1 ml of H$_2$O. The frozen solution was lyophilized directly (without prior removal of acetonitrile on a speed vac) to give 4.2 mg of 82% pure H-[Taeg]$_{10}$-Lys-NH$_2$.

(g) Cleavage, Purification, and Identification of Ac-[Taeg]$_{10}$-Lys-NH$_2$

A 400.0 mg portion of protected Ac-[Taeg]$_{10}$-Lys(ClZ)-BHA resin (dry weight) was cleaved as described in Example 17c, except for the TFA treatment to yield 11.9 mg of crude material. The main peak at 15.8 min accounted for about 75% of the total absorbance. A 4.8 mg portion of the crude product was purified to give approximately 3.5 mg of >95% pure Ac-[Taeg]$_{10}$-Lys-NH$_2$. For (M+H)$^+$ the calculated m/z value=2849.8 and the measured m/z value=2848.8.

(h) Synthetic Protocol 3

(1) Boc-deprotection with TFA/CH$_2$Cl$_2$ (1:1, v/v), 100 ml, 3×1 min and 1×30 min; (2) washing with CH$_2$Cl$_2$, 100 ml, 6×1 min; (3) neutralization:with DIEA/CH$_2$Cl$_2$ (1:19, v/v), 100 ml, 3×2 min; (4) washing with CH$_2$Cl$_2$, 100 ml, 6×1 min and drain for 1 min; (5) 2–5 mg sample of PNA-resin is taken out and dried thoroughly for a quantitative ninhydrin analysis to determine the substitution; (6) addition of 2.5 equiv. (3.75 mmol; 2.064 g) BocTaeg-OPfp dissolved in 35 ml CH$_2$Cl$_2$ (final concentration of pentafluorophenylester~0.1 M); the coupling reaction was allowed to proceed for a total of 20–24 h with shaking; (7) washing with DMF, 100 ml, 1×2 min (to remove precipitate of BocTaeg-OH); (8) washing with CH$_2$Cl$_2$, 100 ml, 4×1 min; (9) neutralization with DIEA/CH$_2$Cl$_2$ (1:19, v/v), 100 ml, 2×2 min; (10) washing with CH$_2$Cl$_2$, 100 ml, 6×1 min; (11) 2–5 mg sample of protected PNA-resin is taken but for a rapid qualitative ninhydrin test and a further 2–5 mg is dried thoroughly for a quantitative ninhydrin analysis to determine the extent of coupling; (12) blocking of unreacted amino groups by acetylation with a 100 ml mixture of acetic anhydride/pyridine/CH$_2$Cl$_2$ (1:1:2, v/v/v) for 2 h; (13) washing with CH$_2$Cl$_2$, 100 ml, 6×1 min; (14) 2×2–5 mg samples of protected PNA-resin are taken out, neutralized with DIEA/CH$_2$Cl$_2$ (1:19, v/v) and washed with CH$_2$Cl$_2$ for qualitative and quantitative ninhydrin analyses.

(i) Synthetic Protocol 4

(1) Boc-deprotection with TFA/CH$_2$Cl$_2$ (1:1, v/v), 25 ml, 3×1 min and 1×30 min; (2) washing with CH$_2$Cl$_2$, 25 ml, 6×1 min; (3) neutralization with DIEA/CH$_2$Cl$_2$ (1:19, v/v), 25 ml, 3×2 min; (4) washing with CH$_2$Cl$_2$, 25 ml, 6×1 min, and drain for 1 min; (5) 2–5 mg sample of PNA-resin is taken out and dried thoroughly for a quantitative ninhydrin analysis to determine the substitution; (6) addition of 2.5 equiv. (0.92 mmol; 0.506 g) BocTaeg-OPfp dissolved in 6 ml CH$_2$Cl$_2$ followed by addition of 3 ml DMF (final concentration of pentafluorophenylester ~0.1 M); the coupling reaction was allowed to proceed for a total of 20–24 hrs with shaking; (7) washing with DMF, 25 ml, 1×2 min; (8) washing with CH$_2$Cl$_2$, 25 ml, 4×1 min; (9) neutralization with DIEA/CH$_2$Cl$_2$ (1:19, v/v), 25 ml, 2×2 min; (10) washing with CH$_2$Cl$_2$, 25 ml, 6×1 min; (11) 2–5 mg sample of protected PNA-resin is taken out for a rapid qualitative ninhydrin test and a further 2–5 mg is dried thoroughly for a quantitative ninhydrin analysis to determine the extent of coupling; (12) blocking of unreacted amino groups by acetylation with a 25 ml mixture of acetic anhydride/pyridine/CH$_2$Cl$_2$ (1:1:2, v/v/v) for 2 h (except after the first cycle); (13) washing with CH$_2$Cl$_2$, 25 ml, 6×1 min; (14) 2×2–5 mg samples of protected PNA-resin are taken out, neutralized with DIEA/CH$_2$Cl$_2$ (1:19, v/v) and washed with CH$_2$Cl$_2$ for qualitative and quantitative ninhydrin analyses.

EXAMPLE 20

Solid-Phase Synthesis of H-[Taeg]$_5$-Caeg-[Taeg]$_4$-Lys-NH$_2$ (a) Stepwise Assembly of Boc-[Taeg]$_5$-C(z)aeg-[Taeg]$_4$-Lys (ClZ)-MBHA Resin About 2.5 g of wet Boc-[Taeg]$_3$-Lys(ClZ)-MBHA resin (~⅙ of the total remaining about 16 g wet resin; ~0.75 g dry resin ~0.15 mmol growing chains) was placed in a 6 ml SPPS reaction vessel. Boc-[Taeg]$_5$-Caeg-[Taeg]$_4$-Lys(ClZ)-MBHA resin was assembled by double coupling of all Taeg-residues utilizing the usual 2.5 equivalents of BocTaeg-OPfp in 2.5 ml about 30% DMF/CH$_2$Cl$_2$, except that the first residue was single-coupled. Incorporation of the C(Z)aeg-residue was accomplished by coupling with 2.0 equivalents of BocC(Z)aeg-OPfp in TFE/CH$_2$Cl$_2$ (1:2, v/v). The progress of the synthesis was monitored at all stages by the quantitative ninhydrin reaction (see Table III).

| Synthetic Residue | | Substitution After Deprotection (mmol/g) | | Remaining Free Amino Groups After ($\mu$mol/g) | | | Estimated Extent of Coupling |
|---|---|---|---|---|---|---|---|
| Step | Coupled | Measd. | Theoret. | 1st Coupl | 2nd Coupl | Acetylation | |
| 3 |  | 0.19 | 0.23 | 1.00 |  | 0.57 |  |
| 4 | BocTaeg | 0.17 | 0.21 | 4.88 |  | 97.3 | 97.3 |
| 5 | BocC(Z)aeg | 0.11 | 0.20 | 70.20 | 27.98 | 1.33 | 78.4 (46) |
| 6 | BocTaeg | 0.10 | 0.19 | 24.79 | 4.58 | 2.40 | 95.4 (75) |
| 7 | BocTaeg | 0.09 | 0.18 | 8.55 | 1.61 | 0.20 | >99.9 (93) |
| 8 | BocTaeg | 0.08 | 0.17 | 6.53 | 0.80 | 0.45 | 99.0 (91) |
| 9 | BocTaeg | 0.07 | 0.16 | 9.26 | 3.66 | 0.61 | 94.8 (86) |
| 10 | BocTaeg | 0.07 | 0.15 | 5.32 | 1.48 | 0.60 | 98.8 (93) |

(b) Cleavage, Purification, and Identification of H-[Taeg]$_5$-Caeg-[Taeg]$_4$-Lys-NH$_2$ A portion of protected Boc-[Taeg]$_5$-Caeg-[Taeg]$_4$-Lys (ClZ)-BHA resin was treated as described in Example I section (c) to yield about 14.4 mg of crude material upon HF cleavage of 66.9 mg dry H-[Taeg]$_5$-Caeg-[Taeg]$_4$-Lys(ClZ)-BHA resin. The main peak at 14.5 min accounted for >50% of the total absorbance. A 100.0 mg portion of the crude product was purified (8 batches; each dissolved in 1 ml H$_2$O) to give approximately 9.1 mg of 96% pure H-[Taeg]$_5$-Caeg-[Taeg]$_4$-Lys-NH$_2$ (FIG. 13b). For (M+H)$^+$ the calculated m/z value=2793.8 and the measured m/z value=2790.6.

EXAMPLE 21

Binding of Acr$^1$-(Taeg)$_{10}$-Lys-NH$_2$ to dA$_{10}$ (FIG. 11a)

Acr$^1$-(Taeg)$_{10}$-Lys (100 ng) was incubated for 15 min at room temperature with 50 cps 5'-[$^{32}$P]-end-labelled oligonucleotide [d(GATCCA$_{10}$G)] in 20 $\mu$l TE buffer (10 mM Tris-HCl, 1 mM EDTA, pH 7.4). The sample was cooled in ice (15 min) and analyzed by gel electrophoresis in polyacrylamide (PAGE). To 10 $\mu$l of the sample was added 2 $\mu$l 50% glycerol, 5 TBE (TBE=90 mM Tris-borate, 1 mM EDTA, pH 8.3), and the sample was analysed by PAGE (15% acrylamide, 0.5% bisacrylamide) in TBE buffer at 4° C. A 10 $\mu$l portion of the sample was lyophilized and redissolved in 10 $\mu$l 80% formamide, 1 TBE, heated to 90° C. (5 min), and analyzed by urea/PAGE (15% acrylamide, 0.5% bisacrylamide, 7 M urea) in TBE. [$^{32}$P]-containing DNA bands were visualized by autoradiography using intensifying screens and Agfa Curix RPI X-ray films exposed at −80° C. for 2 h.

Oligonucleotides were synthesized on a Biosearch 7500 DNA synthesizer, labelled with $\gamma$[$^{32}$P]-ATP (Amersham, 5000 Ci/mmol) and polynucleotide kinase, and purified by PAGE using standard techniques (Maniatis et al. (1986): A laboratory manual, Cold Spring Harbor Laboratories).

EXAMPLE 22

Formation of Strand Displacement Complex

A dA$_{10}$-dT$_{10}$ target sequence contained within a plasmid DNA sequence was constructed by cloning of two oligonucleotides (d(GATCCA$_{10}$G)+d(GATCCT$_{10}$G)) into the BamHI restriction enzyme site of pUC19 using the *Eschericia coli* JM101 strain by standard techniques (Maniatis et al., 1986). The desired plasmid (designated pT10) was isolated from one of the resulting clones and purified by the alkaline extraction procedure and CsCl centrifugation (Maniatis et al., 1986). A 3'-[$^{32}$P]-end-labelled DNA fragment of 248 bp containing the dA$_{10}$/dT$_{10}$ target sequence was obtained by cleaving the pT10 DNA with restriction enzymes EcoRI and PvuII, labelling of the cleaved DNA with $\alpha$[$^{32}$P]-DATP (4000 Ci/mmol, Amersham) using the Klenow fragment of *E. coli* DNA polymerase (Boehringer Mannheim), and purifying the 248 bp DNA fragment by PAGE (5% acrylamide, 0.06% bisacrylamide, TBE buffer). This DNA fragment was obtained with [$^{32}$P]-end labelling at the 5'-end by treating the EcoRI-cleaved pT10 plasmid with bacterial alkaline phosphatase (Boehringer Mannheim), purifying the plasmid DNA by gel electrophoresis in low melting agarose, and labelling with $\gamma$[$^{32}$P]ATP and polynucleotide kinase. Following treatment with PvuII, the 248 bp DNA fragment was purified as above.

The complex between Acr$^1$-(Taeg)$_{10}$-Lys-NH$_2$ and the 248 bp DNA fragment was formed by incubating 50 ng of Acr$^1$-(Taeg)$_{10}$-Lys-NH$_2$ with 500 cps $^{32}$P-labelled 248 bp fragment and 0.5 $\mu$g calf thymus DNA in 100 $\mu$l buffer for 60 min at 37° C.

EXAMPLE 23

Probing of Strand Displacement Complex with (a) Staphylococcus Nuclease (FIG. 12b)

The strand displacement complex was formed in 25 mM Tris-HCl, 1 mM MgCl$_2$, 0.1 mM CaCl$_2$, pH 7.4 as described above. The comples was treated with Staphylococcus nuclease (Boehringer Mannheim) at 750 U/ml for 5 min at 20° C. and the reaction was stopped by addition of EDTA to 25 mM. The DNA was precipitated with 2 vols. of ethanol, 2% potassium acetate redissolved in 80% formamide, TBE, heated to 90° C. (5 min), and analyzed by high resolution PAGE (10% acrylamide, 0.36 bisacrylamide, 7 M urea) and autoradiography.

(b) Affinity Photocleavage (FIGS. 12a+12b)

The complex was formed in TE buffer. A sample contained in an Eppendorf tube was irradiated from above at 300 nm (Philips TL 20 W/12 fluorescent light tube, 24 Jm$^{-2}$s$^{-1}$) for 30 min. The DNA was precipitated as above, taken up in 1 M piperidine, and heated to 90° C. for 20 min. Following lyophilization, the DNA was analysed by PAGE as above.

(c) Potassium Permanganate (FIG. 12b)

The complex was formed in 100 $\mu$l TE and 5 $\mu$l 20 mM KMnO$_4$ was added. After 15 s at 20° C., the reaction was stopped by addition of 50 $\mu$l 1.5 M sodium acetate, pH 7.0, 1 M 2-mercaptoethanol. The DNA was precipitated, treated with piperidine and analyzed, as above.

(d) Photofootprinting (FIG. 12b)

The complex was formed in 100 $\mu$l TE and diazo-linked acridine (0.1 $\mu$g/$\mu$l) (DHA, Nielsen et al. (1988) Nucl. Acids Res. 16, 3877–88) was added. The sample was irradiated at 365 nm (Philips TL 20 W/09N, 22 Jm$^{-2}$s$^{-1}$) for 30 min and treated as described for "affinity photocleavage".

(e) S$_1$-nuclease (FIG. 12c)

The complex was formed in 50 mM sodium acetate, 200 mM NaCl, 0.5% glycerol, 1 mM ZnCl$_2$, pH 4.5 and treated with nuclease S$_1$ (Boehringer Mannheim) at 0.5 U/ml for 5 min at 20° C. The reaction was stopped and treated further as described under "Staphylococcus nuclease".

EXAMPLE 24

N-Benzyloxycarbonyl-N-'(bocaminoethyl)glycine

Aminoethyl glycine (52.86 g; 0.447 mol) was dissolved in water (900 ml) and dioxane (900 ml) was added. The pH was adjusted to 11.2 with 2N NaOH. While the pH was kept at 11.2, tert-butyl-p-nitrophenyl carbonate (128.4 g; 0.537 mol) was dissolved in dioxane (720 ml) and added dropwise over the course of 2 hours. The pH was kept at 11.2 for at least three more hours and then left with stirring overnight. The yellow solution was cooled to 0° C. and the pH was adjusted to 3.5 with 2 N HCl. The mixture was washed with chloroform (4×100 ml), and the pH of the aqueous phase was readjusted to 9.5 with 2 N NaOH at 0° C. Benzyloxycarbonyl chloride (73.5 ml; 0.515 mol) was added over half an hour, while the pH was kept at 9.5 with 2 N NaOH. The pH was adjusted frequently over the next 4 hours, and the solution was left with stirring overnight. On the following day the solution was washed with ether (3×600 ml) and the pH of the solution was afterwards adjusted to 1.5 with 2 N HCl at 0° C. The title compound was isolated by extraction with ethyl acetate (5×1000 ml). The ethyl acetate solution was dried over magnesium sulfate and evaporated to dryness, in vacuo. This afforded 138 g, which was dissolved in ether (300 ml) and precipitated by the addition of petroleum ether (1800 ml). Yield 124.7 g (79%). M.p. 64.5–85° C. Anal. for C$_{17}$H$_{24}$N$_2$O$_6$ found(calc.) C, 58.40(57.94); H, 7.02(6.86); N, 7.94(7.95). $^1$H-NMR (250 MHz, CDCl$_3$) 7.33 & 7.32 (5H, Ph); 5.15 & 5.12 (2H, PhC$\underline{H}_2$); 4.03 & 4.01 (2H, NC$\underline{H}_2$CO$_2$H); 3.46 (b, 2H, BocNHCH$_2$C$\underline{H}_2$); 3.28 (b, 2H, BocNHC$\underline{H}_2$CH$_2$); 1.43 & 1.40 (9H, $^t$Bu). HPLC (260 nm) 20.71 min. (80.2%) and 21.57 min. (19.8%). The UV-spectra (200 nm–300 nm) are identical, indicating that the minor peak consists of Bis-Z-AEG.

EXAMPLE 25

N'-Boc-aminoethyl Glycine Ethyl Ester

N-Benzyloxycarbonyl-N'-(bocaminoethyl)glycine (60.0 g; 0.170 mol) and N,N-dimethyl-4-aminopyridine (6.00 g) were dissolved in absolute ethanol (500 ml), and cooled to 0° C. before the addition of DCC (42.2 g; 0.204 mol). The ice bath was removed after 5 minutes and stirring was continued for 2 more hours. The precipitated DCU (32.5 g dried) was removed by filtration and washed with ether (3×100 ml). The combined filtrate was washed successively with diluted potassium hydrogen sulfate (2×400 ml), diluted sodium hydrogencarbonate (2×400 ml) and saturated sodium chloride (1×400 ml). The organic phase was filtered, then dried over magnesium sulfate, and evaporated to dryness, in vacuo, which yielded 66.1 g of an oily substance which contained some DCU.

The oil was dissolved in absolute ethanol (600 ml) and was added 10% palladium on carbon (6.6 g) was added. The solution was hydrogenated at atmospheric pressure, where the reservoir was filled with 2 N sodium hydroxide. After 4 hours, 3.3 L was consumed out of the theoretical 4.2 L. The reaction mixture was filtered through celite and evaporated to dryness, in vacuo, affording 39.5 g (94%) of an oily substance. A 13 g portion of the oily substance was purified by silica gel (600 g SiO$_2$) chromatography. After elution with 300 ml 20% petroleum ether in methylene chloride, the title compound was eluted with 1700 ml of 5% methanol in methylene chloride. The solvent was removed from the fractions with satisfactory purity, in vacuo and the yield was 8.49 g. Alternatively 10 g of the crude material was purified by Kugel Rohr distillation. $^1$H-NMR (250 MHz, CD$_3$OD); 4.77 (b. s, NH); 4.18 (q, 2H, MeC$\underline{H}_2$—); 3.38 (s, 2H, NC$\underline{H}_2$CO$_2$Et); 3.16 (t, 2H, BocNHC$\underline{H}_2$CH$_2$); 2.68 (t, 2H, BocNHCH$_2$C$\underline{H}_2$); 1.43 (s, 9H, $^t$Bu) and 1.26 (t, 3H, CH$_3$) $^{13}$C-NMR 171.4 ($\underline{C}$OEt); 156.6 (CO); 78.3 ((CH$_3$)$_3$$\underline{C}$); 59.9 (CH$_2$); 49.0 (CH$_2$); 48.1 (CH$_2$); 39.0 (CH$_2$); 26.9 (CH$_2$) and 12.6 (CH$_3$).

EXAMPLE 26

N'-Boc-aminoethyl Glycine Methyl Ester

The above procedure was used, with methanol being substituted for ethanol. The final product was purified by column purification.

EXAMPLE 27

1-(Boc-aeg)thymine Ethyl Ester

N'-Boc-aminoethyl glycine ethyl ester (13.5 g; 54.8 mmol), DhbtOH (9.84 g; 60.3 mmol) and 1-carboxymethyl thymine (11.1 g; 60.3 mmol) were dissolved in DMF (210 ml). Methylene chloride (210 ml) then was added. The solution was cooled to 0° C. in an ethanol/ice bath and DCC (13.6 g; 65.8 mmol) was added. The ice bath was removed after 1 hour and stirring was continued for another 2 hours at ambient temperature. The precipitated DCU was removed by filtration and washed twice with methylene chloride (2×75 ml). To the combined filtrate was added more methylene chloride (650 ml). The solution was washed successively with diluted sodium hydrogen carbonate (3×500 ml), diluted potassium hydrogen sulfate (2×500 ml), and saturated sodium chloride (1×500 ml). Some precipitate was removed from the organic phase by filtration, The organic phase was dried over magnesium sulfate and evaporated to dryness, in vacuo. The oily residue was dissolved in methylene chloride (150 ml), filtered, and the title compound was precipitated by the addition of petroleum ether (350 ml) at 0° C. The methylene chloride/petroleum ether procedure was repeated once. This afforded 16.0 g (71%) of a material which was more than 99% pure by HPLC.

EXAMPLE 28

1-(Boc-aeg)thymine

The material from above was suspended in THF (194 ml, gives a 0.2 M solution), and 1 M aqueous lithium hydroxide (116 ml) was added. The mixture was stirred for 45 minutes at ambient temperature and then filtered to remove residual DCU. Water (40 ml) was added to the solution which was then washed with methylene chloride (300 ml). Additional water (30 ml) was added, and the alkaline, solution was washed once more with methylene chloride (150 ml). The aqueous solution was cooled to 0° C. and the pH was adjusted to 2 by the dropwise addition of 1 N HCl (approx. 110 ml). The title compound was extracted with ethyl acetate (9×200 ml), the combined extracts were dried over magnesium sulfate and were evaporated to dryness, in vacuo. The residue was evaporated once from methanol, which after drying overnight afforded a colorless glassy solid. Yield 9.57 g (64%). HPLC>98% $R_T$=14.8 min. Anal. for $C_{16}H_{24}N_4O_7 \cdot 0.25\ H_2O$ Found (calc.) C, 49.29(49.42); H, 6.52(6.35); N, 14.11(14.41). Due to the limited rotation around the secondary amide, several of the signals were doubled in the ratio 2:1 (indicated in the list by mj. for major and mi. for minor). $^1$H-NMR (250 MHz, DMSO-$d_6$): 12.75 (b.s., 1H, $CO_2H$); 11.28 (s, "1H", mj., imide NH); 11.26 (s, "1H", mi., imide NH); 7.30 (s, "1H", mj., T H-6); 7.26 (s, "1H", mi., T H-6); 6.92 (b.t., "1H", mj., BocNH); 6.73 (b.t., "1H", mi., BocNH); 4.64 (s, "2H", mj., $CH_2CON$); 4.46 (s, "2H", mj., $CH_2CON$); 4.19 (s, "2H", mi., $CH_2CO_2H$); 3.97 (s, "2H", mj., $CH_2CO_2H$); 3.63–3.01 (unresolved m, includes water, $CH_2CH_2$); 1.75 (s, 3H, $CH_3$) and 1.38 (s, 9H, $^tBu$).

EXAMPLE 29

$N^4$-Benzyloxycarbonyl-1-(Boc-aeg)cytosine

N'-Boc-aminoethyl glycine ethyl ester (5.00 g; 20.3 mmol), DhbtOH (3.64 g; 22.3 mmol) and $N^4$-benzyloxycarbonyl-1-carboxymethyl cytosine (6.77 g; 22.3 mmol) were suspended in DMF (100 ml). Methylene chloride (100 ml) then was added. The solution was cooled to 0° C. and DCC (5.03 g; 24.4 mmol) was added. The ice bath was removed after 2 h and stirring was continued for another hour at ambient temperature. The reaction mixture then was evaporated to dryness, in vacuo. The residue was suspended in ether (100 ml) and stirred vigorously for 30 min. The solid material was isolated by filtration and the ether wash procedure was repeated twice. The material was then stirred vigorously for 15 min with dilute sodium hydrogencarbonate (approx. 4% solution, 100 ml), filtered and washed with water. This procedure was then repeated once, which after drying left 17.0 g of yellowish solid material. The solid was then boiled with dioxane (200 ml) and filtered while hot. After cooling, water (200 ml) was added. The precipitated material was isolated by filtration, washed with water, and dried. According to HPLC (observing at 260 nm) this material has a purity higher than 99%, besides the DCU. The ester was then suspended in THF (100 ml), cooled to 0° C., and 1 N LiOH (61 ml) was added. After stirring for 15 minutes, the mixture was filtered and the filtrate was washed with methylene chloride (2×150 ml). The alkaline solution then was cooled to 0° C. and the pH was adjusted to 2.0 with 1 N HCl. The title compound was isolated by filtration and was washed once with water, leaving 11.3 g of a white powder after drying. The material was suspended in methylene chloride (300 ml) and petroleum ether (300 ml) was added. Filtration and wash afforded 7.1 g (69%) after drying. HPLC showed a purity of 99% $R_T$=19.5 min, and a minor impurity at 12.6 min (approx. 1%) most likely the Z-de protected monomer. Anal. for $C_{23}H_{29}N_5O_8$ found(calc.) C, 54.16(54.87); H, 5.76(5.81) and N, 13.65(13.91). $^1$H-NMR (250 MHz, DMSO-$d_6$). 10.78 (b.s, 1H, $CO_2H$) 7.88 (2 overlapping dublets, 1H, Cyt H-5); 7.41–7.32 (m, 5H, Ph); 7.01 (2 overlapping doublets, 1H, Cyt H-6); 6.94 & 6.78 (unres. triplets, 1H, BocNH); 5.19 (s, 2H, $PhCH_2$); 4.81 & 4.62 (s, 2H, $CH_2CON$); 4.17 & 3.98 (s, 2H, $CHCO_2H$); 3.42–3.03 (m, includes water, $CH_2CH_2$) and 1.38 & 1.37 (s, 9H, $^tBu$). $^{13}$C-NMR. 150.88; 128.52; 128.18; 127.96; 93.90; 66.53; 49.58 and 28.22. IR: Frequency in cm$^{-1}$ (intensity). 3423 (26.4), 3035 (53.2), 2978(41.4), 1736(17.3), 1658(3.8), 1563(23.0), 1501(6.8) and 1456 (26.4).

EXAMPLE 30

9-Carboxymethyl Adenine Ethyl Ester

Adenine (10.0 g, 74 mmol) and potassium carbonate (10.29 g; 74.0 mmol) were suspended in DMF and ethyl bromoacetate (8.24 ml, 74 mmol) was added. The suspension was stirred for 2.5 h under nitrogen at room temperature and then filtered. The solid residue was washed three times with DMF (10 ml). The combined filtrate was evaporated to dryness, in vacuo. The yellow-orange solid material was poured into water (200 ml) and 4 N HCl was added to pH≈6. After stirring at 0° C. for 10 min, the solid was filtered off, washed with water, and recrystallized from 96% ethanol (150 ml). The title compound was isolated by filtration and washed thoroughly with ether. Yield 3.4 g (206). M.p. 215.5–220° C. Anal. for $C_9H_{11}N_5O_2$ found(calc.): C, 48.86 (48.65); H, 5.01(4.91); N, 31.66(31.42). $^1$H-NMR (250 MHz; DMSO-$d_6$) (s, 2H, H-2 & H-8), 7.25 (b. s., 2H, $NH_2$), 5.06 (s, 2H, $NCH_2$), 4.17 (q, 2H, J=7.11 Hz, $OCH_2$) and 1.21 (t, 3H, J=7.13 Hz, $NCH_2$). $^{13}$C-NMR. 152.70, 141.30, 61.41, 43.97 and 14.07. FAB-MS. 222 (MH+). IR: Frequency in cm$^{-1}$ (intensity). 3855 (54.3), 3274(10.4), 3246(14.0), 3117 (5.3), 2989(22.3), 2940(33.9), 2876(43.4), 2753(49.0), 2346 (56.1), 2106(57.1), 1899(55.7), 1762(14.2), 1742(14.2), 1742(1.0), 1671(1.8), 1644(10.9), 1606(0.6), 1582(7.1), 1522(43.8), 1477(7.2), 1445(35.8) and 1422(8.6). The position of alkylation was verified by X-ray crystallography on crystals, which were obtained by recrystallization from 96% ethanol.

Alternatively, 9-carboxymethyl adenine ethyl ester can be prepared by the following procedure. To a suspension of adenine (50.0 g, 0.37 mol) in DMF (1100 ml) in 2 L three-necked flask equipped with a nitrogen inlet, a mechanical stirrer and a dropping funnel was added 16.4 g (0.407 mol) haxane washed sodium hydride-mineral oil dispersion. The mixture was stirred vigorously for 2 hours, whereafter ethyl bromacetate 75 ml, 0.67 mol) was added dropwise over the course of 3 hours. The mixture was stirred for one additional hour, whereafter tlc indicated complete conversion of adenine. The mixture was evaporated to dryness at 1 mmHg and water (500 ml) was added to the oily residue which caused crystallisation of the title compound. The solid was recrystallised from 06% ethanol (600 ml). Yield after drying 53.7 (65.6%). HPLC (215 nm) purity>99.5%.

EXAMPLE 31

$N^6$-Benzyloxycarbonyl-9-carboxymethyl Adenine Ethyl Ester

9-Carboxymethyladenine ethyl ester (3.40 g, 15.4 mmol) was dissolved in dry DMF (50 ml) by gentle heating, cooled to 20° C., and added to a solution of N-ethyl-benzyloxycarbonylimidazole tetrafluoroborate (62 mmol) in methylene chloride (50 ml) over a period of 15 min with ice-cooling. Some precipitation was observed. The ice bath was removed and the solution was stirred overnight. The reaction mixture was treated with saturated sodium hydrogen carbonate (100 ml). After stirring for 10 min, the phases were separated and the organic phase was washed successively with one volume of water, dilute potassium hydrogen sulfate (twice), and with saturated sodium chloride. The solution was dried over magnesium sulfate and evaporated to dryness, in vacuo, which afforded 11 g of an oily material. The material was dissolved in methylene chloride (25 ml), cooled to 0° C., and precipitated with petroleumeum ether (50 ml). This procedure was repeated once to give 3.45 g (63%) of the title compound. M.p. 132–35° C. Analysis for $C_{17}H_{17}N_5O_4$ found (calc.): C, 56.95(57.46); H, 4.71(4.82); N, 19.35(19.71). $^1$H-NMR (250 MHz; CDCl$_3$): 8.77 (s, 1H, H-2 or H-8); 7.99 (s, 1H, H-2 or H-8); 7.45–7.26 (m, 5H, Ph); 5.31 (s, 2H, N—C$\underline{H}_2$); 4.96 (s, 2H, Ph—C$\underline{H}_2$); 4.27 (q, 2H, J=7.15 Hz, C$\underline{H}_2$CH$_3$) and 1.30 (t, 3H, J=7.15 Hz, CH$_2$C$\underline{H}_3$). $^{13}$C-NMR: 153.09; 143.11; 128.66; 67.84; 62.51; 44.24 and 14.09. FAB-MS: 356 (MH+) and 312 (MH+—CO$_2$). IR: frequency in cm$^{-1}$ (intensity) 3423 (52.1); 3182 (52.8); 3115(52.1); 3031(47.9); 2981(38.6); 1747(1.1); 1617 (4.8); 15.87(8.4); 1552(25.2); 1511(45.2); 1492(37.9); 1465 (14.0) and 1413(37.3).

EXAMPLE 32

N$^6$-Benzyloxycarbonyl-9-carboxymethyl Adenine

N$^6$-Benzyloxycarbonyl-9-carboxymethyladenine ethyl ester (3.20 g; 9.01 mmol) was mixed with methanol (50 ml) cooled to 0° C. Sodium Hydroxide Solution (50 ml; 2N) was added, whereby the material quickly dissolved. After 30 min at 0° C., the alkaline solution was washed with methylene chloride (2×50 ml). The aqueous solution was brought to pH 1.0 with 4 N HCl at 0° C., whereby the title compound precipitated. The yield after filtration, washing with water, and drying was 3.08 g (104%). The product contained salt and elemental analysis reflected that. Anal. for $C_{15}H_{13}N_5O_4$ found(calc.): C, 46.32(55.05); H, 4.24(4.00); N, 18.10 (21.40) and C/N, 2.57(2.56). $^1$H-NMR(250 MHz; DMSO-d$_6$): 8.70 (s, 2H, H-2 and H-8); 7.50–7.35 (m, 5H, Ph); 5.27 (s, 2H, N—C$\underline{H}_2$); and 5.15 (s, 2H, Ph—C$\underline{H}_2$). $^{13}$C-NMR. 168.77, 152.54, 151.36, 148.75, 145.13, 128.51, 128.17, 127.98, 66.76 and 44.67.IR (KBr) 3484(18.3); 3109(15.9); 3087(15.0); 2966(17.1); 2927(19.9); 2383(53.8); 1960 (62.7); 1739(2.5); 1688(5.2); 1655(0.9); 1594(11.7); 1560 (12.3); 1530(26.3); 1499(30.5); 1475(10.4); 1455(14.0); 1429(24.5) and 1411(23.6). FAB-MS: 328 (MH+) and 284 (MH+—CO$_2$). HPLC (215 nm, 260 nm) in system 1:15.18 min, minor impurities all less than 2%.

EXAMPLE 33

N$^6$-Benzyloxycarbonyl-1-(Boc-aeg)adenine Ethyl Ester

N'-Boc-aminoethyl glycine ethyl ester (2.00 g; 8.12 mmol), DhbtOH (1.46 g; 8.93 mmol) and N$^6$-benzyloxycarbonyl-9-carboxymethyl adenine (2.92 g; 8.93 mmol) were dissolved in DMF (15 ml). Methylene chloride (15 ml) then was added. The solution was cooled to 0° C. in an ethanol/ice bath. DCC (2.01 g; 9.74 mmol) was added. The ice bath was removed after 2.5 h and stirring was continued for another 1.5 hour at ambient temperature. The precipitated DCU was removed by filtration and washed once with DMF (15 ml), and twice with methylene chloride (2×15 ml). To the combined filtrate was added more methylene chloride (100 ml). The solution was washed successively with dilute sodium hydrogen carbonate (2×100 ml), dilute potassium hydrogen sulfate (2×100 ml), and saturated sodium chloride (1×100 ml). The organic phase was evaporated to dryness, in vacuo, which afforded 3.28 g (73%) of a yellowish oily substance. HPLC of the raw product showed a purity of only 66% with several impurities, both more and less polar than the main peak. The oil was dissolved in absolute ethanol (50 ml) and activated carbon was added. After stirring for 5 minutes, the solution was filtered. The filtrate was mixed with water (30 ml) and was left with stirring overnight. The next day, the white precipitate was removed by filtration, washed with water, and dried, affording 1.16 g (26%) of a material with a purity higher than 98% by HPLC. Addition of water to the mother liquor afforded another 0.53 g with a purity of approx. 95%. Anal. for $C_{26}H_{33}N_7O_7\cdot H_2O$ found(calc.) C, 55.01(54.44; H, 6.85 (6.15) and N, 16.47(17.09). $^1$H-NMR (250 MHz, CDCl$_3$) 8.74 (s, 1H, Ade H-2); 8.18 (b. s, 1H, ZNH); 8.10 & 8.04 (s, 1H, H-8); 7.46–7.34 (m, 5H, Ph); 5.63 (unres. t, 1H, BocNH); 5.30 (s, 2H, PhCH$_2$); 5.16 & 5.00 (s, 2H, C$\underline{H}_2$CON); 4.29 & 4.06 (s, 2H, C$\underline{H}_2$CO$_2$H); 4.20 (q, 2H, OC$\underline{H}_2$CH$_3$); 3.67–3.29 (m, 4H, C$\underline{H}_2$C$\underline{H}_2$); 1.42 (s, 9H, $^t$Bu) and 1.27 (t, 3H, OCH$_2$C$\underline{H}_3$). The spectrum shows traces of ethanol and DCU.

EXAMPLE 34

N$^6$-Benzyloxycarbonyl-1-(Boc-aeg)adenine

N$^6$-Benzyloxycarbonyl-1-(Boc-aeg)adenine ethyl ester (1.48 g; 2.66 mmol) was suspended in THF (13 ml) and the mixture was cooled to 0° C. Lithium hydroxide (8 ml; 1 N) was added. After 15 min of stirring, the reaction mixture was filtered, extra water (25 ml) was added, and the solution was washed with methylene chloride (2×25 ml). The pH of the aqueous solution was adjusted to pH 2.0 with 1 N HCl. The precipitate was isolated by filtration, washed with water, and dried, and brief affording 0.82 g (58%). The product reprecipitated twice with methylene chloride/petroleum ether, 0.77 g (55%) after drying. M.p. 119° C.(decomp.) Anal. for $C_{24}H_{29}N_7O_7\cdot H_2O$ found(calc.) C, 53.32(52.84); H, 5.71 (5.73); N, 17.68(17.97). FAB-MS. 528.5 (MH+). $^1$H-NMR (250 MHz, DMSO-d$_6$). 12.75 (very b, 1H, CO$_2$H); 10.65 (b. s, 1H, ZNH); 8.59 (d, 1H, J=2.14 Hz, Ade H-2); 8.31 (s, 1H, Ade H-8); 7.49–7.31 (m, 5H, Ph); 7.03 & 6.75 (unresol. t, 1H, BocNH); 5.33 & 5.16 (s, 2H, CH$_2$CON); 5.22 (s, 2H, PhC$\underline{H}_2$); 4.34–3.99 (s, 2H, CH$_2$CO$_2$H); 3.54–3.03 (m's, includes water, C$\underline{H}_2$C$\underline{H}_2$) and 1.39 & 1.37 (s, 9H, $^t$Bu). $^{13}$C-NMR. 170.4; 166.6; 152.3; 151.5; 149.5; 145.2; 128.5; 128.0; 127.9; 66.32; 47.63; 47.03; 43.87 and 28.24.

EXAMPLE 35

2-Amino-6-chloro-9-carboxymethylpurine

To a suspension of 2-amino-6-chloropurine (5.02 g; 29.6 mmol) and potassium carbonate (12.91 g; 93.5 mmol) in DMF (50 ml) was added bromoacetic acid (4.70 g; 22.8 mmol). The mixture was stirred vigorously for 20 h. under nitrogen. Water (150 ml) was added and the solution was filtered through Celite to give a clear yellow solution. The solution was acidified to a pH of 3 with 4 N hydrochloric acid. The precipitate was filtered and dried, in vacuo, over sicapent. Yield (3.02 g; 44.8%). $^1$H-NMR(DMSO-d6): d=4.88 ppm (s,2H); 6.95 (s,2H); 8.10 (s,1H).

EXAMPLE 36

2-Amino-6-benzyloxy-9-carboxymethylpurine

Sodium (2.0 g; 87.0 mmol) was dissolved in benzyl alcohol (20 ml) and heated to 130° C. for 2 h. After cooling to 0° C., a solution of 2-amino-6-chloro-9-carboxymethylpurine (4.05 g; 18.0 mmol) in DMF (85 ml) was slowly added, and the resulting suspension stirred overnight at 20° C. Sodium hydroxide solution (1N, 100 ml) was added and the clear solution was washed with ethyl acetate (3×100 ml). The water phase then was acidified to a pH of 3 with 4 N hydrochloric acid. The precipitate was taken up in ethyl acetate (200 ml), and the water phase was extracted with ethyl acetate (2×100 ml). The combined organic phases were washed with saturated sodium chloride solution (2×75 ml), dried with anhydrous sodium sulfate, and taken to dryness by evaporation, in vacuo. The residue was recrystallized from ethanol (300 ml). Yield after drying, in vacou, over sicapent: 2.76 g (52%). M.p. 159–65° C. Anal. (calc., found) C,(56.18; 55.97); H,(4.38; 4.32); N,(23.4; 23.10). $^1$H-NMR (DMSO-d$_6$): 4.82 ppm. (s,2H); 5.51 (s,2H); 6.45 (s,2H); 7.45 (m,5H); 7.82 (s,1H).

EXAMPLE 37

N-([2-Amino-6-benzyloxy-purine-9-yl]-acetyl)-N-(2-Boc-aminoethyl)-glycine [BocGaeg-OH Monomer]

2-Amino-6-benzyloxy-9-carboxymethyl-purine (0.50 g; 1.67 mmol), methyl-N(2-[tert-butoxycarbonylamino]ethyl)-glycinate (0.65 g; 2.80 mmol), diisopropylethyl amine (0.54 g; 4.19 mmol), and bromo-tris-pyrrolidino-phosphonium-hexafluorophosphate (PyBroP®) (0.798 g; 1.71 mmol) were stirred in DMF (2 ml) for 4 h. The clear solution was poured into an ice-cooled solution of sodium hydrogen carbonate (1 N; 40 ml) and extracted with ethyl acetate (3×40 ml). The organic layer was washed with potassium hydrogen sulfate solution (1 N; 2×40 ml), sodium hydrogen carbonate (1 N; 1×40 ml) and saturated sodium chloride solution (60 ml). After drying with anhydrous sodium sulfate and evaporation, in vacuo, the solid residue was recrystallized from ethyl acetate/hexane (20 ml (2:1)) to give the methyl ester in 63% yield (MS-FAB 514 (M+1). Hydrolysis was accomplished by dissolving the ester in ethanol/water (30 ml (1:2)) containing conc. sodium hydroxide (1 ml). After stirring for 2 h, the solution was filtered and acidified to a pH of 3, by the addition of 4 N hydrochloric acid. The title compound was obtained by filtration. Yield: 370 mg (72% for the hydrolysis). Purity by HPLC was more than 99%. Due to the limited rotation around the secondary amide several of the signals were doubled in the ratio 2:1 (indicated in the list by mj. for major and mi. for minor). $^1$H-NMR(250, MHz, DMSO-d$_6$): d=1.4 ppm. (s,9H); 3.2 (m,2H); 3.6 (m,2H); 4.1 (s, mj., CONRC$\underline{H}_2$COOH); 4.4 (s, mi., CONR C$\underline{H}_2$COOH); 5.0 (s, mi., Gua-C$\underline{H}_2$CO—); 5.2 (s, mj., Gua-C$\underline{H}_2$CO); 5.6 (s,2H); 6.5 (s,2H) 6.9 (m, mi., BocNH); 7.1 (m, mj., BocNH); 7.5 (m.,3H); 7.8 (s,1H); 12,8 (s;1H). $^{13}$C-NMR. 170.95; 170.52; 167.29; 166.85; 160.03; 159.78; 155.84; 154.87; 140.63; 136.76; 128.49; 128.10; 113.04; 78.19; 77.86; 66.95; 49.22; 47.70; 46.94; 45.96; 43.62; 43.31 and 28.25.

EXAMPLE 38

3-Boc-amino-1,2-propanediol

3-Amino-1,2-propanediol (40.00 g, 0.440 mol, 1.0 eq.) was dissolved in water (1000 ml) and cooled to 0° C. Di-tert-butyl dicarbonate (115.0 g, 0.526 mol, 1.2 eq.) was added in one portion. The reaction mixture was heated to room temperature on a water bath during stirring. The pH was maintained at 10.5 with a solution of sodium hydroxide (17.56 g, 0.440 mol, 1.0 eq.) in water (120 ml). When the addition of aqueous sodium hydroxide was completed, the reaction mixture was stirred overnight at room temperature. Subsequently, ethyl acetate (750 ml) was added to the reaction mixture, followed by cooling to 0° C. The pH was adjusted to 2.5 with 4 N sulphuric acid with vigorous stirring. The phases were separated and the water phase was washed with additional ethyl acetate (6×350 ml). The volume of the organic phase was reduced to 900 ml by evaporation under reduced pressure. The organic phase then was washed with a saturated aqueous solution of potassium hydrogen sulfate diluted to twice its volume (1×1000 ml) and with saturated aqueous sodium chloride (1×500 ml). The organic phase was dried (MgSO$_4$) and evaporated under reduced pressure to yield 50.12 g (600%) of the title compound. The product could be solidified by evaporation from methylene chloride and subsequent freezing. $^1$H-NMR (CDCl$_3$/TMS): d=1.43 (s, 9H, Me$_3$C), 3.25 (m, 2H, CH$_2$), 3.57 (m, 2H, CH$_2$), 3.73 (m, 1H, CH) $^{13}$C-NMR (CDCl$_3$/TMS): d=28.2 (Me$_3$C), 42.6 (CH$_2$), 63.5, 71.1 (CH$_2$OH, CHOH), 79.5 (Me$_3$C), 157.0 (C=O).

EXAMPLE 39

2-(Boc-amino)ethyl-L-alanine Methyl Ester

3-Bocamino-1,2-propanediol (20.76 g, 0.109 mol, 1 eq.) was suspended in water (150 ml). Potassium m-periodate (24.97 g, 0.109 mol, 1 eq.) was added and the reaction mixture was stirred for2 h at room temperature under nitrogen. The reaction mixture was filtered and the water phase extracted with chloroform (6×250 ml) The organic phase was dried (MgSO$_4$) and evaporated to afford an almost quantitative yield of Boc-aminoacetaldehyde as a colourless oil, which was used without further purification in the following procedure.

Palladium-on-carbon (10%, 0.8 g) was added to MeOH (250 ml) under nitrogen with cooling (0° C.) and vigorous stirring. Anhydrous sodium acetate (4.49 g, 54.7 mmol, 2 eqv) and L-alanine methyl ester, hydrochloride (3.82 g, 27.4 mmol, 1 eqv) were added. Boc-aminoacetaldehyde (4.79 g, 30.1 mmol, 1.1 eqv) was dissolved in MeOH (150 ml) and added to the reaction mixture. The reaction mixture was hydrogenated at atmospheric pressure and room temperature until hydrogen uptake had ceased. The reaction mixture was filtered through celite, which was washed with additional MeOH. The MeOH was removed under reduced pressure. The residue was suspended in water (150 ml) and pH adjusted to 8.0 by dropwise addition of 0.5 N NaOH with vigorous stirring. The water phase was extracted with methylene chloride (4×250 ml). The organic phase was dried (MgSO$_4$), filtered through celite, and evaporated under reduced pressure to yield 6.36 g (94%) of the title compound as a clear, slightly yellow oil. MS (FAB-MS): m/z (%)=247 (100, M+1), 191 (90), 147 (18). $^1$H-NMR (250 MHz, CDCl$_3$). 1.18, (d, J=7.0 Hz, 3H, Me), 1.36 (s, 9H, Me$_3$C), 1.89 (b, 1H, NH), 2.51 (m, 1H, CH$_2$), 2.66 (m, 1H, CH$_2$), 3.10 (m, 2H, CH$_2$), 3.27 (q, J=7.0 Hz, 1H, CH), 3.64 (s, 3H, OMe), 5.06 (b, 1H, carbamate NH). $^{13}$C-NMR. d=18.8 (Me), 28.2 (Me$_3$C), 40.1, 47.0 (CH$_2$), 51.6 (OMe), 56.0 (CH), 155.8 (carbamate C=O), 175.8 (ester C=O).

EXAMPLE 40

N-(Boc-aminoethyl)-N-(1-thyminylacetyl)-L-alanine Methyl Ester

To a solution of Boc-aminoethyl-(L)-alanine methyl ester (1.23 g, 5.0 mmol) in DMF (10 ml) was added Dhbt-OH (0.90 g, 5.52 mmol) and 1-thyminylacetic acid (1.01 g, 5.48 mmol). When the 1-thyminylacetic acid was dissolved, dichloromethane (10 ml) was added and the solution was cooled on an ice bath. After the reaction mixture had reached 0° C., DCC (1.24 g, 6.01 mmol) was added. Within 5 min after the addition, a precipitate of DCU was seen. After a further 5 min, the ice bath was removed. Two hours later, TLC analysis showed the reaction to be finished. The mixture was filtered and the precipitate washed with dichloromethane (100 ml). The resulting solution was extracted twice with 5% sodium hydrogen carbonate (150 ml) and twice with saturated potassium hydrogen sulfate (25 ml) in water (100 ml). After a final extraction with saturated sodium chloride (150 ml), the solution was dried with magnesium sulfate and evaporated to give a white foam. The foam was purified by column chromatography on silica gel using dichloromethane with a methanol gradient as eluent. This yielded a pure compound (>99% by HPLC) (1.08 g, 52.4%). FAB-MS: 413 (M+1) and 431 (M+1+water). $^1$H-NMR (CDCl$_3$): 4.52 (s, 2 H, CH'$_2$); 3.73 (s, 3 H, OMe); 3.2–3.6 (m, 4 H, ethyl CH$_2$'s); 1.90 (s, 3 H, Me in T); 1.49 (d, 3 H, Me in Ala, J=7.3 Hz); 1.44 (s, 9 H, Boc).

EXAMPLE 41

N-(Boc-aminoethyl)-N-(1-thyminylacetyl)-L-alanine

The methyl ester of the title compound (2.07 g, 5.02 mmol) was dissolved in methanol (100 ml), and cooled on an ice bath. 2 M sodium hydroxide (100 ml) was added. After stirring for 10 min, the pH of the mixture was adjusted to 3 with 4 M hydrogen chloride. The solution was subsequently extracted with ethyl acetate (3×100 ml). The combined organic extracts were dried over magnesium sulfate. After evaporation, the resulting foam was dissolved in ethyl acetate (400 ml) and a few ml of methanol to dissolve the solid material. Petroleum ether then was added until precipitation started. After standing overnight at −20° C., the precipitate was removed by filtration. This gave 1.01 g (50.5%) of pure compound (>99% by HPLC). The compound can be recrystallized from 2-propanol. FAB-MS: 399 (M+1). $^1$H-NMR (DMSO-d$_6$): 11.35 (s, 1 H, COO); 7.42 (s, 1 H, H'$_6$); 4.69 (s, 2 H, CH'$_2$); 1.83 (s, 3 H, Me in T); 1.50–1.40 (m, 12 H, Me in Ala+Boc).

EXAMPLE 42

(a) N-(Boc-aminoethyl)-N-(1-thyminylacetyl)-D-alanine Methyl Ester

To a solution of Boc-aminoethyl alanine methyl ester (2.48 g, 10.1 mmol) in DMF (20 ml) was added Dhbt-OH (1.80 g, 11.0 mmol) and thyminylacetic acid (2.14 g, 11.6 mmol). After dissolution of the 1-thyminylacetic acid, methylene chloride (20 ml) was added and the solution cooled on an ice bath. When the reaction mixture had reached 0° C., DCC (2.88 g, 14.0 mmol) was added. Within 5 min after the addition a precipitate of DCU was seen. After 35 min the ice bath was removed. The reaction mixture was filtered 3.5 h later and the precipitate washed with methylene chloride (200 ml). The resulting solution was extracted twice with 5% sodium hydrogen carbonate (200 ml) and twice with saturated potassium hydrogen sulfate in water (100 ml). After a final extraction with saturated sodium chloride (250 ml), the solution was dried with magnesium sulfate and evaporated to give an oil. The oil was purified by short column silica gel chromatography using methylene chloride with a methanol gradient as eluent. This yielded a compound which was 96% pure according to HPLC (1.05 g, 25.3%) after precipitation with petroleum ether. FAB-MS: 413 (M+1). $^1$H-NMR (CDCl$_3$): 5.64 (t, 1 H, BocNH, J=5.89 Hz); 4.56 (d, 2 H, CH'$_2$); 4.35 (q, 1 H, CH in Ala, J=7.25 Hz); 3.74 (s, 3 H, OMe); 3.64–3.27 (m, 4 H, ethyl H's); 1.90 (s, 3 H, Me in T); 1.52–1.44 (t, 12 H, Boc+Me in Ala).

(b) N-(Boc-aminoethyl)-N-(1-thyminylacetyl)-D-alanine

The methyl ester of the title compound (1.57 g, 3.81 mmol) was dissolved in methanol (100 ml) and cooled on an ice bath. Sodium hydroxide (100 ml; 2 M) was added. After stirring for 10 min the pH of the mixture was adjusted to 3 with 4 M hydrogen chloride. The solution then was extracted with ethyl acetate (3×100 ml). The combined organic extracts were dried over magnesium sulfate. After evaporation, the oil was dissolved in ethyl acetate (200 ml). Petroleum ether was added (to a total volume of 600 ml) until precipitation started. After standing overnight at −20° C., the precipitate was removed by filtration. This afforded 1.02 g (67.3%) of the title compound, which was 94% pure according to HPLC. FAB-MS: 399 (M+1). $^1$H-NMR: 11.34 (s, 1 H, COOH); 7.42 (s, 1 H, H'$_6$) 4.69 (s, 2 H, CH'$_2$); 4.40 (q, 1 H, CH in Ala, J=7.20 Hz); 1.83 (s, 3 H, Me in T); 1.52–1.40 (m, 12 H, Boc+Me in Ala).

EXAMPLE 43

N-(N'-Boc-3'-aminopropyl)-N-[(1-thyminyl)acetyl] glycinemethyl Ester

N-(N'-Boc-3'-aminopropyl)glycine methyl ester (2.84 g, 0.0115 mol) was dissolved in DMF (35 ml), followed by addition of DhbtOH (2.07 g, 0.0127 mol) and 1-thyminylacetic acid (2.34 g, 0.0127 mol). Methylene chloride (35 ml) was added and the mixture cooled to 0° C. on an ice bath. After addition of DCC (2.85 g, 0.0138 mol), the mixture was stirred at 0° C. for 2 h, followed by 1 h at room temperature. The precipitated DCU was removed by filtration, washed with methylene chloride (25 ml), and a further amount of methylene chloride (150 ml) was added to the filtrate. The organic phase was extracted with sodium hydrogen carbonate (1 volume saturated diluted with 1 volume water, 6×250 ml), potassium sulfate (1 volume saturated diluted with 4 volumes water, 3×250 ml), and saturated aqueous sodium chloride (1×250 ml), dried over magnesium sulfate, and evaporated to dryness, in vacuo. The solid residue was suspended in methylene chloride (35 ml) and stirred for 1 h. The precipitated DCU was removed by filtration and washed with methylene chloride (25 ml). The filtrate was evaporated to dryness, in vacuo, and the residue purified by column chromatography on silica gel, eluting with a mixture of methanol and methylene chloride (gradient from 3–7% methanol in methylene chloride). This afforded the title compound as a white solid (3.05 g, 64%). M.p. 76–79° C. (decomp.). Anal. for $C_{18}H_{28}N_4O_7$, found (calc.) C, 52.03; (52.42); H, 6.90; (6.84); N, 13.21; (13.58). The compound showed satisfactory $^1$H and $^{13}$C-NMR spectra.

EXAMPLE 44

N-(N'-Boc-3'-aminopropyl)-N-[(1-thyminyl)acetyl] glycine

N-(N'-Boc-3'-aminopropyl)-N-[(1-thyminyl)acetyl] glycine methyl ester (3.02 g, 0.00732 mol) was dissolved in methanol (25 ml) and stirred for 1.5 h with 2 M sodium hydroxide (25 ml). The methanol was removed by evaporation, in vacuo, and pH adjusted to 2 with 4 M hydrochloric acid at 0° C. The product was isolated as white crystals by filtration, washed with water (3×10 ml), and dried over sicapent, in vacuo. Yield 2.19 g (75%). Anal. for $C_{17}H_{26}N_4O_7$, $H_2O$, found (calc.) C, 49.95; (49.03); H, 6.47; (6.29); N, 13.43; (13.45). The compound showed satisfactory $^1$H and $^{13}$C-NMR spectra.

EXAMPLE 45

3-(1-Thyminyl)-propanoic Acid Methyl Ester

Thymine (14.0 g, 0.11 mol) was suspended in methanol. Methyl acrylate (39.6 ml, 0.44 mol) was added, along with catalytic amounts of sodium hydroxide. The solution was refluxed in the dark for 45 h, evaporated to dryness, in vacuo, and the residue dissolved in methanol (8 ml) with heating. After cooling on an ice bath, the product was precipitated by addition of ether (20 ml), isolated by filtration, washed with ether (3×15 ml), and dried over sicapent, in vacuo. Yield 11.23 g (48%). M.p. 112–119° C. Anal. for $C_9H_{12}N_2O_4$, found (calc.) C, 51.14; (50.94); H, 5.78; (5.70); N, 11.52; (13.20). The compound showed satisfactory $^1H$ and $^{13}C$-NMR spectra.

EXAMPLE 46

3-(1-Thyminyl)-propanoic Acid 3-(1-Thyminyl)-propanoic acid methyl ester (1.0 g, 0.0047 mol) was suspended in 2 M sodium hydroxide (15 ml), boiled for 10 min. The pH was adjusted to 0.3 with conc. hydrochloric acid. The solution was extracted with ethyl acetate (10×25 ml). The organic phase was extracted with saturated aqueous sodium chloride, dried over magnesium sulfate, and evaporated to dryness, in vacuo, to give the title compound as a white solid (0.66 g, 71%). M.p. 118–121° C. Anal. for $C_8H_{10}N_2O_4$, found (calc.) C, 48.38; (48.49); H, 5.09; (5.09); N, 13.93; (14.14). The compound showed satisfactory $^1H$ and $^{13}C$-NMR spectra.

EXAMPLE 47

N-(N'-Boc-aminoethyl)-N-[(1-thyminyl)propanoyl] glycine Ethyl Ester

N-(N'-Boc-aminoethyl)glycine ethyl ester (1.0 g, 0.0041 mol) was dissolved in DMF (12 ml). DhbtOH (0.73 g, 0.0045 mol) and 3-(1-thyminyl)-propanoic acid (0.89 g, 0.0045 mol) were added. Methylene chloride (12 ml) then was added and the mixture was cooled to 0° C. on an ice bath. After addition of DCC (1.01 g, 0.0049 mol), the mixture was stirred at 0° C. for 2 h, followed by 1 h at room temperature. The precipitated DCU was removed by filtration, washed with methylene chloride (25 ml), and a further amount of methylene chloride (50 ml) was added to the filtrate. The organic phase was extracted with sodium hydrogen carbonate (1 volume saturated diluted with 1 volume water, 6×100 ml), potassium sulfate (1 volume saturated diluted with 4 volumes water, 3×100 ml), and saturated aqueous sodium chloride (1×100 ml), dried over magnesium sulfate, and evaporated to dryness, in vacuo. The solid residue was suspended in methylene chloride (15 ml), and stirred for 1 h. The precipitated DCU was removed by filtration and washed with methylene chloride. The filtrate was evaporated to dryness, in vacuo, and the residue purified by column chromatography on silica gel, eluting with a mixture of methanol and methylene chloride (gradient from 1 to 6% methanol in methylene chloride). This afforded the title compound as a white solid (1.02 g, 59%). Anal. for $C_{19}H_{30}N_4O_7$, found (calc.) C, 53.15; (53.51); H, 6.90; (7.09); N, 12.76; (13.13). The compound showed satisfactory $^1H$ and $^{13}C$-NMR spectra.

EXAMPLE 48

N-(N'-Boc-aminoethyl)-N-[(1-thyminyl)propanoyl] glycine

N-(N'-Boc-aminoethy)-N-[(1-thyminyl)propanoyl] glycine ethyl ester (0.83 g, 0.00195 mol) was dissolved in methanol (25 ml). Sodium hydroxide (25 ml; 2 M) was added. The solution was stirred for 1 h. The methanol was removed by evaporation, in vacuo, and the pH adjusted to 2 with 4 M hydrochloric acid at 0° C. The product was isolated by filtration, washed with ether (3×15 ml), and dried over sicapent, in vacuo. Yield 0.769 g, 99%). M.p. 213° C. (decomp.).

EXAMPLE 49

Mono-Boc-ethylenediamine (2)

tert-Butyl-4-nitrophenyl carbonate (1) (10.0 g; 0.0418 mol) dissolved in DMF (50 ml) was added dropwise over a period of 30 min to a solution of ethylenediamine (27.9 ml; 0.418 mol) and DMF (50 ml) and stirred overnight. The mixture was evaporated to dryness, in vacuo, and the resulting oil dissolved in water (250 ml). After cooling to 0° C., pH was adjusted to 3.5 with 4 M hydrochloric acid. The solution then was filtered and extracted with chloroform (3×250 ml). The pH was adjusted to 12 at 0° C. with 2 M sodium hydroxide, and the aqueous solution extracted with methylene chloride (3×300 ml). After treatment with sat. aqueous sodium chloride (250 ml), the methylene chloride solution was dried over magnesium sulfate. After filtration, the solution was evaporated to dryness, in vacuo, resulting in 4.22 g (63%) of the product (oil). $^1H$-NMR (90 MHz; $CDCl_3$): δ1.44 (s, 9H); 2.87 (t, 2H); 3.1 (q, 2H); 5.62 (s, broad).

EXAMPLE 50

(N-Boc-aminoethyl)-β-alanine Methyl Ester, HCl

Mono-Boc-ethylenediamine (2) (16.28 g; 0.102 mol) was dissolved in acetonitrile (400 ml) and methyl acrylate (91.50 ml; 1.02 mol) was transferred to the mixture with acetonitrile (200 ml). The solution was refluxed overnight under nitrogen in the dark to avoid polymerization of methyl acrylate. After evaporation to dryness, in vacuo, a mixture of water and ether (200+200 ml) was added, and the solution was filtered and vigorously stirred. The aqueous phase was extracted one more time with ether and then freeze dried to yield a yellow solid. Recrystallization from ethyl acetate yielded 13.09 g (46%) of the title compound. M.p. 138–140° C. Anal. for $C_{11}H_{23}N_2O_4Cl$, found (calc.) C, 46.49; (46.72); H, 8.38; (8.20); N, 9.83; (9.91); Cl, 12.45; (12.54). $^1H$-NMR (90 MHz; DMSO-$d_6$): δ1.39 (s, 9H) 2.9 (m, 8H); 3.64 (s, 3H).

EXAMPLE 51

N-[(1-Thyminyl)acetyl]-N'-Boc-aminoethyl-β-alanine Methyl Ester (N-Boc-amino-ethyl)-β-alanine methyl ester, HCl (3) (2.0 g; 0.0071 mol) and 1-thyminylacetic acid pentafluorophenyl ester (5) (2.828 g; 0.00812 mol) were dissolved in DMF (50 ml). Triethyl amine (1.12 ml; 0.00812 mol) was added and the mixture stirred overnight. After addition of methylene chloride (200 ml) the organic phase was extracted with aqueous sodium hydrogen carbonate (3×250 ml), half-sat. aqueous potassium hydrogen sulfate (3×250 ml), and sat. aqueous sodium chloride (250 ml) and dried over magnesium sulfate. Filtration and evaporation to dryness, in vacuo, resulted in 2.9 g (99%) yield (oil). $^1H$-NMR (250 MHz; $CDCl_3$): due to limited rotation around the secondary amide several of the signals were doubled; δ1.43 (s, 9H); 1.88 (s, 3H); 2.63 (t, 1H); 2.74 (t, 1H); 3.25–3.55 (4xt, 8H); 3.65 (2xt, 2H); 3.66 (s, 1.5); 3.72 (s, 1.5); 4.61 (s, 1H); 4.72 (s, 2H); 5.59 (s, 0.5H); 5.96 (s, 0.5H); 7.11 (s, 1H); 10.33 (s, 1H).

EXAMPLE 52

N-[(1-Thyminyl)acetyl]-N'-Boc-aminoethyl-β-alanine

N-[(1-Thyminyl)acetyl]-N'-Boc-aminoethyl-β-alanine methylester (3.0 g; 0.0073 mol) was dissolved in 2 M sodium hydroxide (30 ml), the pH adjusted to 2 at 0° C. with 4 M hydrochloric acid, and the solution stirred for 2 h. The precipitate was isolated by filtration, washed three times with cold water, and dried over sicapent, in vacuo. Yield 2.23 g (77%). M.p. 170–176° C. Anal. for $C_{17}H_{26}N_4O_7$, $H_2O$, found (calc.) C, 49.49; (49.03); H, 6.31; (6.78); N, 13.84; (13.45). $^1$H-NMR (90 MHz; DMSO-$d_6$): δ1.38 (s, 9H); 1.76 (s, 3H); 2.44 and 3.29 (m, 8H); 4.55 (s, 2H); 7.3 (s, 1H); 11.23 (s, 1H). FAB-MS: 399 (M+1).

EXAMPLE 53

N-[(1-($N^4$-Z)-cytosyl)acetyl]-N'-Boc-aminoethyl-β-alanine Methyl Ester (N-Boc-amino-ethyl)-β-alanine methyl ester, HCl (3) (2.0 g; 0.0071 mol) and 1-(N-4-Z)-cytosylacetic acid pentafluorophenyl ester (5) (3.319 g; 0.0071 mol) were dissolved in DMF (50 ml). Triethyl amine (0.99 ml; 0.0071 mol) was added and the mixture stirred overnight. After addition of methylene chloride (200 ml), the organic phase was extracted with aqueous sodium hydrogen carbonate (3×250 ml), half-sat. aqueous potassium hydrogen sulfate (3×250 ml), and sat. aqueous sodium chloride (250 ml), and dried over magnesium sulfate. Filtration and evaporation to dryness, in vacuo, resulted in 3.36 g of solid compound which was recrystallized from methanol. Yield 2.42 g (64%). M.p. 158–161° C. Anal. for $C_{25}H_{33}N_5O_8$, found (calc.) C, 55.19; (56.49); H, 6.19; (6.26); N, 12.86; (13.18). $^1$H-NMR (250 MHz; $CDCl_3$): due to limited rotation around the secondary amide several of the signals were doubled; δ1.43 (s, 9H); 2.57 (t, 1H); 3.60–3.23 (m's, 6H); 3.60 (s, 1.5H); 3.66 (s, 1.5H); 4.80 (s, 1H); 4.88 (s, 1H); 5.20 (s, 2H); 7.80–7.25 (m's, 7H). FAB-MS: 532 (M+1).

EXAMPLE 54

N-[(1-($N^4$-Z)-cytosyl)acetyl]-N'-Boc-aminoethyl-β-alanine

N-[(1-(N-4-Z)-cytosyl)acetyl]-N'-Boc-aminoethyl-β-alanine methyl ester (0.621 g; 0.0012 mol) was dissolved in 2 M sodium hydroxide (8.5 ml) and stirred for 2 h. Subsequently, pH was adjusted to 2 at 0° C. with 4 M hydrochloric acid and the solution stirred for 2 h. The precipitate was isolated by filtration, washed three times with cold water, and dried over sicapent, in vacuo. Yield 0.326 g (54%). The white solid was recrystallized from 2-propanol and washed with petroleum ether. Mp.163° C. (decomp.). Anal. for $C_{24}H_{31}N_5O_8$, found (calc.) C, 49.49; (49.03); H, 6.31; (6.78); N, 13.84; (13.45). $^1$H-NMR (250 MHz; $CDCl_3$): due to limited rotation around the secondary amide several of the signals were doubled; δ1.40 (s, 9H); 2.57 (t, 1H); 2.65 (t, 1H); 3.60–3.32 (m's, 6H); 4.85 (s; 1H); 4.98 (s, 1H); 5.21 (s, 2H); 5.71 (s, 1H, broad); 7.99–7.25 (m's, 7H). FAB-MS: 518 (M+1).

EXAMPLE 55

Example of a PNA-oligomer with a Guanine Residue (a) Solid-Phase Synthesis of H-[Taeg]$_5$-[Gaeg]-[Taeg]$_4$-Lys-$NH_2$ The protected PNA was assembled onto a Boc-Lys(ClZ) modified MBHA resin with a substitution of approximately 0.15 mmol/g (determined by quantitative Ninhydrin reaction). Capping of uncoupled amino groups was only carried out before the incorporation of the BocGaeg-OH monomer.

(b) Stepwise Assembly of H-[Taeg]$_5$-[Gaeg]-[Taeg]$_4$-Lys-$NH_2$ (Synthetic Protocol)

Synthesis was initiated on 102 mg (dry weight) of pre-swollen (overnight in DCM) and neutralized Boc-Lys(ClZ)-MBHA resin. The steps performed were as follows: (1). Boc-deprotection with TFA/DCM (1:1, v/v), 1×2 min and 1×½ h, 3 ml; (2) washing with DCM, 4×20 sec, 3 ml; washing with DMF, 2×20 sec, 3 ml; washing with DCM, 2×20 sec, 3 ml, and drain for 30 sec; (3) neutralization with DIEA/DCM (1:19 v/v), 2×3 min, 3 ml; (4) washing with DCM, 4×20 sec, 3 ml, and drain for 1 min.; (5) addition of 4 equiv. diisopropyl carbodiimide (0.06 mmol; 9.7 μl) and 4 equiv. (0.06 mmol; 24 mg) BocTaeg-OH or (0.06 mmol; 30 mg) BocGaeg-OH dissolved in 0.6 ml DCM/DMF (1:1, v/v) (final concentration of monomer 0.1 M), the coupling reaction was allowed to proceed for ½ h shaking at room temperature; (6) drain for 20 sec; (7) washing with DMF, 2×20 sec and 1×2 min, 3 ml; washing with DCM 4×20 sec, 3 ml; (8) neutralization with DIEA/DCM (1:19 v/v), 2×3 min, 3 ml; (9) washing with DCM 4×20 sec, 3 ml, and drain for 1 min.; (10) qualitative Kaiser test; (11) blocking of unreacted amino groups by acetylation with $Ac_2O$/pyridine/DCM (1:1:2, v/v), 1×½ h, 3 ml; and (12) washing with DCM, 4×20 sec, 2×2 min and 2×20 sec, 3 ml. Steps 1–12 were repeated until the desired sequence was obtained. All qualitative Kaiser tests were negative (straw-yellow colour with no coloration of the beads) indicating near 100% coupling yield. The PNA-oligomer was cleaved and purified by the normal procedure. FAB-MS: 2832.11 [$M^+$+1] (calc. 2832.15)

EXAMPLE 56

Solid-Phase Synthesis of H-Taeg-Aaeg-[Taeg]$_8$-Lys-$NH_2$ (a) Stepwise Assembly of Boc-Taeg-A(Z)aeg-[Taeg]$_8$-Lys(ClZ)-MBHA Resin About 0.3 g of wet Boc-[Taeg]$_8$-Lys(ClZ)-MBHA resin was placed in a 3 ml SPPS reaction vessel. Boc-Taeg-A(Z) aeg-[Taeg]$_8$-Lys(ClZ)-MBHA resin was assembled by in situ DCC coupling (single) of the A(Z)aeg residue utilizing 0.19 M of BocA(Z)aeg-OH together with 0.15 M DCC in 2.5 ml 50% DMF/$CH_2Cl_2$ and a single coupling with 0.15 M BocTaeg-OPfp in neat $CH_2Cl_2$ ("Synthetic Protocol 5"). The synthesis was monitored by the quantitative ninhydrin reaction, which showed about 50% incorporation of A(Z)aeg and about 96% incorporation of Taeg.

(b) Cleavage, Purification, and Identification of H-Taeg-Aaeg-[Taeg]$_8$-Lys-$NH_2$ The protected Boc-Taeg-A(Z)aeg-[Taeg]$_8$-Lys(ClZ)-BAH resin was treated as described in Example 40c to yield about 15.6 mg of crude material upon HF cleavage of 53.1 mg dry H-Taeg-A(Z)aeg-[Taeg]$_8$-Lys(ClZ)-BHA resin. The main peak at 14.4 min accounted for less than 50% of the total absorbance. A 0.5 mg portion of the crude product was purified to give approximately 0.1 mg of H-Taeg-Aaeg-[Taeg]$_8$-Lys-$NH_2$. For $(MH+)^+$ the calculated m/z value was 2816.16 and the measured m/z value was 2816.28.

(c) Synthetic Protocol 5

(1) Boc-deprotection with TFA/$CH_2Cl_2$ (1:1, v/v), 2.5 ml, 3×1 min and 1×30 min; (2) washing with $CH_2Cl_2$, 2.5 ml, 6×1 min; (3) neutralization with DIEA/$CH_2Cl_2$ (1:19, v/v), 2.5 ml, 3×2 min; (4) washing with $CH_2Cl_2$, 2.5 ml, 6×1 min, and drain for 1 min; (5) 2–5 mg sample of PNA-resin is taken out and dried thoroughly for a quantitative ninhydrin analysis to determine the substitution; (6) addition of 0.47 mmol (0.25 g) BocA(Z)aeg-OH dissolved in 1.25 ml DMF followed by addition of 0.47 mmol (0.1 g) DCC in 1.25 ml $CH_2Cl_2$ or 0.36 mmol (0.20 g) BocTaeg-OPfp in 2.5 ml $CH_2Cl_2$; the coupling reaction was allowed to proceed for a total of 20–24 hrs shaking; (7) washing with DMF, 2.5 ml, 1×2 min; (8) washing with $CH_2Cl_2$, 2.5 ml, 4×1 min; (9) neutralization with $DIEA/CH_2Cl_2$ (1:19, v/v), 2.5 ml, 2×2 min; (10) washing with $CH_2Cl_2$, 2.5 ml, 6×1 min; (11) 2–5 mg sample of protected PNA-resin is taken out and dried thoroughly for a quantitative ninhydrin analysis to determine the extent of coupling; (12) blocking of unreacted amino groups by acetylation with a 25 ml mixture of acetic anhydride/-pyridine/$CH_2Cl_2$ (1:1:2, v/v/v) for 2 h (except after the last cycle); and (13) washing with $CH_2Cl_2$, 2.5 ml, 6×1 min; (14) 2×2–5 mg samples of protected PNA-resin are taken out, neutralized with $DIEA/CH_2Cl_2$ (1:19, v/v) and washed with $CH_2Cl_2$ for ninhydrin analyses.

EXAMPLE 57

Solid-Phase Synthesis of H-[Taeg]$_2$-Aaeg-[Taeg]-Lys-NH$_2$ (a) Stepwise Assembly of Boc-[Taeg]$_2$-A(Z)aeg-[Taeg]$_5$-Lys(ClZ)-MBHA Resin About 0.5 g of wet Boc-[Taeg]$_5$-Lys(ClZ)-MBHA resin was placed in a 5 ml SPPS reaction vessel. Boc-[Taeg]$_2$-A(Z)aeg-[Taeg]$_5$-Lys(ClZ)-MBHA resin was assembled by in situ DCC coupling of both the A(Z)aeg and the Taeg residues utilising 0.15 M to 0.2 M of protected PNA monomer (free acid) together with an equivalent amount of DCC in 2 ml neat $CH_2Cl_2$ ("Synthetic Protocol 6"). The synthesis was monitored by the quantitative ninhydrin reaction which showed a total of about 82% incorporation of A(Z)aeg after coupling three times (the first coupling gave about 50% incorporation; a fourth HOBt-mediated coupling in 50% DMF/$CH_2Cl_2$ did not increase the total coupling yield significantly) and quantitative incorporation (single couplings) of the Taeg residues.

(b) Cleavage, Purification, and Identification of H-[Taeg]$_2$-Aaeg-[Taeg]$_5$-Lys-NH$_2$ The protected Boc-[Taeg]$_2$-A(Z)aeg-[Taeg]$_5$-Lys(ClZ)-BHA resin was treated as described in Example 40c to yield about 16.2 mg of crude material upon HF cleavage of 102.5 mg dry H-[Taeg]$_2$-A(Z)aeg-[Taeg]$_5$-Lys(ClZ)-BHA resin. A small portion of the crude product was purified. For (MH+)$^+$, the calculated m/z value was 2050.85 and the measured m/z value was 2050.90

(c) Synthetic Protocol 6

(1) Boc-deprotection with TFA/$CH_2Cl_2$ (1:1, v/v), 2 ml, 3×1 min and 1×30 min; (2) washing with $CH_2Cl_2$, 2 ml, 6×1 min; (3) neutralization with $DIEA/CH_2Cl_2$ (1:19, v/v), 2 ml, 3×2 min; (4) washing with $CH_2Cl_2$, 2 ml; 6×1 min, and drain for 1 min; (5) 2–5 mg sample of PNA-resin was taken out and dried thoroughly for a quantitative ninhydrin analysis to determine the substitution; (6) addition of 0.44 mmol (0.23 g) BocA(Z)aeg-OH dissolved in 1.5 ml $CH_2Cl_2$ followed by addition of 0.44 mmol (0.09 g) DCC in 0.5 ml $CH_2Cl_2$ or 0.33 mmol (0.13 g) BocTaeg-OH in 1.5 ml $CH_2Cl_2$ followed by addition of 0.33 mmol (0.07 g) DCC in 0.5 ml $CH_2Cl_2$; the coupling reaction was allowed to proceed for a total of 20–24 hrs with shaking; (7) washing with DMF, 2 ml, 1×2 min; (8) washing with $CH_2Cl_2$, 2 ml, 4×1 min; (9) neutralization with $DIEA/CH_2Cl_2$ (1:19, v/v), 2 ml, 2×2 min; (10) washing with $CH_2Cl_2$, 2 ml, 6×1 min; (11) 2–5 mg sample of protected PNA-resin is taken out and dried thoroughly for a quantitative ninhydrin analysis to determine the extent of coupling; (12) blocking of unreacted amino groups by acetylation with a 25 ml mixture of acetic anhydride/pyridine/$CH_2Cl_2$ (1:1:2, v/v/v) for 2 h (except after the last cycle); (13) washing with $CH_2Cl_2$, 2 ml, 6×1 min; and (14) 2×2–5 mg samples of protected PNA-resin were taken out, neutralized with $DIEA/CH_2Cl_2$ (1:19, v/v) and washed with $CH_2Cl_2$ for ninhydrin analyses.

EXAMPLE 58

The PNA-oligomer H-T4C2TCT-LysNH$_2$ was prepared as described in Example 93. Hybridization experiments with this sequence should resolve the issue of orientation, since it is truly asymmetrical. Such experiments should also resolve the issues of pH-dependency of the Tm, and the stoichiometry of complexes formed.

Hybridization experiments with the PNA-oligomer H-T$_4$C$_2$TCTC-LysNH$_2$ were performed as follows:

| Row | Hybridized With | pH | Tm | § |
|---|---|---|---|---|
| 1 | 5'-(dA)$_4$(dG)$_2$(dA) (dG) (dA) (dG) | 7.2 | 55.5 | 2:1 |
| 2 | 5'-(dA)$_4$(dG)$_2$(dA) (dG) (dA) (dG) | 9.0 | 26.0 | 2:1 |
| 3 | 5'-(dA)$_4$(dG)$_2$(dA) (dG) (dA) (dG) | 5.0 | 88.5 | 2:1 |
| 4 | 5'-(dG) (dA) (dG) (dA) (dG)$_2$(dA)$_4$ | 7.2 | 38.0 | 2:1 |
| 5 | 5'-(dG) (dA) (dG) (dA) (dG)$_2$(dA)$_4$ | 9.0 | 31.5 | — |
| 6 | 5'-(dG) (dA) (dG) (dA) (dG)$_2$(dA)$_4$ | 5.0 | 52.5 | — |
| 7 | 5'-(dA)$_4$(dG) (dT) (dA) (dG) (dA) (dG) | 7.2 | 39.0 | — |
| 8 | 5'-(dA)$_4$(dG) (dT) (dA) (dG) (dA) (dG) | 9.0 | <20 | — |
| 9 | 5'-(dA)$_4$(dG) (dT) (dA) (dG) (dA) (dG) | 5.0 | 51.5 | — |
| 10 | 5'-(dA)$_4$(dG)$_2$(dT) (dG) (dA) (dG) | 7.2 | 31.5 | — |
| 11 | 5'-(dA)$_4$(dG)$_2$(dT) (dG) (dA) (dG) | 5.0 | 50.5 | — |
| 12 | 5'-(dG) (dA) (dG) (dA) dT) (dG) (dA)$_4$ | 7.2 | 24.5 | — |
| 13 | 5'-(dG) (dA) (dG) (dA) dT) (dG) (dA)$_4$ | 9.0 | <20 | — |
| 14 | 5'-(dG) (dA) (dG) (dA) dT) (dG) (dA)$_4$ | 5.0 | 57.0 | — |
| 15 | 5'-(dG) (dA) (dG) (dT) (dG)$_2$(dA)$_4$ | 7.2 | 25.0 | — |
| 16 | 5'-(dG) (dA) (dG) (dT) (dG)$_2$(dA)$_4$ | 5.0 | 39.5 52.0 | — |

§ = stoichiometry determined by UV-mixing curves
— = not determined

These results show that a truly mixed sequence gave rise to well defined melting curves. The PNA-oligomers can actually bind in both orientations (compare row 1 and 4), although there is preference for the N-terminal/5'-orientation. Introducing a single mismatch opposite either T or C caused a lowering of $T_m$ by more than 16° C. at pH 7.2; at pH 5.0 the $T_m$-value was lowered more than 27° C. This shows that there is a very high degree a sequence-selectivity which should be a general feature for all PNA C/T sequences.

As indicated above, there is a very strong pH-dependency for the $T_m$-value, indicating that Hoogsteen basepairing is important for the formation of hybrids. Therefore, it is not surprising that the stoichiometry was found to be 2:1.

The lack of symmetry in the sequence and the very large lowering of $T_m$ when mismatches are present show that the Watson-Crick strand and the Hoogsteen strand are parallel when bound to complementary DNA. This is true for both of the orientations, i.e., 5'/N-terminal and 3'/N-terminal.

EXAMPLE 59

The results of hybridization experiments with H-T$_5$GT$_4$-LysNH$_2$ to were performed as follows:

| Row | Deoxyoligonucleotide | Tm |
|---|---|---|
| 1 | 5'-(dA) 5 (dA) (dA)4-3' | 55.0 |
| 2 | 5'-(dA) 5 (dG) (dA)4-3' | 47.0 |

-continued

| Row | Deoxyoligonucleotide | Tm |
|---|---|---|
| 3 | 5'-(dA) 5 (dG) (dA)4-3' | 56.5 |
| 4 | 5'-(dA) 5 (dT) (dA)4-3' | 46.5 |
| 5 | 5'-(dA) 4 (dG) (dA)5-3' | 48.5 |
| 6 | 5'-(dA) 4 (dC) (dA)5-3' | 55.5 |
| 7 | 5'-(dA) 4 (dT) (dA)5-3' | 47.0 |

As shown by comparing rows 1, 3, and 6 with rows 2, 4, 5, and 7, G can in this mode discriminate between C/A and G/T in the DNA-strand, i.e., sequence discrimination is observed. The complex in row 3 was furthermore determined to be 2 PNA: 1 DNA complex by UV-mixing curves.

EXAMPLE 60

The masses of some synthesized PNA-oligomers, as determined by FAB mass spectrometry, are as follows:

| SEQUENCE | CALC. | FOUND |
|---|---|---|
| H-T$_4$C$_2$TCTC-LysNH$_2$ | 2747.15 | 2746.78 |
| H-T$_5$GT$_4$-LysNH$_2$ | 2832.15 | 2832.11 |
| H-T$_7$-LysNH$_2$ | 2008.84 | 2540.84 |
| H-T$_9$-LysNH$_2$ | 2541.04 | 2540.84 |
| H-T$_{10}$-LysNH$_2$ | 2807.14 | 2806.69 |
| H-T$_2$CT$_5$-LysNH$_2$ | 2259.94 | 2259.18 |
| H-T$_3$(L-alaT)T$_4$-LysNH$_2$ | 2287.95 | 2288.60 |
| H-T$_4$(Ac)T$_5$-LysNH$_2$ | 2683.12 | 2683.09 |

EXAMPLE 61

Hybridization data for a PNA-oligomer with a single unit with an extended backbone (the β-alanine modification) is as follows:

| PNA | DNA | T$_m$ |
|---|---|---|
| H-T$_{10}$-LysnH$_2$ | (dA)$_{10}$ | 73° C. |
| H-T$_4$(βT)T$_5$-LysNH$_2$ | (dA)$_{10}$ | 57° C. |
| H-T$_4$(βT)T$_5$-LysNH$_2$ | (dA)$_4$(dG) (dA)$_5$ | 47° C. |
| H-T$_4$(βT)T$_5$-LysNH$_2$ | (dA)$_4$(dT) (dA)$_5$ | 49° C. |
| H-T$_4$(βT)T$_5$-LysNH$_2$ | (dA)$_4$(dT) (dA)$_5$ | 47° C. |

Although the melting temperature decreases, the data demonstrates that base specific recognition is retained.

EXAMPLE 62

An example with a "no base" substitution.

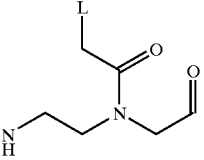

| PNA | DNA | T$_m$ |
|---|---|---|
| H—T$_{10}$—LysNH$_2$ | (dA)$_{10}$ | 73° C. |
| H—T$_4$(Ac)T$_5$—LysNH$_2$ | (dA)$_{10}$ | 49° C. |

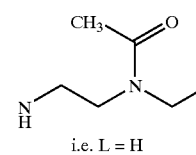

| PNA | DNA | T$_m$ |
|---|---|---|
| H—T$_4$(Ac)T$_5$—LysNH$_2$ | (dA)$_4$ (dG) (dA)$^5$ | 37° C. |
| H—T$_4$(Ac)T$_5$—LysNH$_2$ | (dA)$_4$ (dC) (dA)$^5$ | 41° C. |
| H—T$_4$(Ac)T$_5$—LysNH$_2$ | (dA)$_4$ (dT) (dA)$^5$ | 41° C. |
| H—T$_4$(Ac)T$_5$—LysNH$_2$ | (dA)$_5$ (dG) (dA)$^4$ | 36° C. |
| H—T$_4$(Ac)T$_5$—LysNH$_2$ | (dA)$_5$ (dC) (dA)$^4$ | 40° C. |
| H—T$_4$(AC)T$_5$—LysNH$_2$ | (dA)$_5$ (dT) (dA)$^4$ | 40° C. |

EXAMPLE 63

Iodination Procedure

A 5 μg portion of Tyr-PNA-T$_{10}$-Lys-NH$_2$ is dissolved in 40 μl 100 mM Na-phosphate, pH 7.0, and 1 mCi Na$^{125}$I and 2 μl chloramine-T (50 mM in CH$_3$CN) are added. The solution is left at 20° C. for 10 min and then passed through a 0.5+5 cm Sephadex G10 column. The first 2 fractions (100 μl each) containing radioactivity are collected and purified by HPLC: reversed phase C-18 using a 0–60% CH$_3$CN gradient in 0.1% CF$_3$COOH in H$_2$O. The $^{125}$I-PNA elutes right after the PNA peak. The solvent is removed under reduced pressure.

EXAMPLE 64

Figure 20:
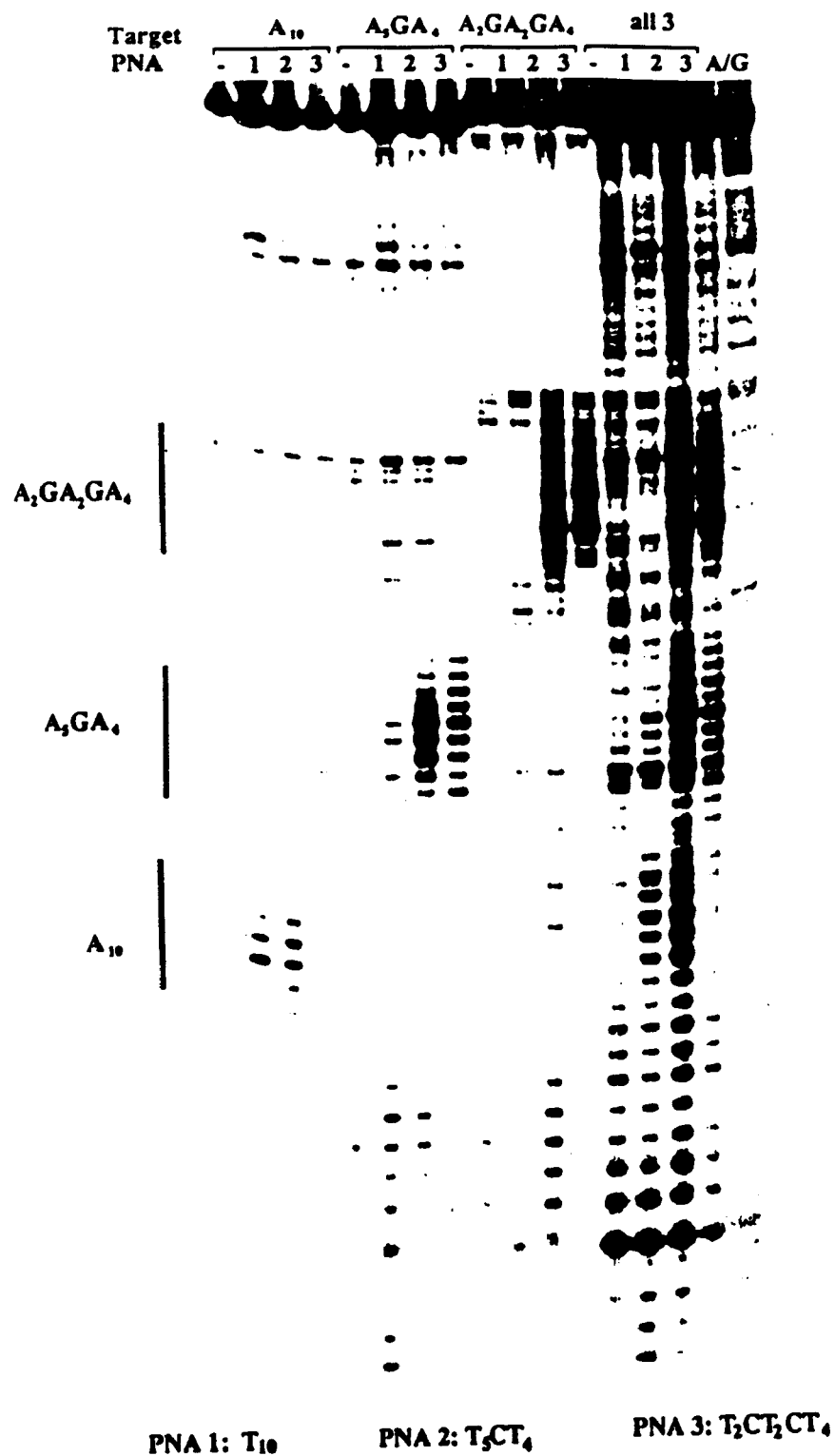
FIG. 20 shows a PAGE autoradiograph demonstrating that PNAs-$T_{10}$, -$T_9C$ and -$T_8C_2$ bind to double stranded DNA with high sequence specificity.

Binding of PNAs-T$_{10}$/T$_9$C/T$_8$C$_2$ to Double Stranded DNA Targets A$_{10}$/A$_9$G/A$_8$G$_2$ (FIG. 20)

A mixture of 200 cps $^{32}$P-labeled EcoRI-PvuII fragment (the large fragment labeled at the 3'-end of the EcoRI site) of the indicated plasmid, 0.5 μg carrier calf thymus DNA, and 300 ng PNA in 100 μl buffer (200 mM NaCl, 50 mM Na-acetate, pH 4.5, 1 mM ZnSO$_4$) was incubated at 37° C. for 120 min; A 50 unit portion of nuclease S$_1$ was added and incubated at 20° C. for 5 min. The reaction was stopped by addition of 3 μl 0.5 M EDTA and the DNA was precipitated by addition of 250 μl 2% potassium acetate in ethanol. The DNA was analyzed by electrophoresis in 10% polyacrylamide sequencing gels and the radiolabeled DNA bands visualized by autoradiography.

The target plasmids were prepared by cloning of the appropriate oligonucleotides into pUC19. Target A$_{10}$: oligonucleotides GATCCA$_{10}$G & GATCCT$_{10}$G cloned into the BamHI site (plasmid designated pT$_{10}$). Target A$_5$GA$_4$: oligonucleotides TCGACT$_4$CT$_5$G & TCGACA$_5$GA$_4$G cloned into the SalI site (plasmid pT9C). Target A$_2$GA$_2$GA$_4$: oligonucleotides GA$_2$GA$_2$GA$_4$TGCA & GT$_4$CT$_2$CT$_2$CTGCA into the PstI site (plasmid pT8C2). The positions of the targets in the gel are indicated by bars to the left. A/G is an A+G sequence ladder of target P10.

EXAMPLE 65

Inhibition of Restriction Enzyme-cleavage by PNA (FIG. 23)

A 2 μg portion of plasmid pT10 was mixed with the indicated amount of PNA-T$_{10}$ in 20 μl TE buffer (10 mM Tris-HCl, 1 mM EDTA, pH 7.4) and incubated at 37° C. for 120 min. 2 μl 10×buffer (10 mM Tris-HCl, pH 7.5, 10 mM, MgCl$_2$, 50 mM NaCl, 1 mM DTT). PvuII (2 units) and BamHI (2 units) were added and the incubation was continued for 60 min. The DNA was analyzed by gel electrophoresis in 5% polyacrylamide and the DNA was visualized by ethidium bromide staining.

EXAMPLE 66

Kinetics of PNA-T$_{10}$—dsDNA Strand Displacement Complex Formation (FIG. 21)

A mixture of 200 cps $^{32}$P-labeled EcoRI-PvuII fragment of pT10 (the large fragment labeled at the 3'-end of the EcoRI site), 0.5 µg carrier calf thymus DNA, and 30.0 ng of PNA-T$_{10}$-LysNH$_2$ in 100 µl buffer (200 mM NaCl, 50 mM Na-acetate, pH 4.5, 1 mM ZnSO$_4$) were incubated at 37° C. At the times indicated, 50 U of S$_1$ nuclease was added to each of 7 samples and incubation was continued for 5 min at 20° C. The DNA was then precipitated by addition of 250 µl 2% K-acetate in ethanol and analyzed by electrophoresis in a 10% polyacrylamide sequencing gel. The amount of strand displacement complex was calculated from the intensity of the S$_1$-cleavage at the target sequence, as measured by densitometric scanning of autoradiographs.

EXAMPLE 67

Figure 22:
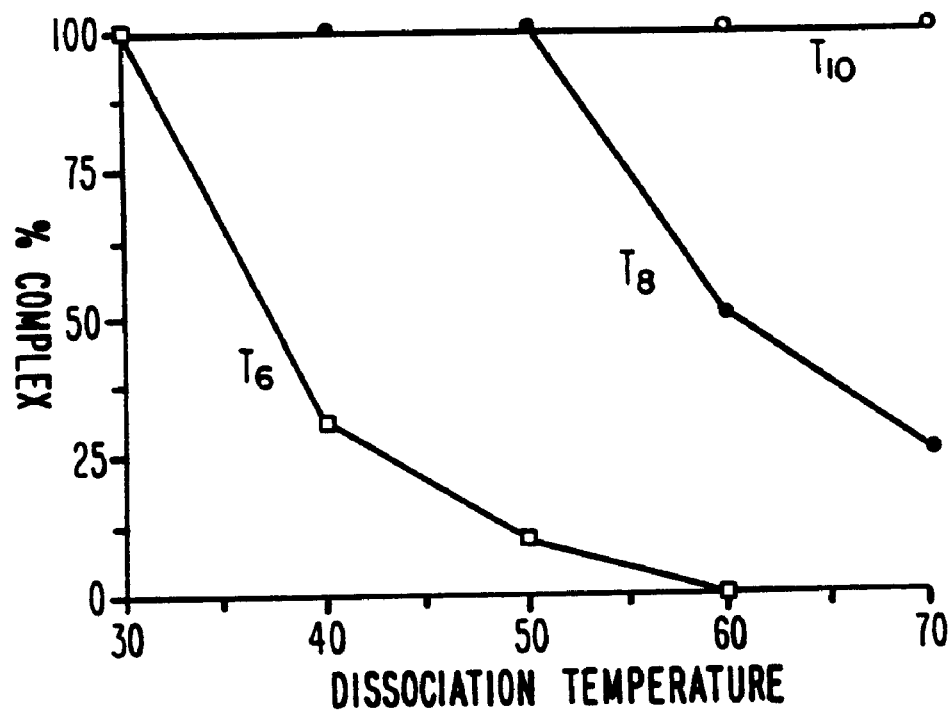
FIG. 22 shows a graph based on densitometric scanning of PAGE autoradiographs demonstrating the thermal stabilities of PNAs of varying lengths bound to an $A_{10}/T_{10}$ double stranded DNA target.

Stability of PNA-dsDNA Complexes (FIG. 22)

A mixture of 200 cps $^{32}$P-pT10 fragment, 0.5 µg calf thymus DNA and 300 ng of the desired PNA (either T$_{10}$-LysNH$_2$, T$_8$-LysNH$_2$ or T$_6$-LysNH$_2$) was incubated in 100 µl 200 mM NaCl, 50 mM Na-acetate, pH 4.5, 1 mM ZnSO$_4$ for 60 min at 37° C. A 2 µg portion of oligonucleotide GATCCA$_{10}$G was added and each sample was heated for 10 min at the temperature indicated, cooled in ice for 10 min and warmed to 20° C. A 50 U portion of S$_1$ nuclease was added and the samples treated and analyzed and the results quantified.

EXAMPLE 68

Inhibition of Transcription by PNA

A mixture of 100 ng plasmid DNA (cleaved with restriction enzyme PvuII (see below) and 100 ng of PNA in 15 µl 10 mM Tris-HCl, 1 mM EDTA, pH 7.4 was incubated at 37° C. for 60 min. Subsequently, 4 µl 5×concentrated buffer (0.2 M Tris-HCl (pH 8.0), 40 MM MgCl$_2$, 10 mM spermidine, 125 mM NaCl) were mixed with 1 µl NTP-mix (10 mM ATP, 10 mM CTP, 10 mM GTP, 1 mM UTP, 0.1 µCi/µl $^{32}$P-UTP, 5 mM DTT, 2 µg/ml tRNA, 1 µg/ml heparin) and 3 units RNA polymerase. Incubation was continued for 10 min at 37° C. The RNA was then precipitated by addition of 60 µl 2% postassium acetate in 96% ethanol at −20° C. and analyzed by electrophoresis in 8% polyacrylamide sequencing gels. RNA transcripts were visualized by autoradiography. The following plasmids were used: pT8C2-KS/pA8G2-KS: oligonucleotides GA$_2$GA$_2$GA$_4$GTGAC & GT$_4$CT$_2$CT$_2$CTGCA cloned into the PstI site of pBluescript-KS$^+$; pT10-KS/pA10-KS (both orientations of the insert were obtained). pT10UV5: oligonucleotides GATCCA$_{10}$G & GATCCT$_{10}$G cloned into the BamHI site of a pUC18 derivative in which the lac UV5 *E.coli* promoter had been cloned into the EcoRI site (Jeppesen, et al., *Nucleic Acids Res.*, 1988, 16, 9545).

Figure 25:
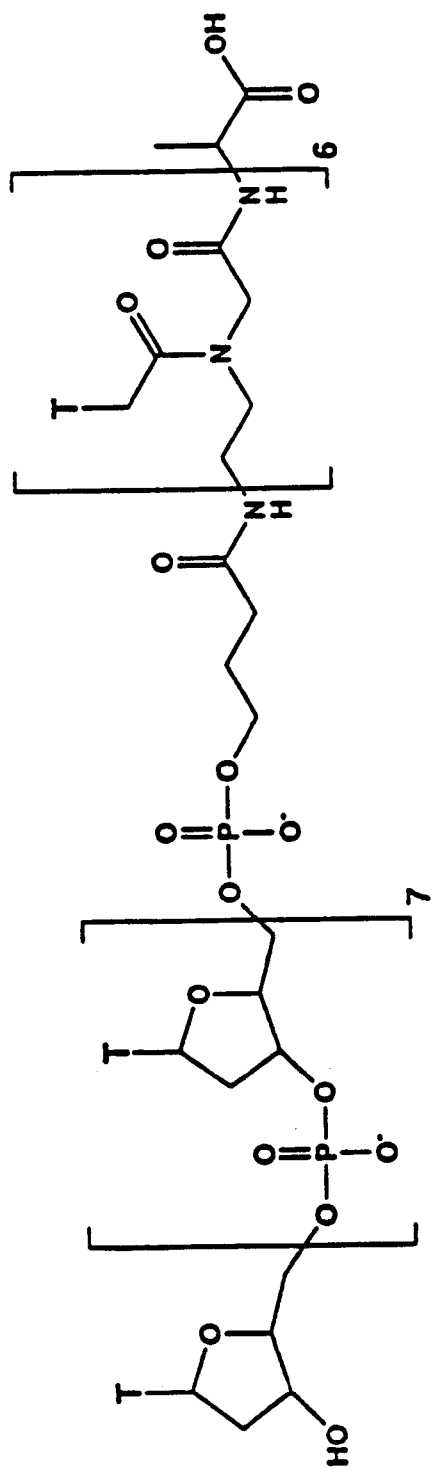
FIG. 25 shows a peptide nucleic acid according to the invention.

Using T$_3$-RNA polymerase, transcription elongation arrest was obtained with PNA-T$_8$C$_2$-LysNH$_2$ and the pA8G2-KS plasmid having the PNA recognition sequence on the template strand, but not with pT8C2-KS having the PNA recognition sequence on the non-template strand. Similar results were obtained with PNA-T10-LysNH$_2$ and the plasmids pA10-KS and pT10-KS. (see, FIG. 25) Using *E.coli* RNA polymerase and the pT10UV5 plasmid (A$_{10}$-sequence on the template strand) transcription elongation arrest was obtained with PNA-T$_{10}$-LysNH$_2$.

EXAMPLE 69

Biological Stability of PNA

A mixture of PNA-T$_5$ (10 µg) and a control, "normal" peptide (10 µg) in 40 µl 50 mM Tris-HCl, pH 7.4 was treated with varying amounts of peptidase from porcine intestinal mucosa or protease from Streptomyces caespitosus for 10 min at 37° C. The amount of PNA and peptide was determined by HPLC analysis (reversed phase C-18 column: 0–60% acetonitrile, 0.1% trifluoroacetic acid).

At peptidase/protease concentrations where complete degradation of the peptide was observed (no HPLC peak) the PNA was still intact.

EXAMPLE 70

Inhibition of Gene Expression

A preferred assay to test the ability of peptide nucleic acids to inhibit expression of the E2 mRNA of papillomavirus is based on the well-documented transactivation properties of E2. Spalholtz, et al., *J. Virol.*, 1987, 61, 2128–2137. A reporter plasmid (E2RECAT) was constructed to contain the E2 responsive element, which functions as an E2 dependent enhancer. E2RECAT also contains the SV40 early promoter, an early polyadenylation signal, and the chloramphenicol acetyl transferase gene (CAT). Within the context of this plasmid, CAT expression is dependent upon expression of E2. The dependence of CAT expression on the presence of E2 has been tested by transfection of this plasmid into C127 cells transformed by BPV-1, uninfected C127 cells and C127 cells cotransfected with E2RECAT and an E2 expression vector.

A. Inhibition of BPV-1 E2 Expression

BPV-1 transformed C127 cells are plated in 12 well plates. Twenty four hours prior to transfection with E2RE1, cells are pretreated by addition of antisense PNAs to the growth medium at final concentrations of 5, 15 and 30 mM. The next day cells are transfected with 10 µg of E2RE1CAT by calcium phosphate precipitation. Ten micrograms of E2RE1CAT and 10 µg of carrier DNA (PUC 19) are mixed with 62 µl of 2 M CaCl$_2$ in a final volume of 250 µl of H$_2$O, followed by addition of 250 µl of 2×HBSP (1.5 mM Na$_2$PO$_2$. 10 mM KCl, 280 mM NaCl, 12 mM glucose and 50 mM HEPES, pH 7.0) and incubated at room temperature for 30 minutes. One hundred microliters of this solution is added to each test well and allowed to incubate for 4 hours at 37° C. After incubation, cells are glycerol shocked for 1 minute at room temperature with 15% glycerol in 0.75 mM Na$_2$PO$_2$, 5 mM KCl, 140 mM NaCl, 6 mM glucose and 25 mM HEPES, pH 7.0. After shocking, cells are washed 2 times with serum free DMEM and refed with DMEM containing 10% fetal bovine serum and antisense oligonucleotide at the original concentration. Forty eight hours after transfection cells are harvested and assayed for CAT activity.

For determination of CAT activity, cells are washed 2 times with phosphate buffered saline and collected by scraping. Cells are resuspended in 100 μl of 250 mM Tris-HCl, pH 8.0 and disrupted by freeze-thawing 3 times. Twenty four microliters of cell extract is used for each assay. For each assay the following are mixed together in an 1.5 ml Eppendorf tube and incubated at 37° C. for one hour: 25 μl of cell extract, 5 μl of 4 mM acetyl coenzyme A, 18 μl H$_2$O and 1 μl $^{14}$C-chloramphenicol, 40–60 mCi/mM. After incubation, chloramphenicol (acetylated and nonacetylated forms) is extracted with ethyl acetate and evaporated to dryness. Samples are resuspended in 25 μl of ethyl acetate, spotted onto a TLC plate and chromatographed in chloroform:methanol (19:1). Chromatographs are analyzed by autoradiography. Spots corresponding to acetylated and nonacetylated $^{14}$C-chloramphenicol are excised from the TLC plate and counted by liquid scintillation for quantitation of CAT activity. Peptide nucleic acids that depress CAT activity in a dose dependent fashion are considered positives.

B. Inhibition of HPV E2 Expression

The assay for inhibition of human papillomavirus (HPV) E2 by peptide nucleic acids is essentially the same as that for BPV-1 E2. For HPV assays appropriate HPVs are co-transfected into either CV-1 or A431 cells with PSV2NEO using the calcium phosphate method described above. Cells which take up DNA are selected for by culturing in media containing the antibiotic G418. G418-resistant cells are then analyzed for HPV DNA and RNA. Cells expressing E2 are used as target cells for antisense studies. For each PNA, cells are pretreated as above, transfected with E2RE1CAT, and analyzed for CAT activity as above. Peptide nucleic acids are considered to have a positive effect if they can depress CAT activity in a dose dependent fashion.

EXAMPLE 71

Synthesis of PNA 15-mer Containing Four Naturally Occurring Nucleobases; H-[Taeg]-[Aaeg]-[Gaeg]-[Taeg]-[Taeg]-[Aaeg]-[Taeg]-[Caeg]-[Taeg]-[Caeg]-[Taeg]-[Aaeg]-[Taeg]-[Caeg]-[Taeg]-LYS—NH2

The protected PNA was assembled onto a Boc-Lys(ClZ) modified MBHA resin with a substitution of approximately 0.145 mmol/g. Capping of uncoupled amino groups was only carried out before the incorporation of the BocGaeg-OH monomer.

Synthesis was initiated on 100 mg (dry weight) of neutralised Boc-Lys(ClA)-MBHA resin that had been preswollen overnight in DCM. The incorporation of the monomers followed the protocol of Example 32, except at step 5 for the incorporation of the BocAaeg-OH monomer. Step 5 for the present synthesis involved addition of 4 equiv. dilsopropyl carbodiimide (0.06 ml; 9.7 μl) and 4 equiv. BocAaeg-OH (0.06 mmol; 32 mg) dissolved in 0.6 ml DCM/DMF (1:1, v/v) (final concentration of monomer 0.1M). The coupling reaction was allowed to proceed for 1×15 min and 1×60 min. (recoupling).

All qualitative Kaiser tests were negative (straw-yellow color with no coloration of the beads). The PNA-oligomer was cleaved and purified by the standard procedure. FAB-MS average mass found(calc.) (M+H) 4145.1 (4146.1).

EXAMPLE 72

Hybridization of H-TAGTTATCTCTATCT-LysNH$_2$

| DNA -target | pH | Tm |
|---|---|---|
| 5'----3' | 5 | 60.5 |
| 5'----3' | 7.2 | 43.0 |
| 5'----3' | 9 | 38.5 |
| 3'----5' | 5 | 64.5/49.0 |
| 3'----5' | 7.2 | 53.5 |
| 3'----5' | 9 | 51.5 |

The fact that there is almost no loss in Tm in going from pH 7.2 to 9.0 indicates that Hoogsteen basepairing is not involved. The increase in Tm in going from 7.2 to 5 is large for the parallel orientation and is probably due to the formation of a 2:1 complex. It is believed that the most favorable orientation in the Watson-Crick binding motif is the 3'/N-orientation and that in the Hoogsteen motif the 5'/N-orientation is the most stable. Thus, it may be the case that the most stable complex is with the two PNA's strands anti parallel.

There is apparently a very strong preference for a parallel orientation of the Hoogsteen strand. This seems to explain why even at pH 9 a 2:1 complex is seen with the 5'/N-orientation. Furthermore, it explains the small loss in going from pH 7.2 to 9 in the 3'/N, as this is probably a 1:1 complex.

EXAMPLE 73

Solid-Phase Synthesis of H-[Taeg]$_2$-Aaeg-Taeg-Caeg-Aaeg-Taeg-Caeg-Taeg-Caeg-Lys-NH2

(a) Stepwise Assembly of Boc-[Taeg]2-A(Z)aeg-Taeg-C(Z)aeg-A(Z)aeg-Taeg-C(Z)aeg-Taeg-C(Z)aeg-Lys(ClZ)-MBHA Resin About 1 g of wet Boc-Lys(ClZ)-MBHA (0.28 mmol Lys/g) resin was placed in a 5 ml SPPS reaction vessel. Boc-[Taeg]2-A(Z)aeg-Taeg-C(Z)aeg-A(Z)aeg-Taeg-C(Z)aeg-Taeg-C(Z)aeg-Lys(ClZ)-MBHA resin was assembled by in situ DCC coupling of the five first residues utilizing 0.16 M of BocC[Z]-OH, BbcTaeg-OH or BocA(Z)aeg-OH, together with 0.16 M DCC in 2.0 ml 50% DMF/CH$_2$Cl$_2$ ("Synthetic Protocol 9") and by analogous in situ DIC coupling of the five last residues ("Synthetic Protocol 10"). Each coupling reaction was allowed to proceed for a total of 20–24 hrs with shaking. The synthesis was monitored by the ninhydrin reaction, which showed nearly quantitative incorporation of all residues except of the first A(Z)aeg residue, which had to be coupled twice. The total coupling yield was about 96% (first coupling, about 89% efficiency).

(b) Cleavage, Purification, and Identification of H-[Taeg]2-Aaeg-Taeg-Caeg-Aaeg-Taeg-Caeg-Taeg-Caeg-Lys-NH2

The protected Boc-[Taeg]2-A(Z)aeg-Taeg-C(Z)aeg-A(Z)aeg-Taeg-C(Z)aeg-Taeg-C(Z)aeg-Lys(ClZ)-MBHA resin was treated as described in Example 17c to yield about 53.4 mg of crude material upon HF cleavage of 166.1 mg dry. Boc-[Taeg]2-A(Z)aeg-Taeg-C(Z)aeg-A(Z)aeg-Taeg-C(Z)aeg-Taeg-C(Z)aeg-Lys(ClZ)-MBHA resin. The crude product (53.4 mg) was purified to give 18.3 mg of H-[Taeg]2-Aaeg-Taeg-Caeg-Aaeg-Taeg-Caeg-Taeg-Caeg-Lys-NH2. For (M+H)+, the calculated m/z value=2780.17 and the measured m/z value=2780.07.

EXAMPLE 74

Hybridization Properties of H-TTA TCA TCT C-Lys-NH$_2$

The title compound hybridized with the following oligonucleotides:

| Oligodeoxynucleotide | pH | Tm(° C.) |
|---|---|---|
| 5'-AAT AGT AGT G-3 | 5 | 31.5† |
| 5'-ATT AGT AGT G-3' | 7.2 | 28.5† |
| 5'-AAT AGT AGT G-3" | 9 | 28.0† |
| 5'-GTG ATG ATA A-3' | 7.2 | 30.5 |
| 5'-GTG ATG ATA A-3' | 9 | 28.0 |

†Low hypochromicity

EXAMPLE 75

Synthesis of a PNA with Two Parallel Strings Tied Together

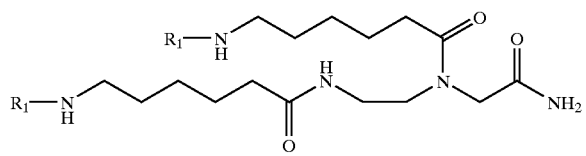

A 375 mg portion of MBHA resin (loading 0.6 mmol/g) was allowed to swell over night in dichloromethane (DCM). After an hour in DMF/DCM, the resin was neutralized by washing 2 times with 5% diisopropylethyla mine in DCM (2 min.), followed by washing with DCM (2ml; 6×1 min.) N,N'-di-Boc-aminoethyl glycine (41,9 mg; 0,132 mmol) disolved in 2 ml DMF was added to the resin, followed by DCC (64.9 mg; 0,315 mmol) dissolved in 1 ml of DCM. After 2.5 hours, the resin was washed with DMF 3 times (1 min.) and once with DCM (1 min.). The unreacted amino groups were then capped by treatment with acetic anhydride/DCM/pyridine (1 ml\2 ml\2 ml) for 72 hours. After washing with DCM (2 ml; 4×1 min), a Kaiser test showed no amino groups were present. The resin was deprotected and washed as described above. This was followed by reaction with 6-(Bocamino)-hexanoic acid DHBT ester (255.8 mg; 67 mmol) dissolved in DMF/DCM 1:1 (4 ml) overnight. After washing and neutraliation, a Kaiser test and an isatin test were performed. Both were negative. After capping, the elongenation of the PNA-chains was performed according to standard procedures for DCC couplings. All Kaiser tests performed after the coupling reactions were negative (Yellow). Qualitative Kaiser tests were done after deprotection of PNA units number 1, 2, 4, and 6. Each test was blue. The PNA oligomers were cleaved and purified by standard procedures. The amount of monomer and DCC used for each coupling was as follows (total volume 4.5 ml):

| Coupling | Monomer(T) | DCC |
|---|---|---|
| 1. | 173 mg | 95 mg |
| 2. | 176 mg | 101 mg |
| 3. | 174 mg | 97 mg |
| 4. | 174 mg | 103 mg |
| 5. | 178 mg | 97 mg |
| 6. | 173 mg | 99 mg |
| 7. | 174 mg | 95 mg |
| 8. | 175 mg | 96 mg |

For the PNA having the Structure (70) where $R_{70}=T_6$, there was 24.5 mg of crude product, which resulted in 6.9 mg. after purification. For the PNA where $R_1=T_8$, there was 28.8 mg of crude product, which resulted in 2.8 mg. after purification. The products had a high tendency of aggregation, as indicated by a complex HPLC chromatogram after a few hours at room temperature in concentration above 1 mg/ml. The PNA-$(T_6)_2$ and PNA-$(T_8)_2$ were hybridised to $(dA)6$ and $(dA)_8$, respectively, with recorded Tm of 42° C. and 59° C., respectively.

EXAMPLE 76

Solid-Phase Synthesis of H-[Taeg]$_5$-Lys(ClZ)-MBHA Resin

The PNA oligomer was assembled onto 500 mg (dry weight) of MBHA resin that had been preswollen overnight in DCM. The resin was initially substituted with approximately 0.15 mmol/g Boc-Lys(ClZ) as determined by quantitative ninhydrin reaction. The stepwise synthesis of the oligomer followed the synthetic protocol described in Example 32 employing 0.077 g (0.2 mmol) BocTaeg-OH and 31.3 μl (0.2 mmol) duisopropyl carbodiimide in 2.0 ml 50% DMF/CH$_2$Cl$_2$ in each coupling. Capping of uncoupled amino groups was carried out before deprotection in each step. All qualitative Kaiser tests were negative indicating near 100% coupling yield.

EXAMPLE 77

Solid-Phase Synthesis of H-[Taeg]$_4$-[apgT]-[Taeg]$_5$-Lys-NH$_2$

Synthesis was initiated on approximately ¼ of the wet H-[Taeg]$_5$-Lys(ClZ)-MBHA resin from Example 76. In situ diisopropyl carbodiimide (DIC) couplings of both Boc-(apgT)-OH and BocTaeg-OH were carried out in 1.2 ml 50% DMF/CH$_2$Cl$_2$ using 119 0.048 g (0.12 mmol) and 0.046 g (0.12 mmol) monomer, respectively, and 18.7 μl (0.12 mmol) diisopropyl carbodiimide in each coupling. All qualitative Kaiser tests were negative, indicating near 100% coupling yield. The PNA oligomer was cleaved and purified by standard procedures. For (M+H)+, the calculated m/z value was 2820.15 and the measured m/z value was 2820.92.

EXAMPLE 78

Solid-Phase Synthesis of H-[Taeg]$_4$-[proT]-[Taeg]$_5$-Lys-NH$_2$

Synthesis was initiated on approximately ¼ of the wet H-[Taeg]$_5$-Lys(ClZ)-MBHA resin from Example 76. In situ diisopropyl carbodiimide couplings of BocTaeg-OH were carried out in 1.2 ml 50% DMF/CH$_2$Cl$_2$ using 0.046 g (0.12 mmol) monomer and 18.7 μl (0.12 mmol) diisopropyl carbodiimide in each coupling. Due to solubility problems, Boc-(proT)-OH 0.048 g (0.12 mmol) was suspended in 2.5 ml 50% DMF/DMSO prior to coupling, the suspension filtered, and approximately 2 ml of the filtrate used in the overnight coupling. All qualitative Kaiser tests were negative, indicating near 100% coupling yield. The PNA oligomer was cleaved and purified by standard procedures.

EXAMPLE 79

Hybridization Properties of H-[Taeg]$_4$-[proT]-[Taeg]$_5$Lys-NH$_2$

| Oligodeoxynucleotide | Tm (° C.) |
| --- | --- |
| 5'-AAA AAA AAA A | 53.5 |
| 5-'AAA AGA AAA A | 44.0 |
| 5'-AAA AAG AAA A | 43.5 |
| 5'-AAA ACA AAA A | 46.5 |
| 5'-AAA AAC AAA A | 46.5 |
| 5'-AAA ATA AAA A | 46.5 |
| 5'-AAA AAT AAA A | 46.0 |

EXAMPLE 80

Solid-Phase Synthesis of H-[Taeg]$_4$-[bC]-[Taeg]$_5$-Lys-NH$_2$

The PNA oligomer was assembled onto 100 mg (dry weight) MBHA resin that had been preswollen overnight in DCM. The resin was initially substituted with approximately 0.25 mmol/g Boc-Lys(ClZ) as determined by quantitative ninhydrin reaction. The stepwise synthesis of the oligomer followed synthetic Protocol 9 employing 0.023 g (0.06 mmol) BocTaeg-OH, 0.062 g (0.12 mmol) BocbC(Z)-OH and 0.012 g (0.06 mmol) DCC in 1.2 ml 50% DMF/CH$_2$Cl$_2$ in each coupling. Capping of uncoupled amino groups was carried out before deprotection in each step. All qualitative Kaiser tests were negative, indicating near 100% coupling yield. The PNA-oligomer was cleaved and purified by standard procedures.

EXAMPLE 81

Hybridization properties of H-T$_4$bCT$_5$-Lys-NH$_2$

| Oligodeoxynucleotide | Tm (° C.) |
| --- | --- |
| 5'-AAA AAA AAA A | 43.5 |
| 5-'AAA AGA AAA A | 58.0 |
| 5'-AAA AAG AAA A | 60.0 |
| 5'-AAA ACA AAA A | 34.5 |
| 5'-AAA AAC AAA A | 34.5 |
| 5'-AAA ATA AAA A | 34.0 |
| 5'-AAA AAT AAA A | 36.0 |

EXAMPLE 82

Stepwise Assembly of H-[Taeg]-[Taeg]-[Taeg]-[Taeg]-[Aaeg]-[Taeg]-[Taeg]-[Taeg]-[Taeg]-[Taeg]-LYS—NH$_2$ Synthesis was initiated on a Boc-[Taeg]$_5$-Lys(ClZ)-MBHA resin (from example 76) that had been preswollen overnight in DCM. The resin resembled approximately 100 mg (dry Weight) of Boc-Lys(ClZ)-MBHA resin (loading 0.15 mmol/g). The incorporation of the monomers followed the protocol of example 55, except for step 5 (incorporation of the BocA(Z)aeg-OH monomer). New step 5 (incorporation of A(Z)aeg) involved addition of 4 equiv. diisopropyl carbodiimide (0.06 mmol; 9.7 µl) and 4 equiv. BocA(Z)aeg-OH (0.06 mmol; 32 mg) dissolved in 0.6 ml DCM/DMF (1:1, v/v) (final concentration of monomer 0.1 M). The coupling reaction was allowed to proceed for 1×15 min. and 1×60 min. (recoupling).

Capping of uncoupled amino groups was only carried out before the incorporation of the BocA(Z)aeg-OH monomer. The coupling reaction was monitored by qualitative ninhydrin reaction (Kaiser test). All qualitative Kaiser tests were negative (straw-yellow color with no coloration of the beads) The PNA oligomer was cleaved and purified by standard procedures.

EXAMPLE 84

Hybridization properties of H-T$_4$AT$_5$-LysNH$_2$

| Oligodeoxynucleotide | Tm (° C.) |
| --- | --- |
| 5'-AAA AAA AAA A | 59.5 |
| 5-'AAA AGA AAA A | 45.0 |
| 5'-AAA AAG AAA A | 45.5 |
| 5'-AAA ACA AAA A | 48.0 |
| 5'-AAA AAC AAA A | 48.0 |
| 5'-AAA ATA AAA A | 52.0 |
| 5'-AAA AAT AAA A | 52.5 |

EXAMPLE 85

Stepwise Assembly of H-[Taeg]-[Taeg]-[Taeg]-[Taeg]-[Gaeg]-[Gaeg]-[Taeg]-[Gaeg]-[Taeg]-[Gaeg]-LYS—NH$_2$ The protected PNA was assembled onto a Boc-Lys(ClZ) modified MBHA resin with a substitution of 0.15 mmol/g. The incorporation of the monomers followed the protocol of example 32, except that the capping step 11 and the washing step 12 were omitted. After the incorporation and deprotection of the first, second, and fourth G(Bzl)aeg-monomer there were some difficulties getting the resin to swell properly. Three hours of shaking in neat DCM gave acceptable swelling. For the incorporation of residues Taeg-4, G(Bzl)aeg-6, and Taeg-7 to Taeg-10, recoupling was necessary to obtain near quantitative coupling yields. Taeg$_4$ (2× in 50 DMF/DCM), Gaeg$_6$ (2× in 50% DMF/DCM), Taeg$_7$ (2× in 50% DMF/DCM, 1× in 50% NMP/DCM and 1× in neat DCM), Taeg$_8$ (1× in 50% DMF/DCM and 2× in neat DCM), Taeg$_9$ (2× in 50% DMF/DCM), Taeg$_{10}$(2× in 50% DMF/DCM). All qualitative Kaiser tests were negative (straw-yellow color with no coloration of the beads). The PNA oligomer was cleaved and purified by standard procedures

EXAMPLE 86

Hybridization Properties of Crude (approx. 50%) H-T$_4$G$_2$TGTG-LysNH$_2$

| Oligodeoxynucleotide | Tm |
| --- | --- |
| 5'-A4C2ACAC | 38 |
| 5'-CACAC2A4 | 55 |

EXAMPLE 87

Large Scale Solid-Phase Synthesis of H-[Taeg]$_6$-Lys-NH$_2$, H-[Taeg]$_7$-Lys-NH$_2$, H-[Taeg]$_8$-Lys-NH$_2$, H-[Taeg]$_9$-Lys-NH$_2$, and H-[Taeg]$_{10}$-Lys-NH$_2$ (a) Stepwise Assembly of Boc-[Taeg]$_{10}$-Lys(ClZ)-MBHA Resin and Shorter Fragments About 9 g of wet Boc-[Taeg]$_3$-Lys(ClZ)-MBHA (see, Example 19b) resin was placed in a 60 ml SPPS reaction vessel. Boc-[Taeg]$_5$-Lys(ClZ)-MBHA resin was assembled by single coupling of both residues with 0.15 M of BocTaeg-OPfp in 10 ml neat CH$_2$Cl$_2$ ("Synthetic Protocol 8"). Both coupling reactions were allowed to proceed overnight. The synthesis was monitored by the ninhydrin reaction, which showed close to quantitative incorporation of both residues. After deprotection of the N-terminal Boc group, about 4.5 g of H-[Taeg]$_5$-Lys(ClZ)-MBHA was placed in a 20 ml SPPS reaction vessel and elongated to Boc-[Taeg]$_8$-Lys(ClZ)-MBHA by single in situ DCC coupling of all residues (close to quantitative, except for residue number eight) overnight with 0.2 M of BocTaeg-OH together with 0.2 M DCC in 7.5 ml neat CH$_2$Cl$_2$ ("Synthetic Protocol 9"). Before coupling of Taeg residues number seven and eight, respectively, small portions of H-[Taeg]$_6$-Lys(ClZ)-MBHA and H-[Taeg]$_7$-Lys (ClZ)-MBHA, respectively, were taken out for HF cleavage.

Taeg residue number eight was coupled twice (overnight) to give close to quantitative incorporation. After deprotection of the N-terminal Boc group, a large portion of H-[Taeg]$_8$-Lys(ClZ)-MBHA was taken out for HF cleavage. Boc-[Taeg]$_{10}$-Lys(ClZ)-MBHA resin was assembled by double in situ DCC coupling of 0.16 M BocTaeg-OH, together with 0.16 M DCC in 2.0 ml 50% DMF/CH$_2$Cl$_2$ ("Synthetic Protocol" 9). Before coupling of the final residue, a small portion of H-[Taeg]$_9$-Lys(ClZ)-MBHA was taken out for HF cleavage.

(b) Cleavage, Purification, and Identification of H-[Taeg]$_6$-Lys-NH$_2$

The protected Boc-[Taeg]$_6$-Lys(ClZ)-MBHA resin was treated as described in Example 17c to yield about 14.0 mg of crude material upon HF cleavage of 52.4 mg dry H-Taeg]$_6$-Lys(ClZ)-MBHA resin. The crude product was not purified (about 99% purity).

(c) Cleavage, Purification, and Identification of H-[Taeg]$_7$-Lys-NH$_2$

The protected Boc-[Taeg]$_7$-Lys(ClZ)-MBHA resin was treated as described in Example 17c to yield about 5.2 m g of crude material upon HF cleavage of 58.4 mg dry H-Taeg]$_7$-Lys(ClZ)-MBHA resin.

(d) Cleavage, Purification, and Identification of H-[Taeg]$_8$-Lys-NH$_2$

The protected Boc-[Taeg]$_8$-Lys(ClZ)-MBHA resin was treated as described in Example 17c to yield about 114 mg of crude material upon HF cleavage of about 604 mg dry H-Taeg]$_8$-Lys(ClZ)-MBHA resin.

(e) Cleavage, Purification, and Identification of H-[Taeg]$_9$-Lys-NH$_2$

The protected Boc-[Taeg]$_9$-Lys(ClZ)-MBHA resin was treated as described in Example 17c to yield about 19.3 mg of crude material upon HF cleavage of 81.0 mg dry H-Taeg]$_9$-Lys(ClZ)-MBHA resin.

(f) Cleavage, Purification, and Identification of H-[Taeg]$_{10}$-Lys-NH$_2$

The protected Boc-[Taeg]$_{10}$-Lys(ClZ)-MBHA resin was treated as described in Example 17c to yield about 141 mg of crude material upon HF cleavage of about 417 mg dry H-Taeg]$_{10}$-Lys(ClZ)-MBHA resin.

(g) Synthetic Protocol 8 (General Protocol)

(1) Boc-deprotection with TFA/CH$_2$Cl$_2$ (1:1, v/v), 3×1 min and 1×30 min; (2) washing with CH$_2$Cl$_2$, 6×1 min; (3) neutralization with DIEA/CH$_2$Cl$_2$ (1:19, v/v), 3×2 min; (4) washing with CH$_2$Cl$_2$, 6×1 min, and drain for 1 min; (5) at some stages of the synthesis, 2–5 mg sample of PNA-resin is taken out and dried thoroughly for a ninhydrin analysis to determine the substitution; (6) addition of Boc-protected PNA monomer (Pfp ester); the coupling reaction was allowed to proceed for a number of hours with shaking; (7) washing with DMF, 1×2 min; (8) washing with CH$_2$Cl$_2$, 4×1 min; (9) neutralization with DIEA/CH$_2$Cl$_2$ (1:19, v/v), 2×2 min; (10) washing with CH$_2$Cl$_2$, 6×1 min; (11) occasionally, 2–5 mg sample of protected PNA-resin is taken out and dried thoroughly for a ninhydrin analysis to determine the extent of coupling; (12) at some stages of the synthesis, unreacted amino groups are blocked by acetylation with a mixture of acetic anhydride/pyridine/CH$_2$Cl$_2$ (1:1:2, v/v/v) for 2 h followed by washing with CH$_2$Cl$_2$, 6×1 min, and, occasionally, ninhydrin analysis.

EXAMPLE 88

Solid-Phase Synthesis of H-[Taeg]4-Caeg-[Taeg]5-Lys-NH$_2$ (a) Stepwise Assembly of Boc-[Taeg]4-C[Z]aeg-[Taeg]5-Lys(ClZ)-MBHA Resin About 1 g of wet Boc-[Taeg]5-Lys(ClZ)-MBHA resin was placed in a 5 ml SPPS reaction vessel. Boc-[Taeg]4-C[Z]aeg-[Taeg]5-Lys(ClZ)-MBHA resin was assembled by in situ DCC coupling of all residues utilizing 0.16 M of BocC[Z]aeg-OH together with 0.16 M DCC in 2.0 ml 50% DMF/CH$_2$Cl$_2$ or 0.16 M BocTaeg-OH together with 0.16 M DCC in 2.0 ml 50% DMF/CH$_2$Cl$_2$ ("Synthetic Protocol 9"). Each coupling reaction was allowed to proceed for a total of 20–24 hrs with shaking. The synthesis was monitored by the ninhydrin reaction, which showed about 98% incorporation of C[Z]aeg and close to quantitative incorporation of all the Taeg residues.

(b) Cleavage, Purification, and Identification of H-[Taeg]4-C[Z]aeg-[Taeg]5-Lys-NH$_2$ The protected Boc-[Taeg]4-C[Z]aeg-[Taeg]5-Lys(ClZ)-MBHA resin was treated as described in Example 17c to yield about 22.5 mg of crude material upon HF cleavage of 128.2 mg dry H-[Taeg]4-C[Z]aeg-[Taeg]5-Lys(ClZ)-MBHA resin. Crude product (5.8 mg) was purified to give 3.1 mg of H-[Taeg]4-Caeg-[Taeg]5-Lys-NH$_2$.

(c) Synthetic Protocol 9 (General Protocol)

(1) Boc-deprotection with TFA/CH$_2$Cl$_2$ (1:1, v/v), 3×1 min and 1×30 min; (2) washing with CH$_2$Cl$_2$, 6×1 min; (3) neutralization with DIEA/CH$_2$Cl$_2$ (1:19, v/v), 3×2 min; (4) washing with CH$_2$Cl$_2$, 6×1 min, and drain for 1 min; (5) at some stages of the synthesis, 2–5 mg sample of PNA-resin is taken out and dried thoroughly for a ninhydrin analysis to determine the substitution; (6) addition of Boc-protected PNA monomer (free acid) in X ml DMF followed by addition of DCC in X ml CH$_2$Cl$_2$; the coupling reaction was allowed to proceed for a total of Y hrs shaking; (7) washing with DMF, 1×2 min; (8) washing with CH$_2$Cl$_2$, 4×1 min; (9) neutralization with DIEA/CH$_2$Cl$_2$ (1:19, v/v), 2×2 min; (10) washing with CH$_2$Cl$_2$, 6×1 min; (11) occasionally, 2–5 mg sample of protected PNA-resin is taken out and dried thoroughly for a ninhydrin analysis to determine the extent of coupling; (12) at some stages of the synthesis, unreacted amino groups are blocked by acetylation with a mixture of acetic anhydride/pyridine/CH$_2$Cl$_2$ (1:1:2, v/v/v) for 2 h followed by washing with CH$_2$Cl$_2$, 6×1 min, and, occasionally, ninhydrin analysis.

EXAMPLE 89

Solid-Phase Synthesis of H-[Taeg]4-(NBaeg)-[Taeg]5-Lys-NH$_2$. (NB=COCH3)

(a) Stepwise Assembly of Boc-[Taeg]4-(NBaeg)-[Taeg]5-Lys(ClZ)-MBHA Resin

About 1 g of wet Boc-[Taeg]5-Lys(ClZ)-MBHA resin was placed in a 5 ml SPPS reaction vessel. Boc-[Taeg]4-(NBaeg)-[Taeg]5-Lys(ClZ)-MBHA resin was assembled by in situ DCC coupling utilizing 0.16 M of Boc(NBaeg)-OH together with 0.16 M DCC in 2.0 ml neat $CH_2Cl_2$ or 0.16 M BocTaeg-OH together with 0.16 M DCC in 2.0 ml 50% $DMF/CH_2Cl_2$ ("Synthetic Protocol 9"). Each coupling reaction was allowed to proceed for a total of 20–24 hrs with shaking. The NBaeg residue was coupled three times and the Taeg residues were all coupled once. The synthesis was monitored by the ninhydrin reaction which showed >99% total incorporation of NBaeg (about 88% after the first coupling and about 93% after the second coupling) and close to quantitative incorporation of all the Taeg residues.

(b) Cleavage, Purification, and Identification of H-[Taeg]4-(NBaeg)-[Taeg]5-Lys-$NH_2$ The protected Boc-[Taeg]4-(NBaeg)-[Taeg]5-Lys(ClZ)-MBHA resin was treated as described in Example 17c to yield about 33.6 mg of crude material upon HF cleavage of 108.9 mg dry H-[Taeg]4-(NBaeg)-[Taeg]5-Lys(ClZ)-MBHA resin. Crude product (20.6 mg) was purified to give 4.6 mg of H-[Taeg]4-(NBaeg)-[Taeg]5-Lys-$NH_2$. For (M+H)+, the calculated m/z value was 2683.12 and the measured m/z value was 2683.09.

EXAMPLE 90

Solid-Phase Synthesis of H-[Taeg]4-aeg-[Taeg]5-Lys-$NH_2$ (a) Stepwise Assembly of Boc-[Taeg]4-aeg-[Taeg]5-Lys(ClZ)-MBHA Resin About 1 g of wet Boc-[Taeg]5-Lys(ClZ)-MBHA resin was placed in a 5 ml SPPS reaction vessel. Boc-[Taeg]4-aeg-[Taeg]5-Lys(ClZ)-MBHA resin was assembled by in situ DCC single coupling of all residues utilizing: (1) 0.16 M of Bocaeg-OH together with 0.16 M DCC in 2.0 ml 50% $DMF/CH_2Cl_2$ or (2) 0.16 M BocTaeg-OH together with (2) 0.16 M DCC in 2.0 ml 50% $DMF/CH_2Cl_2$ ("Synthetic Protocol 9"). Each coupling reaction was allowed to proceed for a total of 20–24 hrs with shaking. The synthesis was monitored by the ninhydrin reaction, which showed close to quantitative incorporation of all the residues.

(b) Cleavage, Purification, and Identification of H-[Taeg]4-aeg-[Taeg]5-Lys-$NH_2$ The protected Boc-[Taeg]4-aeg-[Taeg]5-Lys(ClZ)-MBHA resin was treated as described in Example 17c to yield about 22.2 mg of crude material upon HF cleavage of 126.0 mg dry H-[Taeg]4-aeg-[Taeg]5-Lys(ClZ)-MBHA resin. Crude product (22.2 mg) was purified to give 7.6 mg of H-[Taeg]4-aeg-[Taeg]5-Lys-$NH_2$. For (M+H)+, the calculated m/z value was 2641.11 and the measured m/z value was 2641.16.

EXAMPLE 91

Solid-Phase Synthesis of H-[Taeg]4-Gly-[Taeg]5-Lys-$NH_2$ (a) Stepwise Assembly of Boc-[Taeg]4-Gly-[Taeg]5-Lys(ClZ)-MBHA Resin About 1 g of wet Boc-[Taeg]5-Lys(ClZ)-MBHA resin was placed in a 5 ml SPPS reaction vessel. Boc-[Taeg]4-Gly-[Taeg]5-Lys(ClZ)-MBHA resin was assembled by in situ DCC single coupling of all residues utilizing: (1) 0.16 M of BocGly-OH together with 0.16 M DCC in 2.0 ml 50% $DMF/CH_2Cl_2$ or (2) 0.16 M BocTaeg-OH together with 0.16 M DCC in 2.0 ml 50% $DMF/CH_2Cl_2$ ("Synthetic Protocol 9"). Each coupling reaction was allowed to proceed for a total of 20–24 hrs with shaking. The synthesis was monitored by the ninhydrin reaction, which showed close to quantitative incorporation of all the residues.

(b) Cleavage, Purification, and Identification of H-[Taeg]4-Gly-[Taeg]5-Lys-$NH_2$ The protected Boc-[Taeg]4-Gly-[Taeg]5-Lys(ClZ)-MBHA resin was treated as described in Example 18c to yield about 45.0 mg of crude material upon HF cleavage of 124.1 mg dry H-[Taeg]4-Gly-[Taeg]5-Lys(ClZ)-MBHA resin. Crude product (40.4 mg) was purified to give 8.2 mg of H-[Taeg]4-Gly-[Taeg]5-Lys-$NH_2$.

EXAMPLE 92

Solid-Phase Synthesis of H-[Taeg]4-Gly2-[Taeg]5-Lys-$NH_2$ (a) Stepwise Assembly of Boc-[Taeg]4-Gly2-[Taeg]5-Lys (ClZ)-MBHA Resin About 1 g of wet Boc-[Taeg]5-Lys(ClZ)-MBHA resin was placed in a 5 ml SPPS reaction vessel. Boc-[Taeg]4-[C[Z]aeg]2-Taeg-C[Z]aeg-Taeg-C[Z]aeg-Lys(ClZ)-MBHA resin was assembled by in situ DCC single coupling of all residues utilizing: (1) 0.16 M of BocGly-OH together with 0.16 M DCC in 2.0 ml 50% $DMF/CH_2Cl_2$ or (2) 0.16 M BocTaeg-OH together with 0.16 M DCC in 2.0 ml 50% $DMF/CH_2Cl_2$ ("Synthetic Protocol 9"). Each coupling reaction was allowed to proceed for a total of 20–24 hrs with shaking. The synthesis was monitored by the ninhydrin reaction, which showed close to quantitative incorporation of all the residues.

(b) Cleavage, Purification, and Identification of H-[Taeg]4-Gly2-[Taeg]5-Lys-$NH_2$ The protected Boc-[Taeg]4-Gly2-[Taeg]5-Lys(ClZ)-MBHA resin was treated as described in Example 17c to yield about 32.6 mg of crude material upon HF cleavage of 156.6 mg dry H-[Taeg]4-Gly2-[Taeg]5-Lys(ClZ)-MBHA resin. Crude product (30 mg) was purified to give 7.8 mg of H-[Taeg]4-Gly2-[Taeg]5-Lys-$NH_2$. For (M+H)+, the calculated m/z value was 2655.09 and the measured m/z value was 2655.37.

EXAMPLE 93

Solid-Phase Synthesis of H-[Taeg]4-[Caeg]2-Taeg-Caeg-Taeg-Caeg-Lys-$NH_2$ (a) Stepwise Assembly of Boc-[Taeg]4-[C[Z]aeg]2-Taeg-C[Z]aeg-Taeg-C[Z]aeg-Lys(ClZ)-MBHA Resin About 1.5 g of wet Boc-Lys(ClZ)-MBHA (0.28 mmol Lys/g) resin was placed in a 5 ml SPPS reaction vessel. Boc-[Taeg]4-[C[Z]aeg]2-Taeg-C[Z]aeg-Taeg-C[Z]aeg-Lys(ClZ)-MBHA resin was assembled by in situ DCC single coupling of all residues utilizing: (1) 0.16 M of BocC[Z]-OH together with 0.16 M DCC in 2.0 ml 50% $DMF/CH_2Cl_2$ or (2) 0.16 M BocTaeg-OH together with 0.16 M DCC in 2.0 ml 50% $DMF/CH_2Cl_2$ ("Synthetic Protocol 9"). Each coupling reaction was allowed to proceed for a total of 20–24 hrs with shaking. The synthesis was monitored by the ninhydrin reaction, which showed close to quantitative incorporation of all the residues.

(b) Cleavage, Purification, and Identification of H-[Taeg]4-[Caeg]2-Taeg-Caeg-Taeg-Caeg-Lys-$NH_2$ The protected Boc-[Taeg]4-[C[Z]aeg]2-Taeg-C[Z]aeg-Taeg-C[Z]aeg-Lys(ClZ)-MBHA resin was treated as described in Example 17c to yield about 52.1 mg of crude material upon HF cleavage of 216.7 mg dry H-[Taeg]4-[C[Z]aeg]2-Taeg-C[Z]aeg-Taeg-C[Z]aeg-Lys(ClZ)-MBHA resin. Crude product (30.6 mg) was purified to give 6.2 mg of H-[Taeg]4-[Caeg]2-Taeg-Caeg-Taeg-Caeg-Lys-$NH_2$. For (M+H)+ the calculated m/z value was 2747.15 and the measured m/z value was 2746.78.

EXAMPLE 94

Solid-Phase Synthesis of H-Caeg-Taeg-Caeg-Taeg-[Caeg]3-Taeg-Caeg-Taeg-Lys-NH$_2$ (a) Stepwise Assembly of Boc-C[Z]aeg-Taeg-C[Z]aeg-Taeg-[C[Z]aeg]3-Taeg-C[Z]aeg-Taeg-Lys(ClZ)-MBHA Resin About 1.5 g of wet Boc-Lys(ClZ)-MBHA (0.28 mmol Lys/g) resin was placed in a 5 ml SPPS reaction vessel. Boc-C[Z]aeg-Taeg-C[Z]aeg-Taeg-[C[Z]aeg]3-Taeg-C[Z]aeg-Taeg-Lys(ClZ)-MBHA resin was assembled by in situ DCC single coupling of all residues utilizing: (1) 0.16 M of BocC[Z]-OH together with 0.16 M DCC in 2.0 ml 50% DMF/CH$_2$Cl$_2$ or (2) 0.16 M BocTaeg-OH together with 0.16 M DCC in 2.0 ml 50% DMF/CH$_2$Cl$_2$ ("Synthetic Protocol 9"). Each coupling reaction was allowed to proceed for a total of 20–24 hrs with shaking. The synthesis was monitored by the ninhydrin reaction, which showed close to quantitative incorporation of all the residues.

(b) Cleavage, Purification, and Identification of H-Caeg-Taeg-Caeg-Taeg-[Caeg]3-Taeg-Caeg-Taeg-Lys-NH 2

The protected Boc-C[Z]aeg-Taeg-C[Z]aeg-Taeg-[C[Z]aeg]3-Taeg-C[Z]aeg-TaegLys(ClZ)-MBHA resin was treated as described in Example 17c to yield about 56.1 mg of crude material upon HF cleavage of 255.0 mg dry H-C[Z]aeg-Taeg-C[Z]aeg-Taeg-[C[Z]aeg]3-Taeg-C[Z]aeg-TaegLys(ClZ)-MBHA resin. Crude product (85.8 mg) was purified to give 46.2 mg of H-Caeg-Taeg-Caeg-Taeg-[Caeg]3-Taeg-Caeg-Taeg-LysNH$_2$. For (M+H)+ the calculated m/z value was 2717.15 and the measured m/z value was 2716.93.

EXAMPLE 95

Solid-Phase Synthesis of H-[Taeg]2-[Caeg]3-[Taeg]2-[Caeg]2-Lys-NH$_2$, H-Caeg-[Taeg]2-[Caeg]3-[Taeg]2-[Caeg]2-Lys-NH$_2$, and H-Tyr-[Taeg]2-[Caeg]3-[Taeg]2-[Caeg]2-Lys-NH$_2$ (a) Stepwise Assembly of Boc-[Taeg]2-[C(Z)aeg]3-[Taeg]2-[C(Z)aeg]2-Lys(ClZ)-MBHA Resin, Boc-Caeg-[Taeg]2-[C(Z)aeg]3-[Taeg]2-[C(Z)aeg]2-Lys(ClZ)-MBHA Resin, and Boc-Tyr(BrZ)-[Taeg]2-[C(Z)aeg]3-[Taeg]2-[C(Z)aeg]2-Lys(ClZ)-MBHA Resin About 3 g of wet Boc-Lys(ClZ)-MBHA (0.28 mmol Lys/g) resin was placed in a 20 ml SPPS reaction vessel. Boc-[Taeg]2-[C(Z)aeg]3-[Taeg]2-[C(Z)aeg]2-Lys(ClZ)-MBHA resin was assembled by in situ DCC single coupling of all residues utilizing: (1) 0.16 M of BocC[Z]-OH together with 0.16 M DCC in 3.0 ml 50% DMF/CH$_2$Cl$_2$ or (2) 0.16 M BocTaeg-OH together with 0.16 M DCC in 3.0 ml 50% DMF/CH$_2$Cl$_2$ ("Synthetic Protocol 9"). Each coupling reaction was allowed to proceed for a total of 20–24 hrs with shaking. The synthesis was monitored by the ninhydrin reaction, which showed close to quantitative incorporation of all the residues. After deprotection of the N-terminal Boc group, half of the PNA-resin was coupled quantitatively onto Tyr(BrZ)-OH and a small portion was coupled quantitatively onto one more Caeg residue. Both couplings employed the above-mentioned synthetic protocol.

(b) Cleavage, Purification, and Identification of H-[Taeg]2-[Caeg]3-[Taeg]2-[Caeg]2-Lys-NH$_2$ The protected Boc-[Taeg]2-[C(Z)aeg]3-[Taeg]2-[C(Z)aeg]2-Lys(ClZ)-MBHA resin was treated as described in Example 17c to yield about 50.9 mg of crude material upon HF cleavage of 182.5 mg dry H-[Taeg]2-[C(Z)aeg]3-[Taeg]2-[C(Z)aeg]2-Lys(ClZ)-MBHA resin. Crude product (50.9 mg) was purified to give 13.7 mg of H-[Taeg]2-[Caeg]3-[Taeg]2-[Caeg]2-LysNH$_2$. For (M+H)+ the calculated m/z value was 2466.04; the m/z value was not measured.

(c) Cleavage, Purification, and Identification of H-Tyr-[Taeg]2-[Caeg]3-[Taeg]2-[Caeg]2-Lys-NH$_2$ The protected Boc-Tyr(BrZ)-[Taeg]2-[C(Z)aeg]3-[Taeg]2-[C(Z)aeg]2-Lys(ClZ)-MBHA resin was treated as described in Example 17c to yield about 60.8 mg of crude material upon HF cleavage of 188.8 mg dry H-Tyr(BrZ)-[Taeg]2-[C(Z)aeg]3-[Taeg]2-[C(Z)aeg]2-Lys(ClZ)-MBHA resin. Crude product (60.8 mg) was purified to give 20.7 mg of H-Tyr-[Taeg]2-[Caeg]3-[Taeg]2-[Caeg]2-LysNH$_2$. For (M+H)+ the calculated m/z value was 2629.11 and the measured m/z value was 2629.11.

(d) Cleavage, Purification, and Identification of H-Caeg-[Taeg]2-[Caeg]3-[Taeg]2-[Caeg]2-Lys-NH$_2$ The protected Boc-C(Z)aeg-[Taeg]2-[C(Z)aeg]3-[Taeg]2-[C(Z)aeg]2-Lys(ClZ)-MBHA resin was treated as described in Example 17c to yield about 11.7 mg of crude material upon HF cleavage of 42.0 mg dry H-C(Z)aeg-[Taeg]2-[C(Z)aeg]3-[Taeg]2-[C(Z)aeg]2-Lys(ClZ)-MBHA resin. Crude product (11.6 mg) was purified to give 3.1 mg of H-Caeg-[Taeg]2-[Caeg]3-[Taeg]2-[Caeg]2-LysNH$_2$. For (M+H)+ the calculated m/z value was 2717.15; the m/z value was not measured.

EXAMPLE 96

Solid-Phase Synthesis of H-[Caeg]2-[Taeg]2-[Caeg]3-[Taeg]2-Lys-NH$_2$, H-Taeg-[Caeg]2-[Taeg]2-[Caeg]3-[Taeg]2-Lys-NH$_2$, and H-Tyr-[Caeg]2-[Taeg]2-[Caeg]3-[Taeg]2-Lys-NH$_2$ (a) Stepwise Assembly of Boc-[C(Z)aeg]2-[Taeg]2-[C(Z)aeg]3-[Taeg]2-Lys(ClZ)-MBHA Resin, Boc-Taeg-[C(Z)aeg]2-[Taeg]2-[C(Z)aeg]3-[Taeg]2-Lys(ClZ)-MBHA Resin, and Boc-Tyr(BrZ)-[C(Z)aeg]2-[Taeg]2-[C(Z)aeg]3-[Taeg]2-Lys(ClZ)-MBHA Resin About 3 g of wet Boc-Lys(ClZ)-MBHA (0.28 mmol Lys/g) resin was placed in a 20 ml SPPS reaction vessel. Boc-[Taeg]2-[C(Z)aeg]3-[Taeg]2-[C(Z)aeg]2-Lys(ClZ)-MBHA resin was assembled by in situ DCC single coupling of all residues utilizing: (1) 0.16 M of BocC[Z]-OH together with 0.16 M DCC in 3.0 ml 50% DMF/CH$_2$Cl$_2$ or (2) 0.16 M BocTaeg-OH together with 0.16 M DCC in 3.0 ml 50% DMF/CH$_2$Cl$_2$ ("Synthetic Protocol 9"). Each coupling reaction was allowed to proceed for a total of 20–24 hrs with shaking. The synthesis was monitored by the ninhydrin reaction, which showed close to quantitative incorporation of all the residues. After deprotection of the N-terminal Boc group, half of the PNA-resin was coupled quantitatively onto Tyr(BrZ)-OH and a small portion was coupled quantitatively onto one more Taeg residue. Both couplings employed the above-mentioned synthetic protocol.

(b) Cleavage, Purification, and Identification of H-[C(Z)aeg]2-[Taeg]2-[C(Z)aeg]3-[Taeg]2-Lys-NH$_2$ The protected Boc-[C(Z)aeg]2-[Taeg]2-[C(Z)aeg]3-[Taeg]2-Lys(ClZ)-MBHA resin was treated as described in Example 17c to yield about 57.6 mg of crude material upon HF cleavage of 172.7 mg dry H-[C(Z)aeg]2-[Taeg]2-[C(Z)aeg]3-[Taeg]2-Lys(ClZ)-MBHA resin. Crude product (57.6 mg) was purified to give 26.3 mg of H-[Caeg]2-[Taeg]2-[Caeg]3-[Taeg]2-Lys-NH$_2$. For (M+H)+ the calculated m/z value was 2466.04; the m/z value was not measured.

(c) Cleavage, Purification, and Identification of H-Tyr-[C(Z)aeg]2-[Taeg]2-[C(Z)aeg]3-[Taeg]2-Lys-NH$_2$ The protected Boc-Tyr(BrZ)-[C(Z)aeg]2-[Taeg]2-[C(Z)aeg]3-[Taeg]2-Lys(ClZ)-MBHA resin was treated as described in Example 17c to yield about 57.6 mg of crude material upon HF cleavage of 172.7 mg dry H-Tyr(BrZ)-[C(Z)aeg]2-[Taeg]2-[C(Z)aeg]3-[Taeg]2-Lys(ClZ)-MBHA resin. Crude product (47.1 mg) was purified to give 13.4 mg of H-Tyr-[Caeg]2-[Taeg]2-[Caeg]3-[Taeg]2-Lys-NH$_2$. For (M+H)+ the calculated m/z value was 2629.11 and the measured m/z value was 2629.11.

(d) Cleavage, Purification, and Identification of H-Taeg-[C(Z)aeg]2-[Taeg]2-[C(Z)aeg]3-[Taeg]2-Lys-NH$_2$ The protected Boc-Taeg-[C(Z)aeg]2-[Taeg]2-[C(Z)aeg]3-[Taeg]2-Lys(ClZ)-MBHA resin was treated as described in Example 17c to yield about 53.4 mg of crude material upon HF cleavage of 42.4 mg dry H-Taeg-[C(Z)aeg]2-[Taeg]2-[C(Z)aeg]3-[Taeg]2-Lys(Cl Z)-MBHA resin. Crude product (11.9 mg) was purified to give 4.3 mg of H-Taeg-[Caeg]2-[Taeg]2-[Caeg]3-[Taeg]2-Lys-NH$_2$. For (M+H)+ the calculated m/z value was 2732.15; the m/z value was not measured.

(e) Synthetic Protocol 10 (General Protocol)

Same protocol as "Synthetic Protocol 9", except that DCC has been replaced with DIC.

EXAMPLE 97

Synthesis of the Backbone Moiety for Scale Up by Reductive Amination (a) Preparation of (bocamino)acetaldehyde 3-Amino-1,2-propanediol (80.0 g; 0.88 mol) was dissolved in water (1500 ml) and the solution was cooled to 4° C., whereafter Boc anhydride (230 g; 1.05 mol) was added at once. The solution was gently heated to room temperature with a water bath. The pH was kept at 10.5 by the dropwise addition of sodium hydroxide. Over the course of the reaction a total of 70.2 g NaOH, dissolved in 480 ml water, was added. After stirring overnight, ethyl acetate (1000 ml) was added and the mixture was cooled to 0° C. and the pH was adjusted to 2.5 by the addition of 4 M hydrochloric acid. The ethyl acetate layer was removed and the acidic aqueous solution was extracted with more ethyl acetate (8×500 ml). The combined ethyl acetate solution was reduced to a volume of 1500 ml using a rotary evaporator. The resulting solution was washed with half saturated potassium hydrogen sulphate (1500 ml) and then with saturated sodium chloride. It then was dried over magnesium sulphate and evaporated to dryness, in vacuo. Yield. 145.3 g (86%)

3-Bocamino-1,2-propanediol (144.7 g; 0.757 mol) was suspended in water (750 ml) and potassium periodate (191.5 g; 0.833 mol) was added. The mixture was stirred under nitrogen for 2.5 h and the precipitated potassium iodate was removed by filtration and washed once with water (100 ml). The aqueous phase was extracted with chloroform (6×400 ml). The chloroform extracts were dried and evaporated to dryness, in vacuo. Yield 102 g (93%) of an oil. The (bocamino)acetaldehyde was purified by kugelrohr distillation at 84° C. and 0.3 mmHg in two portions. The yield 79 g (77%) of a colorless oil.

(b) Preparation of (N'-bocaminoethyl)glycine Methyl Ester

Palladium on carbon (10%; 2.00 g) was added to a solution of (bocamino)acetaldehyde (10.0 g; 68.9 mmol) in methanol (150 ml) at 0° C. Sodium acetate (11.3 g; 138 mmol) in methanol (150 ml), and glycine methyl ester hydrochloride (8.65 g; 68.9 mmol) in methanol (75 ml) then were added. The mixture was hydrogenated at atmospheric pressure for 2.5 h, then filtered through celite and evaporated to dryness, in vacuo. The material was redissolved in water (150 ml) and the pH was adjusted to 8.0 with 0.5 N NaOH. The aqueous solution was extracted with methylene chloride (5×150 ml). The combined extracts were dried over sodium sulphate and evaporated to dryness, in vacuo. This resulted in 14.1 g (88%) of (N'-bocaminoethyl)glycine methyl ester. The crude material was purified by kugelrohr destination at 120° C. and 0.5 mmHg to give 11.3 g (70%) of a colorless oil. The product had a purity that was higher than the material produced in example 26 according to tlc-analysis (10% methanol in methylene chloride).

Alternatively, sodium cyanoborohydride can be used as reducing agent instead of hydrogen (with Pd(C) as catalyst), although the yield (42%) was lower.

(c) Preparation of (N'-bocaminoethyl)glycine Ethyl Ester

The title compound was prepared by the above procedure with glycine ethyl ester hydrochloride substituted for glycine methyl ester hydrochloride. Also, the solvent used was ethanol. The yield was 78%.

EXAMPLE 98

Solid-Phase Synthesis of H-Tyr-[Taeg]$_{10}$-Lys-NH$_2$ (a) Stepwise Assembly of Boc-Tyr(BrZ)-[Taeg]$_{10}$-Lys(ClZ)-MBHA Resin About 0.2 g of wet Boc-[Taeg]$_{10}$-Lys(ClZ)-MBHA resin was placed in a 5 ml SPPS reaction vessel. Boc-Tyr(BrZ)-[Taeg]$_{10}$-Lys(ClZ)-MBHA resin was assembled by standard in situ DCC coupling utilizing 0.32 M of BocCTyr (BrZ)-OH together with 0.32 M DCC in 3.0 ml neat CH$_2$Cl$_2$ overnight. The ninhydrin reaction showed about 97% incorporation of BocTyr(BrZ).

(b) Cleavage, Purification, and Identification of H-Tyr-[Taeg]$_{10}$-Lys-NH$_2$ The protected Boc-Tyr(BrZ)-[Taeg]$_{10}$-Lys(ClZ)-MBHA resin was treated as described in Example 17c to yield about 5.5 mg of crude material upon HF cleavage of 20.7 mg dry H-Tyr(BrZ)-[Taeg]$_{10}$-Lys(ClZ)-MBHA resin. The crude product was purified to give 2.5 mg of H-Tyr-[Taeg]$_{10}$-Lys-NH$_2$.

EXAMPLE 99

Solid-Phase Synthesis of Dansyl-[Taeg]$_{10}$-Lys-NH$_2$ (a) Stepwise Assembly of Dansyl-[Taeg]$_{10}$-Lys(ClZ)-MBHA Resin About 0.3 g of wet Boc-[Taeg]$_{10}$-Lys(ClZ)-MBHA resin was placed in a 5 ml SPPS reaction vessel. Dansyl-[Taeg]$_{10}$-Lys(ClZ)-MBHA resin was assembled by coupling of 0.5 M dansyl-Cl in 2.0 ml neat pyridine overnight. The ninhydrin reaction showed about 95% incorporation of dansyl.

(b) Cleavage, Purification, and Identification of Dansyl-[Taeg]$_{10}$-Lys-NH$_2$ The protected dansyl-[Taeg]$_{10}$-Lys(ClZ)-MBHA resin was treated as described in Example 17c to yield about 12 mg of crude material upon HF cleavage of 71.3 mg dry dansyl-[Taeg]$_{10}$-Lys(ClZ)-MBHA resin. The crude product was purified to give 5.4 mg of dansyl-[Taeg]$_{10}$-Lys-NH$_2$.

EXAMPLE 100

Solid-Phase Synthesis of Gly-Gly-His-[Taeg]$_{10}$-Lys-NH$_2$ (a) Stepwise Assembly of Boc-Gly-Gly-His(Tos)-[Taeg]$_{10}$-Lys(ClZ)-MBHA Resin About 0.05 g of Boc-[Taeg]$_{10}$-Lys(ClZ)-MBHA resin was placed in a 5 ml SPPS reaction vessel. Boc-Gly-Gly-His(Tos)-[Taeg]$_{10}$-Lys(ClZ)-MBHA resin was assembled by standard double in situ DCC coupling of Boc-protected amino acid (0.1 M) in 2.5 ml 25% DMF/CH$_2$Cl$_2$, except for the first coupling of BocHis(Tos), which was done by using a preformed symmetrical anhydride (0.1M) in 25% DMF/CH$_2$Cl$_2$. All couplings were performed overnight and ninhydrin reactions were not carried out.

(b) Cleavage, Purification, and Identification of Gly-Gly-His-[Taeg]$_{10}$-Lys-NH$_2$ The protected Boc-Gly-Gly-His(Tos)-[Taeg]$_{10}$-Lys(ClZ)-MBHA resin was treated as described in Example 17c to yield about 10.3 mg of crude material (about 40% purity) upon HF cleavage of 34.5 mg dry Boc-Gly-Gly-His(Tos)-[Taeg]$_{10}$-Lys(ClZ)-MBHA resin. A small portion of the crude product (taken out before lyophilization) was purified to give 0.1 mg of Gly-Gly-His-[Taeg]$_{10}$-Lys-NH$_2$.

EXAMPLE 101

Solid-Phase Synthesis of H-[Taeg]$_5$-[Caeg]$_2$-NH$_2$ (a) Stepwise Assembly of Boc-[Taeg]$_5$-[C(Z)aeg]$_2$-MBHA Resin About 0.2 g of MBHA resin was placed in a 3 ml SPPS reaction vessel and neutralized. The loading was determined to be about 0.64 mmol/g. BocC(Z)aeg-OPfp was coupled onto the resin using a concentration of 0.13 M in 2.5 ml 25% phenol//CH$_2$Cl$_2$. The ninhydrin analysis showed a coupling yield of about 40%. The remaining free amino groups were acetylated as usual. Boc-[Taeg]$_5$-[C(Z)aeg]$_2$-MBHA resin was assembled by single in situ DCC coupling of the next residue utilizing 0.11 M of BocC(Z)aeg-OH together with 0.11 M DCC in 2.5 ml 50% DMF/CH$_2$Cl$_2$ and by coupling with 0.13 M BocTaeg-OPfp in neat CH$_2$Cl$_2$ for the remaining residues ("Synthetic Protocol 8"). Each coupling reaction was allowed to proceed with shaking overnight. The synthesis was monitored by the ninhydrin reaction, which showed close to quantitative incorporation of all the residues.

(b) Cleavage, Purification, and Identification of H-[Taeg]$_5$-[Caeg]$_2$-NH$_2$ The protected Boc-[Taeg]$_5$-[C(Z)aeg]$_2$-MBHA resin was treated as described in Example 17c to yield about 21.7 mg of crude material (>80% purity) upon HF cleavage of 94.8 mg dry H-[Taeg]$_5$-[C(Z)aeg]$_2$-MBHA resin. Crude product (7.4 mg) was purified to give 2.0 mg of H-[Taeg]$_5$-[Caeg]$_2$-NH$_2$ (>99% purity).

EXAMPLE 102

Solid-Phase Synthesis of H-[Taeg]$_3$-Caeg-[Taeg]$_4$-NH$_2$ (a) Stepwise Assembly of Boc-[Taeg]$_3$-C(Z)aeg-[Taeg]$_4$-MBHA Resin About 0.2 g of the above-mentioned MBHA resin was placed in a 5 ml SPPS reaction vessel and neutralized. Boc-[Taeg]$_3$-C(Z)aeg-[Taeg]$_4$-MBHA resin was assembled by single in situ DCC coupling of the C(Z)aeg residue utilizing 0.13 M of BocC[Z]aeg-OH together with 0.13 M DCC in 2.5 ml 50% DMF/CH$_2$Cl$_2$ and by coupling the Taeg residues with 0.13 M BocTaeg-OPfp in 2.5 ml neat CH$_2$Cl$_2$. Each coupling reaction was allowed to proceed with shaking overnight. The synthesis was monitored by the ninhydrin reaction, which showed close to quantitative incorporation of all the residues.

(b) Cleavage, Purification, and Identification of H-[Taeg]$_3$-Caeg-[Taeg]$_4$-NH$_2$ The protected Boc-[Taeg]$_3$-C(Z)aeg-[Taeg]$_4$-MBHA resin was treated as described in Example 17c to yield about 44.4 mg of crude material upon HF cleavage of about 123 mg dry H-[Taeg]$_3$-C(Z)aeg-[Taeg]$_4$-MBHA resin. Crude product (11.0 mg) was purified to give 3.6 mg of H-[Taeg]$_3$-Caeg-[Taeg]$_4$-NH$_2$.

EXAMPLE 103

Solid-Phase Synthesis of H-Taeg-Caeg-[Taeg]$_8$-LysNH$_2$ (a) Stepwise Assembly of Boc-Taeg-C(Z)aeg-[Taeg]$_8$-Lys(ClZ)-MBHA Resin About 0.3 g of wet Boc-[Taeg]$_8$-Lys(ClZ)-MBHA resin was placed in a 3 ml SPPS reaction vessel. Boc-Taeg-C(Z)aeg-[Taeg]$_8$-Lys(ClZ)-MBHA resin was assembled by single in situ DCC coupling overnight of the C(Z)aeg residue ("Synthetic Protocol" 9) utilizing 0.2 M of BocC[Z]aeg-OH together with 0.2 M DCC in 2.5 ml 50% DMF/CH$_2$Cl$_2$ (incorporation was about 80% as judged by ninhydrin analysis; remaining free amino groups were acetylated) and by overnight coupling the Taeg residue with 0.15 M BocTaeg-OPfp in 2.5 ml neat CH$_2$Cl$_2$ (nearly quantitatively).

(b) Cleavage, Purification, and Identification of H-Taeg-Caeg-[Taeg]$_8$-LysNH$_2$ The protected Boc-Taeg-C(Z)aeg-[Taeg]$_8$-Lys(ClZ)-MBHA resin was treated as described in Example 17c to yield about 22.3 mg of crude material upon HF cleavage of about 76.5 mg dry H-Taeg-C(Z)aeg-[Taeg]$_8$-Lys(ClZ)-MBHA resin. Crude product (6.7 mg) was purified to give 2.6 mg of H-Taeg-Caeg-[Taeg]$_8$-LysNH$_2$. For (M+H)$^+$ the calculated m/z value was 2792.15 and the measured m/z value was 2792.21.

EXAMPLE 104

Solid-Phase Synthesis of H-Caeg-[Taeg]$_5$-Lys-NH$_2$ and H-[Taeg]$_2$-Caeg-[Taeg]$_5$-Lys-NH$_2$ (a) Stepwise Assembly of Boc-[Taeg]$_2$-C(Z)aeg-[Taeg]$_5$-Lys(ClZ)-MBHA Resin About 0.5 g of wet Boc-[Taeg]-Lys(ClZ)-MBHA resin was placed in a 5 ml SPPS reaction vessel. Boc-[Taeg]$_2$-C(Z)aeg-[Taeg]$_5$-Lys(ClZ)-MBHA resin was assembled by single in situ DCC coupling of all residues utilizing: (1) 0.12 M of BocC[Z]aeg-OH together with 0.12 M DCC in 3.0 ml 50% DMF/CH$_2$Cl$_2$ or (2) 0.12 M BocTaeg-OH together with 0.12 M DCC in 3.0 ml 50% DMF/CH$_2$Cl$_2$ ("Synthetic Protocol 9"). Each coupling reaction was allowed to proceed overnight with shaking. The synthesis was monitored by the ninhydrin reaction, which showed close to quantitative incorporation of all the residues. During the synthesis, a small portion of H-C(Z)aeg-[Taeg]$_5$-Lys(ClZ)-MBHA resin was taken out for HF cleavage.

(b) Cleavage, Purification, and Identification of H-Caeg-[Taeg]$_5$-Lys-NH$_2$

The protected Boc-C[Z]aeg-[Taeg]$_5$-Lys(ClZ)-MBHA resin was treated as described in Example 17c to yield about 3.0 mg of crude material upon HF cleavage of 37.5 mg dry H-C[Z]aeg-[Taeg]$_5$-Lys(ClZ)-MBHA resin. About 0.7 mg of the crude product was purified to give about 0.5 mg of H-Caeg-[Taeg]$_5$-Lys-NH$_2$.

(c) Cleavage, Purification, and Identification of H-[Taeg]$_2$-Caeg-[Taeg]$_5$-Lys-NH$_2$ The protected Boc-[Taeg]$_2$-C[Z]aeg-[Taeg]$_5$-Lys(ClZ)-MBHA resin was treated as described in Example 17c to yield about 37.7 mg of crude material upon HF cleavage of 118.6 mg dry H-[Taeg]$_2$-C[Z]aeg-[Taeg]$_5$-Lys(ClZ)-MBHA resin.

EXAMPLE 105

Solid-Phase Synthesis of H-[Caeg]$_5$-Lys-NH$_2$, H-[Caeg]$_6$-Lys-NH$_2$, H-[Caeg]$_8$-Lys-NH$_2$, and H-[Caeg]$_{10}$-Lys-NH$_2$ (a) Stepwise Assembly of Boc-[C(Z)aeg]$_{10}$-Lys(ClZ)-MBHA Resin and Shorter Fragments About 5 g of wet Boc-Lys(ClZ)-MBHA resin (substitution=0.3 mmol Lys/g) was placed in a 30 ml SPPS reaction vessel. Boc-[C(Z)aeg]$_{10}$-Lys(ClZ)-MBHA resin was assembled by single in situ DCC coupling of the first three residues with 0.1 M of BocC(Z)aeg-OH together with 0.1 M DCC in 10 ml 50% DMF/CH$_2$Cl$_2$ ("Synthetic Protocol 9") and by single in situ DIC coupling of the remaining seven residues with 0.1 M of BocC(Z)aeg-OH together with 0.1 M DIC in 1.0 ml 50% DMF/CH$_2$Cl$_2$ ("Synthetic Protocol 10"). All the coupling reactions were allowed to proceed overnight. The synthesis was monitored by the ninhydrin reaction, which showed close to quantitative incorporation of all residues. During the synthesis, portions of the shorter fragments H-[C(Z)aeg]$_5$-Lys(ClZ)-MBHA resin, H-[C(Z)aeg]$_6$-Lys(ClZ)-MBHA resin, H-[C(Z)aeg]$_7$-Lys(ClZ)-MBHA resin, H-[C(Z)aeg]$_8$-Lys(ClZ)-MBHA resin, and H-[C(Z)aeg]$_9$-Lys(ClZ)-MBHA resin were taken out for HF cleavage.

(b) Cleavage, Purification, and Identification of H-[Caeg]$_5$-Lys-NH$_2$

The protected Boc-[C(Z)aeg]$_5$-Lys(ClZ)-MBHA resin was treated as described in Example 17c to yield about 10.8 mg of crude material upon HF cleavage of 60.1 mg dry H-[C(Z)aeg]$_5$-Lys(ClZ)-MBHA resin.

(c) Cleavage, Purification, and Identification of H-[Caeg]$_6$-Lys-NH$_2$

The protected Boc-[C(Z)aeg]$_6$-Lys(ClZ)-MBHA resin was treated as described in Example 17c to yield about 13.4 mg of crude material upon HF cleavage of 56.2 mg dry H-[C(Z)aeg]$_6$-Lys(ClZ)-MBHA resin.

(d) Cleavage, Purification, and Identification of H-[Caeg]$_8$-Lys-NH$_2$

The protected Boc-[C(Z)aeg]$_8$-Lys(ClZ)-MBHA resin was treated as described in Example 17c to yield about 16.8 mg of crude material upon HF cleavage of 65.6 mg dry H-[C(Z)aeg]$_8$-Lys(ClZ)-MBHA resin.

(e) Cleavage, Purification, and Identification of H-[Caeg]$_{10}$-Lys-NH$_2$

The protected Boc-[C(z)aeg]$_{10}$-Lys(ClZ)-MBHA resin was treated as described in Example 17c to yield about 142.4 mg of crude material upon HF cleavage of 441 mg dry H-[C(Z)aeg]$_{10}$-Lys(ClZ)-MBHA resin.

EXAMPLE 106

Solid-Phase Synthesis of H-[Taeg]$_2$-Caeg-[Taeg]$_2$-Caeg-[Taeg]$_4$-Lys-NH$_2$ (a) Stepwise Assembly of Boc-[Taeg]$_2$-C(Z)aeg-[Taeg]$_2$-C(Z)aeg-[Taeg]$_4$-Lys(ClZ)-MBHA Resin About 0.3 g of wet H-[Taeg]$_2$-C(Z)aeg-[Taeg]$_4$-Lys(ClZ)-MBHA resin from the earlier synthesis of Boc-[Taeg]$_5$-C(Z)aeg-[Taeg]$_4$-Lys(ClZ)-MBHA resin was placed in a 5 ml SPPS reaction vessel. After coupling of the next residue five times, a total incorporation of BocC(Z)aeg of 87% was obtained. The five repeated couplings were carried out with 0.18 M BocC(Z)aeg-OPfp in 2 ml of TFE/CH$_2$Cl$_2$ (1:2, v/v), 2 ml of TFE/CH$_2$Cl$_2$ (1:2, v/v), 2 ml of TFE/CH$_2$Cl$_2$ (1:2, v/v) with two drops of dioxane and two drops of DIEA (this condition gave only a few per cent coupling yield), 2 ml of TFE/CH$_2$Cl$_2$ (1:2, v/v) plus 0.5 g phenol, and 1 ml of CH$_2$Cl$_2$ plus 0.4 g of phenol, respectively. The two final Taeg residues were incorporated close to quantitatively by double couplings with 0.25 M BocTaeg-OPfp in 25% phenol/CH$_2$Cl$_2$. All couplings were allowed to proceed overnight.

(b) Cleavage, Purification, and Identification of H-[Taeg]$_2$-Caeg-[Taeg]$_2$-Caeg-[Taeg]$_4$-Lys-NH$_2$ The protected Boc-[Taeg]$_2$-C(Z)aeg-[Taeg]$_2$-C(Z)aeg-[Taeg]$_4$-Lys(ClZ)-MBHA resin was treated as described in Example 17c to yield about 7 mg of crude material upon HF cleavage of 80.7 mg dry H-[Taeg]$_2$-C(Z)aeg-[Taeg]$_2$-C(Z)aeg-[Taeg]$_4$-Lys(ClZ)-MBHA resin. The crude product was purified to give 1.2 mg of H-[Taeg]$_2$-Caeg-[Taeg]$_2$-Caeg-[Taeg]$_4$-Lys-NH$_2$ (>99.9% purity).

EXAMPLE 107

Figure 26:
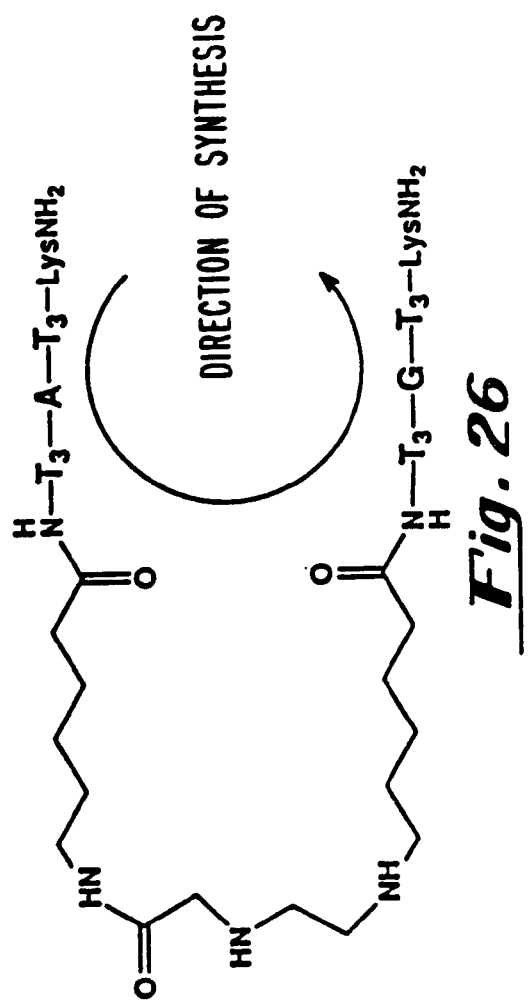
FIG. 26 shows the direction of synthesis for a peptide nucleic acid according to the invention.

Synthesis of a PNA with Two Anti Parallel Strands Tied Together Synthesis of H-[Taeg]-[Taeg]-[Taeg]-[Gaeg]-[Taeg]-[Taeg]-[Taeg]-[6-AHA]-[aeg]-[6-AHA]-[Taeg]-[Taeg]-[Taeg]-[Aaeg]-[Taeg]-[Taeg]-[Taeg]-LYS-NH$_2$. (6-AHA=6-aminohexanoic acid) (FIG. 26)

The protected, PNA was assembled onto a Boc-Lys(ClZ) modified MBHA resin with a substitution of approximately 0.30 mmol/g. Capping of uncoupled amino groups was only carried out before the incorporation of the BocGaeg-OH monomer. Synthesis was initiated on 1.00 g (dry weight) of preswollen (overnight in DCM) and neutralized Boc-Lys (ClZ)-MBHA resin. The incorporation of the monomers followed the protocol of Example 32 and Example 71. The coupling reaction was monitored by qualitative ninhydrin reaction (kaiser test). In case of a positive Kaiser test, the coupling reaction was repeated until the test showed no coloration of the beads. Final deprotection, cleavage from support, and purification were performed according to standard procedures.

EXAMPLE 108

Figure 27:
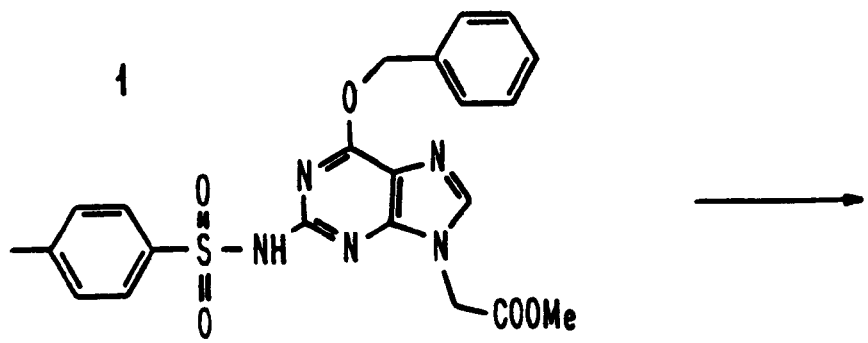
FIG. 27 provides a test for the tosyl group as a nitrogen protecting group in the synthesis of peptide nucleic acids.
Figure 27:
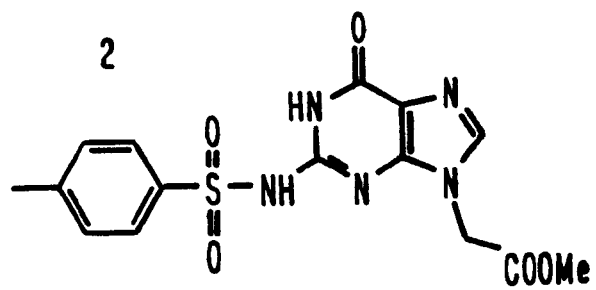
Figure 27:
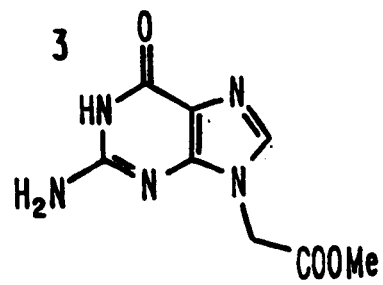

Alternative Protecting Group Strategy for PNA-synthesis (FIG. 27)

(a) Synthesis of Test Compounds 2-amino-6-O-benzyl purine. To a solution of 2.5 g (0.109 mol) of sodium in 100 ml of benzyl alcohol was added 10.75 g (0.063 mol) of 2-amino-6-chloropurine. The mixture was stirred for 12 h at 120 0° C. The solution was cooled to room temperature and neutralized with acetic acid and extracted with 10 portions of 50 ml of 0.2 N sodium hydroxide. The collected sodium hydroxide phases were washed with 100 ml of diethyl ether and neutralized with acetic acid, whereby precipitation starts. The solution was cooled to 0° C. and the yellow precipitate was collected by filtration. Recrystallization from ethanol gave 14.2 g 92% of pure white crystals of the target compound. 1H-NMR (250 MHz-DMSO-d6) d ppm: 8-H, 7.92; benzyl aromatic, 7.60–7.40; 2NH$_2$, 6.36; benzyl CH2, 5.57.

(2-amino-6-O-benzyl purinyl)methylethanoate. A mixture of 5 g (0.0207 mol) of 2-amino-6-O-benzyl-purine, 30 ml of DMF and 2.9 g (0.021 mol) of potassium carbonate was stirred at room temperature. Methyl bromoacetate (3.2 g; 1.9 ml; 0,0209 mol) was added dropwise. The solution was filtrated after 4 h and the solvent was removed under reduced pressure (4 mmHg, 40° C.). The residue was recrystallized two times from ethyl acetate to give 3.7 g (57%) of the target compound. 1H-NMR (250 MHz, DMSO-d6) d ppm: 8-H, 7.93; benzyl aromatic 7.4–7.6; 2-NH$_2$, 6.61; benzyl CH2, 5.03; CH2, 5.59; OCH3, 3.78.

(2N-p-Toluene sulfonamido-6-O-benzyl purinyl)methyl ethanoate. To a solution of 0.5 g (1.6 mmol) of (2-amino-6-O-benzyl purinyl)methyl ethanoate in 25 ml methylene chloride was added 0.53 g (1.62 mmol) of p-toluenesulfonic anhydride and 0.22 g (1.62 mmol) of potassium carbonate. The mixture was stirred at room temperature. The mixture was filtered and the solvent was removed at reduced pressure (15 mmHg, 40° C.). Diethyl ether was added to the oily residue. The resulting solution was stirred overnight, whereby the target compound (0.415 mg; 55%) precipitated and was collected by filtration. 1H-NMR (250 MHz, DMSO-d6) d ppm: 8-H, 8.97; aromatic 7.2–7.8; benzyl CH2, 5.01; CH2, 4.24; OCH3, 3.73; CH3, 2.43.

(b) Stability of the Tosyl Protected Base-residue in TFA and HF

The material was subjected to the standard deprotection conditions (TFA-deprotection) and the final cleavage conditions with HF. The products were then subjected to HPLC-analysis using a 4 $\mu$ RCM 8×10 Nova pack column and solvents A (0.1% TFA in water) and B (0.1% TFA in acetonitrile) according to the following time gradient with a flow of 2 ml/min.

| Time | % A | % B |
|------|-----|-----|
| 0    | 100 | 0   |
| 5    | 100 | 0   |
| 35   | 0   | 100 |
| 37   | 0   | 100 |
| 39   | 100 | 0   |

The following retention times were found: (a) Compound 1: 30.77 min; (b) compound 2: 24.22 min; and (c) compound 3: 11.75 min. The analysis showed that the O6-benzyl group was removed both by TFA and HF, whereas there was no cleavage of the tosyl group in TFA, but quantitative removal in HF under the standard cleavage conditions.

EXAMPLE 109

5-Bromouracil-$N^1$-methyl Acetate

5-Bromouracil (5.00 g; 26.2 mmol) and potassium carbonate (7.23 g; 52.3 mmol) were suspended in DMF (75 ml). Methyl bromoacetate (2.48 ml; 26.1 mmol) was added over a period of 5 min. The suspension was stirred for 2 h at room temperature, and then filtered. The solid residue was washed twice with DMF, and the combined filtrates were evaporated to dryness, in vacuo. The residue was an oil containing the title compound, DMF and some unidentified impurities. It is not necessary to purify the title compound before hydrolysis. $^1$H-NMR (DMSO-$d_6$, 250 MHz); 8.55 (impurity); 8.27 (CBr=CHN); 8.02 (impurity); 4.76 (impurity); 4.70 (impurity); 4.62 (NCH$_2$COOCH$_3$); 3.78 (COOCH$_3$); 2.96 (DMF); 2.80 (DMF). $^{13}$C-NMR (DMSO-$d_6$, 250 MHz); 168.8 (COOCH$_3$); 172.5 (CH=CBrCON); 161.6 (DMF); 151.9 (NCON); 145.0 (CO—CBr=CHN); 95.6 (COCBr=CHN); 52.6 (impurity); 52.5 (OCH$_3$); 49.7 (impurity); 48.8 (NCH$_2$COOMe); 43.0 (impurity); 36.0 (DMF). UV(Methanol; $_{max}$nm); 226; 278. IR (KBr;cm$^{-1}$__; 3158s (_NH); 1743vs (_C=O, COOMe); 1701vs (_C=O, CONH); 1438vs ($\partial$ CH, CH$_3$O); 1223vs (_C—O, COOMe); 864 m ($\partial$ CH, Br=C—H). FAB-MS m/z (assignment): 265/263 (M+H).

EXAMPLE 110

(5-Bromouracil)acetic Acid

Water (30 ml) was added to the oil of the crude product from Example 109 and the mixture was dissolved by adding sodium hydroxide (2M, 60 ml). After stirring at 0° C. for 10 min, hydrochloric acid (4M, 45 ml) was added to pH=2 and the title compound precipitated. After 50 min, the solid residue was isolated by filtration, washed once with cold water, and then dried in vacuo over sicapent. Yield: 2.46 g (38%). Mp, 250°–251° C. Anal. for $C_6H_5BrN_2O_4$. Found (calc.): C, 28.78; (28.94); H, 2.00; (2.02); Br, 32.18; (32.09); N, 11.29; (11.25). $^1$H-NMR (DMSO-$d_6$, 250 MHz): 12.55 (1H.s,COOH); 11.97 (1H,s,NH); 8.30 (1H,s,C=C—H); 4.49 (2H,s,NCH$_2$COOH). $^{13}$C-NMR (DMSO-$d_6$, 250 MHz); 169.4 (COOH); 159.8 (NHCOCBr=CH); 150.04 (NCON); 145.8 (COCBr=CHN); 94.6 (COCBr=CHN); 48.8 (NCH$_2$COOH). UV (Methanol; $_{max}$nm); 226; 278. IR (KBr; cm$^{-1}$); 3187s (_NH); 1708vs (_C=O,COOH); 1687vs; 1654VS (_C=O, CONH); 1192s (_C—O, COOH); 842 m ($\partial$ CH, Br—C=C—H). FAB-MS m/z (assignment, relative intensity); 251/249 (M+H,5).

EXAMPLE 111

N-(Boc-aminoethyl)-N-(5-bromouracil) methylenecarbonoylglycine Ethyl Ester

Boc-aminoethylglycine ethyl ester (1.80 g; 7.30 mmol) was dissolved in DMF (10 ml). Dhbt-OH (1.31 g; 8.03 mmol) was added, whereby a precipitate was formed. DMF (2×10 ml) was added until the precipitate was dissolved. The product of Example 110 (2.00 g; 8.03 mmol) was added slowly to avoid precipitation. Methylene chloride (30 ml) was added, and the mixture was cooled to 0° C. and then filtered. The precipitate, DCU, was washed twice with methylene chloride. To the combined filtrate was added methylene chloride (100 ml). The mixture was washed with half saturated NaHCO$_3$-solution (3×100 ml, H$_2$O:saturated NaHCO$_3$-solution 1:1 v/v), then with dilute KHSO$_4$-solution (2×100 ml, H$_2$O:saturated KHSO$_4$-solution 4:1 v/v), and finally with saturated NaCl-solution (1×100 ml). The organic phase was dried over magnesium sulphate, filtered, and evaporated to dryness in vacuo (about 15 mmHg and then about 1 mmHg). The residue was suspended in methylene chloride (35 ml), stirred for 45 min at room temperature, and filtered (the precipitate was DCU). Petroleum ether (2 volumes) was added dropwise to the filtrate at 0° C., whereby an oil precipitated. The liquor was decanted and the remaining oil dissolved in methylene chloride (20–50 ml). Precipitated was effected by the addition of petroleum ether (2 volumes). This procedure was repeated 5 times until an impurity was removed. The impurity can be seen at TLC with 10% MeOH/CH$_2$Cl$_2$ as the developing solvent. The resulting oil was dissolved in methylene chloride (25 ml) and evaporated to dryness in vacuo, which caused solidification of the title compound. Yield: 2.03 g ((58%). Mp. 87°–90° C. Anal. for $C_{17}H_{25}BrN_4O_7$. Found (calc.): C, 42.33; (42.78); H, 5.15; (5.28); Br, 17.20; (16.74); N, 1.69; (11.74). $^1$H-NMR (DMSO-$d_6$, 250 MHz, J in Hz): 1.93 & 11.92 (1H,s,C=ONHC=O); 8.09 & 8.07 (1H,s, C=C—H); 7.00 & 6.80 (1H,t,b,BocNH); 4.80 & 4.62 (2H,s,NCH$_2$CON); 4.35 & 4.24 (2H,s,NCH$_2$COOEt); 4.27–4.15 (2H,m's, COOCH$_2$CH$_3$O); 3.47–3.43 (2H,m's, BocNHCH$_2$CH$_2$N); 3.28–3.25 & 3.12–3.09 (2H,m's, BocNHCH$_2$CH—$_2$N): 1.46 & 1.45 (9H,s,$^t$Bu); 1.26 & 1.32 (3H,t,J=7.1, COOCH$_2$CH$_3$). $^{13}$C-NMR (DMSO-$d_6$, 250 MHz); 169.3 & 169.0 ($^t$BuOC=O); 167.4 & 167.1 (COOEt); 159.8 (C=C—CON); 155.9 (NCH$_2$CON); 150.4 (NCON); 145.9 (COCBr—CHN); 94.5 (COCBr=CHN); 78.2 (Me$_3$C); 61.3 & 60.7 (COCH$_2$CH$_3$); 49.1 & 48.0 (NCH$_2$COOH); 48.0 & 47.0 (NCH$_2$CON); 38.6 (BocNHCH$_2$CH$_2$N); 38.2 (BocNHCH$_2$CH$_2$N); 26.3

(C(C$\underline{H}$₃)₃); 14.1 (COC$\underline{H}$₂C$\underline{H}$₃). UV (Methanol; $_{max}$NM): 226; 280. IR (KBr, CM$^{-1}$): 3200 ms, broad (_NH); 168vs, vbroad (_C=O, COOH, CONH); 1250s (_C—O, COOEt); 1170s (_C—O, COO$^t$Bu); 859 m (∂ CH, Br—C=C—H). FAB-MS m/z (assignment, relative intensity): 479/477 (M+H, 5); 423/421 (M+2H–$^t$Bu, 8); 379/377 (M+2H–Boc, 100); 233/231 (M–backbone, 20).

EXAMPLE 112

N-(Boc-aminoethyl)-N-(5-bromouracyl-N$^1$-methylenecarbonoyl)glycine

The product of Example 111 (1.96 g; 4.11 mmol) was dissolved in methanol (30 ml) by heating, and then cooled to 0° C. Sodium hydroxide (2M, 30 ml) was added, and the mixture stirred for 30 min. HCl (1M, 70 ml) was added to pH=2.0. The water phase was extracted with ethyl acetate (3×65 ml+7×40 ml). The combinedethyl acetate extractions were washed with saturated NaCl-solution (500 ml). The ethyl acetate phase was dried over magnesium sulphate, filtered and evaporated to dryness in vacuo. Yield: 1.77 g (96%). Mp. 92°–97° C. Anal. for C$_{15}$H$_{21}$BrN$_4$O$_7$. Found (calc.): C, 40.79; (40.10); H, 5.15; (4.71); Br, 14.64; (17.70); N, 11.35; (12.47). $^1$H-NMR (DMSO-d$_6$, 250 MHz, J in Hz): 12.83 (1H,s,COO$\underline{H}$); 11.93 & 11.91 (1H,s,C=ON$\underline{H}$C=O); 8.10 & 8.07 (1H,s,C=C—$\underline{H}$); 7.00 & 6.81 (1H,t,b,BocN$\underline{H}$); 4.79 & 4.61 (2H,s,NC$\underline{H}$₂CON); 4.37 & 4.25 (2H,s,NC$\underline{H}$₂COOH); 3.46–3.39 (2H,m's, BocNHCH₂C$\underline{H}$₂N); 3.26–3.23 & 3.12–3.09 .(2H,m's, BocNHC$\underline{H}$₂CH₂N); 1.46 (9H,s,$^t$Bu). $^{13}$C-NMR 9DMSO-d$_6$, 250 MHz); 170.4 ($^t$BUO$\underline{C}$=O); 166.9($\underline{C}$OOH); 159.7 (C=C—$\underline{C}$ON); 155.8 (N$\underline{C}$H₂CON); 150.4 (N$\underline{C}$ON); 145.9 (COCBr=$\underline{C}$HN); 94.4 (CO$\underline{C}$Br=CHN); 78.1 (Me₃$\underline{C}$); 49.1 & 48.0 (N$\underline{C}$H₂COOH); 47.7 & 47.8 (N$\underline{C}$H₂CON); 38.6 (BocNHC$\underline{C}$H₂N); 38.1 (Boc NH $\underline{C}$H₂CH₂N); 28.2 (C(C$\underline{H}$₃)₃). UV (Methanol; $_{max}$nm); 226; 278. IR (KBr,cm$^{-1}$): 3194ms, broad (_NH); 1686vs, vbroad (_C=O COOH, CONH); 1250s (_C—O,COOH); 1170s (_C—O,COO$^t$Bu); 863m (∂ CH, Br—C=C—H). FAB-MS m/z (assignment, relative intensity): 449/451 (M+H, 70); 349/351 (M+2H–Boc, 100); 231/233 (M–backbone, 20).

EXAMPLE 113

Uracil-N$^1$-methyl Acetate

Uracil (10.0 g; 89.2 mmol) and potassium carbonate (24.7 g; 178 mmol) were suspended in DMF (250 ml). Methyl bromoacetate (8.45 ml; 89.2 mmol) was added over a period of 5 min. The suspension was stirred overnight under nitrogen at room temperature, and then filtered. TLC (10% methanol in ethylene chloride) indicated incomplete conversion of uracil. The solid residue was washed twice with DMF, and the combined filtrates were evaporated to dryness in vacuo. The precipitate was suspended in water (60 ml) and HCl (2.5 ml, 4M) was added to pH=2. The suspension was stirred for 30 min at 0° C., and then filtered. The precipitated title compound was washed with water and dried, in vacuo, over sicapent. Yield: 9.91 g (60%). Mp. 182°–183° C. Anal. for C$_6$H$_8$N$_2$O$_4$. Found (calc.): C, 45.38; (45.66); H, 4.29; (4.38); N, 15.00; (15.21). $^1$H-NMR (DMSO-d$_6$, 250 MHz, J in Hz): 1.47 (1H,s, N$\underline{H}$); 7.68 (1H,d, J$_{H—C=C—H}$=7.9), CH=C$\underline{H}$N); 5.69 (1H, d, J$_{H—C=C—H}$= 7.9), C$\underline{H}$=CHN); 4.59 (2H, s, NC$\underline{H}$₂COOMe); 3.76 (3H,s, COOC$\underline{H}$₃). $^{13}$C-NMR (DMSO-d$_6$, 250 MHz); 168.8 ($\underline{C}$OOMe); 164.0 (C=C—$\underline{C}$ON); 151.1 (N$\underline{C}$ON); 146.1 (CO$\underline{C}$H=$\underline{C}$HN); 101.3 (CO$\underline{C}$H=CHN); 52.5 (COOC$\underline{H}$₃); 48.7 (N$\underline{C}$H₂COOMe). UV (Methanol; $_{max}$nm): 226; 261. IR (KBr; cm$^{-1}$); 3164s (_NH); 1748vs (_C—O, COOMe); 1733vs (_C=O, CONH); 1450vs (∂ CH, CH₃O); 1243VS (_C—O,COOMe); 701m (∂ CH, H—C=C—H). FAB-MS m/z (assignment); 185 (M+H).

EXAMPLE 114

Uracilacetic Acid

Water (90 ml) was added to the product of Example 113 (8.76 g; 47.5 mmol), followed by sodium hydroxide (2M, 40 ml). The mixture was heated for 40 min, until all the methyl ester has reacted. After stirring at 0° C. for 15 min, hydrochloric acid (4M, 25 ml) was added to pH=2. The title compound precipitated and the mixture was filtered after 2–3 h. The precipitate was washed once with the mother liquor and twice with cold water and dried in vacuo over sicapent. Yield: 6.66 g (82%). Mp. 288°–289° C. Anal. for C$_6$H$_6$N$_2$O$_4$. Found (calc.): C, 42.10; (42.36); H, 3.43; (3.55); N, 16.25; (16.47)/$^1$H-NMR (DMSO-d$_6$), 250 MHz, J in Hz): 13.19 (1H,s,COO$\underline{H}$); 11.41 (1H,s,N$\underline{H}$); 7.69 (1H,d, J$_{H—C=C—H}$=7.8, J$_{H—C—C—N—H}$=2.0, COC$\underline{H}$=CHN); 4.49 (2H,s,NC$\underline{H}$₂COOH). $^{13}$C-NMR (DMSO-d$_6$, 2509 MHz); 169.9 ($\underline{C}$OOH); 163.9 (CH=CH$\underline{C}$ON); 151.1 (N$\underline{C}$ON); 146.1 (CO$\underline{C}$H=$\underline{C}$HN); 100.9 (CO$\underline{C}$H=CHN); 48.7 N$\underline{C}$H₂COOH. UV (Methanol; $_{max}$nm): 246; 263. IR (KBr; cm$^{-1}$): 3122s (_NH); 1703vs (_C=O, COOH); 1698vs, 1692vs (_C=O, CONH); 1205s (_C—O,COOH); 676 (∂ CH, H—C=C—H). FAB-MS m/z (assignment): 171 (M+H).

EXAMPLE 115

N-(Bocaminoethyl)-N-(uracil-N$^1$-methylenecarbonoyl)glycine Ethyl Ester (Bocaminoethyl)glycine ethyl ester (2.00 g; 8.12 mmol) was dissolved in DMF (10 ml). Dhbt-OH (1.46 g; 8.93 mmol) was added and a precipitate was formed. DMF (2×10 ml) was added until all was dissolved. The product of Example 114 (1.52 g; 8.93 mmol) was added slowly to avoid precipitation. Methylene chloride (30 ml) was added, and the mixture was cooled to 0° C., whereafter DDC (2.01 g; 9.74 mmol) was added. The mixture was stirred for 1 h at 0° C., at 2 h at room temperature, and then filtered. The precipitated DCU was washed twice with methylene chloride. To combined filtrate was added methylene chloride (100 ml), and the solution washed with half-saturated NaHCO3-solution (3×100 ml, H₂O:saturated NaHCO₃-solution 1:1 v/v), then with dilute KHSO₄-solution (2×100 ml, H₂O:saturated KHSO₄-solution 4:1 v/v) and finally with saturated NaCl-solution (1×100 ml). The organic phase was dried over magnesium sulphate, filtered and evaporated to dryness in vacuo (about 15 mmHg and then about 1 mmHg). The residue was suspended in methylene chloride (32 ml), and stirred for 35 min at room temperature, and 30 min at 0° C., and then filtered. The precipitate (DCU) was washed with methylene chloride. Petroleum ether (2 volumes) was added dropwise to the combined filtrate at 0° C., which caused separation of an oil. The mixture was decanted, the remaining oil was then dissolved in methylene chloride (20 ml), and then again precipitated by addition of petroleum ether (2 volumes). This procedure was repeated5 times until an impurity was removed. The impurity can be seen by TLC with 10% MeOH/CH₂Cl₂ as the developing solvent. The resulting oil was dissolved in methylene chloride (20 ml) and evaporated to dryness in vacuo, which caused solidification of the title compound. Yield: 1.71 g (53%). Mp. 68.5°–75.7° C. Anal for C$_{17}$H$_{26}$N$_4$O$_7$. Found (calc.): C, 50.61; (51.25); H, 6.48; (6.58); N, 13.33; (14.06). $^1$H-NMR (DMSO-d$_6$,250 MHz,J in Hz): 11.36 (1H,s,C=ONHC=O); 7.51 & 7.47 (1H,d,J$_{H—C=C—H}$+6.1; COCH=X—H); 7.00 & 6.80 (1H,t,b, BocNH); 5.83 & 5.66 (1H,d,J$_{H—C=C—H}$=5.7, COCH=CH); 4.78 & 4.60 (2H,s,NCH$_2$CON); 4.37 & 4.12 (2H,s,NCH$_2$COOEt); 4.30–4.15 (2H,m's,COOCH$_2$CH$_3$); 3.49–3.46 (2H,m's, BocNHCH$_2$CH$_2$n); 3.27 3.23 & 3.11–3.09 (2H, m's, BocNHCH$_2$CH$_2$N; 1.46 (9H, s, $^t$Bu); 1.39–1.23 (3H, m's, COOCH$_2$CH$_3$). $^{13}$C-NMR (DMSO-d$_6$, 250 MHz): 169.4 & 169.0 ($^t$BuOC=O); 167.6 & 167.3 (COOEt); 163.8 (CH=CHCON); 155.8 (NCH$_2$CON); 151.0 (NCON); 146.3 (COCH=CHN); 100.8 (COCH=CHN); 78.1 (Me$_3$C); 61.2 & 60.6 (COOCH$_2$CH$_3$); 49.1 (NCH$_2$COOEt); 47.8 & 47.0 (NCH$_2$CON); 38.6 (BocNHCH$_2$CH$_2$N); 38.1 & 37.7 (BocNHCH$_2$N); 28.2 (C(CH$_3$)$_3$); 14.1 (CO—OCH$_2$CH$_3$. UV (Methanol; $_{max}$ nm); 226; 264. IR (KBr; cm$^{-1}$): 3053m (_NH); 1685vs, vbroad (_C=O, COOH, CONH); 1253s (_C—O, COOEt); 1172s (_C—O, COO$^t$Bu); 718w ($\partial$ CH, C—C—C—H), FAB-MS m/z (assignment, relative intensity); 399 (M+H, 35); 343 (M+2H-$^t$Bu, 100); 299 (M+2H-Boc, 100); 153 (M-backbone, 30).

EXAMPLE 116

N-(Bocaminoethyl)-N-(uracilmethylenecarbonoyl) glycine

The product of Example 115 (1.56 g; 3.91 mmol) was dissolved in methanol (20 ml) and then cooled to 0° C. Sodium hydroxide (2M, 20 ml) was added, and the mixture was stirred for 75 min at 0° C. Hydrochloric acid (1M, 46 ml) was added to pH=2.0. The water phase was extracted was ethyl acetate (3×50 ml+7×30 ml). The combined ethyl acetate extractions were washed with saturated NaCl solution (360 ml). The ethyl acetate phase was dried over magnesium sulphate, filtered, and evaporated to dryness, in vacua. The residue was dissolved in methanol and evaporated to dryness, in vacuo. Yield: 0.55 g (38%). Mp 164°–170° C. Anal. for C$_{15}$H$_{22}$N$_4$O$_7$. Found (calc.): C, 46.68; (48.65); H, 6.03; (5.99); N, 1461; (15.13). $^1$H-NMR (DMSO-d$_6$, 250 MHz, J in Hz); 12.83 (1H, s, COOH); 11.36 (1H, s, C=ONHC=O); 7.52–7.45 (1H, m's, COCH=CHN); 7.00 & 6.82 (1H, t,b, BocNH); 5.67–5.62 (1H, M's, COCH=CHN); 4.76 & 4.58 (2H, s, NCH$_2$CON); 4.26 & 4.05 (2H, s, NCH$_2$COOH); 3.46–3.39 (2H, m's, BocNHCH$_2$CH$_2$N); 3.25–3.23 & 3.15–3.09 (2H, m's, Boc-NHCH$_2$CH$_2$N); 1.46 (9H, s, $^t$Bu). $^{13}$C-NMR (DMSO-d$_6$, 250 MHz); 170.5 ($^t$BuOC=O); 167.2 (COOH); 163.9 (C=C—CON); 155.8 (NCH$_2$CON); 151.1 (NCON); 146.4 (COCH=CHN); 100.8 (COCH=CHN); 78.1 (Me$_3$C); 49.1 & 47.8 (NCH$_2$ COOH); 47.6 & 46.9 (NCH$_2$CON); 38.6 (BocNHCH$_2$CH$_2$N); 38.1 & 37.6 (BocNHCH$_2$CH$_2$N); 28.2 (C(CH$_3$)$_3$). UV (Methanol; $_{max}$nm); 226; 264. IR (KBr; cm$^{-1}$); 3190 (_NH); 1685vs, vbroad (_C=O, COOH, CONH); 1253s (_C—O, COOH); 1171s (_C—O, COO$^t$BU); 682w ($\partial$ CH, H—C=C—H). FAB-MS m/z (assignment, relative intensity): 371 (M+H, 25); 271 (M+H-Boc, 100).

EXAMPLE 117

H-U10-LysNH$_2$

Synthesis of the title compound was accomplished by using "Synthetic Protocol 10". The synthesis was initiated on approximately 100 mg Lys-(ClZ)-MHBA-resin. The crude product (12 mg) was pure enough for hybridization studies. The hybrid between 5'-(dA)10 and H-U10 had Tm of 67.5° C.

EXAMPLE 118

N-(Carbamoylmethyl)-β-alanine Ethylester

A suspension of 2-chloroacetamide (2.34 g, 25.0 mmol), β-alanine ethyl ester hydrochloride (15.36 g, 100 mmol) and K$_2$CO$_3$ (42.0 g) in dry DMF (200 mL) was heated at 90° C. for 24 hours. After cooling to room temperature the reaction mixture was filtered to remove any unreacted β-alanine ethyl ester and the solvent and was removed by distillation under reduced pressure (50° C., 1 Torr). The resulting yellow oil (6.0 g) was purified by silica gel flash column chromatography using ethyl acetate, ethyl acetate/ethanol (2:1, v/v), and finally ethanol as the eluent, to give 2.24 g (50%) of the title compound as a colorless oil. TLC (methanol, det. ninhydrin, R$_f$=0.65). $^1$H NMR (DMSO-d$_6$) δ1.18 (t, J=7.1 Hz, 3H, CH$_3$), 2.42, 2.70 (2t, J=6.7 Hz, 4H, CH$_2$CH$_2$), 3.03 (s, 2H, CH$_2$), 4.06 (q, J=7.1 Hz, 2H, OCH$_2$), 7.02, 7.24 (2s (br), 2H, NH$_2$) ppm. $^{13}$C NMR (DMSO) δ14.1 (CH$_3$), 34.5 (CH$_2$CO), 44.7 (NCH$_2$CH$_2$), 51.8 (NCH$_2$CN), 59.8 (OCH$_2$), 172.1 (C=O), 173.5 (C=O) ppm. FAB-MS: m/z 175.1 (M+1)$^+$.

A solution of N-(carbamoylmethyl)-β-alanine ethylester (530 mg) in diethyl ether was treated with HCl (4.7 M in diethyl ether). The precipitated HCl of N-(carbamoylmethyl)-β-alanine ethylester was filtered, rinsed with cold diethyl ether and dried in vacuo, to a white powder. $^1$H NMR (DMSO-d$_6$) δ1.2.1 (t, J=7.1 Hz, 3H, CH$_3$), 2.80, 3.16 (2t, J=7.5 Hz, 4H, CH$_2$CH$_2$), 3.69 (s, 2H, CH$_2$), 4.10 (q, J=7.1 Hz, 2H, OCH$_2$), 7.53, 7.96 (2s, 2H, NH$_2$), 9.22 (s, 2H, NH$_2$). $^{13}$C NMR (DMSO-d$_6$) δ14.0 (CH$_3$), 30.2 (CH$_2$C(O)), 42.4 (NCH$_2$CH$_2$), 47.6 (NCH$_2$C(O)), 60.5 (OCH$_2$), 166.8 (amide C=O), 170.0 (ester C=O). Anal. Calcd for C$_7$H$_{15}$ClN$_2$O$_3$ (210.66): C, 39.91; H, 7.18; N, 13.30. found C, 39.45; H, 7.10; N, 13.22.

EXAMPLE 119

N-(Carbamoylmethyl)-N-(thymin-1-ylacetyl)-β-alanine Ethyl Ester

DhbtOH (9.37 g, 57.4 mmol), N$^1$-thyminyl acetic acid (10.57 g, 57.4 mmol) and CH$_2$Cl$_2$ (100 mL) were added to a solution of N-(carbamoylmethyl)-β-alanine ethylester (10.0 g, 57.4 mmol) in dry DMF (100 mL). The solution was cooled to 0° C. in an ice bath and a solution of DCC (1.90 g, 9.18 mmol) in DMF/CH$_2$Cl$_2$ (100 mL, 1:1 v/v) was added dropwise within 20 minutes. The ice bath was removed and after stirring for 1 hour at room temperature. The reaction mixture was filtered and the precipitate (DCU) was rinsed with CH$_2$Cl$_2$ (50 mL). The organic solution and the CH$_2$Cl$_2$ rinse were combined. A colorless precipitate formed overnight which was filtered and rinsed with CH$_2$Cl$_2$. The precipitate was dried in vacuo to give 12.0 g (61%) (mp 207–208° C.) of the title compound.

Due to restricted conformations at the tertiary amide group two sets of signals (ratio 1:1) are observed for most protons and carbons in the NMR spectras, the coalescence temperature is 85° C. $^1$H NMR (DMSO-d$_6$) δ1.16 to 1.18 (2t, J=7.1 Hz, 3H, CH$_2$CH$_3$), 1.73 (s, 3H, T-CH$_3$), 2.49, 2.70, 3.45, 3.58 (4t, J=7 Hz, 4H, CH$_2$CH$_2$), 3.84, 4.04 (2s, 2H, CH$_2$), 4.03, 4.07 (2q, J=7 Hz, 2H, OCH$_2$), 4.42, 4.65 (2s, 2H, T(N1)-CH$_2$), 7.01, 7.22, 7.26, 7.54 (4s, 2H, NH$_2$), 7.28, 7.32 (2s, 1H, CH), 11.22, 11.24 (2s, T, NH) ppm. $^{13}$C NMR (DMSO-d$_6$) δ11.92 to 11.95 (T, CH$_3$), 14.1 (CH$_2$CH$_3$), 32.1, 32.7 (CH$_2$CO), 43.4, 43.9 (NCH$_2$CH$_2$), 47.85, 47.91 (NCC CH$_2$N), 48.5, 50.2 (T(N1)—CH$_2$), 60.1, 60.2 (OCH$_2$), 108.0, 108.1 (CCH$_3$), 142.2, 142.3 (CH), 151.0, 151.1 (T, NC(O)N), 164.4 (T, C=O), 167.1, 167.7 (tert. amide C=O), 169.8, 170.0 (prim. amide C=O), 171.2 (ester C=O) ppm. FAB-MS: m/z=341.1 (M+1)$^+$. Anal. Calcd for $C_{14}H_{20}N_4O_6$ (340.34): 49.41; H, 5.92; N, 16.46. found C, 48.76; H, 5.76; N, 16.34.

EXAMPLE 120

N-(Carbamoylmethyl)-N-(N6-(benzyloxycarbonyl) adenin-9-ylacetyl)-β-alanine Ethyl Ester As per the above procedure for the preparation of N-(carbamoylmethyl)-N-(thymin-1-ylacetyl)-β-alanine ethyl ester, N-(carbamoylmethyl)-β-alanine ethylester (2.00 g, 11.5 mmol) was reacted with N9-(N6-benzyloxycarbonyl) adeninyl acetic acid (3.76 g, 11.5 mmol), DhbtOH (1.88 g, 11.5 mmol) and DCC (2.37 g, 11.5 mmol). The crude material was purified by silica gel flash column chromatography using ethylacetate/methanol 3:1 as the eluent, to give 4.0 g (DCU content ca. 15%) of the title compound.

Using HBTU as the activating agent the title compound was isolated having higher purity.

To a solution of N-(carbamoylmethyl)-β-alanine ethylester.HCl (211 mg, 1.0 mmol) in DMF (2.5 mL) was added pyridine (2.5 mL), N-diisopropylethyl amine (0.64 mL), N9-(N6-benzyloxycarbonyl)adeninyl acetic acid (327 mg, 1.0 mmol) and HBTU (380 mg, 1.0 mmol). After stirring of the reaction mixture for 1 hour at room temperature a precipitate formed and was isolated by filtration. The precipitate was purified by silica gel flash column chromatography using methanol/ethyl acetate 1:1 as the eluent. Combination of the appropriate fractions and concentration in vacuo gave 280 mg (58%) of the title compound as a white amorphous solid, mp 202–203° C. $^1$H NMR (DMSO-d$_6$) δ(two rotamers, ratio 1:1) 1.25, 1.30 (2t, J=7.1 Hz, 3H, CH$_3$), 2.60 (overl. with solvent), 2.89, 3.57, 3.81 (4t, J=7.1 Hz, 4H, CH$_2$CH$_2$), 3.96, 4.29 (2s, 2H, CH$_2$), 4.12, 4.21 (2q, 2H, CH$_2$CH$_3$), 5.23, 5.48 (2s, 2H, CH$_2$), 5.30 (s, 2H, CH$_2$Ph), 7.12, 7.77 (2s, 1H, NH$_2$), 7.40–7.55 (m, 6H, aromatic H, NH$_2$), 8.41 (s, 1H, A-H), 8.67, 8.68 (2s, 1H, A-H), 10.71 (s, 1H, HNCbz) ppm. $^{13}$C NMR (DMSO-d$_6$) δ(two rotamers) 14.08, 14.13 (CH$_3$), 32.08, 32.64 (CCH$_2$CO), 43.51, 43.95, 44.12, 44.16 (CH$_2$NCH$_2$), 48.47, 50.29 (A(N9)CH$_2$), 60.05, 60.23 (OCH$_2$CH$_3$), 66.27 (OCH$_2$Ph), 122.90, 122.96, 127.83, 127.96, 128.40, 136.40, 145.27, 145.32, 149.31, 151.43, 152.18, 152.40, 152.44, 166.44, 167.12 (tert. amide C=O), 169.78, 169.83 (prim. amide C=O), 171.22 (ester C=O) ppm. FAB-MS: m/z=484.12 (M$^{H+}$). Anal. Calcd for $C_{22}H_{25}N_7O_6$ (483.48): C, 54.65; H, 5.21; N, 20.28. found C, 52.93; H, 5.09; N, 19.84.

EXAMPLE 121

N-(N-tert-Butyloxycarbonyl-aminomethyl)-N-(N1-thyminylacetyl)-β-alanine Ethylester A solution of [bis(trifluoroacetoxy)iodo]benzene (16.71 g., 38.8 mmol) in CH$_3$CN (55 mL) was added dropwise within 10 minutes to a stirred solution of N-(carbamoylmethyl)-N-(thymin-1-ylacetyl)-β-alanine ethyl ester (11.5 g, 33.8 mmol) in CH$_3$CN/H$_2$O (275 mL, 2:3 v/v). After 20 hours at room temperature the volume was reduced to about 50 mL under reduced pressure (1 Torr, 30° C.) and the solution was extracted with diethyl ether (150 mL). The aqueous phase was evaporated to dryness in vacuo (1 Torr, 30° C.). The remaining solid was rinsed with diethyl ether (20 mL) and dried in vacuo. 1,4-Dioxane (150 mL), K$_2$CO$_3$ (12.2 g) and a solution of di-tert-butyl dicarbonate (8.4 g, 38.5 mmol) in 1,4-dioxane (50 mL) were added. After stirring for 1 hour at room temperature the reaction mixture was filtered and the solvent was removed under reduced pressure. The resulting residue was purified by silica gel flash column chromatography using hexane/acetone 1:1, v/v and subsequent precipitation from MeOH (60 mL) by addition of hexane (300 mL) gave 8.6 g (64%) of the title compound, mp 174–175° C. TLC (MeOH, det. UV, ninhydrin): R$_f$ N-(Carbamoylmethyl)-N-(thymin-1-ylacetyl)-β-alanine ethyl ester=0.73, R$_f$(title compound)= 0.85. $^1$H NMR (DMSO-d$_6$)(*=major rotamer) δ1.17 (t, J=7 Hz, 3H, CH$_2$CH$_3$), 1.38, 1.42* (2s, 9H, t-Bu), 1.75 (s, 3H, T-CH$_3$), 2.50*, 2.72 (2t, J=7.9 Hz, 2H, NCH$_2$CH$_2$), 3.31*, 3.50 (2t, 2H, NCH$_2$CH$_2$), 4.05*, 4.08 (2q, 2H, OCH$_2$), 4.58, 4.61* (2d, 2H, CH$_2$), 4.61 (overlap.), 4.74* (s, 2H, CH$_2$), 7.26*, 7.35 (2s, 1H, CH), 7.4, 7.8 (2m, 1H, NH), 11.25 (s, 1H, NH) ppm. $^{13}$C NMR (major rotamer) (DMSO-d$_6$) δ11.9 (T, CH$_3$), 14.1 (CH$_2$CH$_3$), 28.0 (tBu-CH$_3$), 32.2 (CH$_2$CO), 41.4 (NCH$_2$CH$_2$), 48.1 (T(N1)CH$_2$), 53.1 (NCH$_2$N), 60.0 (OCH$_2$), 78.8 (C(CH$_3$)$_3$) 108.2 (T, CCH$_3$), 142.0 (CH), 151.1(T, NC(O)N), 155.7 (carbamate C=O), 164.4 (T, C=O), 167.0 (tert. amide C=O), 171.1 (ester C=O) ppm.FAB-MS: m/z=413.20 (M+H)$^+$. Anal. Calcd. for $C_{18}H_{28}N_4O_7$ (412.44) C, 52.42; H, 6.84; N, 13.58. found C, 52.37; H, 6.68; N, 13.57.

EXAMPLE 122

N-(N-tert-Butyloxycarbonyl-aminomethyl)-N-(N9-benzyloxycarbonyl-adenin-9-ylacetyl)-β-alanine Ethylester A solution of N-(carbamoylmethyl)-N-(N6-(benzyloxycarbonyl)adenin-9-ylacetyl)-β-alanine ethyl ester (2.60 g, 5.38 mmol) and [bis(trifluoroacetoxy)iodo] benzene (2.77 g, 6.45 mmol) in CH$_3$CN/H$_2$O 1:1, v/v, (50 mL) was stirred for 20 hours at room temperature. The mixture was filtered and the solution was evaporated to a residue under reduced pressure. 1,4-Dioxane (50 mL) and Na$_2$CO$_3$ (5.0 g) were added, followed by addition of a solution of di-tert-butyl dicarbonate (1.65 g, 7.56 mmol) in 1,4-dioxane (10 mL). The resulting mixture was stirred at room temperature for 24 hours and then filtered. The filtrate was concentrated in vacuo to a residue. The residue was purified by silica gel column chromatography using ethyl acetate/methanol 97:3 to give 2.24 g (75%) of the title compound. TLC (MeOH/ethyl acetate 1:1, det. UV, ninhydrin): R$_f$(N-(carbamoylmethyl)-N-(N6-(benzyloxycarbonyl)adenin-9-ylacetyl)-β-alanine ethyl ester)=0.65, R$_f$(the title compound)=0.85. $^1$H NMR (DMSO-d$_6$) δ1.23*, 1.30 (2t, J=7.0 Hz, 3H, CH$_2$CH$_3$), 1.46, 1.52* (2s, 9H, t-Bu), 2.6* (overl. with solvent), 2.90 (2t, CH$_2$CO$_2$), 3.60*, 3.90 (2t, J=7.3 Hz, 2H, NCH$_2$CH$_2$), 4.11*, 4.20 (2q, J=7.1 Hz, 2H, CH$_2$CH$_3$), 4.65, 4.82* (2d, 2H, NCH$_2$N), 5.30 (s, 2H, CH$_2$Ph), 5.41, 5.53* (2s, 2H, CH$_2$—A), 7.40–7.60 (m, 5H, aromatic H), 8.02 (t, NH), 8.37, 8.40, 8.66 (3s, A-H), 10.72 (s, NH) ppm. FAB-MS:m/z=556.4 (M+1)$^+$. Anal. Calcd. for $C_{26}H_{33}N_7O_7$ (555.59) C, 56.21; H, 5.99; N, 17.65; found C, 55.65; H, 5.89; N, 17.16.

EXAMPLE 123

N-(N-tert-Butyloxycarbonyl-aminomethyl)-N-(N$^1$-thyminylacetyl)-β-alanine

A solution of N-(N-tert-butyloxycarbonyl-aminomethyl)-N-(N1-thyminylacetyl)-β-alanine ethylester (5.45 g, 13.2 mmol) in THF (80 mL) and aqueous LiOH (0.5 M, 80 mL) was stirred at room temperature for 1 hour and extracted with ethyl acetate. The aqueous layer was acidified to pH 3.5 by dropwise addition of hydrochloric acid (4 M) and kept at 4° C. for 3 hours. The colorless precipitate was filtered, rinsed with water and dried in vacuo to give 4.40 g of the title compound, mp 196° C. (dec.). The filtrate was extracted with ethyl acetate, the organic phase dried over $Na_2SO_4$ and the solvent was removed under reduced pressure. The residue was crystallized from MeOH/ethyl acetate/hexane to give 280 mg additional title compound for an overall yield of 92%. TLC ($CHCl_3$/MeOH/$NEt_3$ 7:2:1, UV-detection): $R_f$(N-(N-tert-butyloxycarbonyl-aminomethyl)-N-(N1-thyminylacetyl)-β-alanine ethylester)=0.94, $R_f$(the title compound)=0.52). $^1$H NMR (DMSO-$d_6$) (two rotamers, ratio 3:1) δ1.46, 1.50* (2s, 9H, t-Bu), 1.83 (s, 3H, T-$CH_3$), 2.52*, 2.73 (2t, J=7.5 Hz, 2H, $NCH_2C\underline{H}_2$), 3.54*, 3.64 (2t, J=7.3 Hz, 2H, $NC\underline{H}_2CH_2$), 4.64, 4.69 (2d, J=6.4 Hz, J=7.0 Hz. $^{13}$C NMR (major rotamer) (DMSO-$d_6$) δ11.9 (T, $CH_3$), 28.1 (t-Bu-$CH_3$), 32.2 ($\underline{C}H_2$CO), 41.6 ($N\underline{C}H_2CH_2$), 48.1 (T(N1)$CH_2$), 53.2 ($NCH_2$N), 60.0 ($OCH_2$), 78.9 (C($CH_3$)$_3$) 108.2 (T, $\underline{C}CH_3$), 142.0 (CH), 151.1(T, NC(O)N), 155.7 (carbamate C=O), 164.4 (T, C=O), 166.9 (tert. amide C=O), 172.7 (carboxylic acid C=O) ppm. FAB-MS: m/z= 385.15 (M+H)$^+$. Anal. Calcd. for $C_{16}H_{24}N_4O_7$ (384.39): C, 50.00; H, 6.29; N, 14.58. found C, 49.95, H, 6.40; N, 14.23.

EXAMPLE 124

N-(N-tert-Butyloxycarbonyl-aminomethyl)-N-(N6-benzyloxycarbonyladenin-9-ylacetyl)-β-alanine (4b)

A mixture of N-(N-tert-butyloxycarbonyl-aminomethyl)-N-(N9-benzyloxycarbonyl-adenin-9-ylacetyl)-β-alanine ethylester (2.34 g, 4.21 mmol) in THF (25 mL) and aqueous LiOH (0.5 M, 25 mL) was stirred at room temperature. AT 1.5 hour TLC indicated that hydrolysis was complete. The reaction mixture was extracted with $CH_2Cl_2$, acidified with HCl (2N) and extracted with $CH_2Cl_2$ to give 2.1 g (95%) of the title compound. $^1$H NMR (DMSO-$d_6$) δ1.47, 1.53* (2s, 9H, t-Bu), 2.51*, 2.78 (2t, J=7.5 Hz, 2H, $NCH_2C\underline{H}_2$), 3.57*, 3.75 (2t, J=7.2 Hz, 2H, $NC\underline{H}_2CH_2$), 4.65, 4.83* (2d, $NCH_2$N), 5.29 (s, 2H, $CH_2$Ph), 5.44, 5.54* (2s, 2H, $CH_2$), 7.4–7.6 (5H, aromat.), 8.02 (NH), 8.39, 8.67 (2s, aromat.), 10.7 ppm. FAB-MS: m/z=528.1 (M+1)$^+$. Anal. Calcd. for $C_{24}H_{29}N_7O_7$ (527.53): C, 54.64; H, 5.54; N, 18.59. found C, 54.86; H, 5.50; N, 18.81.

EXAMPLE 125

General coupling procedures for amino alkyl-β-alanine PNA's having letters attached through acetyl linkage

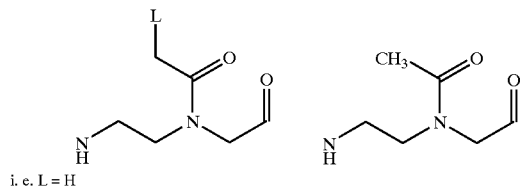

i. e. L = H

A. Preparation of the C Terminus Fragment

In general the PNA monomer, dimer or larger fragment such as N-(N-tert-butyloxycarbonyl-aminomethyl)-N-(N1-thyminylacetyl)-β-alanine ethylester, or N-(N-tert-butyloxycarbonyl-aminomethyl)-N-(N9-benzyloxycarbonyl-adenin-9-ylacetyl)-β-alanine ethylester prepared above, to be attached at the C terminus of another PNA monomer or larger fragment is dissolved in trifluoroacetic acid/$CH_2Cl_2$ (0.2–2 mL, 1:1, v/v). After stirring for 20 min at room temperature the clear solution is evaporated to dryness in vacuo (0.5 Torr) Diethylether (2 mL) is added and the mixture is evaporated to dryness. This process removes the t-Boc protecting group from the N terminus.

B. Preparation of the N Terminus Fragment

In general a PNA monomer, dimer or larger fragment having a free carboxyl group at the C terminus such as N-(N-tert-butyloxycarbonyl-aminomethyl)-N-(N1-thyminylacetyl)-β-alanine, or N-(N-tert-butyloxycarbonyl-aminomethyl)-N-(N6-benzyloxycarbonyladenin-9-ylacetyl)-β-alanine prepared above, is mixed with an equimolar amount of HBTU (0.1–1 mmol) in a solution of DMF/pyridine (0.5–5 mL, 1:1, v/v) and diisopropylethyl amine (0.2–2 mL).

C. Coupling of the Two Fragments

The solution prepared in part B is mixed with the solid residue obtained in part A and the mixture is stirred for 2 hours at room temperature. The reaction mixture is purified by silica gel flash column chromatography using a gradient of methanol and ethyl acetate as the eluent to give the corresponding oligomer.

Using the procedures illustrated a number of PNA's having the amino alkyl-β-alanine backbone were prepared. These PNA'S are listed in Table IV, as is MS characterization data and yields.

TABLE IV

| x | R$^1$ | R$^2$ | R$^3$ | n | yield$^a$ [%] | FAB-MS m/z found | (calcd.) |
|---|---|---|---|---|---|---|---|
| 1 | T | T | Et | 2 | 66 | 693.6 | (693.3) |
| 1 | T | T | H | 2 | 97 | 671.3 | (665.3) |
| 1 | T | T | Et | 1 | 56 | 679.5 | (679.3) |
| 1 | T | T | H | 1 | 99 | 657.3$^b$ | (651.3) |
| 2 | T | T | Et | 1 | 42 | 1211.5 | (1211.5) |
| 2 | T | T | H | 1 | 90 | 1183.2 | (1183.5) |
| 4 | T | T | Et | 1 | 31 | 2276.8 | (2276.9) |
| 1 | A (Cbz) | T | Et | 1 | 66 | 822.1 | (822.4) |
| 1 | A (Cbz) | T | H | 1 | 96 | 795.0 | (794.3) |
| 2 | A (Cbz) | T | Et | 1 | 33 | 1497.4 | (1497.6) |
| 2 | A | T | Et | 1 | 99 | 1229.9 | (1229.5) |
| 1 | A (Cbz) | A (Cbz) | Et | 1 | 62 | 965.8 | (965.4) |
| 1 | A (Cbz) | A (Cbz) | H | 1 | 95 | 938.9 | (937.4) |

$^a$Purity established by HPLC
$^b$[M+Li]+

EXAMPLE 126

General Procedure for Hydrolysis Amino Alkyl-β-alanine PNA's Having Letters Attached Through Acetyl Linkage In general the PNA monomer, dimer or larger fragment having its carbonyl group as an ester is hydrolyzed by adding (0.1–1 mmol) to a mixture of THF (0.8–8 mL) and LiOH (0.5 M, 0.8–8 mL). The mixture is stirred at room temperature until TLC indicated that hydrolysis is complete (ca. 2 hours) After extraction with n-butanol, the aqueous phase is acidified with HCl (2N). A precipitate is isolated by filtration and/or the solution is extracted with n-butanol a second time. The organic layer is separated and dried over $Na_2SO_4$, evaporated and the crude products are combined and purified by silica gel flash column chromatography using a methanol/ethyl acetate gradient as eluent.

EXAMPLE 127

PNA Uptake and Protein Inhibition by PNA 20-mer

The PNA 20-mer H-Gly-TTT AGG ATT CGT GCT CAT GG-Lys-CONH2 was labeled with fluorescein isothiocycanate (FITC) and used in an uptake study. Transformed human hepatocytes (H8ad17) expressing HCV sequences were seeded onto 4-chamber slides at approximately $4 \times 10^4$ cells per well in 10% fbs media. FITC labeled PNA was prehybridized with 4 different lengths of oligodeoxyribonucleotides with a first region having from 6 to 12 deoxyribonucleotides that are complementary to the PNA and a second region having 10 deoxyribonucleotides that are not hybridized e.g. a tail. The sequences of the oligodeoxynucleotides used were 5'-ACG AAT CCT AAA CCT CAA AGA A-3' (SEQ ID NO: 40) 5'-GAA TCC TAA ACC TCA AAG AAA-3' (SEQ ID NO: 41) 5'-ATC CTA AAC CTC AAA GAA-3' (SEQ ID NO: 42) and 5'-CCT AAA CCT CAA AGA A-3' (SEQ ID NO: 43) with the underlined portion denoting the portion of the oligodeoxyribonucleotide that is complementary to the PNA 20-mer. Each deoxyribonucleotide (22, 20, 18, and 16-mer) was independently hybridized with 5 equivalents of the above PNA 20-mer in 100mM NaCl and 100mm tris-HCl buffer. The mixture was preheated to 65° C. for 15 minutes and cooled to 37° C. for 30 minutes. The cells were washed twice with 1 mL of optimem. Then 1 mL of optimem with lipofectin was placed on the cells. Cells were treated with DNA prehybridized with oligodeoxyribonucleotides for 4 hours. The cells were rinsed with complete media and wet mounts were prepared immediately in order to study the cells under a fluorescent scope.

The cells treated with FITC labeled PNA 20-mer that were prehybridized with 20-mer 5'-GAA TCC TAA ACC TCA AAG AA-3' (SEQ ID NO: 41) where the underlined portion is hybridized to the PNA deoxyribonucleotide, showed staining consistent with cellular uptake. The cells treated with FITC labeled PNA 20-mer that were not prehybridized with deoxyribonucleotides did not show staining.

In a similar study the effects of the above PNA on HCV core protein were examined. Cells are seeded in 6-well plates at approximately $3 \times 10^5$ cells per well, and the harvesting was done in 100 $\mu$l per well of laemmli buffer. Other than that the process was exactly the same as the uptake study above.

The results show that unhybridized PNA had an inhibitory affect on the HCV core protein. The PNA hybridized to the oligodeoxyribonucleotides also showed inhibition.

EXAMPLE 128

Preparation of N-(trifluoroacetyl)-3-[O-(dimethoxytrityl)]-1-aminopropan-3-ol

To a solution of 3-amino-1-propanol (1 g, 13.31 mmol) in dichloromethane (50 ml) was added ethyltrifluoromethylacetate (1.58 ml, 13.31 mmol). The reaction was complete as indicated by TLC (10% MeOH/CH$_2$Cl$_2$) in 2 hours. The solvent was removed by evaporation in vacuo. The residue was coevaporated four times with dry pyridine. The residue was then dissolved in a mixture of dry pyridine (50 ml) and triethylamine (1.87 ml, 13.31 mmol). While the reaction mixture was stirred, dimethoxytrityl chloride (4.51 g, 13.31 mmol) was added in four portions. The reaction was complete in 20 hours as indicated by TLC (25% EtOAc/hexanes). The solvent was reduced in vacuo and the residue was partitioned between dichloromethane and water. The dichloromethane was collected and washed with water (2×25 ml) and once with brine (25 ml). The dichloromethane was dried (MgSO$_4$) and concentrated in vacuo. The residue was neutralized with a solution of 5% EtOAc in hexanes with 1% pyridine and was purified by silica gel flash chromatography eluted with 5% EtOAc in hexanes. The appropriate fractions were collected and concentrated in vacuo to yield title compound in 84% yield (5.29 g). $^1$H NMR (DMSO) δ: 1.79 (m, 2H, CH$_2$), 3.01 (t, 2H, CH$_2$), 3.75 (s, 6H 2×CH$_3$), 6.88–7.36 (m, 13H, aromatics), 9.36 (bs, 1H, NH).

EXAMPLE 129

Preparation of Methyl N-(3-O-dimethoxytritylprop-1-yl)-N-(trifluoroacetyl)glycinate To a solution of N-(triflubroacetyl)-3-[O-(dimethoxytrityl)]-1-aminopropan-3-ol (40 g, 84.50 mmol) in DMF (550 ml) at 0° C. was added NaH (4 g, 101.40 mmol) in four 1 g portions. The reaction mixture was stirred until the evolution of gas stopped. Then methylbromoacetate (10.31 ml, 92.95 mmol) was added to the reaction mixture dropwise via addition funnel. The reaction was complete as indicated by TLC (20% EtOAc in hexanes) in 20 hours. The solvent volume was reduced in vacuo to approximately 200 ml and then partitioned between water (100 ml) and dichloromethane (200 ml). The aqueous layer was extracted with dichloromethane (4×75 ml). The organic fractions were collected and dried over MgSO$_4$ and concentrated in vacuo. The residue was purified by silica gel flash chromatography eluted with 20% EtOAc in Hexanes. The appropriate fractions were collected and concentrated in vacuo to yield title compound 35.90 g (83%). $^1$N NMR (CDCl$_3$) δ: 1.90 (m, 2H, CH$_2$), 3.18 (m, 2H, CH$_2$), 3.65 (m, 2H, CH$_2$), 3.78 (d, 3H, CH$_3$), 3.83 (s, 6H, 2×CH$_3$), 4.10 (s, 2H, CH$_2$), 6.81–7.48 (m, 13H, aromatics).

EXAMPLE 130

Preparation of Sodium Salt of N-[3-O-(dimethoxytrityl)prop-1-yl]glycine

Methyl N-(3-O-dimethoxytritylprop-1-yl)-N-(trifluoroacetyl)glycinate (1.57 g, 3.08 mmol) was suspended in 20% aq. NaOH (50 ml) and the reaction mixture was refluxed. The reaction was complete as indicated by TLC (20% EtOAc in hexanes) in 4 hours. The reaction was allowed to cool to room temperature and was extracted with EtOAc (4×25 ml). The organic fractions were collected and washed once with brine (25 ml) and dried over MgSO$_4$ then concentrated in vacuo to yield 1.19 g (85%) of the title compound. ES/MS Positive mode m/z=434.30. $^1$N NMR (DMSO) δ: 1.65 (m, 2H, CH$_2$), 2.79 (bt, 2H, CH$_2$), 2.47 (m, 6H, CH$_2$+DMSO), 3.02 (bt, 2H, CH$_2$), 3.78 (s, 6H, 2×CH$_3$), 6.88–7.41 (m, 13H, aromatics).

EXAMPLE 131

Preparation of Sodium Salt of N-[3-O-(dimethoxytrityl)prop-1-yl]-N-[thymidylmethylenecarbonyl]glycine N$_1$-acetic acid thymidine (722 mg, 1.58 mmol), hydroxybenzyltriazole (74 mg, 0.482 mmol), EDC HCl salt (92 mg, 482 mmol) were dissolved in pyridine (25 ml) and DMF (25 ml) and stirred for 1 hour. The sodium salt of N-[3-O-(dimethoxytrityl)prop-1-yl]glycine then was added and reaction mixture was stirred for 20 hours at which time TLC (10% MeOH in CH$_2$Cl$_2$) indicated that the reaction was complete. Dichloromethane (50 ml) and water (50 ml) were added to the reaction mixture and separated. The water was extracted with dichloromethane (3×50 ml). The organic layers were pooled and washed with brine (1×50 ml), dried over MgSO$_4$ and concentrated in vacuo. The product was purified by silica gel flash chromatography eluting with 10% MeOH in $CH_2Cl_2$ then 15% MeOH in $CH_2Cl_2$. The appropriate fractions were collected and concentrated in vacuo to yield title compound 164 mg (60%). $^1$N NMR (DMSO) Delta: 1.65–1.71 (bs, 5H, $CH_2+CH_3$), 2.95 (m, 2H, $CH_2$), 3.33 (m, 2H, $CH_2$), 3.71 (bs, 8H, $CH_2+2\times CH_3$), 4.50 (d, 2H, $CH_2$), 6.84–7.5 (m, 14H, aromatics), 11.3 (bs, 1H, NH).

EXAMPLE 132

Preparation of N-(trifluoroacetyl)-3-[O-(dimethoxytrityl)]-1-aminobutan-4-ol

The procedure of Example 128 was repeated using 4-amino-1-propanol as the starting material. $^1$N NMR (DMSO) δ: 1.53 (m, 4H, 2×$CH_2$), 2.98 (t, 2H, $CH_2$), 3.27 (m, 2H, $CH_2$), 3.73 (s, 6H, 2×$CH_3$), 6.85–7.40 (m, 13H, aromatics), 9.40 (bt, 1H, NH).

EXAMPLE 133

Preparation of Methyl N-(3-O-dimethoxytritylprop-1-yl)-N-(trifluoroacetyl)glycinate The procedure of Example 129 was repeated using N-(trifluoroacetyl)-3-[O-(dimethoxytrityl)]-1-aminobutan-4-olas the starting material. $^1$N NMR (DMSO) δ: 1.60 (m, 4H, 2×$CH_2$), 2.99 (t, 2H, $CH_2$), 3.45 (m, 2H, $CH_2$), 3.71 (d, 3H, $CH_3$), 3.78 (s, 6H, 2×$CH_3$), 4.30 (d, 2H, $CH_2$), 6.89–7.41 (m, 13H, aromatics)

EXAMPLE 134

Preparation of Sodium Salt of N-[3-O-(dimethoxytrityl)prop-1-yl]glycine

The procedure of Example 130 was repeated using methyl N-(3-O-dimethoxytritylprop-1-yl)-N-(trifluoroacetyl)-glycinate as the starting material. $^1$N NMR (DMSO) δ: 1.61 (bm, 4H, 2×$CH_2$), 2.71 (bt, 2H, $CH_2$), 2.98 (bs, 2H, $CH_2$), 3.14 (bt, 2H, $CH_2$), 3.72 (bs, 6H, 2×$CH_3$), 6.84–7.44 (m, 13H, aromatics).

EXAMPLE 135

Preparation of Sodium Salt of N-[3-O-(dimethoxytrityl) prop-1-yl]-N-[thymidylmethylenecarbonyl]glycine The procedure of Example 131 was repeated using the odium salt of N-[3-O-(dimethoxytrityl)prop-1-yl]glycine as the starting material. $^1$N NMR (DMSO) δ: 1.55 (bm, 4 H, 2×$CH_2$), 1.80 (bs, 3H, $CH_3$), 2.95 (bm, 2H, $CH_2$), 3.23 (bm, 2H, $CH_2$), 3.75 (bs, 8H, 2×$CH_3+CH_2$), 4.50 (d, 2H, $CH_2$), 6.82–7.50 (m, 14H, aromatics), 11.22 (bs, 1H, NH).

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A process for preparing a compound comprising a polyamide backbone bearing a plurality of ligands that are individually bound to aza nitrogen atoms located within said backbone, comprising the steps of:

A) providing a polymer substrate, said polymer being functionalized with a chemical group capable of forming an anchoring linkage with an amino acid;

B) coupling said polymer with a first amino acid through said anchoring linkage, said first amino acid having formula (IV):

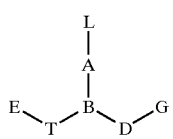

(IV)

wherein:

L is selected from the group consisting of naturally occurring nucleobases, non-naturally occurring nucleobases, provided that at least one L is a naturally occurring nucleobase; aromatic moieties, DNA intercalators, nucleobase-binding groups, heterocyclic moieties, and reporter ligands, wherein amino groups are, optionally, protected by amino protecting groups; provided that at least one L is a naturally occurring nucleobase;

A is a single bond or a group of the formula:

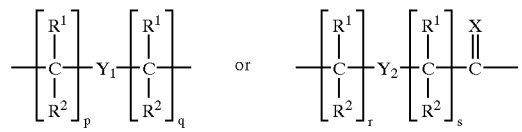

where:
X is O, S, Se, $NR^3$, $CH_2$ or $C(CH_3)_2$;
$Y_1$ is a single bond, O, S or $NR^4$;
$Y_2$ is single bond, O or S;
p and q are zero or integers from 1 to 5;
r and s are zero or integers from 1 to 5;
$R^1$ and $R^2$ are independently selected from the group consisting of hydrogen, $(C_1-C_4)$alkyl, hydroxy- or alkoxy- or alkylthio-substituted $(C_1-C_4)$alkyl, hydroxy, alkoxy, alkylthio, amino and halogen; and
$R^3$ and $R^4$ are independently selected from the group consisting of hydrogen, $(C_1-C_4)$alkyl, hydroxy- or alkoxy- or alkylthio-substituted $(C_1-C_4)$alkyl, hydroxy, alkoxy, alkylthio and amino;

B is N or $R^3N^+$, where $R^3$ is as defined above;

T is $CR^6R^7$, $CHR^6CHR^7$ or $CR^6R^7CH_2$, where $R^6$ is hydrogen and $R^7$ is selected from the group consisting of the side chains of naturally occurring alpha amino acids, or $R^6$ and $R^7$ are independently selected from the group consisting of hydrogen, $(C_2-C_6)$alkyl, aryl, aralkyl, heteroaryl, hydroxy, $(C_1-C_6)$alkoxy, $(C_1-C_6)$alkythio, $NR^3R^4$ and $SR^5$, where $R^3$ and $R^4$ are as defined above, and $R^5$ is hydrogen or $(C_1-C_6)$alkyl, hydroxy-, alkoxy-, or alkylthio-substituted $(C_1-C_6)$alkyl, or $R^6$ and $R^7$ taken together complete an alicyclic or heterocyclic system;

D is $CR^6R^7$, $CH_2CR^6R^7$ or $CHR^6CHR^7$, where $R^6$ and $R^7$ are as defined above;

E is COOH or an activated or protected derivative thereof; and

G is $NPgR^3$ where $R^3$ is as defined above and Pg is an amino protecting group;

C) removing said amino protecting group from said coupled first amino acid to generate a free amino group; and D) reacting said free amino group with a second amino acid having formula (IV) to form said compound.

2. The process of claim 1 further comprising the steps of:

E) removing said amino protecting group from said second amino acid to generate a terminal free amino group on said peptide chain; and F) reacting said free amino group on said peptide chain with a further amino acid having formula (IV) to lengthen said peptide chain.

3. The process of claim 2 wherein steps E and F are performed a plurality of times.

4. The process of claim 2 further comprising removing at least one protecting group remaining on the amino acid moieties of the peptide chain.

5. The process of claim 1 further comprising cleaving said anchoring linkage without substantially degrading said peptide chain.

6. The process of claim 1 wherein the polymer substrate contains polystrene, polyacrylamide, silica, a composite material, or cotton.

7. The process of claim 1 wherein the chemical group capable of forming said anchoring linkage is chloro-, bromo- and iodo-substituted alkyl, amino-substituted alkyl, amino and aryl-substituted alkyl, amino- and alkylaryl-substituted alkyl, hydroxy-substituted alkyl, or a derivative thereof having a spacer group that can be cleaved substantially without degradation of said polypeptide.

8. The process of claim 7 wherein chloro-substituted alkyl is chloromethyl, amino-substituted alkyl is aminomethyl, amino- and alkyl-substituted aryl is α-aminobenzyl, amino- and alkylaryl-substituted alkyl is selected from the group consisting of α-amino-3- and α-amino-4-methylbenzyl, and hydroxy-substituted alkyl is hydroxymethyl.

9. The process of claim 7 wherein:

the chemical group is derived from an amino-containing moiety selected from amino-substituted alkyl, amino- and aryl substituted alkyl, and amino- and alkylaryl-substituted alkyl; and the chemical group includes a spacer group derived from the group consisting of 4-(haloalkyl)aryl-lower alkanoic acids, Boc-aminoacyl-4-(oxymethyl)aryl-lower alkanoic acids, N-Boc-p-acylbenzhydrylamines, N-Boc-4'-(lower alkyl)-p-acylbenzhydrylamines, N-Boc-4'-(lower alkoxy)-p-acylbenzhydrylamines, and 4-hydroxymethylphenoxy-lower alkanoic acids.

* * * * *

UNITED STATES PATENT AND TRADEMARK OFFICE
CERTIFICATE OF CORRECTION

PATENT NO.   : 6,713,602 B1
DATED        : March 30, 2004
INVENTOR(S)  : Ole Buchardt et al.

It is certified that error appears in the above-identified patent and that said Letters Patent is hereby corrected as shown below:

Column 103,
Line 65, please delete "provided that at least one L is a naturally occurring nucleobase;";

Column 106,
Line 8, please delete "polystrene" and insert therefor -- polystyrene --.

Signed and Sealed this

Fifth Day of April, 2005

JON W. DUDAS
*Director of the United States Patent and Trademark Office*

SEQUENCE LISTING

<160> NUMBER OF SEQ ID NOS: 43

<210> SEQ ID NO 1
<211> LENGTH: 16
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 1
gatccaaaaa aaaaag        16

<210> SEQ ID NO 2
<211> LENGTH: 16
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 2
gatccttttt tttttg        16

<210> SEQ ID NO 3
<211> LENGTH: 10
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 3
aaaaaaaaaa        10

```
<210> SEQ ID NO 4
<211> LENGTH: 20
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 4
aaaaagaaaa aaaaaaaaag                                               20

<210> SEQ ID NO 5
<211> LENGTH: 20
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 5
aagaagaaaa aaaaaaaagg                                               20

<210> SEQ ID NO 6
<211> LENGTH: 8
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 6 aaaaaaaa                                                             8

<210> SEQ ID NO 7
<211> LENGTH: 10
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 7
tttttttttt                                                          10

<210> SEQ ID NO 8
<211> LENGTH: 10
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 8
aaaaagaaaa                                                          10

<210> SEQ ID NO 9
<211> LENGTH: 10
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 9
aagaagaaaa                                                          10
```

```
<210> SEQ ID NO 10
<211> LENGTH: 10
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 10
aaaagaaaaa                                                          10

<210> SEQ ID NO 11
<211> LENGTH: 10
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 11
aaaagaagaa                                                          10

<210> SEQ ID NO 12
<211> LENGTH: 10
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 12
ttttcttttt                                                          10

<210> SEQ ID NO 13
<211> LENGTH: 10
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 13
ttttcttctt                                                          10

<210> SEQ ID NO 14
<211> LENGTH: 10
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 14
tttttctttt                                                          10

<210> SEQ ID NO 15
<211> LENGTH: 10
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 15
tttttcttct                                                          10
```

```
<210> SEQ ID NO 16
<211> LENGTH: 10
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 16
ttcttctttt                                                            10

<210> SEQ ID NO 17
<211> LENGTH: 15
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 17
tttttttttt ttttt                                                      15

<210> SEQ ID NO 18
<211> LENGTH: 15
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 18
aaaaaaaaaa aaaaa                                                      15

<210> SEQ ID NO 19
<211> LENGTH: 10
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 19
aaaaggagag                                                            10

<210> SEQ ID NO 20
<211> LENGTH: 10
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 20
gagaggaaaa                                                            10

<210> SEQ ID NO 21
<211> LENGTH: 10
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 21
aaaagtagag                                                            10

<210> SEQ ID NO 22
```

```
<211> LENGTH: 10
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 22
aaaaggtgag                                                                    10

<210> SEQ ID NO 23
<211> LENGTH: 10
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 23
gagatgaaaa                                                                    10

<210> SEQ ID NO 24
<211> LENGTH: 10
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 24
gagtggaaaa                                                                    10

<210> SEQ ID NO 25
<211> LENGTH: 10
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 25
aaaaataaaa                                                                    10

<210> SEQ ID NO 26
<211> LENGTH: 10
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 26
aaaacaaaaa                                                                    10

<210> SEQ ID NO 27
<211> LENGTH: 10
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 27
aaaataaaaa                                                                    10

<210> SEQ ID NO 28
<211> LENGTH: 10
```

```
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 28
aaaaacaaaa                                                          10

<210> SEQ ID NO 29
<211> LENGTH: 16
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 29
tcgacttttc tttttg                                                   16

<210> SEQ ID NO 30
<211> LENGTH: 16
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 30
tcgacaaaaa gaaaag                                                   16

<210> SEQ ID NO 31
<211> LENGTH: 15
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 31
gaagaagaaa atgca                                                    15

<210> SEQ ID NO 32
<211> LENGTH: 16
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 32
gttttcttct tctgca                                                   16

<210> SEQ ID NO 33
<211> LENGTH: 16
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 33
gaagaagaaa agtgac                                                   16

<210> SEQ ID NO 34
<211> LENGTH: 16
<212> TYPE: DNA
```

```
<213> ORGANISM: Artificial Sequence
<220> FEATURE:
<221> NAME/KEY: misc_feature
<223> OTHER INFORMATION: Novel Sequence

<400> SEQUENCE: 34
gttttcttct tctgca                                                    16

<210> SEQ ID NO 35
<211> LENGTH: 10
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 35
aatagtagtg                                                           10

<210> SEQ ID NO 36
<211> LENGTH: 10
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 36
attagtagtg                                                           10

<210> SEQ ID NO 37
<211> LENGTH: 10
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 37
gtgatgataa                                                           10

<210> SEQ ID NO 38
<211> LENGTH: 10
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 38
aaaaccacac                                                           10

<210> SEQ ID NO 39
<211> LENGTH: 10
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 39
cacaccaaaa                                                           10

<210> SEQ ID NO 40
<211> LENGTH: 22
<212> TYPE: DNA
<213> ORGANISM: Artificial Sequence
```

```
-continued

<220> FEATURE:
<221> NAME/KEY: misc_feature
<223> OTHER INFORMATION: Novel Sequence

<400> SEQUENCE: 40
acgaatccta aacctcaaag aa                                              22

<210> SEQ ID NO 41
<211> LENGTH: 20
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 41
gaatcctaaa cctcaaagaa                                                 20

<210> SEQ ID NO 42
<211> LENGTH: 18
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 42
atcctaaacc tcaaagaa                                                   18

<210> SEQ ID NO 43
<211> LENGTH: 16
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 43
cctaaacctc aaagaa                                                     16
```